US011555061B2

(12) United States Patent
Finnis et al.

(10) Patent No.: US 11,555,061 B2
(45) Date of Patent: *Jan. 17, 2023

(54) ALBUMIN VARIANTS AND CONJUGATES

(71) Applicant: Albumedix Ltd, Nottingham (GB)

(72) Inventors: Christopher John Arthur Finnis, Nottingham (GB); Joanna Mary Hay, Nottingham (GB); Esben Peter Friis, Herlev (DK); Jason Cameron, Nottingham (GB); Darrell Sleep, Nottingham (GB)

(73) Assignee: ALBUMEDIX, LTD, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/827,356

(22) Filed: Mar. 23, 2020

(65) Prior Publication Data

US 2020/0392206 A1  Dec. 17, 2020

Related U.S. Application Data

(60) Continuation of application No. 15/280,733, filed on Sep. 29, 2016, now abandoned, which is a division of application No. 13/201,123, filed as application No. PCT/EP2010/051751 on Feb. 11, 2010, now Pat. No. 9,493,545.

(60) Provisional application No. 61/154,555, filed on Feb. 23, 2009.

(30) Foreign Application Priority Data

Feb. 11, 2009 (EP) .................................... 09152625
Feb. 12, 2009 (EP) .................................... 09152686

(51) Int. Cl.
*C07K 14/765* (2006.01)
*G16B 5/00* (2019.01)
*C07K 14/76* (2006.01)

(52) U.S. Cl.
CPC ............ *C07K 14/765* (2013.01); *C07K 14/76* (2013.01); *G16B 5/00* (2019.02); *C07K 2319/00* (2013.01)

(58) Field of Classification Search
None
See application file for complete search history.

(56) References Cited

U.S. PATENT DOCUMENTS

| 2,714,586 | A | 8/1955 | Lynch et al. |
| 4,302,386 | A | 11/1981 | Stevens |
| 4,741,900 | A | 5/1988 | Alvarez et al. |
| 4,757,006 | A | 7/1988 | Toole, Jr. et al. |
| 4,784,950 | A | 11/1988 | Hagen et al. |
| 4,795,805 | A | 1/1989 | Itoh et al. |
| 4,868,112 | A | 9/1989 | Toole, Jr. |
| 5,073,627 | A | 12/1991 | Curtis et al. |
| 5,208,020 | A | 5/1993 | Chari et al. |
| 5,223,409 | A | 6/1993 | Ladner et al. |
| 5,264,586 | A | 11/1993 | Nicolaou et al. |
| 5,294,699 | A | 3/1994 | Ohmura et al. |
| 5,380,712 | A | 1/1995 | Ballance et al. |
| 5,625,041 | A | 4/1997 | Johnson et al. |
| 5,698,426 | A | 12/1997 | Huse |
| 5,712,374 | A | 1/1998 | Kuntsmann et al. |
| 5,714,377 | A | 2/1998 | Tanner et al. |
| 5,714,586 | A | 2/1998 | Kunstmann et al. |
| 5,716,808 | A | 2/1998 | Raymond |
| 5,728,553 | A | 3/1998 | Goodey et al. |
| 5,736,383 | A | 4/1998 | Raymond |
| 5,766,883 | A | 6/1998 | Ballance et al. |
| 5,773,001 | A | 6/1998 | Hamann et al. |
| 5,824,837 | A | 10/1998 | Chen et al. |
| 5,854,039 | A | 12/1998 | Raymond et al. |
| 5,876,969 | A | 3/1999 | Fleer et al. |
| 5,888,768 | A | 3/1999 | Raymond |
| 5,948,609 | A | 9/1999 | Carter et al. |
| 6,509,313 | B1 | 1/2003 | Smith |
| 6,528,313 | B1 | 3/2003 | Le Mouellic et al. |
| 6,528,314 | B1 | 3/2003 | Le Mouellic et al. |
| 6,599,873 | B1 | 7/2003 | Sommer et al. |
| 6,638,768 | B1 | 10/2003 | Le Mouellic et al. |
| 6,686,179 | B2 | 2/2004 | Fleer et al. |
| 6,905,688 | B2 | 6/2005 | Rosen et al. |
| 6,926,898 | B2 | 8/2005 | Rosen et al. |
| 6,949,691 | B2 | 9/2005 | Carter |
| 6,972,322 | B2 | 12/2005 | Fleer et al. |
| 6,987,006 | B2 | 1/2006 | Fleer et al. |
| 6,989,365 | B2 | 1/2006 | Fleer et al. |

(Continued)

FOREIGN PATENT DOCUMENTS

| CA | 2611540 | 5/2009 |
| CA | 2562249 | 4/2016 |

(Continued)

OTHER PUBLICATIONS

Elzoghby et al., 2012. Albumin-based nanoparticles as potential controlled release drug delivery systems, J Control Release. 157(2):168-182.

(Continued)

*Primary Examiner* — Suzanne M Noakes

(74) *Attorney, Agent, or Firm* — Knobbe, Martens, Olson & Bear LLP

(57) ABSTRACT

Based on the three-dimensional structure of albumin, the inventors have designed variant polypeptides (muteins) which have one or more cysteine residues with a free thiol group (hereinafter referred to as "thio-albumin"). The variant polypeptide may be conjugated through the sulphur atom of the cysteine residue to a conjugation partner such as a bioactive compound.

17 Claims, 75 Drawing Sheets

Specification includes a Sequence Listing.

(56) References Cited

U.S. PATENT DOCUMENTS

| | | |
|---|---|---|
| 6,994,857 B2 | 2/2006 | Rosen et al. |
| 7,041,478 B2 | 5/2006 | Fleer et al. |
| 7,041,802 B2 | 5/2006 | Young et al. |
| 7,041,803 B2 | 5/2006 | Ni et al. |
| 7,045,318 B2 | 5/2006 | Ballance |
| 7,053,190 B2 | 5/2006 | Ruben et al. |
| 7,056,701 B2 | 6/2006 | Fleer et al. |
| 7,081,354 B2 | 7/2006 | Fleer et al. |
| 7,094,577 B2 | 8/2006 | Fleer et al. |
| 7,141,547 B2 | 11/2006 | Rosen et al. |
| 7,196,164 B2 | 3/2007 | Rosen et al. |
| 7,253,259 B2 | 8/2007 | Otagiri et al. |
| 7,271,149 B2 | 9/2007 | Glaesner et al. |
| 7,358,416 B2 | 4/2008 | Roopenian |
| 7,410,779 B2 | 8/2008 | Fleer et al. |
| 7,425,622 B2 | 9/2008 | Rosen |
| 7,435,410 B2 | 10/2008 | Fleer et al. |
| 7,465,707 B2 | 12/2008 | Ni et al. |
| 7,482,013 B2 | 1/2009 | Ballance et al. |
| 7,507,413 B2 | 3/2009 | Rosen et al. |
| 7,507,414 B2 | 3/2009 | Rosen et al. |
| 7,514,079 B2 | 4/2009 | Rosen et al. |
| 7,550,432 B2 | 6/2009 | Ballance |
| 7,569,215 B2 | 8/2009 | Wittrup et al. |
| 7,572,619 B2 | 8/2009 | Hauser et al. |
| 7,592,010 B2 | 9/2009 | Rosen et al. |
| 7,597,886 B2 | 10/2009 | Yu et al. |
| 7,615,537 B2 | 11/2009 | Scaria et al. |
| 7,785,599 B2 | 8/2010 | Ballance et al. |
| 7,833,521 B2 | 11/2010 | Fleer et al. |
| 7,850,963 B2 | 12/2010 | Rosen et al. |
| 7,851,596 B2 | 12/2010 | Gentz et al. |
| 7,862,818 B2 | 1/2011 | Raschke et al. |
| 7,951,360 B2 | 5/2011 | Wittrup et al. |
| 7,998,691 B2 | 8/2011 | Kulaksiz et al. |
| 8,012,464 B2 | 9/2011 | Rosen et al. |
| 8,080,651 B2 | 12/2011 | Goldberg |
| 8,541,378 B2 | 9/2013 | Ahn et al. |
| 8,697,650 B2 | 4/2014 | Gao et al. |
| 8,748,380 B2 | 6/2014 | Plumridge et al. |
| 8,822,417 B2 | 9/2014 | Andersen et al. |
| 9,493,545 B2 | 11/2016 | Finnis et al. |
| 9,944,691 B2 | 4/2018 | Delahay |
| 10,208,102 B2 | 2/2019 | Andersen et al. |
| 10,233,228 B2 | 3/2019 | Plumridge et al. |
| 10,329,340 B2 | 6/2019 | Delahay |
| 10,501,524 B2 | 12/2019 | Cameron et al. |
| 10,633,428 B2 | 4/2020 | Delahay et al. |
| 10,696,732 B2 | 6/2020 | Sleep et al. |
| 10,711,050 B2 | 7/2020 | Schmidt et al. |
| 10,934,341 B2 | 3/2021 | Cameron et al. |
| 2002/0123080 A1 | 9/2002 | Sonnenschein et al. |
| 2002/0151011 A1 | 10/2002 | Fleer et al. |
| 2003/0091565 A1 | 5/2003 | Beltzer et al. |
| 2003/0104578 A1 | 6/2003 | Ballance |
| 2004/0063635 A1 | 4/2004 | Yu |
| 2004/0171154 A1 | 9/2004 | Storici et al. |
| 2005/0142106 A1 | 6/2005 | Wittrup et al. |
| 2005/0222026 A1 | 10/2005 | Otagiri |
| 2005/0256303 A1 | 11/2005 | Otagiri et al. |
| 2006/0018859 A1 | 1/2006 | Carter |
| 2006/0051859 A1 | 3/2006 | Fu |
| 2006/0171892 A1 | 8/2006 | Woodrow |
| 2006/0178301 A1 | 8/2006 | Jurs |
| 2007/0041987 A1 | 2/2007 | Carter et al. |
| 2007/0092940 A1 | 4/2007 | Eigenbrot |
| 2008/0108560 A1 | 5/2008 | Beals et al. |
| 2008/0167238 A1 | 7/2008 | Rosen et al. |
| 2009/0029914 A1 | 1/2009 | Rosen et al. |
| 2010/0129846 A1 | 5/2010 | Goldknopf |
| 2011/0091412 A1 | 4/2011 | Wittrup et al. |
| 2011/0151490 A1 | 6/2011 | Hillman |
| 2011/0172398 A1 | 7/2011 | Borges et al. |
| 2013/0053322 A1 | 2/2013 | Gao |
| 2013/0225496 A1 | 8/2013 | Plumridge |
| 2014/0128326 A1 | 5/2014 | Cameron |
| 2014/0148392 A1 | 5/2014 | Gao et al. |
| 2014/0234311 A1 | 8/2014 | Sleep et al. |
| 2014/0248682 A1 | 9/2014 | Gao et al. |
| 2014/0315816 A1 | 10/2014 | Andersen et al. |
| 2014/0315817 A1 | 10/2014 | Schmidt et al. |
| 2015/0210752 A1 | 7/2015 | Cameron |
| 2016/0009787 A1 | 1/2016 | Sleep et al. |
| 2016/0033523 A1 | 2/2016 | Cameron et al. |
| 2016/0052993 A1 | 2/2016 | Schmidt et al. |
| 2016/0075756 A1 | 3/2016 | Sleep et al. |
| 2016/0075757 A1 | 3/2016 | Sleep et al. |
| 2016/0075758 A1 | 3/2016 | Sleep et al. |
| 2016/0075759 A1 | 3/2016 | Sleep et al. |
| 2016/0075760 A1 | 3/2016 | Sleep et al. |
| 2016/0075761 A1 | 3/2016 | Sleep et al. |
| 2016/0075762 A1 | 3/2016 | Sleep et al. |
| 2016/0075763 A1 | 3/2016 | Sleep et al. |
| 2017/0081389 A1 | 3/2017 | Finnis et al. |
| 2018/0072792 A1 | 3/2018 | Sleep et al. |
| 2018/0105576 A1 | 4/2018 | Sleep et al. |
| 2018/0105577 A1 | 4/2018 | Sleep et al. |
| 2018/0105578 A1 | 4/2018 | Sleep et al. |
| 2018/0162925 A1 | 6/2018 | Sleep et al. |
| 2018/0222963 A1 | 8/2018 | Sleep et al. |
| 2018/0265568 A1 | 9/2018 | Delahay et al. |
| 2018/0265570 A1 | 9/2018 | Sleep et al. |
| 2018/0334491 A1 | 11/2018 | Schmidt et al. |
| 2019/0113519 A1 | 4/2019 | Cameron et al. |
| 2019/0315836 A1 | 10/2019 | Delahay et al. |
| 2020/0102367 A1 | 4/2020 | Cameron et al. |
| 2020/0102368 A1 | 4/2020 | Andersen et al. |
| 2020/0385442 A1 | 12/2020 | Sleep et al. |
| 2021/0070839 A1 | 3/2021 | Delahay et al. |

FOREIGN PATENT DOCUMENTS

| | | |
|---|---|---|
| CN | 1405182 | 3/2003 |
| CN | 101065151 A | 10/2007 |
| CN | 101875693 B | 7/2012 |
| EP | 0286424 | 10/1988 |
| EP | 0319067 | 6/1989 |
| EP | 0413622 | 2/1991 |
| EP | 0438102 | 7/1991 |
| EP | 0464590 | 1/1992 |
| EP | 0510693 | 4/1992 |
| EP | 0305216 | 8/1995 |
| EP | 1681304 | 7/2006 |
| JP | 2005-206577 | 8/2005 |
| JP | 4983148 | 7/2012 |
| KR | 2005-0075134 | 7/2005 |
| RU | 2369404 | 10/2009 |
| WO | WO 1990/13653 | 11/1990 |
| WO | WO 1991/09125 | 6/1991 |
| WO | WO 1992/04367 | 3/1992 |
| WO | WO 1992/06204 | 4/1992 |
| WO | WO 1993/21232 | 10/1993 |
| WO | WO 1994/04687 | 3/1994 |
| WO | WO 1994/11026 | 5/1994 |
| WO | WO 1995/17413 | 6/1995 |
| WO | WO 1995/22625 | 8/1995 |
| WO | WO 1995/23857 | 9/1995 |
| WO | WO 1995/24427 | 9/1995 |
| WO | WO 1997/24445 | 7/1997 |
| WO | WO 1999/28348 | 6/1999 |
| WO | WO 2000/008207 | 2/2000 |
| WO | WO 2000/044772 | 8/2000 |
| WO | WO 2000/069902 | 11/2000 |
| WO | WO 2000/071079 | 11/2000 |
| WO | WO 2001/079258 | 10/2001 |
| WO | WO 2001/079271 | 10/2001 |
| WO | WO 2001/079442 | 10/2001 |
| WO | WO 2001/079443 | 10/2001 |
| WO | WO 2001/079444 | 10/2001 |
| WO | WO 2001/079480 | 10/2001 |
| WO | WO 2002/022809 | 3/2002 |
| WO | WO 2002/043658 | 6/2002 |
| WO | WO 2002/083897 | 10/2002 |
| WO | WO 2002/102830 | 12/2002 |

(56) References Cited

FOREIGN PATENT DOCUMENTS

| | | |
|---|---|---|
| WO | WO 2003/059934 | 7/2003 |
| WO | WO 2003/060071 | 7/2003 |
| WO | WO 2003/066085 | 8/2003 |
| WO | WO 2003/066824 | 8/2003 |
| WO | WO 2004/101620 | 1/2004 |
| WO | WO 2004/011499 | 2/2004 |
| WO | WO 2004/071536 | 8/2004 |
| WO | WO 2004/082640 | 9/2004 |
| WO | WO 2004/083245 | 9/2004 |
| WO | WO 2005/003296 | 1/2005 |
| WO | WO 2005/061718 | 7/2005 |
| WO | WO 2005/061719 | 7/2005 |
| WO | WO 2005/077042 | 8/2005 |
| WO | WO 2005/082423 | 9/2005 |
| WO | WO 2006/066595 | 6/2006 |
| WO | WO 2006/067511 | 6/2006 |
| WO | WO 2006/073195 | 7/2006 |
| WO | WO 2006/118772 | 11/2006 |
| WO | WO 2006/136831 | 12/2006 |
| WO | WO 2007/021494 | 2/2007 |
| WO | WO 2007/071068 | 6/2007 |
| WO | WO 2007/090584 | 8/2007 |
| WO | WO 2007/112940 | 10/2007 |
| WO | WO 2007/144173 | 12/2007 |
| WO | WO 2007/146038 | 12/2007 |
| WO | WO 2008/007146 | 1/2008 |
| WO | WO 2008/030558 | 3/2008 |
| WO | WO 2009/019314 | 2/2009 |
| WO | WO 2009/081201 | 7/2009 |
| WO | WO 2009/126920 | 10/2009 |
| WO | WO 2009/134808 | 11/2009 |
| WO | WO 2010/059315 | 5/2010 |
| WO | WO 2010/065950 | 6/2010 |
| WO | WO 2010/068278 | 6/2010 |
| WO | WO 2010/092135 | 8/2010 |
| WO | WO 2010/118169 | 10/2010 |
| WO | WO 2010/129023 | 11/2010 |
| WO | WO 2010/138814 | 12/2010 |
| WO | WO 2010/141329 | 12/2010 |
| WO | WO 2011/011315 | 1/2011 |
| WO | WO 2011/011797 | 1/2011 |
| WO | WO 2011/018611 | 2/2011 |
| WO | WO 2011/044563 | 4/2011 |
| WO | WO 2011/051489 | 5/2011 |
| WO | WO 2011/079175 | 6/2011 |
| WO | WO 2011/103076 | 8/2011 |
| WO | WO 2011/124718 | 10/2011 |
| WO | WO 2011/146902 | 11/2011 |
| WO | WO 2011/161127 | 12/2011 |
| WO | WO 2012/020143 | 2/2012 |
| WO | WO 2012/059486 | 5/2012 |
| WO | WO 2012/112188 | 8/2012 |
| WO | WO 2012/150319 | 11/2012 |
| WO | WO 2013/010840 | 1/2013 |
| WO | WO 2013/075066 | 5/2013 |
| WO | WO 2013/135896 | 9/2013 |
| WO | WO 2014/005596 | 1/2014 |
| WO | WO 2014/072481 | 5/2014 |
| WO | WO 2014/179657 | 11/2014 |
| WO | WO 2015/036579 | 3/2015 |

OTHER PUBLICATIONS

Adams et al., 2013. The Adaptable Major Histocompatibility Complex (MHC) Fold: Structure and Function of Nonclassical and MHC Class I-Like Molecules. Annu Rev Immunol. 31:529-561.
Akilesh et al., 2007. Neonatal FcR expression in bone marrow-derived cells functions to protect serum IgG from catabolism. J Immunol. (Baltimore, Md.: 1950) 179:4580-4588.
Allan et al "Enhanced albumins and albumin fusion technology" May 4, 2012 XP055109701 Retrieved from the Internet: URL: http:\\www.biopharma.novozymes.com/en/information-centre/posters-and-presentations/Documents/PEGS%20poster%202012_EZAL.pdf.
Altschul et al., 1997, Gapped BLAST and PSI-BLAST: A new genertion of protein database search programs. Nucleic Acids Res. 25(17):3389-3402.
Amthor et al., 2004, Albumin targeting of damaged muscle fibres in the mdx mouse can be monitored by MRI. Neuromuscular Disorders 14(12): 791-796.
Andersen et al., 2006, The conserved histidine 166 residue of the human neonatal Fc receptor heavy chain is critical for the pH-dependent binding to albumin, Eur J Immunol, 36:3044-3051.
Andersen et al., 2007, A receptor-mediated mechanism to support clinical observation of altered albumin variants, Clinic Chem, 53(12):2216.
Andersen et al., 2008, Ligand binding and antigenic properties of a human neonatal Fc receptor with mutation of two unpaired cysteine residues, FEBS Journal, 275(16):4097-4110.
Andersen et al., 2009, The versatile MCH class I-related FcRn protects IgG and albumin from degradation: implications for development of new diagnostics and therapeutics, Drug Metab Pharmacokinet, 24(4):318-332.
Andersen et al., 2010, Cross-species binding analyses of mouse and human neonatal Fc receptor show dramatic differences in immunoglobulin G and albumin binding. J Biol Chem. 285(7):4826-4836.
Andersen et al., 2010, FcRn binding properties of an abnormal truncated analbuminemic albumin variant, Clinical Biochem, 43:367-372.
Andersen et al., 2012, Structure-based mutagenesis reveals the albumin-binding site of the neonatal Fc receptor, Nature Comm. 3:610 in 9 pages and Supplemental Information in 13 pages.
Andersen et al., 2013, Single-chain variable fragment albumin fusions bind the neonatal Fc receptor (FcRn) in a species-dependent manner: implications for in vivo half-life evaluation of albumin fusion therapeutics, J Biol Chem., 288(33):24277-24285.
Andersen et al., May 2014, Extending serum half-life of albumin by engineering neonatal Fc receptor (FcRn) binding, J Biol Chem., 289(19):13492-502.
Anderson et al., 2006, Perspective—FcRn transports albumin: relevance to immunology and medicine, Trends Immunol, 27(7):343-348.
Averyhart-Fullard et al., 1990. Cloning and Thyroid Hormone Regulation of Albumin mRNA in Rana catesbeiana Tadpole Liver, Mol Endocrinol. 4(10):1556-1563.
Balan et al., 2006, A phase I/II study evaluating escalating doses of recombinant human albumin-interferon-α fusion protein in chronic hepatitis C patients who have failed previous interferon-α-based therapy, Antiviral Therapy, 11(1):35-45.
Ballesta-Claver et al., 2011, Disposable luminol copolymer-based biosensor for uric acid in urine, Analytica Chimica Acta, 702:254-261.
Barash et al., 1993, Synthesis and secretion of human serum albumin by mammary gland explants of virgin and lactating transgenic mice, Trans Res, 2:266-276.
Bar-Or et al., 2006, The formation and rapid clearance of a truncated albumin species in a critically ill patient, Clin Chim Acta 365(1-2):346-349.
Barr et al., 1996, C-Type Natriuretic Peptide, Peptides 17(7):1243-1251.
Barton et al., 1990, Site-directed, recombination-mediated mutagenesis of a complex gene locus. Nucleic Acids Res. 18(24):7349-4955.
Basle, Mar. 26, 2010, Protein chemical modification on endogenous amino acids, Chemistry & Biology, 17:213-227.
Beeken et al., 1962. Studies of I131-albumin catabolism and distribution in normal young male adults. The Journal of clinical investigation 41, 1312-1333.
Bennhold et al., 1959. Comparative studies on the half-life of I131-labeled albumins and nonradioactive human serum albumin in a case of analbuminemia. J Clin Invest. 38:863-872.
Benotti et al., 1979, Protein and caloric or macronutrient metabolic management of the critically ill patient, Crit Care Med, 7(12):520-525.
Bergmann et al., Jun. 2012, Development of a mathematical model for neonatal Rc receptor recycling to design human serum albumin

(56) References Cited

OTHER PUBLICATIONS mutants with extended half-lives, Medimmune FcRn recycling model for mutant albumins, poster, 21st PAGE meeting, Venice Italy, 1 p.
Berntzen et al., 2005, Prolonged and increased expression of soluble FC receptors, IgG and a TCR-lg fusion protein by transiently transfected adherent 293E cells, J Immun Method. 298:93-104.
Bhattacharya et al., 2000, Binding of the general anesthetics propofol and halothane to human serum albumin. High resolution crystal structures, J Biol Chem. 275(49):38731-38738.
Bhattacharya et al., 2000, Crystallographic analysis reveals common modes of binding of medium and long-chain fatty acids to human serum albumin, J. Mol. Biol., 303:721-732.
Blackburn, 2007, Maternal, Fetal and Neonatal Physiology: a Clinical Perspective, 3rd ed., pp. 197-198.
Boder et al., 1997. Yeast surface display for screening combinatorial polypeptide libraries. Nat Biotechnol. 15(6):553-557.
Boder et al., 2000. Directed evolution of antibody fragments with monovalent femtomolar antigen-binding affinity. PNAS U.S.A. 97:10701-10705.
Bos et al., 1989. The molecular mechanism of the neutral-to-base transition of human serum albumin. J Biol Chem. 264:953-959.
Bosse et al., 2005, Phase I comparability of recombinant human albumin and human serum albumin, J Clin Pharmacol, 35:57-67.
Bowe et al., 2001, FGF-23 inhibits renal tubular phosphate transport and is a PHEX substrate, Biochem Biophys Res Common., 284:977-981.
Bowie et al., 1989, Identifying determinants of folding and activity for a protein of unknown structure. PNAS U.S.A. 86(7):2152-2156.
Brennan et al., 2000, Three truncated forms of serum albumin associated with pancreatic pseudocyst, Biochim Biophys Acta 1481(2):337-343.
Broze et al., Feb. 25, 1980, Purification and properties of human coagulation factor VII, J Biol Chem., 255(4):1242-1247.
Bunting et al., 2012, Enhanced albumins and albumin fusion technology: tuning circulatory half-life with Novozymes Albufuse® Flex to meet medical needs, Poster, Biopharma NZ, 1 p.
Burmeister et al., 1994, Crystal structure at 2.2 Å result ion of the MHC-related neonatal Fc receptor, Nature, 372(6504):336-343.
Burmeister et al., 1994, Crystal structure of the complex of rat neonatal Fc receptor with Fc, Nature, 372(6504):379-383.
Cai et al., Jun. 2010, QPSOBT: One codon usage optimization software for protein heterologous expression, J Bioinformatics Sequence Analysis, 2(2):25-29.
Calissano et al., 1996, In vivo site-directed mutagenesis of Neurospora crassa beta-tubulin gene by spheroplasts transformation with oligonucleotides. Fungal Genetics Reports 43(Article 5) pp. 5.
Cantor et al. [Eds], 1980, Box 21-2. Reoxidation and refolding of reduced proteins, in Biophysical chemistry. Part III: The behavior of biological macromolecules, W.H. Freeman & Co., p. 1104.
CAPlus accession No. 2005:1283404, "Standard Albumin Gene . . . ", STN entry date Dec. 8, 2005; 1 page.
Carlson et al., 1992, Alloalbuminemia in Sweden: structural study and phenotypic distribution of nine albumin variants, PNAS USA 89:8225-8229.
Carter et al., 1989, Three-dimensional structure of human serum albumin, Science, 244(4909):1195-1198.
Chao et al. 2006. Isolating and engineering human antibodies using yeast surface display. Nature protocols 1(2):755-768.
Chapman A.P., 2002, PEGylated antibodies and antibody fragments for improved therapy: A review. Adv. Drug Deliv. Rev. 54:531-545.
Chari et al., 1992, Immunoconjugates Containing Novel Maytansinoids: Promising Anticancer Drugs; Cancer Research 52:127-131.
Chaudhury et al., 2003, The major histocompatibility complex-related Fc receptor for IgG (Fern) binds albumin and prolongs its lifespan, J Exp Med, 197(3):315-322.
Chaudhury et al., 2006, Albumin binding to FcRn: distinct from the FcRn-IgG interaction, Biochem. 45:4983-4990 and Supplemental Material in 4 pages.
Chen et al., 2003, ZDOCK: an initial-stage protein-docking algorithm, Protein, 52:80-87.
Chen et al., 2013, Human serum albumin from recombinant DNA technology: challenges and strategies, Biochimica et Biophysica Acta, 1830:5515-5525.
Condreay et al., 2007, Baculovirus Expression Vectors for Insect and Mammalian Cells, Current Drug Targets, 8:1126-1131.
Cornell et al., 1981, The environment of the sulfhydryl group in human plasma albumin as determined by spin labelling, Arch Biochem Biophys, 209(1):1-6.
Crystal Structure of Human Serum Albumin AT 2.5 A Resolution, PDB Accession: 1A06. publically available in 1999, 125 pp.
Curry et al., 1998, Crystal structure of human serum albumin complexed with fatty acid reveals on asymmetric distribution of binding sites, Nat Struct Biol, 5(9):827-835.
Curry, S., 2009. Lessons from the crystallographic analysis of small molecule binding to human serum albumin. Drug Metab Pharmacokinet. 24(4):342-357.
Dagnino et al., 2010, A novel frameshift deletion in the albumin gene causes analbuminemia in a young Turkish woman, Clinic Chimica Acta, 411:1711-1715.
Dall'Acqua et al., 2002. Increasing the affinity of a human IgG1 for the neonatal Fc receptor: Biological consequences. J Immunol. 169:5171-5180.
Daniels et al., 2006, The transferrin receptor part II: Targeted delivery of therapeutic agents into cancer cells. Clin Immunol. 121(2):159-176.
Database EMBL accession No. BAG37325; Jan. 12, 2008, "*Homo sapiens* hypothetical protein", 2 pages.
Database NCBI—Access No. 1A06_A (Jun. 1998); pp. 4.
Database NCBI—Access No. AAC63407 (Oct. 1998).
Database NCBI—Access No. AAD09358 (Jan. 1999).
Database NCBI—Access No. AAHF01000013.1 (Mar. 2007) Aspergillus fumigatus in 110 pages.
Database NCBI—Access No. AAL08579 (Sep. 2001).
Database NCBI—Access No. AAL56646 (Jan. 2002).
Database NCBI—Access No. AAM46104 (Jun. 2002).
Database NCBI—Access No. AAN17825.1 (Sep. 2002).
Database NCBI—Access No. AAQ20088 (May 2004).
Database NCBI—Access No. ACF10391 (Jul. 2008).
Database NCBI—Access No. AXS56687 (Jan. 2010) 2 pages.
Database NCBI—Access No. NP_001004887 (Feb. 2011).
Database NCBI—Access No. NP_001127106 (May 2011).
Database NCBI—Access No. P02768 (Apr. 2011).
Database NCBI—Access No. P02770 (May 2011).
Database NCBI—Access No. P07724 (May 2011).
Database NCBI—Access No. P21847 (Nov. 2010); Serum Albumin, 2 pages.
Database NCBI Access No. 103600—Albumin (2011); XP-002660221, 47 pages.
Database NCBI—Access No. P21848 (May 2011).
Database NCBI—Access No. P35747 (May 2011).
Database NCBI—Access No. P83517 (May 2011).
Database NCBI—Access No. Q03156 (May 2011).
Database NCBI—Access No. Q6WDN9-1 (Nov. 2006).
Database NCBI—Access No. Q91274 (Aug. 2010).
Database NCBI—Access No. QXLE4 (May 2011).
Database NCBI—Access No. S59517 (Mar. 2000).
Database NCBI—Accession No. AAA98797 (May 1996).
Database NCBI—Accession No. AAH49971 (Jun. 2007).
Database NCBI—Accession No. AAH85359 (Jul. 2006).
Database Swiss prot—Accession No. Q5XLE4.1 (May 2011).
Database Swiss prot—Accession No. A6YF56 (Jun. 2010).
Database NCBI—Accession No. XP-517233.2 (Sep. 2006).
Database NCBI—Accession No. NP_001182578.1 (Mar. 2014).
Database Swiss prot—Access No. P49822 (Jun. 2009).
Database Swissprot—Access No. O73860 (Jun. 2009).
Database Swissprot—Access No. P01012 (Jun. 2009).
Database Swissprot—Access No. P02768 (May 2009).
Database Swissprot—Access No. P02769 (Jun. 2009).
Database Swissprot—Access No. P08835 (May 2009).
Database Swissprot—Access No. P14639 (May 2009).
Database Swissprot—Access No. P19121 (Jun. 2009).

(56) References Cited

OTHER PUBLICATIONS

Database Swissprot—Access No. P49064 (May 2009).
Database Swissprot—Access No. P49065 (May 2009).
Database Swissprot—Access No. Q28522 (May 2009).
Datta-Mannan et al., 2007. Monoclonal antibody clearance: Impact of modulating the interaction of IgG with the neonatal Fc receptor. J Biol Chem. 282(3):1709-1717.
Datta-Mannan et al. 2012. FcRn affinity-pharmacokinetic relationship of five human IgG4 antibodies engineered for improved in vitro FcRn binding properties in cynomolgus monkeys. Drug Metabol Dispos. 40(8):1545-1555.
Debinski W., 2002, Local treatment of brain tumors with targeted chimera cytotoxic proteins. Cancer Invest. 20(5):801-809.
DeMarco et al., 2007, Schistosome albumin is of host, not parasite, origin, Int J Parasit., 37(11):2101-1208.
Derbyshire et al., 1986, A simple and efficient procedure for saturation mutagenesis using mixed oligodeoxynucleotides. Gene 46(2-3):145-152.
Dickinson et al., Oct. 1999, Bidirectional FcRn-dependent IgG transport in a polarized human intestinal epithelial cell line, J Clin Invest., 104(7):903-911.
Di Stefano et al., 2004, A novel method for coupling doxorubicin to lactosaminated human albumin by an acid sensitive hydrazone bond; synthesis, characterization and preliminary biological properties of the conjugate, Eur J Pharm Sci, 23:393-397.
Dockal et al., Oct. 1, 1999, The three recombinant domains of human serum albumin, J Biol Chem, 274(41):29303-29310.
Doronina et al., 2003, Development of potent monoclonal antibody auristatin conjugates for cancer therapy, Nat Biotechnol, 21:778-784.
Dugaiczyk et al., Jan. 1982, Nucleotide sequence and the encoded amino acids of human serum albumin mRNA, PNAS, USA, 79:71-75.
Edgar R.C., 2004, MUSCLE: multiple sequence alignment with high accuracy and high throughput. Nucleic Acids Res. 32(5):1792-1797.
Edgar R.C., 2004, MUSCLE: a multiple sequence alignment method with reduced time and space complexity. BMC Bioinformatics. 5(1):113 in 19 pages.
Elble, 1992, A simple and efficient procedure for transformation of yeasts, Biotechniques 13(1):18-20.
Emsley et al., 2010. Features and development of Coot. Acta crystallographica Section D, Biol. Crystallo. 66:486-501.
Farran et al., 2002, Targeted expression of human serum albumin to potato tubers, Trans Res, 11:337-346.
Feng et al., 2011, Design, expression and characterization of a soluble single-chain functional human neonatal Fc receptor, Prot Expr Purific., 79:66-71.
Ferrara et al., 1999, Pathophysiologic mechanisms of acute graft-vs.-host disease, Biol Blood Marrow Transpl., 5:347-56.
Flanagan, 2009, Protein engineering reaches new frontiers: more detailed knowledge of structure and function drives field forward quickly, Gen Eng Biotech News, 29(12):1-4.
Fleer et al., Oct. 1991, Stable multicopy vestors for high-level secretion of recombinant human serum albumin by kluyveromyces yeasts, Biotech, 9(10):968-975.
Fontaine et al., Long-term stabilization of maleeimide-thiol conjugates. Bioconjug Chem. 26(1):145-152.
Francisco et al., Aug. 2003, cAC10-vcMMAE, an anti-CD30-monomethyl auristatin E conjugate with potent and selective antitumor activity, Blood, 102(4):1458-1465.
Franklin et al., May 1980, Localization of the amino acid substitution site in a new variant of human serum albumin, albumin Mexico-2, PNAS. USA, 77(5):2505-2509.
Fritzer et al., 1996, Cytotoxic effects of a doxorubicin-transferrin conjugate in multidrug-resistant KB cells. Biochem Pharmacol. 51(4):489-493.
Fu et al., 2004, Fibroblast growth factor 19 increases metabolic rate and reverses dietary and leptin-deficient diabetes. Endocrinol., 145(6):2594-2603.

Gabrielsson et al. 2007. Pharmacokinetic and Pharmacodynamic Data Analysis: Concepts and Applications, 4th ed. (Swedish Pharmaceutical Press: Stockholm); Table of Contents in 9 pages.
Galliano et al., 1986, Structural characterization of a chain termination mutant of human serum albumin, J Biol Chem., 261:4283-4287.
Galliano et al., 1993, Protein and DNA sequence analysis of a 'private' genetic variant: albumin ortonovo (Glu-505→Lys), Biochim Biophys Acta, 1225(1)27-32.
Gama Sosa et al., 2010, Animal transgenesis: an overview, Brain Struct Funct, 214:91-109.
Gao et al., 2004, UpGene: Application of a Web-Based DNA Codon Optimization Algorithm, Biotechnol Prog, 20:443-448.
Garnier et al., 1994, Scale-Up of the Adenovirus Expression System for the Production of Recombinant Protein in Human 293S Cells, Cytotechnology, 15:145-155.
Ghetie et al., 1997. Increasing the serum persistence of an IgG fragment by random mutagenesis. Nature Biotech. 15:637-640.
Ghuman et al., 2005, Structural basis of the drug-binding specificity of human serum albumin. J Mol Bol. 353:38-52.
Gibbs et al., Apr. 13, 2007, Evolutionary and biomedical insights from the Rhesus Macaque genome, Science, 316(5822):222-234.
Gough et al., 2001, Assignment of Homology to Genome Sequences using a Library of Hidden Markov Models that Represent all Proteins of Known Structure. J Mol Biol. 313:903-919.
Graf et al., 2000, Concerted Action of Multiple cis-Acting Sequences Is Required for Rev Dependence of Late Human Immunodeficiency Virus Type 1 Gene Expression, J Virol 74(22):10822-10826.
Grantham et al., 1980, Codon Frequencies in 119 Individual Genes Confirm Consistent Choices of Degenerate Bases According to Genome Type, Nuc. Acids Res. 8(9):1893-1912.
Grosjean et al., 1982, Preferential Codon Usage in Prokaryotic Genes; The Optimal Codon-Anticodon Interaction Energy and the Selective Codon Usage in Efficiently Expressed Genes, Gene, 18:199-209.
Guo et al., 1995, 3'-end-forming signals of yeast mRNA. Mol Cell Biol. 15(11):5983-5990.
Gurbaxani et al., 2006. Analysis of a family of antibodies with different half-lives in mice fails to find a correlation between affinity for FcRn and serum half-life. Mol Immunol. 43(9):1462-1473.
Gustafsson et al., 2004, Codon bias and heterologous protein expression, Trends in Biotechnol. 22(7):346-353.
Gutniak et al., 1992, Antidiabetogenic Effect of Glucagon-like Peptide-1 (7-36) amide in Normal Subjects and Patients with Diabetes Mellitus, N Engl J Med., 326:1316-1322.
Ha et al., 2006, Fatty acids bound to human serum albumin and its structural variants modulate apolipoprotein B secretion in HepG2 cells, Biochem Biophys Acta 1761:717-724.
Haas et al., 1996, Codon usage limitation in the expression of HIV-1 envelope glycoprotein, Curr. Biol. 6:315-324.
Hagen et al., 1986, Characterization of a cDNA coding for human factor VII, PNAS USA, 83:2412-2416.
Hall et al., 2012, Interspecies scaling in pharmacokinetics: a novel whole-body physiologically based modeling framework to discovery drug biodistribution mechanisms In Vivo, J Pharma Sci, 101:1221-1241.
Hallstrom et al., 2008, S-nitroso human serum albumin reduces ischaemia/reperfusion injury in the pig heart after unprotected warm ischaemia, Cardiovascular Res, 77:506-514.
Haspel et al., 1999, Effects of barbiturates on facilitative glucose transporters are pharmacologically specific and isoform selective, J Membr Biol, 169:45-53.
Hassan et al., Oct. 1997, All About Albumin, Review, Clin Chem 43(10):2014a-2015.
Hawkins et al., 2008, Protein nanoparticles as drug carriers in clinical medicine. Adv Drug Deliv Rev. 60(8):876-885.
Hay et al., Apr. 9, 2009, ThioTransferrin: a recombinant human transferrin engineered for site specific drug conjugation and delivery, Oral Presentation, 5th Annual PEGS, Boston, MA, Novozymes; 22 pages.
He et al., 1992. Atomic structure and chemistry of human serum albumin. Nature 358(6383):209-215.

(56) References Cited

OTHER PUBLICATIONS

Henrotte et al., 2004, Investigation of non-covalent interactions between paramagnetic complexes and human serum albumin by electrospray mass spectrometry, Rapid Comm Mass Spectro, 18:1919-1924.
Herzog et al., 1999, Long-term correction of canine hemophilia B by gene transfer of blood coagulation factor IX mediated by adena-associated viral vector, Nature Med., 5(1):56-63.
Hillier et al., Apr. 2007, Generation and annotation of the DNA sequences of human chromosomes 2 and 4, Nature, 434:724-731.
Hinman et al., 1993, Preparation and Characterization of Monoclonal Antibody Conjugates of the Calicheamicins: A Novel and Potent Family of Antitumor Antibiotics, Cancer Research 53:3336-3342.
Hinton et al., 2004. Engineered human IgG antibodies with longer serum half-lives in primates. J Biol Chem. 279(8):6213-6216.
Hinton et al., 2006. An engineered human IgG1 antibody with longer serum half-life. J Immunol. 176:346-356.
Ho et al. (1993). X-ray and primary structure of horse serum albumin (Equus caballus) at 0.27-nm resolution. Eur J Biochem. 215(1):205-212.
Holm, 1986, Codon usage and gene expression, Nuc. Acids Res. 14(7):3075-3087.
Holm et al., 1998, Dictionary of recurrent domains in protein structures. Proteins 33(1):88-96.
Holm et al., 2000, DaliLite workbench for protein structure comparison. Bioinformatics 16(6):566-567.
Holt et al., 2003, Definition of a novel growth factor-dependent signal cascade for the suppression of bile acid biosynthesis, Genes Dev, 17:1581 -1591.
Houghton et al., 1980, The complete amino acid sequence of human fibroblast interferon as deduced using synthetic oligodeoxyribonucleotide primers of reverse transcriptase, Nucleic Acids Res., 8(13):2885-2894.
Howard et al., 1989, Intracerebral Drug Delivery in Rats with Lesion-Induced Memory Deficits, J. Neurosurg. 71:105-112.
Huang et al., 2007, Efficient gene delivery targeted to the brain using a transferrin-conjugated polyethyleneglycol-modified polyamidoamine dendrimer. FASEB J. 21(4):1117-1125.
Humphreys et al., 2007, Alternative antibody Fab' fragment PEGylation strategies: combination of strong reducing agents, disruption of the interchain disulphide bond and disulphide engineering. Protein Eng Des Sel. 20(5):227-234.
Humphries et al., 1994, Conjugation of synthetic peptides to carrier proteins for cell adhesion studies. J Tissue Cult Meth. 16(3-4):239-242.
Hussain et al., 2006, Fat-free Albumin as a Novel Drug Delivery System. Int'l J Peptide Res Therapeutics 12(3):311-315.
Ikemura, 1982, Correlation between the abundance of yeast transfer RNAs and the occurrence of the respective codons in protein genes. Differences in synonymous codon choice patterns of yeast and *Escherichia coli* with reference to the abundance of isoaccepting transfer RNAs, J Mol Biol. 158:573-597.
Ishima et al., 2007, S-nitrosylation of human variant albumin liprizzi (R410C) confers potent antibacterial and cytoprotective properties, J Pharma Exp Therapeutics, 320(3):969-977.
Israel et al., 1993. Immunoglobulin G binding sites on the human foetal intestine: a possible mechanism for the passive transfer of immunity from mother to infant. Immunol. 79(1):77-81.
Ito et al., 1983, Transformation of intact yeast cells treated with alkali cations, J Bacteriol, 153(1):163-168.
Iwao et al., 2006, Oxidation of Arg-410 promotes the elimination of human serum albumin, Biochim Biophys Acta, 1764(4):743-749.
Iwao et al., 2007, Changes of net charge and α-helical content affect the pharmacokinetic properties of human serum albumin, Biochim Biophys Acta, 1774:1582-1590.
Iwao et al., 2007, Effect of one point mutation on the structural and pharmacokinetic properties of human serum albumin, The Pharmaceutical Society of Japan, Summary of Annual Meeting, 127(3):154 (w/Translation).
Iwao et al., 2009, Altered chain-length and glycosylation modify the pharmacokinetics of human serum albumin, Biochem Biophys Acta, 1794(4):634-641.
Jaye et al., 1983, Isolation of a human anti-haemophilic factor IX cDNA clone using a unique 52-base synthetic oligonucleotide probe deduced from the amino acid sequence of bovine factor IX, Nucleic Acids Res. 11(8):2325-2335.
Jerdeva et al., Comparison of FcRn- and pIgR-mediated transport in MOCK cells by fluorescence confocal microscopy. Traffic. Sep. 2010;11 (9):1205-20.
Jones D.T., 1999, GenTHREADER: An efficient and reliable protein fold recognition method for genomic sequences. J Mol Biol. 287(4):797-815.
Kabsch et al., 1983, Dictionary of protein secondary structure: pattern recognition of hydrogen-bonded and geometrical features, Biopolymers, 22(12):2577-2637.
Kabsch W., 2010. XDS. Acta crystallographica Section D, Biol Crystallogr. 66:125-132.
Kacskovics et al., 2011, Recent advances using FcRn overexpression, Landes Bioscience 3(5) 431-439.
Kaneko et al., Jan. 2008, Subdomain IIIA of dog albumin contains a binding site similar to site II of human albumin, Drug Metabol Disp. 36:81-86.
Katoh et al., 2002, MAFFT: A novel method for rapid multiple sequence alignment based on fast Fourier transform. Nucleic Acids Res. 30(14):3059-3066.
Katoh et al., 2005, MAFFT Version 5: Improvement in accuracy of multiple sequence alignment. Nucleic Acids Res. 33(2):511-518.
Katoh et al., 2007, PartTree: an algorithm to build an approximate tree from a large number of unaligned sequences. BioInformatics 23(3): 372-374.
Katoh et al., 2009, Multiple alignment of DNA sequences with MAFFT. Methods Mol Biol. 537:39-64.
Katoh et al., 2010, Parallelization of the MAFFT multiple sequence alignment program. Bioinformatics 26(15): 1899-1900.
Kavimandan et al., 2006, Synthesis and characterization of insulin-transferrin conjugates. Bioconjug Chem. 17(6):1376-1384.
Kawamata et al., Aug. 10, 2010 Generation of genetically modified rats from embryonic stem cells, PNAS, 107(32):14223-14228.
Kenanova et al., 2005, Tailoring the pharmacokinetics and positron emission tomography imaging properties of anti-carcinoembryonic antigen single-chain Fv-Fc antibody fragments, Cancer Res, 65(2):622-631.
Kenanova et al., 2007, Radioiodinated versus radiometal-labeled anti-carcinoembryonic antigen single-chain Fv-Fc antibody fragments; optimal pharmacokinetics for therapy, Cancer Res, 67(2):718-726.
Kenanova et al., 2009, HAS domain III as a protein scaffold with defined serum pharmacokinetics, J Nucl Med, 50(Supp 2): 1582—Abstract in 1 page.
Kenanova et al., 2010, Tuning the serum persistence of human serum albumin domain III:diabody fusion proteins, Prot Eng Design Selec, 23(10):789-798.
Khan et al., 2002, Bilirubin binding properties of pigeon serum albumin and its comparison with human serum albumin, J Biol Macromol., 30(3-4):171-178.
Kharitonenkov et al., 2005, FGF-21 as a novel metabolic regulator, J Clin Invest., 115(6):1627-1635.
Kiessling et al., 2002, Magnetic resonance imaging of nude mice with heterotransplanted high-grade squamous cell carcinomas: use of a low-loaded,covalently bound Gd-Has conjugate as contrast agent with high tumor affinity. Invest Radiol.37(4):193-198.
Kim et al., Mar. 2003, Development and characterization of a glucagon-like peptide 1-albumin conjugate: the ability to activate the glucagon-like peptide 1 receptor in vivo, Diabetes, 52:751-759.
Kim et al., 2006. Albumin turnover: FcRn-mediated recycling saves as much albumin from degradation as the liver produces. Am J Physiol Gastrointest Liver Physiol. 290:G352-G360.
Kim et al., 2007. Kinetics of FcRn-mediated recycling of IgG and albumin in human: Pathophysiology and therapeutic implications using a simplified mechanism-based model. Clin Immunol. 122(2):146-155.

(56) References Cited

OTHER PUBLICATIONS

Kjeldsen et al., 1998, Secretory expression of human albumin domains in *Saccharomyces cerevisiae* and their binding of myristic acid and an acylated insulin analogue. Protein Expr Purif. 13(2):163-169.
Kobayashi et al., 1998, The development of recombinant human serum albumin, Thera Apheresis, 2:257-262.
Kontermann, 2011, Strategies for extended serum half-life or protein therapeutics, Curr Opin Biotech. 22:1-9.
Kragh-Hansen et al., 2002, Practical aspects of the ligand-binding and enzymatic properties of human serum albumin, Biol Pharm Bull, 25(6):695-704.
Kragh-Hansen et al., 2004, Structural analysis and fatty acid-binding properties of two Croatian variants of human serum albumin, Clinical Chimica Acta, 349(1-2):105-112.
Kragh-Hansen et al., 2005, Effect of genetic variation on the thermal stability of human serum albumin, Biochim Biophys Acta, 1747(1):81-88.
Kratz, 2008, Albumin as a drub carrier: design of prodrugs, drug conjugates and nanoparticles, J Controlled Release, 132(3):171-183.
Kren et al., 1998, In vivo site-directed mutagenesis of the factor IX gene by chimeric RNA/DNA oligonucleotides. Nat Med. 4(3):285-290.
Krieger et al., Jul. 4, 2014, YASARA View—molecular graphics for all devices—from smartphones to workstations. Bioinformatics 30(20) 2981-2982.
Krissinel et al., 2007. Inference of macromolecular assemblies from crystalline state. Journal of molecular biology 372, 774-797 (2007).
Kuo et al., 2010, Neonatal Fc receptor: from immunity to therapeutics, J Clin Immunol, 30(6):777-789.
Kuo et al., 2011. Neonatal Fc receptor and IgG-based therapeutics. mAbs 3(5):422-430.
Kurtzhals et al., 1995, Albumin binding of insulins acylated with fatty acids; characterization of the ligand-protein interaction and correlation between binding affinity and timing of the insulin effect in vivo, Biochem J, 312:725-731.
Kurtzhals et al., 1997, Effect of fatty acids and selected drugs on the albumin binding of a long-acting, acylated insulin analogue, J Pharma Sci, 86:1365-1368.
Labro et al., 1986. A proton nuclear magnetic resonance study of human serum albumin in the neutral pH region. Biochim Biophys Acta 873(2):267-278.
Laftah et al., May 15, 2004, Effect of hepcidin on intestinal iron absorption in mice, Blood, 103(10):3940-3944.
Larsen et al., 2004, Use of the Gottingen minipig as a model of diabetes, with special focus on type 1 diabetes research,, ILAR Journal, 45(3):303-313.
Lawn et al, 1981, The sequence of human serum albumin cDNA and its expression in *E. coli*, Nucl Acids Res. 9(22):6103-6114.
Lee et al., 2005, Evaluation of transferrin-polyethylenimine conjugate for targeted gene delivery. Arch Pharm Res. 28(6):722-729.
Leger et al., 2004, Identification of CJC-1131-albumin bioconjugate as a stable and bioactive GLP-1 (7-36) analog, Bioorg Med Chem Lttrs, 14(17):4395-4398.
Leger et al., 2003, Synthesis and in vitro analysis of atrial natriuretic peptide-albumin conjugates, Bioorganic Medical Chem Lttrs, 13:3571-3575.
Li et al., 2001, Bipartite regulation of different components of the MHC class 1 antigen-processing machinery during dendritic cell maturation, Inti Immunol, 13(12):1515-1523.
Li et al., 2008, Germline competent embryonic stem cells derived from rat blastocysts, Cell, 135:1299-1310.
Lim et al., 2004, Transferrin-oligomers as potential carriers in anticancer drug delivery. Pharm Res. 21(11):1985-1992.
Lindahl et al., 2000, Identification of related proteins on family, superfamily and fold level. J Mol Biol. 295(3):613-615.
Liu et al., 2009, A high-yield and scaleable adenovirus vector production process based on high density perfusion culture of HEK 293 cells as suspended aggregates, J Bioscience Bioeng., 107(5):524-529.
Lode et al., Jul. 15, 1998, Targeted Therapy with a Novel Enediyene Antibiotic Calicheamicin theta11 Effectively Suppresses Growth and Dissemination of Liver Metastases in a Syngeneic Model of Murine Neuroblastoma, Cancer Research, 58:2925-2928.
Lowman et al., 1991, Selecting high-affinity binding proteins by monovalent phage display. Biochemistry 30(45):10832-10838.
Lubgan et al., 2002, A Transferrin conjugate of adriamycin-synthesis and potential chemotherapeutic efficacy. Cell Mol Biol Lett. 7(Suppl):98.
Luckow et al., 1993, Efficient Generation of Infectious Recombinant Baculoviruses by Site-Specific Transposon-Mediated Insertion of Foreign Genes into a Baculovirus Genome Propagated in *Escherichia coli*, J. Virol. 67(8):4566-4579.
Madison et al., 1994, Genetic variants of human serum albumin in Italy, Proc Nat Acad Sci. USA, 91:6476-6480.
Mahmood, 2004, Chapter 7: Principles, issues and applications of interspecies scaling, in New Drug Development, Sahajwalla ed., Marcel Dekker, Inc., New York, pp. 137-163.
Martin et al., 1982, Irreversible coupling of immunoglobulin fragments to preformed vesicles. An improved method for liposome targeting. J Biol Chem. 257(1):286-288.
Martin et al., 2001. Crystal structure at 2.8 Å of an FcRn/heterodimeric Fc complex: Mechanism of pH-dependent binding. Mol Cell 7(4):867-877.
McClenaghan et al., Aug. 1996, Characterization of a novel glucose-responsive insulin-secreting cell line, BRIN-BD11, produced by electrofusion, Diabetes, 45:1132-1140.
McCoy et al., 2007. Phaser crystallographic software. J Applied Crystallogr. 40:658-674.
McGraw et al., 1987, Functional expression of the human transferring receptor cDNA in Chinese hamster ovary cells deficient in endogenous transferring receptor. J Cell Biol. 105(1):207-214.
McGregor, 2008, Discovering and improving novel peptide therapeutics, Curr Opin Pharmacol, 8(5):616-619.
McGuffin et al., 2003, Improvement of the GenTHREADER method for genomic fold recognition. Bioinformatics 19(7):874-881.
Mezo et al., 2010, X-ray crystal structures of monomeric and dimeric peptide inhibitors in complex with the human neonatal Fc receptor, FcRn, J Biol Chem, 285(36):27694-27701.
Miguel et al., 2003, Cooperative enhancement of insulinotropic action of GLP-1 by acetylcholine uncovers paradoxical inhibitory effect of beta cell muscarinic receptor activation on adenylate cyclase activity Biochem Pharm., 65:283-292.
Minchiotti et al., 1987, Structure characterization of two genetic variants of human serum albumin, Biochim Biophys Acta, 916(3):411-418.
Minchiotti et al., 1990, The molecular defect of albumin Castel di Sangro: 536 Lys →Gllu, Biochem Bioph Acta, 1039:204-208.
Minchiotti et al., 2001, A nucleotide insertion and frameshift cause albumin Kenitra, an extended and O-glycosylated mutant of human serum albumin with two additional disulfide bridges, Eur J Biochem., 268:344-352.
Minchiotti et al., 2008, Mutations and polymorphisms of the gene of the major human blood protein, Serum albumin, Human Mutation 29(8):1007-1016.
Minghetti et al., 1986, Molecular structure of the human albumin gene is revealed by nucleotide sequence within q11-22 of chromosome 4*, J. Bio Chem. 261(15): 6747-6757.
Mishra et al., 2006, Targeted brain delivery of AZT via transferrin anchored pegylated albumin nanoparticles. J Drug Targeting 14(1):45-53.
Montoyo et al., 2009, Conditional deletion of the MHC class I-related receptor FcRn reveals the sites of IgG homeostasis in mice, Proc Natl Acad Sci USA, 106(8):2788-2793.
Morrissey et al., Feb. 1, 1993, Quantitation of activated factor VII levels in plasma using a tissue factor mutant selectively deficient in promoting factor VII activation, Blood, 81(3):734-744.

(56) References Cited

OTHER PUBLICATIONS

Müller et al., 2007, Improved pharmacokinetics of recombinant bispecific antibody molecules by fusion to human serum albumin, J Bio Chem., 282(17):12650-12660.

Munoz et al., 2009, Constraints to progress in embryonic stem cells from domestic species, Stem Cell Rev and Rep, 5:6-9.

Murshudov et al., 1997. Refinement of macromolecular structures by the maximum-likelihood method. Acta Crystallogr D Biol Crystallogr. 53(Pt 3):240-255.

Nauck et al., 1993, Normalization of fasting hyperglycaemia by exogenous glucagon-like peptide 1 (7-36 amide) in type 2 (non-insulin-dependent) diabetic patients, Diabetologia 36:741-744.

Nauck et al., 1993, Preserved incretin activity of glucagon-like peptide 1 [7-36 amide] but not of synthetic human gastric inhibitory polypeptide in patients with type-2 diabetes mellitus. Clin Invest., 91:301-307.

Needleman et al., 1970, A general method applicable to the search for similarities in the amino acid sequence of two proteins. J Mol Biol., 48(3):443-453.

Ner et al., 1988, A simple and efficient procedure for generating random point mutations and for codon replacements using mixed oligodeoxynucleotides. DNA 7(2):127-134.

Ness et al., 1999, DNA shuffling of subgenomic sequences of subtilisin. Nature Biotechnol. 17(9):893-896.

Neumann et al., 2010, Native albumin for targeted drug delivery, Expert Opin. Drug Deliv., 7(8):1-11.

New Century Pharmaceuticals Inc., 2005 Catalog, Recombinant Serum Albumin: Other Proteins & Antibodies, pp. 1-36.

Nobs et al., 2004, Current methods for attaching targeting ligands to liposomes and nanoparticles. J Pharma Sci. 93(8):1980-1992.

Ober et al., 2001, Differences in promiscuity for antibody—FcRn interactions across species: implications for therapeutic antibodies, Int Immunol 13(12):1551-1559.

Ober et al., 2004, Exocytosis of IgG as mediated by the receptor, FcRn: an analysis at the single-molecule level, PNAS USA, 101(30):11076-11081.

Ober et al., 2004, Visualizing the site and dynamics of IgG salvage by the MHC class I-related receptor, FcRn, J Immunol, 172(4):2021-2029.

Oganesyan et al., 2014, Structural insights into neonatal Fc receptor-based recycling mechanisms, J Biol Chem 289(11):7812-24.

O'Hara et al., 1987, Nucleotide sequence of the gene coding for human factor VII, a vitamin K-dependent protein participating in blood coagulation, PNAS USA, 84:5158-5162.

O'Keefe et al., 1985, Characterization of a transferrin-diphtheria toxin conjugate. J Biol Chem. 260(2):932-937.

Olafsen et al., 2006, Tunable pharmacokinetics; modifying the in vivo half-life of antibodies by directed mutagenesis of the Fc fragment, Nature Protocol, 1(4):2048-2060.

O'Neill et al., 2008, Scale-up of Agrobacterium-mediated transient protein expression in bioreactor-grown Nicotiana glutinosa plant cell suspension culture, Biotechnol Prog., 24:372-376.

Öner et al., 1993, Preparation of small gelatin and albumin microparticles by a carbon dioxide atomization. Pharm Res., 10(9):1385-1388.

Osborn et al., 2002, Pharmacokinetic and pharmacodynamic studies of a human serum albumin-interferon-α fusion protein in cynomolgus monkeys, J Pharmacol Exp Ther, 303(2):540-548.

Otagiri et al., Apr. 2009, Pharmaceutically Important Pre- and Postranstional Modifications on Human Serum Albumin, Biol Pharm Bull., 32(4):527-534.

Pandjaitan et al., 2000, *Escherichia coli* expression and purification of recombinant dog albumin, a cross-reactive animal allergen. J Allergy Clin Immunol. 105(2 Pt):279-285.

Payne et al., 2008, Modulation of chaperone gene expression in mutagenized *Saccharomyces cerevisiae* strains developed for recombinant human albumin production results in increased production of multiple heterologous proteins. Appl Environ Microbiol. 74(24):7759-7766.

Peach et al., 1991, Structural characterization of glycoprotein variant of human serum albumin: albumin Casebrook (494 Asp →Asn), Biochim Biophys Acta, 1097:49-54.

Peters, 1985, Serum Albumin, Advances in Protein Chemistry, 37:161-245.

Peters [Ed], 1996, All about Albumin: Biochemistry, Genetics and Medical Applications, Academic Press, Cooperstown, NY, Chapter 2: pp. 9-23.

Peters [Ed], 1996, All about Albumin: Biochemistry, Genetics and Medical Applications, Academic Press, Cooperstown, NY, pp. 10, 170-181, 245-250 in 37 pages.

Petitpas et al., 2001, Crystal Structure Analysis of Warfarin Binding to Human Serum Albumin—Anatomy of Drug Site I. J Biol Chem 276(25):22804-22809.

Petitpas et al., 2001, Crystal structures of human serum albumin complexed with monounsaturated and polyunsaturated fatty acids. J Mol Biol. 314(5):955-960.

Petitpas et al., 2003. Structural basis of albumin-thyroxine interactions and familial dysalbuminemic hyperthyroxinemia. PNAS U.S.A. 100(11):6440-6445 (2003).

Petkova et al., 2006. Enhanced half-life of genetically engineered human IgG1 antibodies in a humanized FcRn mouse model: potential application in humorally mediated autoimmune disease. Int immunol. 18(12):1759-1769.

Piedrahita et al., 2011, Perspectives on transgenic livestock in agriculture and biomedicine: an update, Repro Fertility Develop., 23:56-63.

Pierce, Crosslinking Reagents Technical Handbook, Thermo Fisher Scientific, Rockford, IL, USA; downloaded Feb. 9, 2009 <https://tools.lifetechnologies.com/content/sfs/brochures/1602163-Crosslinking-Reagents>, 48 pp.

Pittman et al., 1993, Biochemical, immunological, and in vivo functional characterization of B-domain-deleted factor VIII, Blood, 81:2925-2935.

Prabhat et al., 2007, Elucidation of intracellular recycling pathways leading to exocytosis of the Fc receptor, FcRn, by using multifocal plane microscopy, Proc Natl Acad Sci USA, 104(14):5889-5894.

Presley et al., 1993, The End2 mutation in CHO cells slows the exit of Transferring receptors from the recycling compartment byt bulk membrane recycling is unaffected. J Cell Biol. 122(6):1231-1241.

Rakestraw et al., 2006. A flow cytometric assay for screening improved heterologous protein secretion in yeast. Biotechnol Prog. 22(4):1200-1208.

Rakestraw et al., 2009, Directed evolution of a secretory leader for the improved expression of heterologous proteins and full-length antibodies in *S. cerevisiae*, Biotech Bioengin. 103(6):1192-1201.

Rao et al, 2003, Interleukin-2 mutants with enhanced alpha-receptor subunit binding affinity, Protein Engin., 16(12):1081-1087.

Rao et al., 2005, High-affinity CD25-binding IL-2 mutants potently stimulate persistent T cell growth, Biochemistry 44:10696-10701.

Reidhaar-Olson et al., 1988, Combinatorial cassette mutagenesis as a probe of the informational content of protein sequences. Science 241 (4861):53-57.

Rice et al., 2000, EMBOSS: The European Molecular Biology Open Software Suite, Trends in Genetics, 16(6):276-277.

Riminucci et al., Sep. 2003, FGF-23 in fibrous dysplasia of bone and its relationship to renal phosphate wasting, J Clin Invest, 112(5):683-92.

Rinderknecht et al., Jun. 10, 1984, Natural Human Interferon-gamma. Complete amino acid sequence and determination of sites of glycosylation, J Biol Chem., 259(11):6790-6797.

Rodewald et al.,1984, Receptor-mediated transport of IgG. J Cell Biol. 99:159s-164s.

Romanos et al., 1992, Foreign gene expression in yeast: a review. Yeast 8: 423-488.

Roopenian et al., 2003, The MHC class I-like IgG receptor controls perinatal IgG transport, IgG homeostasis, and fate of IgG-Fc-coupled drugs, J Immunol, 170(7):3528-3533.

Roopenian et al., 2007, FcRn: the neonatal Fc receptor comes of age, Nat Rev Immunol 7:715-725.

Roopenian et al., 2010, Human FcRn transgenic mice for pharmacokinetic evaluation of therapeutic antibodies, Methods Mol Biol, 602:93-104.

(56) References Cited

OTHER PUBLICATIONS

Sabater-Lleal et al., 2006, Human F7 sequence is split into three deep clades that are related to FVII plasma levels, Hum Genet 118:741-751.
Sand et al, Dec. 12, 2014, Interaction with both domain I and III of albumin is required for optimal pH-dependent binding to the neonatal Fc receptor (FcRn)*, J Biol Chem 289(50):34583-35894.
Sandhu et al., 2008. GASCO: Genetic Algorithm Simulation for Codon Optimization. In Silico Biol. 8(2):187-192.
Sayle et al. Sep. 1995, RASMOL: biomolecular graphics for all, TIBS 20, 374-377.
Scherer et al., 1979, Replacement of chromosome segments with altered DNA sequences constructed in vitro. PNAS U.S.A. 76(10):4951-4955.
Schmidt et al., 2013, Crystal Structure of an HAS/FcRn Complex Reveals Recycling by Competitive Mimicry of HSA Ligands at a pH-Dependent Hydrophobic Interface, Structure 21:1966-1978 and supplemental material.
Schulte, 2008, Use of albumin fusion technology to prolong the half-life of recombinant factor VIIa, Thromb Res. 122 Suppl. 4:S14-19.
Several (definition), dictionary.com, accessed on Oct. 30, 2015, 4 pp.
Sheffield et al., 2000, Modulation of clearance of recombinant serum albumin by either glycosylation or truncation, Thromb Res., 99(6):613-621.
Shimada et al., 2004, FGF-23 Is a Potent Regulator of Vitamin D Metabolism and Phosphate Homeostasis, J. Clin. Invest, 19(3):429-435.
Shindyalov et al., 1998, Protein structure alignment by incremental combinatorial extension (CE) of the optimal path. Protein Eng. 11(9):739-747.
Sijmons et al., 1990, Production of correctly processed human serum albumin in transgenic plants, Biotechnology (NY), 8(3):217-221.
Silveira et al., 1994, Activation of Coagulation Factor VII During Alimentary Lipemia, Arterioscler Thromb Vsc Biol., 14:60-69.
Simard et al., 2005, Locating high-affinity fatty acid-binding sites on albumin by x-ray crystallography and NMR spectroscopy, PNAS USA, 102(50):17958-17963.
Simard et al., 2006, Location of High and Low Affinity Fatty Acid Binding Sites on Human Serum Albumin Revealed by NMR Drug-competition Analysis, J Mol Biol., 361(2):336-351.
Sleep et al., 1990, The secretion of human serum albumin from the yeast *Saccharomyces cerevisiae* using five different leader sequences, Biotech.8:42-46.
Sleep et al., 1991, *Saccharomyces cerevisiae* strains that overexpress heterologous proteins, Biotechnology (NY) 9(2):183-187.
Sleep et al., 2001, Yeast 2 μ m plasmid number is elevated by a mutation in the nuclear gene UBC4, Yeast, 18(5):403-421.
Sleep, 2012, Produce Proteins with Tailored Circulatory Half Life to Meet Patient's Specific Medical Needs, Keynote Address, Drug Delivery Partnerships. Las Vegas, NV. Jan. 25-27, 2012 in 29 pages.
Sleep et al., 2013, Albumin as a versatile platform for drug half-life extension, Biochimca et Biophysica Acta, http://dx/doi/org/10.1016/j.bbagen.2013.04.023; in 9 pages.
Smith et al., Jun. 2015 (online), A platform for efficient, thiol-stable conjugation to albumin's native single accessible cysteine. Org Biomol Chem. 13(29):7946-7949.
Sogami et al., 1968. Isomerization reactions of charcoal-defatted bovine plasma albumin. The N—F transition and acid expansion. Biochemistry 7(6): 2172-2182.
Sogami et al., 1969. The microheterogeneity of plasma albumins. V. Permutations in disulfide pairings as a probable source of microheterogeneity in bovine albumin. Biochemistry 8(1):49-58.
Sorensen et al., 2004, Whole blood clot formation phenotypes in hemophilia A and rare coagulation disorders. Patterns of response to recombinant factor Vila, J Thromb Haemo. 2:102-110.

Spiegelberg et al., 1968, Catabolism of human γG-immunoglobulins of different heavy chain subclasses. I. Catabolism of γG-myeloma proteins in man. J Clin Invest. 47(10):2323-2330.
Spiekermann et al., 2002. Receptor-mediated Immunoglobulin G Transport Across Mucosal Barriers in Adult Life. J Exp Med. 196(3):303-10, and correction.
Stapleton et al., 2011. Competition for FcRn-mediated transport gives rise to short half-life of human IgG3 and offers therapeutic potential. Nature Comm. 2:599; 9 pages.
Stehle et al., 1997, Plasma protein (albumin) catabolism by the tumor itself—implications for tumor metabolism and the genesis of cachexia, Crit Rev Oncol Hematol, 26(2):77-100.
Stewart et al., 2003, Interdomain zinc site on human albumin, PNAS USA, 100(7):3701-3706.
Storici et al., 2001, In vivo site-directed mutagenesis using oligonucleotides. Nat Biotechnol. 19(8):773-776.
Sugio et al., Jun. 1999, Crystal structure of human serum albumin at 2.5 Å resolution, Protein Eng. 12(6):439-446.
Sundaram et al, Aug. 21, 1998, Chimeric constructs between human and rat equilibrative nucleoside transporters (hENT1 and rENT1) reveal hENT1 structural domains interacting with coronary vasoactive drugs, J. Bio Chemistry, 273(34):21519-21525.
Suzuki et al., 2010, Importance of Neonatal FcR in Regulating the Serum Half-Life of Therapeutic Proteins Containing the Fc Domain of Human IgG1: A Comparative Study of the Affinity of Monoclonal Antibodies and Fc- Fusion Proteins to Human Neonatal FcR, J Immunol. 184:1968-1976.
Syed et al., 1997, Potent antithrombin activity and delayed clearance from the circulation characterize recombinant hirudin genetically fused to albumin, Blood 89(9):3243-3252.
Sykes et al., 1994, Interleukin-2 inhibits graft-versus-host disease-promoting activity of CD4+ cells while preserving CD4- and CD8-mediated graft-versus-Leukemia effects, Blood, 83(9):2560-2569.
Takahashi et al., 1987, Amino acid substitutions in genetic variants of human serum albumin and in sequences inferred from molecular cloning, PNAS USA 84:4413-4417.
Tesar et al., 2006. Ligand valency affects transcytosis, recycling and intracellular trafficking mediated by the neonatal Fc receptor. Traffic. 7(9):1127-1142.
Thibaudeau et al., 2005, Synthesis and evaluation of insulin-human serum albumin conjugates, Bioconjug Chem., 16(4):1000-1008.
Thim et al., 1988, Amino acid sequence and posttranslational modifications of human factor Vila from plasma and transfected baby hamster kidney cells, Biochemistry, 27:7785-7793.
Thompson et al., 1994, Clustal W: Improving the sensitivity of progressive multiple sequence alignment through sequence weighting, position-specific gap penalties and weight matrix choice. Nucleic Acids Res. 22(22):4673-4680.
Tian et al., 2004, Accurate multiplex gene synthesis from programmable DNA microchips. Nature 432(7020):1050-1054.
Toole et al., 1984, Molecular cloning of a cDNA encoding human antihaemophilic factor. Nature, 312:342-347.
Tsakiridis et al., 1995, Multiple roles of phosphatidylinositol 3-kinase in regulation of glucose transport, amino acid transport, and glucose transporters in L6 skeletal muscle cells, Endocrinol. 136(10):4315-4322.
Ueda et al., 2009, Chemoenzymatic Synthesis of Glycosylated Glucagon-like Peptide 1: Effect of Glycosylation on Proteolytic Resistance and in Vivo Blood Glucose-Lowering Activity, JACS Articles, 131:6237-6245.
Uniprot Database Accession No. F7HCHO, Jul. 27, 2011, 2 pp.
UniProt Database Accession No. A6NBZ8 (A6NBZ8_HUMAN), Version 24, modified Mar. 8, 2011, accessed at http://www.uniprot.org/uniprot/A6NBZ8 on Mar. 23, 2011.
Urso et al., 1999, Differences in signaling properties of the cytoplasmic domains of the insulin receptor and insulin-like growth factor receptor in 3T3-L 1 adipocytes, J Biol Chem, 274(43):30864-30873.
Valkonen et al., 2003, Effects of inactivation and constitutive expression of the unfolded-protein response pathway on protein production in the yeast *Saccharomyces cerevisiae*. Applied Environ Microbiol., 69(4):2065-2072.

(56) References Cited

OTHER PUBLICATIONS

Van Deijk et al., 1983, Evaluation of a Coagulation Assay Determining the Activity State of Factor VII in Plasma, Haemostasis 13:192-197.
Van der Spoel et al., 2005, GROMACS: Fast, flexible, and free, J Comp Chem, 22:1701-1718.
Van Dongen et al., 2007, Immuno-PET: A Navigator in Monoclonal Antibody Development and Applications, The Oncologist Cancer Imaging 12:1379-1389.
Vestberg et al., 1992, High-affinity binding of warfarin, salicylate and diazepam to natural mutants of human serum albumin modified in the c-terminal end, Biochem Pharmacol, 44(8):1515-1521.
Viuff et al., 2016, Generation of a double transgenic humanized neonatal Fc receptor (FcRn)/albumin mouse to study the pharmacokinetics of albumin-linked drugs, J Controlled Release, 223:22-30.
Wain-Hobson et al. 1981, Preferential codon usage in genes, Gene 13:355-364.
Wang et al., 1997, Regulation of glucose transporters and hexose uptake in 3T3-L 1 adipocytes: glucagon-like peptide-1 and insulin interactions, J Mol Endocrinol, 19:241-248.
Wang et al., 2008, Overexpression of fibroblast growth factor 23 suppresses osteoblast differentiation and matrix mineralization in vitro. J Bone Miner Res. 23(6):939-948.
Wang et al. 2011. Monoclonal antibodies with identical Fc sequences can bind to FcRn differentially with pharmacokinetic consequences. Drug Metabol Disposition. 39:1469-1477.
Wani et al., 2006, Familial hypercatabolic hypoproteinemia caused by deficiency of he neonatal Fc receptor, FcRn, due to a mutant β2-microglobulin gene, Proc Natl Acad Sci USA 103(13):5084-5089 and Correction/Retraction in 2 pages.
Ward et al., 2009, Multitasking by exploitation of intracellular transport functions: the many faces of FcRn, Adv Immunol 103:77-115.
Watkins et al., 1993, A donor splice mutation and a single-base deletion produce two carboxy-terminal variants of human serum albumin, PNAS USA, 88:5959-5963.
Watkins et al., 1993, cDNA and protein sequence of polymorphic macaque albumins that differ in bilirubin binding, PNAS USA, 90:2409-2413.
Weaver et al., 2003, Transferrin receptor ligand-targeted toxin conjugate (Tf-CRM107) for therapy of malignant gliomas. J Neurooncol. 65(1):3-13.
Wenning et al., 1998, Quantitative analysis of protein synthesis inhibition and recovery in CRM107 immunotoxin-treated HeLac cells. Biotechol Bioeng. 57(4):484-496.
Werle et al., 2006, Strategies to improve plasma half life time of peptide and protein drugs, Amino Acids, 30(4):351-367.
West et al., 2000, Crystal structure and immunoglobulin G binding properties of the human major histocompatibility complex-related Fc receptor, Biochemistry 39(32):9698-9708.
Widera et al., 2003, Transcytosis of GCSF-transferring across rat alveolar epithelial cell monolayers. Pharm Res. 20(8):1231-1238.
Wildgoose et al., 1992, Measurement of basal levels of factor VIIa in hemophilia A and B patients, Blood, 80:25-28.
Wood et al., 1984, Expression of active human factor VIII from recombinant DNA clones, Nature 312:330-337.
Wu et al., 1987, Receptor-mediated in vitro gene transformation by a soluble DNA carrier system, J Biol Chem., 262(10):4429-4432.
Wu et al., Dec. 1989, Urate Oxidase: Primary Structure and Evolutionary Implications, PNAS USA, 86:9412-9416.
Wunder et al., 2003, Albumin-based drug delivery as novel therapeutic approach for rheumatoid arthritis, J Immunol. 170:4793-4801.
Xia et al., 2000, Hypoglycemic effect of insulin-transferrin conjugate in streptozotocin-induced diabetic rats. J Pharmacol Exp Ther. 295(2):594-600.
Yang et al., 2012, Genetic modification of domestic animals for agricultre and biomedical applications, in Ghista [Ed], Biomedical Science, Engineering and Technology, Chapter 29, pp. 697-726.
Yazdi et al., 1994, Quantitative Analysis of Protein Synthesis Inhibition by Transferrin-Toxin Conjugates. Cancer Res. 54(24):6387-6394.
Yeung et al., 2009. Engineering human IgG1 affinity to human neonatal Fc receptor: Impact of affinity improvement on pharmacokinetics in primates. J immunol. 182:7663-7671.
Yin et al., 2007, Select what you need: a comparative evaluation of the advantages and limitations of frequently used expression systems for foreign genes, J Biotech., 127:335-347.
Yoshida et al., 2004, Human neonatal Fc receptor mediates transport of IgG into luminal secretions for delivery of antigens to mucosal dendritic cells Immunity. 20(6):769-83.
Zalevsky et al., Feb. 2010, Enhanced antibody half-life improves in vivo activity, Nature Biotechnology, 28(2):157-159.
Zheng et al., 2012, Minipig as a potential translatable model for monoclonal antibody pharmacokinetics after intravenous and subcutaneous administration, mAbs, 4(2):243-255.
Zhu et al., 2005, Calnexin and ERp57 facilitate the assembly of the neonatal Fc receptor for IgG with beta 2-microglobulin in the endoplasmic reticulum. J Immunol., 175(2):967-76.
Zhu et al., 2001, MHC class I-related neonatal Fc receptor for IgG is functionally expressed in monocytes, intestinal macrophages, and dendritic cells, J Immunol., 166(5):3266-76.
International Search Report and Written Opinion of International Application No. PCT/US2012/065733, dated May 21, 2013.
International Search Report of PCT/US2014/036508 dated Oct. 9, 2014.
Written Opinion of the International Searching Authority for PCT/US2014/036508 dated Oct. 9, 2014.
International Search Report, International Patent Application No. PCT/IB2014/003002, dated Aug. 12, 2015.
Ellgaard et al., 2003, Quality Control in the Endoplasmic Reticulum, Mol Cell Biol. 4: 181-191.
Hong et al., 1996, A Pathway for Targeting Soluble Misfolded Proteins to the Yeast Vacuole, J Cell Biol. 135(3): 623-633.
International Search Report and Written Opinion dated Oct. 24, 2016 for corresponding PCT Application No. PCT/EP2016/069748, filed Aug. 19, 2016.

Figure 1

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| n/a | 1 | 25 | D | n/a | n/a | 0 | 40 | 0 | 40 | D25V | 0 | 3 |
| n/a | 2 | 26 | A | n/a | n/a | 0 | 40 | 0 | 20 | | | 1 |
| n/a | 3 | 27 | H | n/a | n/a | 0 | 80 | 0 | 60 | H27Q, H27Y | 0 | 5 |
| n/a | 4 | 28 | K | n/a | n/a | 0 | 80 | 1 | 40 | | | 4 |
| 1 | 5 | 29 | S | 57.8 | 30.65 | 0 | 100 | 1 | 60 | | | 1 |
| 2 | 6 | 30 | E | 41.0 | 30.41 | 1 | 100 | 1 | 40 | | | 4 |
| 3 | 7 | 31 | V | 0.0 | 27.81 | 1 | 60 | 2 | 40 | | | 3 |
| 4 | 8 | 32 | A | 0.0 | 28.93 | 1 | 100 | 1 | 40 | | | 1 |
| 5 | 9 | 33 | H | 57.7 | 29.05 | 1 | 100 | 2 | 40 | | | 5 |
| 6 | 10 | 34 | R | 13.3 | 28.32 | 1 | 100 | 1 | 40 | | | 5 |
| 7 | 11 | 35 | F | 17.1 | 28.41 | 1 | 80 | 1 | 40 | | | 4 |
| 8 | 12 | 36 | K | 72.4 | 32.91 | 1 | 40 | 1 | 20 | | | 4 |
| 9 | 13 | 37 | D | 115.9 | 29.96 | 1 | 100 | 0 | 60 | | | 3 |
| 10 | 14 | 38 | L | 33.0 | 24.52 | 1 | 80 | 2 | 60 | | | 4 |
| 11 | 15 | 39 | G | 62.0 | 24.74 | 1 | 100 | 1 | 60 | | | 2 |
| 12 | 16 | 40 | E | 49.4 | 27.83 | 1 | 100 | 1 | 60 | | | 4 |
| 14 | 18 | 42 | N | 58.8 | 24.75 | 1 | 60 | 2 | 20 | | | 2 |
| 15 | 19 | 43 | F | 0.0 | 22.59 | 1 | 100 | 0 | 20 | | | 4 |
| 16 | 20 | 44 | K | 31.0 | 19.84 | 1 | 60 | 1 | 60 | | | 4 |
| 17 | 21 | 45 | A | 29.0 | 17.31 | 1 | 80 | 1 | 40 | | | 1 |
| 18 | 22 | 46 | L | 1.0 | 15.93 | 1 | 100 | 1 | 40 | | | 4 |
| 19 | 23 | 47 | V | 0.0 | 17.25 | 1 | 100 | 2 | 60 | | | 3 |
| 20 | 24 | 48 | L | 6.2 | 18.56 | 1 | 100 | 1 | 40 | | | 4 |

Figure 1 continued

| 21 | 25 |   |   |   |   |   |   |   |   | 4 |
|---|---|---|---|---|---|---|---|---|---|---|
| 22 | 26 | I | 0.0 | 18.85 | 1 | 40 | 1 | 60 |   | 1 |
| 23 | 27 | A | 11.3 | 18.7 | 1 | 80 | 0 | 20 |   | 4 |
| 24 | 28 | F | 0.8 | 16.67 | 1 | 80 | 0 | 40 |   | 1 |
| 25 | 29 | A | 0.0 | 16.49 | 1 | 80 | 1 | 40 |   | 3 |
| 26 | 30 | Q | 3.1 | 18.47 | 1 | 100 | 0 | 40 |   | 3 |
| 27 | 31 | Y | 10.6 | 21.52 | 1 | 80 | 2 | 60 |   | 4 |
| 28 | 32 | L | 3.1 | 22.77 | 0 | 100 | 1 | 40 |   | 3 |
| 29 | 33 | Q | 8.7 | 19.2 | 0 | 100 | 1 | 60 |   | 3 |
| 30 | 34 | Q | 63.8 | 23.45 | 0 | 60 | 1 | 20 |   | 0 |
| 31 | 35 | C | 1.1 | 31.66 | 0 | 80 | 0 | 20 |   | 3 |
| 32 | 36 | P | 76.1 | 30.42 | 0 | 80 | 0 | 60 |   | 4 |
| 33 | 37 | F | 8.9 | 29.13 | 1 | 60 | 1 | 40 |   | 4 |
| 34 | 38 | E | 78.8 | 34.65 | 1 | 60 | 0 | 20 |   | 3 |
| 35 | 39 | D | 87.0 | 34.73 | 1 | 60 | 1 | 40 |   | 5 |
| 36 | 60 | H | 0.0 | 31.2 | 1 | 100 | 0 | 40 |   | 3 |
| 60 | 37 | V | 35.8 | 30.38 | 1 | 80 | 1 | 40 |   | 4 |
| 37 | 38 | E | 101.3 | 31.14 | 1 | 40 | 1 | 60 |   | 4 |
| 38 | 42 | K | 51.1 | 31.26 | 1 | 100 | 1 | 60 |   | 4 |
| 39 | 43 | L | 1.0 | 26.45 | 1 | 60 | 1 | 40 |   | 3 |
| 40 | 44 | V | 7.4 | 26.21 | 1 | 80 | 1 | 40 |   | 2 |
| 41 | 45 | N | 88.2 | 29.63 | 1 | 40 | 0 | 60 |   | 4 |
| 42 | 46 | E | 41.0 | 29.37 | 1 | 100 | 2 | 40 |   | 3 |
| 43 | 47 | V | 7.4 | 28.93 | 1 | 80 | 0 | 40 |   | 1 |
| 44 | 48 | T | 5.0 | 28.95 | 1 | 100 | 1 | 40 |   | 4 |
| 45 | 49 | E | 91.0 | 31.25 | 1 | 60 | 1 | 40 | F73Y | 0 | 4 |
| 46 | 50 | F | 39.8 | 23.4 | 1 | 80 | 0 | 60 |   | 4 |
| 47 | 51 | A | 0.0 | 23.04 | 1 | 100 | 1 | 60 |   | 1 |
| 48 | 52 | K | 53.4 | 28.74 | 1 | 80 | 1 | 60 |   | 4 |
|    |    | T | 86.3 | 35.9 | 1 | 40 | 1 | 20 |   | 1 |

Figure 1 continued

| | | | | | | | | | | |
|---|---|---|---|---|---|---|---|---|---|---|
| 49 | 53 | 77 | C | 0.0 | 36.73 | 1 | 100 | 0 | 60 | | 0 |
| 50 | 54 | 78 | V | 60.5 | 39.55 | 1 | 60 | 1 | 40 | | 3 |
| 51 | 55 | 79 | A | 148.4 | 43.59 | 1 | 80 | 0 | 40 | | 1 |
| 52 | 56 | 80 | D | 117.4 | 45.92 | 0 | 80 | 0 | 40 | | 3 |
| 53 | 57 | 81 | E | 54.5 | 48.38 | 0 | 80 | 0 | 40 | | 4 |
| 54 | 58 | 82 | S | 164.1 | 53.12 | 0 | 80 | 0 | 40 | | 1 |
| 55 | 59 | 83 | A | 54.8 | 52.13 | 0 | 60 | 0 | 40 | | 1 |
| 56 | 60 | 84 | E | 110.3 | 53.87 | 0 | 40 | 0 | 20 | E84K | 4 0 |
| 57 | 61 | 85 | N | 54.1 | 43.73 | 0 | 80 | 1 | 40 | | 2 |
| 58 | 62 | 86 | C | 1.1 | 36.08 | 0 | 100 | 0 | 80 | | 0 |
| 59 | 63 | 87 | D | 189.9 | 35.65 | 0 | 80 | 2 | 40 | D87N | 3 1 |
| 60 | 64 | 88 | K | 32.2 | 32.63 | 0 | 100 | 0 | 60 | | 4 |
| 61 | 65 | 89 | S | 93.8 | 26.67 | 0 | 80 | 1 | 60 | | 1 |
| 62 | 66 | 90 | L | 9.3 | 23.68 | 1 | 80 | 0 | 40 | L90P | 4 1 |
| 63 | 67 | 91 | H | 20.0 | 20.17 | 1 | 80 | 0 | 40 | | 5 |
| 64 | 68 | 92 | T | 45.0 | 22.6 | 1 | 80 | 0 | 40 | | 1 |
| 65 | 69 | 93 | L | 22.7 | 18.5 | 1 | 80 | 0 | 60 | | 4 |
| 66 | 70 | 94 | F | 13.0 | 19.27 | 1 | 80 | 1 | 60 | | 4 |
| 67 | 71 | 95 | G | 4.0 | 23.14 | 1 | 100 | 1 | 40 | | 2 |
| 68 | 72 | 96 | D | 113.0 | 24.53 | 1 | 100 | 1 | 60 | | 3 |
| 69 | 73 | 97 | K | 32.2 | 22.59 | 1 | 80 | 1 | 60 | | 4 |
| 70 | 74 | 98 | L | 1.0 | 19.05 | 1 | 80 | 1 | 40 | | 4 |
| 71 | 75 | 99 | C | 20.7 | 24.72 | 1 | 100 | 0 | 80 | | 0 |
| 72 | 76 | 100 | T | 105.0 | 32.05 | 1 | 40 | 1 | 20 | | 1 |
| 73 | 77 | 101 | V | 27.2 | 42.97 | 1 | 60 | 0 | 20 | | 3 |
| 74 | 78 | 102 | A | 0.0 | 53.66 | 1 | 60 | 0 | 20 | | 1 |
| 75 | 79 | 103 | T | 103.8 | 67.13 | 0 | 40 | 0 | 20 | | 1 |
| 76 | 80 | 104 | L | 106.2 | 79.71 | 0 | 80 | 0 | 40 | | 4 |
| 77 | 81 | 105 | R | 87.2 | 90.39 | 1 | 80 | 0 | 40 | | 5 |

Figure 1 continued

| 78 | 82 | 106 | E | 130.1 | 96.77 | 1 | 60 | 0 | E106K | 0 | 4 |
|---|---|---|---|---|---|---|---|---|---|---|---|
| 79 | 83 | 107 | T | 113.8 | 98.21 | 1 | 60 | 1 | | | 1 |
| 80 | 84 | 108 | Y | 20.2 | 95.72 | 1 | 100 | 0 | | | 3 |
| 81 | 85 | 109 | G | 74.0 | 93.64 | 0 | 80 | 1 | | | 2 |
| 82 | 86 | 110 | E | 99.4 | 88.78 | 0 | 60 | 0 | | | 4 |
| 83 | 87 | 111 | M | 28.2 | 77.89 | 0 | 40 | 1 | | | 3 |
| 84 | 88 | 112 | A | 22.6 | 66.98 | 0 | 100 | 1 | | | 1 |
| 85 | 89 | 113 | D | 166.7 | 54.86 | 0 | 100 | 2 | | | 3 |
| 86 | 90 | 114 | C | 0.0 | 37.61 | 0 | 100 | 2 | | | 0 |
| 87 | 91 | 115 | C | 32.6 | 33.58 | 0 | 100 | 1 | | | 0 |
| 88 | 92 | 116 | A | 135.5 | 38.25 | 0 | 40 | 2 | | | 1 |
| 89 | 93 | 117 | K | 52.3 | 39.06 | 0 | 100 | 0 | | | 4 |
| 90 | 94 | 118 | Q | 121.3 | 41.84 | 0 | 60 | 1 | | | 3 |
| 91 | 95 | 119 | E | 28.2 | 35.82 | 0 | 80 | 1 | | | 4 |
| 92 | 96 | 120 | P | 125.4 | 32.16 | 0 | 100 | 0 | | | 3 |
| 93 | 97 | 121 | E | 63.5 | 28.49 | 1 | 80 | 2 | E121G | 0 | 4 |
| 94 | 98 | 122 | R | 7.6 | 26.53 | 1 | 100 | 0 | | | 5 |
| 95 | 99 | 123 | N | 1.2 | 30.02 | 1 | 80 | 2 | | | 2 |
| 96 | 100 | 124 | E | 71.8 | 31.84 | 1 | 100 | 1 | | | 4 |
| 97 | 101 | 125 | C | 2.2 | 28.44 | 1 | 100 | 2 | | | 0 |
| 98 | 102 | 126 | F | 3.3 | 22.56 | 1 | 100 | 2 | | | 4 |
| 99 | 103 | 127 | L | 22.7 | 26.39 | 1 | 100 | 1 | | | 4 |
| 100 | 104 | 128 | Q | 111.0 | 32.1 | 1 | 40 | 2 | | | 3 |
| 101 | 105 | 129 | H | 33.8 | 31.12 | 0 | 100 | 1 | | | 5 |
| 102 | 106 | 130 | K | 10.9 | 30.28 | 0 | 100 | 1 | | | 4 |
| 103 | 107 | 131 | D | 60.9 | 30.16 | 0 | 80 | 2 | | | 3 |
| 104 | 108 | 132 | D | 58.0 | 32.21 | 0 | 100 | 0 | | | 3 |
| 105 | 109 | 133 | N | 80.0 | 36.44 | 0 | 60 | 2 | | | 2 |
| 106 | 110 | 134 | P | 28.4 | 37.95 | 0 | 100 | 0 | | | 3 |

Figure 1 continued

| 107 | 111 | 135 | N | 143.5 | | | 49.66 | 0 | 40 | 1 | 20 | | | 2 |
| --- | --- | --- | --- | --- | --- | --- | --- | --- | --- | --- | --- | --- | --- | --- |
| 108 | 112 | 136 | L | 30.9 | | | 49.38 | 0 | 80 | 0 | 40 | | | 4 |
| 109 | 113 | 137 | P | 141.8 | | | 51.5 | 0 | 80 | 0 | 40 | | | 3 |
| 110 | 114 | 138 | R | 88.6 | | | 56.24 | 0 | 40 | 0 | 20 | R138G | 1 | 5 |
| 111 | 115 | 139 | L | 100.0 | | | 54.21 | 0 | 60 | 0 | 20 | | | 4 |
| 112 | 116 | 140 | V | 139.5 | | | 51.82 | 0 | 40 | 0 | 0 | | | 3 |
| 113 | 117 | 141 | R | 46.4 | | | 49.48 | 0 | 40 | 0 | 20 | | | 5 |
| 114 | 118 | 142 | P | 98.5 | | | 47.97 | 0 | 80 | 0 | 60 | | | 3 |
| 115 | 119 | 143 | E | 88.5 | | | 46.63 | 0 | 80 | 0 | 40 | E143K | 0 | 4 |
| 116 | 120 | 144 | V | 22.2 | | | 40.28 | 1 | 40 | 0 | 20 | | | 3 |
| 117 | 121 | 145 | D | 130.4 | | | 46.02 | 1 | 60 | 0 | 40 | | | 3 |
| 118 | 122 | 146 | V | 87.7 | | | 43.96 | 1 | 40 | 0 | 20 | V146E | 0 | 3 |
| 119 | 123 | 147 | M | 26.2 | | | 39.04 | 1 | 40 | 1 | 20 | | | 3 |
| 120 | 124 | 148 | C | 3.3 | | | 34.94 | 1 | 100 | 0 | 60 | | | 0 |
| 121 | 125 | 149 | T | 115.0 | | | 35.32 | 1 | 40 | 1 | 20 | | | 1 |
| 122 | 126 | 150 | A | 74.2 | | | 33.29 | 1 | 60 | 1 | 20 | | | 1 |
| 123 | 127 | 151 | F | 0.0 | | | 33.85 | 1 | 100 | 0 | 60 | | | 4 |
| 124 | 128 | 152 | H | 75.4 | | | 39.69 | 1 | 20 | 1 | 20 | H152R | 0 | 5 |
| 125 | 129 | 153 | D | 211.6 | | | 43.69 | 1 | 40 | 0 | 20 | | | 3 |
| 126 | 130 | 154 | N | 87.1 | | | 42.63 | 0 | 40 | 0 | 20 | | | 2 |
| 127 | 131 | 155 | E | 42.3 | | | 43.42 | 1 | 60 | 0 | 20 | | | 4 |
| 128 | 132 | 156 | E | 70.5 | | | 43.81 | 1 | 20 | 1 | 20 | | | 4 |
| 129 | 133 | 157 | T | 76.3 | | | 36.77 | 1 | 20 | 1 | 20 | | | 1 |
| 130 | 134 | 158 | F | 23.6 | | | 29.94 | 1 | 100 | 0 | 60 | | | 4 |
| 131 | 135 | 159 | L | 24.7 | | | 27.81 | 1 | 40 | 1 | 40 | | | 4 |
| 132 | 136 | 160 | K | 29.9 | | | 26.12 | 1 | 60 | 0 | 40 | | | 4 |
| 133 | 137 | 161 | K | 52.9 | | | 24.22 | 1 | 60 | 1 | 20 | | | 4 |
| 134 | 138 | 162 | Y | 26.0 | | | 20.68 | 1 | 100 | 1 | 60 | | | 3 |
| 135 | 139 | 163 | L | 13.4 | | | 19.07 | 1 | 100 | 1 | 60 | | | 4 |

Figure 1 continued

| | | | | | | | | | | |
|---|---|---|---|---|---|---|---|---|---|---|
| 136 | 140 | Y | 6.7 | 21.43 | 1 | 80 | 2 | 40 | Y164C | 0 | 3 |
| 137 | 141 | E | 17.9 | 22.66 | 1 | 100 | 0 | 60 | | | 4 |
| 138 | 142 | L | 50.0 | 19.7 | 1 | 60 | 1 | 40 | | | 4 |
| 139 | 143 | A | 0.0 | 16.68 | 1 | 80 | 1 | 60 | | | 1 |
| 140 | 144 | R | 11.4 | 16.35 | 1 | 100 | 1 | 60 | | | 5 |
| 141 | 145 | R | 22.7 | 20.06 | 1 | 100 | 2 | 60 | | | 5 |
| 142 | 146 | H | 37.7 | 23 | 0 | 100 | 2 | 60 | | | 5 |
| 143 | 147 | P | 3.0 | 22.35 | 0 | 100 | 2 | 60 | | | 3 |
| 144 | 148 | Y | 24.0 | 22.81 | 0 | 100 | 2 | 60 | | | 3 |
| 145 | 149 | F | 2.4 | 22.42 | 0 | 100 | 2 | 40 | | | 4 |
| 146 | 150 | Y | 16.3 | 20 | 0 | 100 | 1 | 60 | | | 3 |
| 147 | 151 | A | 0.0 | 22.17 | 1 | 80 | 2 | 40 | | | 1 |
| 148 | 152 | P | 9.0 | 23.4 | 1 | 100 | 1 | 60 | | | 3 |
| 149 | 153 | E | 4.5 | 23.39 | 1 | 100 | 2 | 40 | | | 4 |
| 150 | 154 | L | 1.0 | 20.61 | 1 | 100 | 2 | 40 | | | 4 |
| 151 | 155 | L | 14.4 | 22.22 | 1 | 100 | 1 | 60 | | | 4 |
| 152 | 156 | F | 12.2 | 22.38 | 1 | 60 | 1 | 40 | | | 4 |
| 153 | 157 | F | 1.6 | 24.28 | 1 | 40 | 1 | 20 | | | 4 |
| 154 | 158 | A | 21.0 | 24.88 | 1 | 100 | 0 | 60 | | | 1 |
| 155 | 159 | K | 45.4 | 27.29 | 1 | 20 | 1 | 20 | | | 4 |
| 156 | 160 | R | 33.2 | 25.89 | 1 | 40 | 0 | 20 | | | 5 |
| 157 | 161 | Y | 25.0 | 25.3 | 1 | 100 | 1 | 60 | | | 3 |
| 158 | 162 | K | 45.4 | 21.31 | 1 | 60 | 0 | 20 | | | 4 |
| 159 | 163 | A | 87.1 | 21.49 | 1 | 40 | 0 | 20 | | | 1 |
| 160 | 164 | A | 4.8 | 22.78 | 1 | 40 | 0 | 20 | | | 1 |
| 161 | 165 | F | 0.0 | 23.92 | 1 | 60 | 0 | 40 | | | 4 |
| 162 | 166 | T | 77.5 | 30.55 | 1 | 40 | 1 | 40 | | | 1 |
| 163 | 167 | E | 75.0 | 33.84 | 1 | 80 | 1 | 40 | | | 4 |
| 164 | 168 | C | 0.0 | 31.68 | 1 | 100 | 1 | 60 | | | 0 |

Figure 1 continued

| | | | | | | | | | |
|---|---|---|---|---|---|---|---|---|---|
| 165 | 169 | C | 14.1 | 32.95 | 0 | 100 | 1 | | 0 |
| 166 | 170 | Q | 124.4 | 34.61 | 0 | 40 | 1 | | 3 |
| 167 | 171 | A | 58.1 | 31.57 | 0 | 80 | 0 | | 1 |
| 168 | 172 | A | 183.9 | 30.74 | 0 | 40 | 1 | | 1 |
| 169 | 173 | D | 155.1 | 29.21 | 0 | 100 | 1 | | 3 |
| 170 | 174 | K | 32.2 | 30.28 | 1 | 100 | 1 | | 4 |
| 171 | 175 | A | 74.2 | 27.97 | 1 | 40 | 1 | | 1 |
| 172 | 176 | A | 93.5 | 29.27 | 1 | 80 | 1 | | 1 |
| 173 | 177 | C | 30.4 | 28.29 | 1 | 100 | 1 | C201F | 2 | 0 |
| 174 | 178 | L | 0.0 | 28.43 | 1 | 100 | 1 | | 4 |
| 175 | 179 | L | 70.1 | 27.06 | 1 | 40 | 2 | | 4 |
| 176 | 180 | P | 111.9 | 28.36 | 1 | 100 | 1 | | 3 |
| 177 | 181 | K | 33.3 | 27.16 | 1 | 100 | 1 | | 4 |
| 178 | 182 | L | 10.3 | 24.64 | 1 | 60 | 1 | | 4 |
| 179 | 183 | D | 52.2 | 26.6 | 1 | 60 | 0 | | 3 |
| 180 | 184 | E | 80.8 | 28.49 | 1 | 40 | 0 | | 4 |
| 181 | 185 | L | 8.2 | 26.58 | 1 | 60 | 0 | | 4 |
| 182 | 186 | R | 59.2 | 29.18 | 1 | 40 | 0 | | 5 |
| 183 | 187 | D | 118.8 | 28.69 | 1 | 60 | 0 | | 3 |
| 184 | 188 | E | 35.9 | 27.68 | 1 | 60 | 0 | | 4 |
| 185 | 189 | G | 20.0 | 22.68 | 1 | 20 | 0 | | 2 |
| 186 | 190 | K | 37.9 | 23.57 | 1 | 60 | 0 | | 4 |
| 187 | 191 | A | 58.1 | 22.4 | 1 | 40 | 0 | A215V | 0 | 1 |
| 188 | 192 | S | 32.8 | 23.5 | 1 | 80 | 0 | | 1 |
| 189 | 193 | S | 21.9 | 21.41 | 1 | 60 | | | 1 |
| 190 | 194 | A | 45.2 | 21.45 | 1 | 80 | 0 | | 1 |
| 191 | 195 | K | 55.2 | 24.21 | 1 | 40 | 0 | | 4 |
| 192 | 196 | Q | 6.3 | 20.68 | 1 | 60 | 1 | Q220L | 0 | 3 |
| 193 | 197 | R | 9.0 | 16.53 | 1 | 100 | 0 | | 5 |

Figure 1 continued

| | | | | | | | | | |
|---|---|---|---|---|---|---|---|---|---|
| 194 | 198 | L | 27.8 | 18.26 | 1 | 80 | 1 | | 4 |
| 195 | 199 | K | 20.1 | 19.76 | 1 | 60 | 1 | | 4 |
| 196 | 200 | C | 2.2 | 20.47 | 1 | 100 | 0 | | 0 |
| 197 | 201 | A | 4.8 | 21.9 | 1 | 60 | 2 | | 1 |
| 198 | 202 | S | 17.2 | 25.36 | 1 | 100 | 0 | | 1 |
| 199 | 203 | L | 19.6 | 28.06 | 1 | 40 | 1 | | 4 |
| 200 | 204 | Q | 66.1 | 33.17 | 1 | 80 | 0 | | 3 |
| 201 | 205 | K | 75.3 | 34.01 | 1 | 80 | 1 | | 4 |
| 202 | 206 | F | 52.8 | 28.46 | 1 | 100 | 1 | | 4 |
| 203 | 207 | G | 50.0 | 28.59 | 0 | 100 | 1 | | 2 |
| 204 | 208 | E | 67.9 | 29.55 | 1 | 60 | 2 | | 4 |
| 205 | 209 | R | 56.4 | 29.9 | 1 | 100 | 1 | | 5 |
| 206 | 210 | A | 48.4 | 25.17 | 1 | 100 | 1 | | 1 |
| 207 | 211 | F | 1.6 | 24.26 | 1 | 60 | 2 | | 4 |
| 208 | 212 | K | 42.5 | 31.21 | 1 | 100 | 1 | | 4 |
| 209 | 213 | A | 54.8 | 26.47 | 1 | 100 | 2 | | 1 |
| 210 | 214 | W | 49.2 | 23.68 | 1 | 100 | 1 | | 3 |
| 211 | 215 | A | 0.0 | 20.76 | 1 | 40 | 1 | | 1 |
| 212 | 216 | V | 17.3 | 23.85 | 1 | 80 | 0 | | 3 |
| 213 | 217 | A | 0.0 | 26.06 | 1 | 80 | 1 | | 1 |
| 214 | 218 | R | 18.0 | 29.91 | 1 | 100 | 0 | R242H, R242P (1) | 5 |
| 215 | 219 | L | 14.4 | 23.26 | 1 | 80 | 2 | | 4 |
| 216 | 220 | S | 0.0 | 23.79 | 1 | 100 | 1 | | 1 |
| 217 | 221 | Q | 2.4 | 24.52 | 1 | 100 | 1 | | 3 |
| 218 | 222 | R | 19.0 | 24.02 | 1 | 40 | 2 | | 5 |
| 219 | 223 | F | 2.4 | 26.59 | 0 | 100 | 1 | | 4 |
| 220 | 224 | P | 4.5 | 29.7 | 0 | 100 | 1 | | 3 |
| 221 | 225 | K | 54.6 | 37.85 | 0 | 80 | 2 | K249Q (0) | 4 |

Figure 1 continued

| 222 | 222 | A | 1.6 | 35.15 | 0 | 100 | 0 | 60 | | | 1 |
| --- | --- | --- | --- | --- | --- | --- | --- | --- | --- | --- | --- |
| 223 | 226 | E | 89.7 | 38.91 | 0 | 40 | 2 | 20 | | | 4 |
| 224 | 227 | F | 30.9 | 37.46 | 1 | 100 | 0 | 60 | | | 4 |
| 225 | 228 | A | 109.7 | 36.47 | 1 | 60 | 1 | 40 | | | 1 |
| 226 | 229 | E | 17.3 | 32.11 | 1 | 80 | 0 | 40 | | | 4 |
| 227 | 230 | V | 0.0 | 29.49 | 1 | 40 | 0 | 20 | | | 3 |
| 228 | 231 | S | 54.7 | 29.63 | 1 | 60 | 0 | 20 | | | 1 |
| 229 | 232 | K | 43.7 | 28.65 | 1 | 80 | 0 | 60 | | | 4 |
| 230 | 233 | L | 3.1 | 32.28 | 1 | 40 | 0 | 20 | | | 4 |
| 231 | 234 | V | 6.2 | 29.28 | 1 | 80 | 1 | 40 | | | 3 |
| 232 | 235 | T | 92.5 | 29.1 | 1 | 100 | 0 | 40 | | | 1 |
| 233 | 236 | D | 62.3 | 28.36 | 1 | 80 | 1 | 40 | | | 3 |
| 234 | 237 | L | 30.9 | 23.28 | 1 | 80 | 0 | 40 | | | 4 |
| 235 | 238 | T | 6.3 | 24.55 | 1 | 80 | 1 | 40 | | | 1 |
| 236 | 239 | K | 63.8 | 24.54 | 1 | 100 | 0 | 40 | K264E | 0 | 4 |
| 237 | 240 | V | 1.2 | 23.3 | 1 | 80 | 1 | 40 | | | 3 |
| 238 | 241 | H | 3.1 | 20.96 | 1 | 60 | 0 | 40 | | | 5 |
| 239 | 242 | T | 66.3 | 21.82 | 1 | 60 | 1 | 40 | | | 1 |
| 240 | 243 | E | 17.9 | 24.56 | 1 | 100 | 1 | 60 | | | 4 |
| 241 | 244 | C | 10.9 | 22.73 | 1 | 100 | 2 | 60 | | | 0 |
| 242 | 245 | C | 3.3 | 20.77 | 0 | 100 | 2 | 80 | | | 0 |
| 243 | 246 | H | 53.8 | 25.67 | 0 | 100 | 2 | 40 | | | 5 |
| 244 | 247 | G | 16.0 | 19.18 | 0 | 100 | 2 | 80 | | | 2 |
| 245 | 248 | D | 37.7 | 18.57 | 1 | 100 | 2 | 60 | | | 3 |
| 246 | 249 | L | 5.2 | 18.31 | 1 | 100 | 2 | 40 | | | 4 |
| 247 | 250 | L | 3.1 | 16.12 | 1 | 100 | 2 | 40 | | | 4 |
| 248 | 251 | E | 17.3 | 19.95 | 1 | 100 | 2 | 60 | | | 4 |
| 249 | 252 | C | 0.0 | 19.89 | 1 | 100 | 2 | 60 | | | 0 |
| 250 | 253 | A | 21.0 | 20.33 | 1 | 100 | 2 | 40 | | | 1 |

Figure 1 continued

| | | | | | | | | | | |
|---|---|---|---|---|---|---|---|---|---|---|
| 251 | 255 | 279 | D | 10.1 | 21.47 | 1 | 100 | 2 | 40 | | | 3 |
| 252 | 256 | 280 | D | 47.8 | 23.25 | 1 | 100 | 2 | 60 | | | 3 |
| 253 | 257 | 281 | R | 9.0 | 26.57 | 1 | 100 | 1 | 60 | | | 5 |
| 254 | 258 | 282 | A | 38.7 | 25.99 | 1 | 80 | 1 | 40 | | | 1 |
| 255 | 259 | 283 | D | 123.2 | 23.81 | 1 | 60 | 1 | 20 | | | 3 |
| 256 | 260 | 284 | L | 17.5 | 21.77 | 1 | 100 | 0 | 60 | | | 4 |
| 257 | 261 | 285 | A | 8.1 | 27.58 | 1 | 80 | 2 | 40 | | | 1 |
| 258 | 262 | 286 | K | 64.4 | 31.33 | 1 | 100 | 1 | 40 | | | 4 |
| 259 | 263 | 287 | Y | 51.0 | 30.7 | 1 | 100 | 1 | 60 | | | 3 |
| 260 | 264 | 288 | I | 14.3 | 32.27 | 1 | 40 | 2 | 20 | | | 4 |
| 261 | 265 | 289 | C | 18.5 | 38.84 | 1 | 100 | 0 | 80 | | | 0 |
| 262 | 266 | 290 | E | 83.3 | 41.21 | 1 | 80 | 1 | 40 | | | 4 |
| 263 | 267 | 291 | N | 54.1 | 36.4 | 0 | 60 | 1 | 20 | | | 2 |
| 264 | 268 | 292 | Q | 32.3 | 37.75 | 1 | 100 | 0 | 60 | Q292R | 0 | 3 |
| 265 | 269 | 293 | D | 229.0 | 45.46 | 1 | 60 | 1 | 60 | D293G | 1 | 3 |
| 266 | 270 | 294 | D | 114.1 | 43.53 | 1 | 40 | 0 | 20 | | | 1 |
| 267 | 271 | 295 | S | 2.4 | 35.55 | 1 | 80 | 1 | 40 | | | 4 |
| 268 | 272 | 296 | I | 7.8 | 36.26 | 0 | 100 | 0 | 60 | | | 1 |
| 269 | 273 | 297 | S | 112.5 | 40.24 | 0 | 60 | 1 | 40 | | | 1 |
| 270 | 274 | 298 | S | 23.6 | 38.39 | 0 | 80 | 1 | 60 | | | 4 |
| 271 | 275 | 299 | K | 0.0 | 37.35 | 0 | 100 | 0 | 80 | | | 4 |
| 272 | 276 | 300 | L | 64.9 | 45.27 | 0 | 80 | 1 | 40 | K300N | 1 | 4 |
| 273 | 277 | 301 | K | 79.5 | 46.31 | 0 | 60 | 1 | 20 | | | 4 |
| 274 | 278 | 302 | E | 1.1 | 40.66 | 0 | 100 | 1 | 80 | | | 0 |
| 275 | 279 | 303 | C | 20.7 | 40.94 | 0 | 100 | 1 | 80 | | | 0 |
| 276 | 280 | 304 | C | 99.4 | 44.93 | 0 | 60 | 2 | 40 | | | 4 |
| 277 | 281 | 305 | E | 59.2 | 41.28 | 0 | 100 | 0 | 60 | | | 4 |
| 278 | 282 | 306 | K | 116.4 | 40.02 | 0 | 80 | 1 | 60 | | | 3 |
| 279 | 283 | 307 | P | 87.6 | 36.51 | 1 | 40 | 1 | 20 | | | 4 |

Figure 1 continued

| 280 | 284 | 308 |   | 22.7  | 33.27 | 1 | 100 | 0 | 60 |   | 4 |
|-----|-----|-----|---|-------|-------|---|-----|---|----|---|---|
| 281 | 285 | 309 | L | 32.7  | 32.98 | 1 | 60  | 2 | 40 |   | 4 |
| 282 | 286 | 310 | E | 26.4  | 30.79 | 1 | 100 | 0 | 40 |   | 4 |
| 283 | 287 | 311 | K | 12.5  | 31.54 | 1 | 80  | 1 | 40 |   | 1 |
| 284 | 288 | 312 | S | 27.7  | 33.63 | 1 | 80  | 1 | 40 |   | 5 |
| 285 | 289 | 313 | H | 22.8  | 34.65 | 1 | 100 | 0 | 80 |   | 0 |
| 286 | 290 | 314 | C | 14.3  | 34.3  | 1 | 60  | 1 | 40 |   | 4 |
| 287 | 291 | 315 | L | 53.2  | 35.49 | 1 | 60  | 0 | 40 |   | 1 |
| 288 | 292 | 316 | A | 58.3  | 40.82 | 0 | 80  | 0 | 40 |   | 4 |
| 289 | 293 | 317 | E | 32.1  | 40.52 | 0 | 60  | 0 | 40 |   | 3 |
| 290 | 294 | 318 | V | 89.1  | 40.97 | 0 | 40  | 0 | 40 |   | 4 |
| 291 | 295 | 319 | E | 65.9  | 40.65 | 0 | 20  | 1 | 20 |   | 2 |
| 292 | 296 | 320 | N | 15.9  | 44.56 | 0 | 100 | 0 | 60 |   | 3 |
| 293 | 297 | 321 | D | 80.8  | 49.85 | 0 | 40  | 1 | 20 |   | 4 |
| 294 | 298 | 322 | E | 84.5  | 53.49 | 0 | 20  | 1 | 20 |   | 3 |
| 295 | 299 | 323 | M | 44.8  | 59.14 | 0 | 100 | 0 | 60 |   | 3 |
| 296 | 300 | 324 | P | 180.6 | 63.75 | 0 | 40  | 1 | 40 |   | 1 |
| 297 | 301 | 325 | A | 218.8 | 64.56 | 0 | 60  | 0 | 40 |   | 3 |
| 298 | 302 | 326 | D | 44.3  | 61.34 | 0 | 100 | 1 | 60 |   | 4 |
| 299 | 303 | 327 | L | 119.4 | 59.59 | 0 | 80  | 0 | 60 |   | 3 |
| 300 | 304 | 328 | P | 134.4 | 57.01 | 0 | 20  | 1 | 20 |   | 1 |
| 301 | 305 | 329 | S | 13.4  | 53.51 | 0 | 80  | 0 | 40 |   | 4 |
| 302 | 306 | 330 | L | 33.9  | 49.21 | 1 | 60  | 0 | 20 |   | 1 |
| 303 | 307 | 331 | A | 67.7  | 48.5  | 1 | 60  | 0 | 40 |   | 1 |
| 304 | 308 | 332 | A | 131.9 | 47.92 | 1 | 80  | 0 | 40 |   | 3 |
| 305 | 309 | 333 | D | 10.6  | 43.2  | 0 | 80  | 0 | 40 |   | 4 |
| 306 | 310 | 334 | F | 25.9  | 50.47 | 0 | 60  | 1 | 40 |   | 3 |
| 307 | 311 | 335 | V | 92.9  | 55.73 | 0 | 100 | 0 | 60 |   | 4 |
| 308 | 312 | 336 | E | 75.0  | 57.48 | 0 | 60  | 1 | 40 |   | 1 |

Figure 1 continued

| 309 | 313 | 337 | K | 92.0 | 64.18 | 0 | 80 | 0 | 40 | K337N | 1 | 4 |
| --- | --- | --- | --- | --- | --- | --- | --- | --- | --- | --- | --- | --- |
| 310 | 314 | 338 | D | 131.9 | 65.86 | 0 | 40 | 0 | 40 | D338G, D338V | 1 | 3 |
| 311 | 315 | 339 | V | 2.5 | 62.66 | 1 | 80 | 1 | 60 | | | 3 |
| 312 | 316 | 340 | C | 23.9 | 62.19 | 1 | 100 | 1 | 80 | | | 0 |
| 313 | 317 | 341 | K | 79.3 | 62.49 | 1 | 100 | 1 | 60 | | | 4 |
| 314 | 318 | 342 | N | 107.1 | 59.91 | 1 | 80 | 1 | 40 | N342K | 0 | 2 |
| 315 | 319 | 343 | Y | 13.5 | 58.72 | 1 | 80 | 0 | 60 | | | 3 |
| 316 | 320 | 344 | A | 119.4 | 64 | 1 | 40 | 0 | 20 | A344T | 1 | 1 |
| 317 | 321 | 345 | E | 88.5 | 67.18 | 1 | 80 | 1 | 40 | E345K | 0 | 4 |
| 318 | 322 | 346 | A | 75.8 | 66.17 | 0 | 100 | 1 | 40 | | | 1 |
| 319 | 323 | 347 | K | 52.9 | 62.98 | 1 | 100 | 1 | 60 | | | 4 |
| 320 | 324 | 348 | D | 120.3 | 58.69 | 1 | 80 | 1 | 60 | | | 3 |
| 321 | 325 | 349 | V | 100.0 | 50.37 | 1 | 80 | 1 | 40 | | | 3 |
| 322 | 326 | 350 | F | 8.1 | 44.71 | 1 | 100 | 1 | 60 | | | 4 |
| 323 | 327 | 351 | L | 18.6 | 42.37 | 1 | 100 | 2 | 60 | | | 4 |
| 324 | 328 | 352 | G | 30.0 | 38.93 | 1 | 100 | 1 | 60 | | | 2 |
| 325 | 329 | 353 | M | 65.0 | 37.18 | 1 | 40 | 2 | 20 | | | 3 |
| 326 | 330 | 354 | F | 0.8 | 29.72 | 1 | 100 | 1 | 60 | | | 4 |
| 327 | 331 | 355 | L | 8.2 | 29.23 | 1 | 100 | 2 | 60 | | | 4 |
| 328 | 332 | 356 | Y | 13.5 | 30.36 | 1 | 100 | 2 | 60 | | | 3 |
| 329 | 333 | 357 | E | 23.7 | 29.68 | 1 | 100 | 1 | 60 | E357K | 0 | 4 |
| 330 | 334 | 358 | Y | 14.4 | 32.04 | 1 | 100 | 1 | 60 | | | 3 |
| 331 | 335 | 359 | A | 0.0 | 31.27 | 1 | 60 | 2 | 60 | | | 1 |
| 332 | 336 | 360 | R | 8.5 | 31.88 | 1 | 100 | 1 | 60 | | | 5 |
| 333 | 337 | 361 | R | 16.6 | 33.45 | 0 | 100 | 2 | 60 | | | 5 |
| 334 | 338 | 362 | H | 33.1 | 32.11 | 0 | 100 | 2 | 60 | | | 5 |
| 335 | 339 | 363 | P | 62.7 | 28.98 | 0 | 100 | 1 | 60 | | | 3 |
| 336 | 340 | 364 | D | 84.1 | 24.21 | 0 | 40 | 2 | 40 | | | 3 |

Figure 1 continued

| 337 | 341 | Y | 24.0 | 20.57 | 0 | 100 | 0 | 40 | | | 3 |
|---|---|---|---|---|---|---|---|---|---|---|---|
| 338 | 342 | S | 0.0 | 20.06 | 0 | 80 | 1 | 60 | | | 1 |
| 339 | 343 | V | 2.5 | 23.25 | 1 | 80 | 0 | 40 | | | 3 |
| 340 | 344 | V | 14.8 | 24.72 | 1 | 60 | 0 | 20 | | | 3 |
| 341 | 345 | L | 0.0 | 25.04 | 1 | 60 | 1 | 40 | | | 4 |
| 342 | 346 | L | 0.0 | 25.17 | 1 | 100 | 1 | 60 | | | 4 |
| 343 | 347 | L | 16.5 | 25.68 | 1 | 100 | 2 | 60 | | | 4 |
| 344 | 348 | R | 3.3 | 24.63 | 1 | 100 | 1 | 60 | | | 5 |
| 345 | 349 | L | 0.0 | 26.75 | 1 | 60 | 1 | 40 | | | 4 |
| 346 | 350 | A | 27.4 | 27.71 | 1 | 80 | 1 | 60 | | | 1 |
| 347 | 351 | K | 60.3 | 33.28 | 1 | 100 | 0 | 60 | | | 4 |
| 348 | 352 | T | 33.8 | 31.6 | 1 | 20 | 2 | 20 | | | 1 |
| 349 | 353 | Y | 0.0 | 34.39 | 1 | 100 | 1 | 60 | | | 3 |
| 350 | 354 | E | 13.5 | 35.62 | 1 | 100 | 1 | 60 | E378K | 0 | 4 |
| 351 | 355 | T | 86.3 | 40.3 | 1 | 80 | 1 | 40 | | | 1 |
| 352 | 356 | T | 15.0 | 45.68 | 1 | 80 | 1 | 40 | | | 1 |
| 353 | 357 | L | 0.0 | 49.17 | 1 | 100 | 0 | 80 | | | 4 |
| 354 | 358 | E | 66.0 | 53.47 | 1 | 80 | 1 | 60 | E382K | 0 | 4 |
| 355 | 359 | K | 91.4 | 55.14 | 1 | 60 | 1 | 40 | K383N | 2 | 4 |
| 356 | 360 | C | 2.2 | 60.95 | 1 | 100 | 2 | 80 | | | 0 |
| 357 | 361 | C | 42.4 | 66.33 | 0 | 100 | 1 | 80 | | | 0 |
| 358 | 362 | A | 140.3 | 72.72 | 0 | 100 | 1 | 60 | | | 1 |
| 359 | 363 | A | 75.8 | 76.03 | 0 | 20 | 0 | 20 | | | 1 |
| 360 | 364 | A | 164.5 | 80.24 | 0 | 40 | 0 | 20 | | | 1 |
| 361 | 365 | D | 168.1 | 84.23 | 0 | 80 | 1 | 40 | D389H, D389V | 1 | 3 |
| 362 | 366 | P | 35.8 | 82.14 | 1 | 100 | 0 | 60 | | | 3 |
| 363 | 367 | H | 65.4 | 80.75 | 1 | 40 | 1 | 20 | | | 5 |
| 364 | 368 | E | 109.6 | 77.34 | 1 | 60 | 1 | 20 | | | 4 |

Figure 1 continued

| 365 | 369 | C | 48.9 | 1 | 100 | 1 | 80 | | 0 |
|---|---|---|---|---|---|---|---|---|---|
| 366 | 370 | Y | 1.9 | 0 | 100 | 1 | 60 | | 3 |
| 367 | 371 | A | 100.0 | 0 | 60 | 1 | 40 | | 1 |
| 368 | 372 | K | 73.0 | 0 | 40 | 1 | 20 | K396E | 4 |
| 369 | 373 | V | 0.0 | 1 | 100 | 0 | 40 | | 3 |
| 370 | 374 | F | 51.2 | 1 | 60 | 1 | 40 | | 4 |
| 371 | 375 | D | 152.2 | 1 | 80 | 0 | 40 | D399N, D399H | 3 |
| 372 | 376 | E | 66.0 | 1 | 60 | 0 | 20 | E400K, E400Q | 4 |
| 373 | 377 | F | 2.4 | 0 | 60 | 0 | 40 | | 4 |
| 374 | 378 | K | 72.4 | 1 | 40 | 0 | 20 | | 4 |
| 375 | 379 | P | 119.4 | 1 | 80 | 1 | 40 | | 3 |
| 376 | 380 | L | 50.5 | 1 | 100 | 0 | 40 | | 4 |
| 377 | 381 | V | 17.3 | 1 | 80 | 1 | 40 | | 3 |
| 378 | 382 | E | 61.5 | 1 | 40 | 1 | 20 | E406K | 4 |
| 379 | 383 | E | 49.4 | 1 | 100 | 1 | 60 | | 4 |
| 380 | 384 | P | 0.0 | 1 | 100 | 1 | 40 | | 3 |
| 381 | 385 | Q | 68.5 | 1 | 40 | 1 | 20 | | 3 |
| 382 | 386 | N | 94.1 | 1 | 80 | 1 | 40 | | 2 |
| 383 | 387 | L | 21.6 | 1 | 100 | 0 | 60 | | 4 |
| 384 | 388 | I | 11.9 | 1 | 60 | 0 | 40 | | 4 |
| 385 | 389 | K | 69.5 | 1 | 80 | 0 | 60 | | 3 |
| 386 | 390 | Q | 96.9 | 1 | 40 | 1 | 20 | | 2 |
| 387 | 391 | N | 22.4 | 1 | 100 | 1 | 60 | | 0 |
| 388 | 392 | C | 3.3 | 1 | 100 | 1 | 80 | | 4 |
| 389 | 393 | E | 71.2 | 1 | 60 | 1 | 40 | | 4 |
| 390 | 394 | L | 52.6 | 1 | 80 | 0 | 40 | | 4 |
| 391 | 395 | F | 30.1 | 1 | 60 | 0 | 40 | | 4 |

Figure 1 continued

| 392 | 396 | 420 | E | 85.9 | 62.51 | 1 | 80 | 0 | E420K | 0 | 4 |
|---|---|---|---|---|---|---|---|---|---|---|---|
| 393 | 397 | 421 | Q | 101.6 | 58.94 | 1 | 40 | 0 | | | 3 |
| 394 | 398 | 422 | L | 21.6 | 53.27 | 1 | 60 | 1 | | | 4 |
| 395 | 399 | 423 | G | 62.0 | 50.77 | 0 | 100 | 0 | | | 2 |
| 396 | 400 | 424 | E | 51.9 | 50.07 | 1 | 80 | 2 | | | 4 |
| 397 | 401 | 425 | Y | 53.8 | 50.48 | 1 | 100 | 0 | | | 3 |
| 398 | 402 | 426 | K | 66.7 | 46.35 | 1 | 40 | 2 | | | 4 |
| 399 | 403 | 427 | F | 0.8 | 40.68 | 1 | 100 | 1 | | | 4 |
| 400 | 404 | 428 | Q | 0.8 | 37.32 | 1 | 60 | 2 | | | 3 |
| 401 | 405 | 429 | N | 21.2 | 34.37 | 1 | 40 | 2 | | | 2 |
| 402 | 406 | 430 | A | 54.8 | 29.99 | 1 | 60 | 1 | | | 1 |
| 403 | 407 | 431 | L | 8.2 | 28.56 | 1 | 40 | 1 | | | 4 |
| 404 | 408 | 432 | L | 0.0 | 32.59 | 1 | 60 | 1 | | | 4 |
| 405 | 409 | 433 | V | 34.6 | 36.52 | 1 | 40 | 1 | | | 3 |
| 406 | 410 | 434 | R | 31.8 | 38.85 | 1 | 60 | 2 | R434C | 1 | 5 |
| 407 | 411 | 435 | Y | 15.4 | 32.48 | 1 | 80 | 2 | | | 3 |
| 408 | 412 | 436 | T | 0.0 | 29.54 | 1 | 60 | 1 | | | 1 |
| 409 | 413 | 437 | K | 27.6 | 33.11 | 1 | 100 | 1 | | | 4 |
| 410 | 414 | 438 | K | 6.3 | 32.07 | 1 | 60 | 0 | | | 4 |
| 411 | 415 | 439 | V | 0.0 | 28.94 | 0 | 40 | 2 | | | 3 |
| 412 | 416 | 440 | P | 7.5 | 31.07 | 0 | 100 | 1 | | | 3 |
| 413 | 417 | 441 | Q | 45.7 | 31.05 | 0 | 80 | 2 | | | 3 |
| 414 | 418 | 442 | V | 3.7 | 28.94 | 0 | 60 | 2 | | | 3 |
| 415 | 419 | 443 | S | 98.4 | 27.89 | 1 | 60 | 2 | | | 1 |
| 416 | 420 | 444 | T | 13.8 | 27.97 | 1 | 40 | 2 | | | 1 |
| 417 | 421 | 445 | P | 132.8 | 24.74 | 1 | 40 | 2 | | | 3 |
| 418 | 422 | 446 | T | 18.8 | 25.07 | 1 | 60 | 2 | | | 1 |
| 419 | 423 | 447 | L | 3.1 | 24.57 | 1 | 60 | 2 | | | 4 |
| 420 | 424 | 448 | V | 6.2 | 25.83 | 1 | 60 | 2 | | | 3 |

Figure 1 continued

| 421 | 425 | | E | 48.1 | 30.55 | 1 | 100 | 1 | 60 | | | 4 |
|---|---|---|---|---|---|---|---|---|---|---|---|---|
| 422 | 426 | 449 | V | 3.7 | 28 | 1 | 40 | 1 | 20 | | | 3 |
| 423 | 427 | 450 | S | 1.6 | 31.38 | 1 | 40 | 1 | 20 | | | 1 |
| 424 | 428 | 451 | R | 18.0 | 30.58 | 1 | 100 | 0 | 40 | | | 5 |
| 425 | 429 | 452 | N | 22.4 | 29.18 | 1 | 20 | 2 | 20 | | | 2 |
| 426 | 430 | 453 | L | 7.2 | 31.68 | 1 | 100 | 1 | 40 | | | 4 |
| 427 | 431 | 454 | G | 0.0 | 35.59 | 1 | 100 | 1 | 40 | | | 2 |
| 428 | 432 | 455 | K | 27.6 | 36.58 | 0 | 60 | 2 | 40 | | | 4 |
| 429 | 433 | 456 | V | 17.3 | 37.59 | 0 | 100 | 1 | 60 | | | 3 |
| 430 | 434 | 457 | G | 4.0 | 40.74 | 1 | 100 | 1 | 60 | | | 2 |
| 431 | 435 | 458 | S | 73.4 | 41.51 | 1 | 40 | 1 | 20 | | | 1 |
| 432 | 436 | 459 | K | 58.0 | 40.92 | 1 | 60 | 1 | 40 | | | 4 |
| 433 | 437 | 460 | C | 2.2 | 41.74 | 1 | 100 | 1 | 80 | | | 0 |
| 434 | 438 | 461 | C | 13.0 | 46.67 | 0 | 100 | 0 | 80 | | | 0 |
| 435 | 439 | 462 | K | 106.3 | 52.99 | 0 | 40 | 0 | 20 | | | 4 |
| 436 | 440 | 463 | H | 44.6 | 54.37 | 0 | 40 | 0 | 20 | | | 5 |
| 437 | 441 | 464 | P | 119.4 | 55.7 | 0 | 100 | 1 | 60 | | | 3 |
| 438 | 442 | 465 | E | 112.8 | 57.25 | 0 | 100 | 1 | 60 | | | 4 |
| 439 | 443 | 466 | A | 93.5 | 55.15 | 0 | 40 | 0 | 20 | | | 1 |
| 440 | 444 | 467 | K | 63.8 | 50.64 | 0 | 40 | 0 | 20 | | | 4 |
| 441 | 445 | 468 | R | 24.2 | 42.52 | 1 | 100 | 1 | 60 | | | 5 |
| 442 | 446 | 469 | M | 8.7 | 35.96 | 1 | 40 | 1 | 20 | | | 3 |
| 443 | 447 | 470 | P | 35.8 | 36.33 | 1 | 60 | 1 | 40 | | | 3 |
| 444 | 448 | 471 | C | 43.5 | 35.54 | 1 | 100 | 0 | 80 | | | 0 |
| 445 | 449 | 472 | A | 3.2 | 33.69 | 1 | 40 | 2 | 20 | | | 1 |
| 446 | 450 | 473 | E | 0.0 | 29.58 | 1 | 100 | 0 | 60 | | | 4 |
| 447 | 451 | 474 | D | 42.0 | 25.46 | 1 | 80 | 0 | 40 | | | 3 |
| 448 | 452 | 475 | Y | 34.6 | 20.82 | 1 | 80 | 1 | 40 | | | 3 |
| 449 | 453 | 476 | L | 20.6 | 21.5 | 1 | 100 | 0 | 60 | | | 4 |

Figure 1 continued

| | | | | | | | | | | | |
|---|---|---|---|---|---|---|---|---|---|---|---|
| 450 | 454 | S | 23.4 | 20.37 | 1 | 80 | 1 | 40 | | | 1 |
| 451 | 455 | V | 23.5 | 16.54 | 1 | 40 | 0 | 20 | | | 3 |
| 452 | 456 | V | 3.7 | 20.05 | 1 | 40 | 1 | 20 | | | 3 |
| 453 | 457 | L | 3.1 | 17.71 | 1 | 100 | 1 | 60 | | | 4 |
| 454 | 458 | N | 3.5 | 19.76 | 1 | 100 | 1 | 40 | | | 2 |
| 455 | 459 | Q | 25.2 | 25.52 | 1 | 80 | 1 | 40 | | | 3 |
| 456 | 460 | L | 2.1 | 26.58 | 1 | 80 | 1 | 40 | | | 4 |
| 457 | 461 | C | 7.6 | 27.06 | 1 | 100 | 0 | 80 | | | 0 |
| 458 | 462 | V | 12.3 | 25.4 | 1 | 80 | 2 | 40 | | | 3 |
| 459 | 463 | L | 17.5 | 29.09 | 1 | 100 | 1 | 40 | | | 4 |
| 460 | 464 | H | 6.9 | 35.51 | 1 | 100 | 2 | 40 | | | 5 |
| 461 | 465 | E | 60.3 | 42.01 | 1 | 100 | 2 | 60 | | | 4 |
| 462 | 466 | K | 54.0 | 45.63 | 1 | 100 | 2 | 60 | K490E | 0 | 4 |
| 463 | 467 | T | 111.3 | 47.62 | 0 | 100 | 2 | 60 | | | 1 |
| 464 | 468 | P | 128.4 | 44.24 | 0 | 100 | 2 | 40 | | | 3 |
| 465 | 469 | V | 97.5 | 41.69 | 0 | 100 | 2 | 40 | | | 3 |
| 466 | 470 | S | 4.7 | 43.02 | 0 | 100 | 1 | 40 | | | 1 |
| 467 | 471 | D | 205.8 | 45.67 | 1 | 80 | 0 | 40 | | | 3 |
| 468 | 472 | R | 25.6 | 43.1 | 1 | 40 | 1 | 20 | | | 5 |
| 469 | 473 | V | 0.0 | 35.26 | 1 | 80 | 1 | 60 | | | 3 |
| 470 | 474 | T | 66.3 | 36.92 | 1 | 100 | 2 | 40 | | | 1 |
| 471 | 475 | K | 63.2 | 36.72 | 1 | 60 | 2 | 40 | | | 4 |
| 472 | 476 | C | 2.2 | 29.85 | 1 | 100 | 1 | 80 | | | 0 |
| 473 | 477 | C | 9.8 | 29.96 | 1 | 100 | 1 | 40 | | | 0 |
| 474 | 478 | T | 125.0 | 35 | 1 | 60 | 1 | 40 | | | 1 |
| 475 | 479 | E | 94.2 | 40.83 | 1 | 60 | 1 | 20 | E503K | 0 | 4 |
| 476 | 480 | S | 62.5 | 40.31 | 0 | 100 | 0 | 60 | | | 1 |
| 477 | 481 | L | 34.0 | 34.26 | 0 | 100 | 0 | 40 | | | 4 |
| 478 | 482 | V | 32.1 | 32.41 | 0 | 80 | 1 | 40 | | | 3 |

Figure 1 continued

| | | | | | | | | | | |
|---|---|---|---|---|---|---|---|---|---|---|
| 479 | 483 | 507 | N | 85.9 | 30.93 | 0 | 60 | | | 2 |
| 480 | 484 | 508 | R | 8.1 | 26.02 | 1 | 100 | | | 5 |
| 481 | 485 | 509 | R | 2.4 | 27.43 | 1 | 100 | | | 5 |
| 482 | 486 | 510 | P | 26.9 | 27.41 | 1 | 100 | | | 3 |
| 483 | 487 | 511 | C | 34.8 | 28.7 | 1 | 100 | | | 0 |
| 484 | 488 | 512 | F | 0.0 | 26.54 | 1 | 100 | | | 4 |
| 485 | 489 | 513 | S | 39.1 | 29.37 | 1 | 100 | | | 1 |
| 486 | 490 | 514 | A | 130.6 | 32.03 | 1 | 80 | | | 1 |
| 487 | 491 | 515 | L | 12.4 | 36.77 | 0 | 100 | | | 4 |
| 488 | 492 | 516 | E | 83.3 | 48.42 | 0 | 40 | | | 4 |
| 489 | 493 | 517 | V | 67.9 | 54.02 | 0 | 40 | | | 3 |
| 490 | 494 | 518 | D | 26.1 | 62.32 | 0 | 60 | D518N | 1 | 3 |
| 491 | 495 | 519 | E | 100.6 | 69.16 | 0 | 100 | | | 4 |
| 492 | 496 | 520 | T | 148.8 | 70.07 | 0 | 60 | | | 1 |
| 493 | 497 | 521 | Y | 46.2 | 69.63 | 0 | 100 | | | 3 |
| 494 | 498 | 522 | V | 149.4 | 74.11 | 0 | 80 | | | 3 |
| 495 | 499 | 523 | P | 89.6 | 78.71 | 0 | 100 | | | 3 |
| 496 | 500 | 524 | K | 86.8 | 87.39 | 0 | 100 | | | 4 |
| 497 | 501 | 525 | E | 99.4 | 95.25 | 0 | 60 | E525K | 0 | 4 |
| 498 | 502 | 526 | F | 48.8 | 97.09 | 0 | 100 | | | 2 |
| 499 | 503 | 527 | N | 81.2 | 99.86 | 0 | 40 | | | 1 |
| 500 | 504 | 528 | A | 108.1 | 98.55 | 0 | 60 | | | 4 |
| 501 | 505 | 529 | E | 105.8 | 93.84 | 0 | 60 | E529K | 0 | 1 |
| 502 | 506 | 530 | T | 92.5 | 88 | 1 | 60 | | | 4 |
| 503 | 507 | 531 | F | 3.3 | 82.27 | 1 | 100 | | | 1 |
| 504 | 508 | 532 | T | 100.0 | 80.18 | 0 | 100 | | | 4 |
| 505 | 509 | 533 | F | 13.8 | 78.2 | 2 | 100 | | | 1 |
| 506 | 510 | 534 | H | 88.5 | 76.46 | 1 | 100 | | | 5 |
| 507 | 511 | 535 | A | 48.4 | 69.68 | 1 | 80 | | | 1 |

Figure 1 continued

| 508 | 512 | 536 | D | 139.1 | 61.05 | 0 | 80 | 0 | 40 | | | 3 |
| --- | --- | --- | --- | --- | --- | --- | --- | --- | --- | --- | --- | --- |
| 509 | 513 | 537 | I | 4.8 | 50.62 | 0 | 60 | 1 | 40 | | | 4 |
| 510 | 514 | 538 | C | 45.7 | 44.69 | 0 | 100 | 1 | 80 | | | 0 |
| 511 | 515 | 539 | T | 145.0 | 40.33 | 0 | 100 | 2 | 60 | | | 1 |
| 512 | 516 | 540 | L | 46.4 | 40.23 | 0 | 100 | 1 | 40 | | | 4 |
| 513 | 517 | 541 | S | 78.1 | 46.03 | 0 | 60 | 1 | 40 | | | 1 |
| 514 | 518 | 542 | E | 51.9 | 49.65 | 1 | 60 | 0 | 40 | | | 4 |
| 515 | 519 | 543 | K | 62.6 | 49.4 | 1 | 40 | 1 | 20 | | | 4 |
| 516 | 520 | 544 | E | 23.7 | 43.06 | 1 | 100 | 0 | 60 | | | 4 |
| 517 | 521 | 545 | R | 16.6 | 40.16 | 1 | 80 | 1 | 40 | | | 5 |
| 518 | 522 | 546 | Q | 37.0 | 39.72 | 1 | 80 | 0 | 60 | | | 3 |
| 519 | 523 | 547 | I | 71.4 | 36.13 | 1 | 60 | 0 | 40 | | | 4 |
| 520 | 524 | 548 | K | 60.3 | 34.29 | 1 | 80 | 1 | 60 | | | 4 |
| 521 | 525 | 549 | K | 6.9 | 35.18 | 1 | 100 | 1 | 60 | | | 4 |
| 522 | 526 | 550 | Q | 0.0 | 30.63 | 1 | 100 | 1 | 60 | | | 3 |
| 523 | 527 | 551 | T | 53.8 | 28.26 | 1 | 60 | 2 | 20 | | | 1 |
| 524 | 528 | 552 | A | 6.5 | 31.62 | 1 | 100 | 1 | 40 | | | 1 |
| 525 | 529 | 553 | L | 7.2 | 30.26 | 1 | 100 | 1 | 80 | | | 4 |
| 526 | 530 | 554 | V | 0.0 | 33.2 | 1 | 60 | 2 | 40 | | | 3 |
| 527 | 531 | 555 | E | 28.2 | 41.25 | 1 | 100 | 1 | 60 | | | 4 |
| 528 | 532 | 556 | L | 14.4 | 49.88 | 1 | 100 | 2 | 60 | | | 4 |
| 529 | 533 | 557 | V | 2.5 | 54.97 | 1 | 60 | 2 | 40 | V557M | 0 | 3 |
| 530 | 534 | 558 | K | 10.9 | 60.16 | 0 | 100 | 1 | 60 | | | 4 |
| 531 | 535 | 559 | H | 27.7 | 70.44 | 0 | 100 | 2 | 60 | | | 5 |
| 532 | 536 | 560 | K | 23.0 | 79.19 | 0 | 100 | 1 | 60 | K560E | 0 | 4 |
| 533 | 537 | 561 | P | 34.3 | 87.27 | 0 | 100 | 1 | 60 | | | 3 |
| 534 | 538 | 562 | K | 115.5 | 96.73 | 0 | 80 | 2 | 40 | | | 4 |
| 535 | 539 | 563 | A | 90.3 | 99.48 | 0 | 100 | 0 | 40 | | | 1 |
| 536 | 540 | 564 | T | 26.3 | 97.44 | 0 | 80 | 1 | 60 | | | 1 |

Figure 1 continued

| | | | | | | | | | | | |
|---|---|---|---|---|---|---|---|---|---|---|---|
| 537 | 541 | K | 98.3 | 96.84 | 0 | 20 | 0 | 20 | | 1 | 4 |
| 538 | 542 | E | 105.8 | 96.98 | 1 | 80 | 1 | 60 | K565E | | 4 |
| 539 | 543 | Q | 53.5 | 92.83 | 1 | 100 | 0 | 60 | | | 3 |
| 540 | 544 | L | 6.2 | 91.34 | 1 | 80 | 1 | 60 | | | 4 |
| 541 | 545 | K | 63.8 | 92.51 | 1 | 80 | 1 | 60 | | | 4 |
| 542 | 546 | A | 80.6 | 91.51 | 1 | 60 | 1 | 40 | | | 1 |
| 543 | 547 | V | 27.2 | 88.34 | 1 | 100 | 0 | 60 | | | 3 |
| 544 | 548 | M | 8.7 | 86.47 | 1 | 60 | 1 | 40 | | | 3 |
| 545 | 549 | D | 146.4 | 84.68 | 1 | 40 | 0 | 20 | | | 3 |
| 546 | 550 | D | 94.2 | 80.18 | 1 | 40 | 1 | 20 | D574G, D574A | 0 | 3 |
| 547 | 551 | F | 0.8 | 74.2 | 1 | 100 | 0 | 80 | | | 4 |
| 548 | 552 | A | 38.7 | 71.8 | 1 | 40 | 1 | 20 | | | 1 |
| 549 | 553 | A | 69.4 | 71.17 | 1 | 60 | 0 | 40 | | | 1 |
| 550 | 554 | F | 0.8 | 71.18 | 1 | 80 | 0 | 40 | | | 4 |
| 551 | 555 | V | 1.2 | 73.7 | 1 | 60 | 0 | 60 | | | 3 |
| 552 | 556 | E | 60.9 | 77.5 | 1 | 40 | 0 | 20 | | | 4 |
| 553 | 557 | K | 71.8 | 77.55 | 1 | 80 | 1 | 60 | | | 4 |
| 554 | 558 | C | 1.1 | 76.28 | 1 | 100 | 1 | 80 | | | 0 |
| 555 | 559 | C | 40.2 | 71.47 | 0 | 100 | 1 | 80 | | | 0 |
| 556 | 560 | K | 92.5 | 81.9 | 0 | 40 | 0 | 20 | K584E | 0 | 4 |
| 557 | 561 | A | 77.4 | 89.44 | 0 | 80 | 0 | 60 | | | 1 |
| 558 | 562 | D | 217.4 | 95.72 | 0 | 40 | 0 | 40 | | | 3 |
| 559 | 563 | D | 63.8 | 98.46 | 1 | 80 | 0 | 60 | D587N | 1 | 3 |
| 560 | 564 | K | 97.1 | 100.08 | 0 | 80 | 0 | 40 | | | 4 |
| 561 | 565 | E | 87.8 | 98.18 | 0 | 80 | 0 | 40 | E589K | 0 | 4 |
| 562 | 566 | T | 86.3 | 94.83 | 1 | 40 | 1 | 40 | | | 1 |
| 563 | 567 | C | 25.0 | 92.56 | 1 | 100 | 1 | 80 | | | 0 |
| 564 | 568 | F | 1.6 | 95.34 | 1 | 100 | 1 | 60 | | | 4 |

Figure 1 continued

| | | | | | | | | | | | |
|---|---|---|---|---|---|---|---|---|---|---|---|
| 565 | 569 | 593 | A | 74.2 | 96.55 | 1 | 60 | 1 | 20 | | 1 |
| 566 | 570 | 594 | E | 73.1 | 97.9 | 1 | 40 | 0 | 40 | E594K | 2 | 4 |
| 567 | 571 | 595 | E | 48.7 | 96.74 | 1 | 80 | 1 | 60 | | | 4 |
| 568 | 572 | 596 | G | 6.0 | 97.47 | 1 | 100 | 0 | 60 | | | 2 |
| 569 | 573 | 597 | K | 81.6 | 98.2 | 1 | 80 | 1 | 40 | K597E | 0 | 4 |
| 570 | 574 | 598 | K | 90.8 | 99.51 | 1 | 80 | 0 | 40 | K598N | 0 | 4 |
| 571 | 575 | 599 | L | 33.0 | 99.45 | 1 | 80 | 1 | 60 | | | 4 |
| 572 | 576 | 600 | V | 25.9 | 98.42 | 1 | 100 | 0 | 60 | | | 3 |
| 573 | 577 | 601 | A | 93.5 | 97.86 | 1 | 60 | 1 | 40 | | | 1 |
| 574 | 578 | 602 | A | 96.8 | 98.62 | 1 | 20 | 0 | 20 | | | 1 |
| 575 | 579 | 603 | S | 21.9 | 100.74 | 1 | 40 | 0 | 40 | | | 1 |
| 576 | 580 | 604 | Q | 86.6 | 101.91 | 1 | 60 | 0 | 40 | | | 3 |
| 577 | 581 | 605 | A | 133.9 | 103.91 | 1 | 40 | 0 | 40 | | | 1 |
| 578 | 582 | 606 | A | 88.7 | 106.05 | 0 | 80 | 1 | 40 | | | 1 |
| n/a | 583 | 607 | L | n/a | n/a | 0 | 100 | 0 | 60 | | | 4 |
| n/a | 584 | 608 | G | n/a | n/a | 0 | 60 | 1 | 40 | | | 2 |
| n/a | 585 | 609 | L | n/a | n/a | 0 | 0 | 0 | 0 | | | 4 |

```
+ Majority

Majority                            650        660        670        680        690        700        710        720

P02768.pro                          ----------------------------------------------------------------------------    460
P02769.pro                          ----------------------------------------------------------------------------    479
P49064.pro                          ----------------------------------------------------------------------------    490
P49822.pro                          ----------------------------------------------------------------------------    480
Q5XLE4.pro                          ----------------------------------------------------------------------------    479
JC5838.pro                          ----------------------------------------------------------------------------    481
ACF10391.1.pro                      ----------------------------------------------------------------------------    455
AAQ20088.pro                        ----------------------------------------------------------------------------    480
P35747.pro                          ----------------------------------------------------------------------------    479
Q28522.pro                          ----------------------------------------------------------------------------    472
P07724.pro                          ----------------------------------------------------------------------------    480
P08835.pro                          ----------------------------------------------------------------------------    479
P02770.pro                          ----------------------------------------------------------------------------    480
P49065.pro                          ----------------------------------------------------------------------------    480
Q28522.pro                          ----------------------------------------------------------------------------    472
P14639.pro                          ----------------------------------------------------------------------------    479
NP_001127106.pro                    ----------------------------------------------------------------------------    480
P19121.pro                          -----------------SQTAMVLVNAIV------------------------------------------------    484
P01012.pro                          -----------------SQTAMVLVNAIV------------------------------------------------    180
O73860.pro                          ----------------------------------------------------------------------------    180
AAC63407.pro                        ----------------------------------------EGVSSIPSAASCCSL---------------------    42
Q91274.pro                          ADRIMIGLAQRISVASFVNISSVALHFAQSVIKCCDADHERTCFMEQEFALEDQVCSDSEALSHIPSVSRCCBLHFDRS    713
P21847.pro                          ----------------------------------------------------------------------------    256
AAD09358.pro                        ----------------------------------------------------------------------------    477
ABXL68.pro                          ----------------------------------------------------------------------------    480
NP_001004887.pro                    SK----SLPNYLTVKEFLK-----------------SFSPDQFRM--------FCLRSKYKSA              355
AAL56646.pro                        ----------------------------------------------------------------------------    489
Q03156.pro                          ----------------------------------------------------------------------------    479
P21848.pro                          ----------------------------------------------------------------------------    479
AAM46104.pro                        ----------------------------------------------------------------------------    398
P83517.pro                          ----------------------------------------------------------------------------    94
S59517.pro                          ----------------------------------------------------------------------------    484
AAL08579.pro                        ----------------------------------------------------------------------------    480
```

Figure 3 continued

```
                        810         820         830         840         850         860         870         880
+ Majority              |-----------|-----------|-----------|-----------|-----------|-----------|-----------|

Majority

P02768.pro              ----------------------------------------------------------------------------------  484
P02769.pro              ----------------------------------------------------------------------------------  483
P49064.pro              ----------------------------------------------------------------------------------  484
P49822.pro              ----------------------------------------------------------------------------------  484
Q5NLE4.pro              ----------------------------------------------------------------------------------  483
JC5838.pro              ----------------------------------------------------------------------------------  485
ACF10391.1.pro          ----------------------------------------------------------------------------------  459
AAQ20088.pro            ----------------------------------------------------------------------------------  484
P35747.pro              ----------------------------------------------------------------------------------  483
Q28522.pro              ----------------------------------------------------------------------------------  476
P07724.pro              ----------------------------------------------------------------------------------  484
P08835.pro              ----------------------------------------------------------------------------------  483
P02770.pro              ----------------------------------------------------------------------------------  484
P49065.pro              ----------------------------------------------------------------------------------  484
Q28522.pro              ----------------------------------------------------------------------------------  476
P14639.pro              ----------------------------------------------------------------------------------  483
NP_001127106.pro        ----------------------------------------------------------------------------------  484
P19121.pro              ----------------------------------------------------------------------------------  488
P01012.pro              ----------------------------------------------QIGL------------------FRVASMASEKM-------KILEL----------------------------  233
O73860.pro              ----------------------------------------------QIGL------------------FRVASMASEKM-------KILEL----------------------------  233
AAC63407.pro            ----------------------------------------------------------------------------------  42
O91274.pro              LTDADQESCLHTARSQARQEALKSLQRSBRICNTLSAIGKEKFEDRIVIALSQKATDASPEQILEIANRMSRGLARCCEQ  873
P21847.pro              ----------------------------------------------------------------------------------  260
AAD09358.pro            ----------------------------------------------------------------------------------  481
ABXL68.pro              ----------------------------------------------------------------------------------  484
NP_001004887.pro        --------------------------KGQLICQEVQ------------------------------------------  394
AAL56646.pro            ----------------------------------------------------------------------------------  493
O03156.pro              ----------------------------------------------------------------------------------  483
P21848.pro              ----------------------------------------------------------------------------------  483
AAM46104.pro            ----------------------------------------------------------------------------------  402
P83517.pro              ----------------------------------------------------------------------------------  94
S59517.pro              ----------------------------------------------------------------------------------  488
```

Figure 3 continued

```
                          970       980       990      1000      1010      1020      1030      1040
+ Majority       D-----------------------------------------------------------------------------------

Majority         D-----------------------------------------------------------------------------------

P02768.pro       D-----------------------------------------------------------------------------------   518
P02769.pro       D-----------------------------------------------------------------------------------   517
P49064.pro       D-----------------------------------------------------------------------------------   518
P49822.pro       D-----------------------------------------------------------------------------------   518
Q5XLE4.pro       D-----------------------------------------------------------------------------------   517
JC5838.pro       D-----------------------------------------------------------------------------------   519
ACF10391.1.pro   D-----------------------------------------------------------------------------------   493
ARQ20088.pro     D-----------------------------------------------------------------------------------   518
P35747.pro       D-----------------------------------------------------------------------------------   517
Q28522.pro       D-----------------------------------------------------------------------------------   510
P07724.pro       D-----------------------------------------------------------------------------------   518
P08835.pro       D-----------------------------------------------------------------------------------   517
P02770.pro       D-----------------------------------------------------------------------------------   518
P49065.pro       D-----------------------------------------------------------------------------------   519
Q28522.pro       D-----------------------------------------------------------------------------------   510
P14639.pro       D-----------------------------------------------------------------------------------   517
NP_001127106.pro D-----------------------------------------------------------------------------------   519
P19121.pro       D----------------------PFASGTMS----------MLVL---------------------------------------   522
P01012.pro       ----------------------PFASGTMS----------MNVL-----------------------------------------   245
O73860.pro       ----------------------PFASGTMS---------------------------------------------------------  245
AAC63407.pro     NLSIHSVPLAPASQLCHDRRMKSHESFASLLMEFGRRHPRAADSQVEELAERFSKIGDACCDLADEKECITRGREAIHQE           137
Q91274.pro       NVSRAHAPFYSNSQLCLMKLRTPHRFLERFLMEFGRRHPQAALSQVEELAEMYVKMTDSCCGKLHSKSCFTEQRHTIHME          1033
P21847.pro       Y-----------------------------------------------------------------------------------   294
AAD09358.pro     Y-----------------------------------------------------------------------------------   515
ABXL68.pro       D-----------------------------------------------------------------------------------   518
NP_001004887.pro ------------------------EALLW-----------------QRLNETKVNVKAAFSDDFDTPRAVDAVMDLIHHG         433
AAL56646.pro     D-----------------------------------------------------------------------------------   527
Q03156.pro       D-----------------------------------------------------------------------------------   517
P21848.pro       D-----------------------------------------------------------------------------------   517
AAM46104.pro     D-----------------------------------------------------------------------------------   436
P93517.pro       ------------------------------------------------------------------------------------   101
559517.pro       D-----------------------------------------------------------------------------------   522
AAL08579.pro     D-----------------------------------------------------------------------------------   518
```

Figure 3 continued

```
+ Majority                                              ETYVPKE----------------------------------FKAETFTFHADIC--

|        |        |        |        |        |        |        |
                      1050     1060     1070     1080     1090     1100     1110     1120

Majority

P02768.pro     ---------------------------------ETYVPKE----------------------------------FKAETFTFHADIC--    538
P02769.pro     ---------------------------------ETYVPKA----------------------------------PDEKLFTFHADIC--    537
P49064.pro     ---------------------------------ETYVPKE----------------------------------FSAETFTFHADLC--    538
P49822.pro     ---------------------------------ETYVPKE----------------------------------FNAETFTFHADLC--    538
Q5XLE4.pro     ---------------------------------EGYIPKE----------------------------------FKAETFTFHADIC--    537
JC5838.pro     ---------------------------------ETYVPKE----------------------------------FKAETFTFHANIC--    539
ACF10391.1.pro ---------------------------------ETYVPKP----------------------------------FDGESETFHADIC--    513
AAQ20088.pro   ---------------------------------ETYVPKP----------------------------------FHADSFTFHADIC--    538
P35747.pro     ---------------------------------ETYVPKE----------------------------------FKAETFTFHADIC--    537
Q28522.pro     ---------------------------------EGYVPKE----------------------------------FKAETFTFHADMC--    530
P07724.pro     ---------------------------------EAYVPKA----------------------------------FNAETRTFHSDIC--    538
P08835.pro     ---------------------------------ETYVPKE----------------------------------FKAETFTFHSDIC--    537
P02770.pro     ---------------------------------ETYKPKE----------------------------------FVEGTFTFHSDIC--    538
P49065.pro     ---------------------------------ETYVPKE----------------------------------FKAETFTFHSDIC--    538
Q28522.pro     ---------------------------------EAYVPKA----------------------------------FNAETFTFHADMC--    530
P14639.pro     ---------------------------------ETYVPKP----------------------------------FDEKFFTFHADIC--    537
NP_001127106.pro ---------------------------------ETYVPKE----------------------------------FNAETFTFHADIC--    538
P19121.pro     ---------------------------------TKYVPPP----------------------------------FNPDMFSPDEKLC--    542
P01012.pro     ------------------------LPDEVSGLEQLESIINFEKLT------------------------EWTSS---                       271
O73060.pro     ------------------------LPDEVSGLEQLESIINFEKLT------------------------EWISS---                       271
AAC63407.pro   VSAAYADAAQLCSSLQALGAQKFLGRMVLVFSQKAPNATFDQISKELSHRFNSYAQTCCGEGWSRGCFAEQRHLIHDENCH                     217
Q91274.pro     IRHAYAEVQHICGSLRSRGEETPIQREVTLLSQKAPMASFEKVSQLARHFLSLAKKCCAPDHAAGCFLEEFYAIHDEVCR                    1113
P21847.pro     ---------------------------FNYVAPK----------------------------------WDESKLHFNEDLC--                 214
AAQ09258.pro   ---------------------------ANYEAEV----------------------------------WDESKLHFTADMC--                 535
ABX16?.pro     ---------------------------EDYVPPP----------------------------------VTDDTFHFDDKIC--                 538
NP_001004887.pro NRQ----LKAVSKESNSPR----SSVVYGAMISYIEQELEI----                                                         466
RAL56646.pro   ---------------------------ETYVPPP----------------------------------LSVASFNFNDELC--                 547
Q03156.pro     ---------------------------TEFTPPE----------------------------------LDASSFHMGPELC--                 537
P21848.pro     ---------------------------TEFTPPE----------------------------------LDASSFHMGPELC--                 537
AAM46104.pro   ---------------------------BKFVPIB----------------------------------FSADLFTFHEDLC--                 456
P63517.pro                                                                                                        101
S59517.pro     ---------------LSFVPPT---                                                                            542
RAL08579.pro   ---------------------------ETYVPKE----------------------------------FKAETFTFHADIC--                 538
```

| | | |
|---|---|---|
| + Majority | | |
| Majority | ──────────────────── | |
| | 1450 | |
| P02768.pro | | 609 |
| P02769.pro | | 607 |
| P49064.pro | | 608 |
| P49822.pro | | 608 |
| Q5ZLW4.pro | | 607 |
| JC5838.pro | | 609 |
| ACF10391.1.pro | | 583 |
| AAQ20088.pro | | 608 |
| P35747.pro | | 607 |
| Q28522.pro | | 600 |
| P07724.pro | | 608 |
| P98835.pro | | 607 |
| P02770.pro | | 608 |
| P49065.pro | | 600 |
| Q28522.pro | | 607 |
| P14639.pro | | 609 |
| NP_001127106.pro | ────────────────GA | 615 |
| P19121.pro | ───────────────VSP | 386 |
| P01012.pro | ───────────────ISP | 386 |
| O73860.pro | | 551 |
| AAC63407.pro | KSECFSHEIKEMKNSP | 1422 |
| Q91874.pro | KTACFTEKLEAIK-SS | 382 |
| P21847.pro | | 603 |
| AAD09358.pro | | 608 |
| ABXL68.pro | | 572 |
| NP_001004887.pro | RGNTSTMELLDRKEET | 626 |
| AAL56646.pro | ───────────VEVSV | 608 |
| O31156.pro | | 608 |
| P21848.pro | ───────────────A | 527 |
| AAM46104.pro | | 101 |
| P83517.pro | | 614 |
| S59517.pro | ───────────PTTE | 608 |
| AAL08579.pro | | |

Figure 5A

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| n/a | 1 | 25 | D | n/a | n/a | 0 | 40 | 0 | 40 | D25V | 0 | 3 |
| n/a | 585 | 609 | L | n/a | n/a | 0 | 0 | 0 | 0 | | | 4 |
| n/a | 2 | 26 | A | n/a | n/a | 0 | 40 | 0 | 20 | | | 1 |
| 558 | 562 | 586 | D | 217.4 | 95.72 | 0 | 40 | 0 | 40 | | | 3 |
| 360 | 364 | 388 | A | 164.5 | 80.24 | 0 | 40 | 0 | 20 | | | 1 |
| 500 | 504 | 528 | A | 108.1 | 98.55 | 0 | 60 | 0 | 40 | | | 1 |
| 501 | 505 | 529 | E | 105.8 | 93.84 | 0 | 60 | 0 | 40 | E529K | 0 | 4 |
| 75 | 79 | 103 | T | 103.8 | 67.13 | 0 | 40 | 0 | 20 | | | 1 |
| 82 | 86 | 110 | E | 99.4 | 88.78 | 0 | 60 | 0 | 20 | | | 4 |

Figure 5B

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| 125 | 129 | 153 | D | 211.6 | 43.69 | 1 | 40 | 0 | 20 | | | 3 |
| 545 | 549 | 573 | D | 146.4 | 84.68 | 1 | 40 | 0 | 20 | | | 3 |
| 577 | 581 | 605 | A | 133.9 | 103.91 | 1 | 40 | 0 | 40 | | | 1 |
| 117 | 121 | 145 | D | 130.4 | 46.02 | 1 | 60 | 0 | 40 | | | 3 |
| 78 | 82 | 106 | E | 130.1 | 96.77 | 1 | 60 | 0 | 40 | E106K | 0 | 4 |
| 266 | 270 | 294 | S | 114.1 | 43.53 | 1 | 40 | 0 | 20 | | | 1 |
| 393 | 397 | 421 | Q | 101.6 | 58.94 | 1 | 40 | 0 | 20 | | | 3 |
| 574 | 578 | 602 | A | 96.8 | 98.62 | 1 | 20 | 0 | 20 | | | 1 |

Figure 5C

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| n/a | 585 | 609 | L | n/a | n/a | 0 | 0 | 0 | 0 | | | 4 |
| n/a | 2 | 26 | A | n/a | n/a | 0 | 40 | 0 | 20 | | | 1 |
| n/a | 1 | 25 | D | n/a | n/a | 0 | 40 | 0 | 40 | D25V | 0 | 3 |
| n/a | 584 | 608 | G | n/a | n/a | 0 | 60 | 1 | 40 | | | 2 |
| n/a | 4 | 28 | K | n/a | n/a | 0 | 80 | 1 | 40 | | | 4 |
| 297 | 301 | 325 | D | 218.8 | 64.56 | 0 | 60 | 1 | 40 | | | 3 |
| 558 | 562 | 586 | D | 217.4 | 95.72 | 0 | 40 | 0 | 40 | | | 3 |
| 296 | 300 | 324 | A | 180.6 | 63.75 | 0 | 40 | 1 | 40 | | | 1 |
| 361 | 365 | 389 | D | 168.1 | 84.23 | 0 | 80 | 1 | 40 | D389H, D389V | 1 | 3 |
| 360 | 364 | 388 | A | 164.5 | 80.24 | 0 | 40 | 0 | 20 | | | 1 |
| 54 | 58 | 82 | S | 164.1 | 53.12 | 0 | 80 | 0 | 40 | | | 1 |
| 494 | 498 | 522 | V | 149.4 | 74.11 | 0 | 80 | 2 | 60 | | | 3 |
| 492 | 496 | 520 | T | 148.8 | 70.07 | 0 | 60 | 2 | 40 | | | 1 |
| 109 | 113 | 137 | P | 141.8 | 51.5 | 0 | 80 | 0 | 40 | | | 3 |
| 112 | 116 | 140 | V | 139.5 | 51.82 | 0 | 40 | 0 | 0 | | | 3 |
| 508 | 512 | 536 | D | 139.1 | 61.05 | 0 | 80 | 0 | 40 | | | 3 |
| 300 | 304 | 328 | S | 134.4 | 57.01 | 0 | 20 | 0 | 20 | | | 1 |
| 310 | 314 | 338 | D | 131.9 | 65.86 | 0 | 40 | 0 | 40 | D338G, D338V | 1 | 3 |
| 299 | 303 | 327 | P | 119.4 | 59.59 | 0 | 80 | 1 | 60 | | | 3 |
| 534 | 538 | 562 | K | 115.5 | 96.73 | 0 | 80 | 2 | 40 | | | 4 |
| 56 | 60 | 84 | E | 110.3 | 53.87 | 0 | 40 | 0 | 20 | E84K | 0 | 4 |

Figure 5C continued

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| 500 | 504 | 528 | A | 108.1 | 98.55 | 0 | 60 | 0 | 40 | | | 1 |
| 435 | 439 | 463 | K | 106.3 | 52.99 | 0 | 40 | 1 | 20 | | | 4 |
| 501 | 505 | 529 | E | 105.8 | 93.84 | 0 | 60 | 0 | 40 | E529K | 0 | 4 |
| 75 | 79 | 103 | T | 103.8 | 67.13 | 0 | 40 | 0 | 20 | | | 1 |
| 111 | 115 | 139 | L | 100.0 | 54.21 | 0 | 60 | 0 | 20 | | | 4 |
| 367 | 371 | 395 | A | 100.0 | 63.92 | 0 | 60 | 1 | 40 | | | 1 |
| 82 | 86 | 110 | E | 99.4 | 88.78 | 0 | 60 | 0 | 20 | | | 4 |
| 497 | 501 | 525 | E | 99.4 | 95.25 | 0 | 60 | 2 | 40 | E525K | 0 | 4 |
| 537 | 541 | 565 | K | 98.3 | 96.84 | 0 | 20 | 0 | 20 | K565E | 1 | 4 |
| 560 | 564 | 588 | K | 97.1 | 100.08 | 0 | 80 | 0 | 40 | | | 4 |
| 439 | 443 | 467 | A | 93.5 | 55.15 | 0 | 40 | 1 | 20 | | | 1 |
| 556 | 560 | 584 | K | 92.5 | 81.9 | 0 | 40 | 1 | 20 | K584E | 0 | 4 |
| 502 | 506 | 530 | T | 92.5 | 88 | 0 | 60 | 1 | 40 | | | 1 |
| 309 | 313 | 337 | K | 92.0 | 64.18 | 0 | 80 | 0 | 40 | K337N | 1 | 4 |
| 578 | 582 | 606 | A | 88.7 | 106.05 | 0 | 80 | 1 | 40 | | | 1 |
| 561 | 565 | 589 | E | 87.8 | 98.18 | 0 | 80 | 0 | 40 | E589K | 0 | 4 |
| 294 | 298 | 322 | M | 84.5 | 53.49 | 0 | 20 | 1 | 20 | | | 3 |
| 499 | 503 | 527 | N | 81.2 | 99.86 | 0 | 40 | 1 | 20 | | | 2 |

Figure 5D

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| 265 | 269 | 293 | D | 229.0 | 45.46 | 1 | 60 | 1 | 60 | D293G | 1 | 3 |
| 125 | 129 | 153 | D | 211.6 | 43.69 | 1 | 40 | 0 | 20 | | | 3 |
| 467 | 471 | 495 | D | 205.8 | 45.67 | 1 | 80 | 1 | 40 | | | 3 |
| 371 | 375 | 399 | D | 152.2 | 50.78 | 1 | 80 | 0 | 40 | D399N, D399H | 0 | 3 |
| 51 | 55 | 79 | A | 148.4 | 43.59 | 1 | 80 | 0 | 40 | | | 1 |
| 545 | 549 | 573 | D | 146.4 | 84.68 | 1 | 40 | 0 | 20 | | | 3 |
| 577 | 581 | 605 | A | 133.9 | 103.91 | 1 | 40 | 0 | 40 | | | 1 |
| 304 | 308 | 332 | D | 131.9 | 47.92 | 1 | 80 | 0 | 40 | | | 3 |
| 486 | 490 | 514 | A | 130.6 | 32.03 | 1 | 80 | 2 | 40 | | | 1 |
| 117 | 121 | 145 | D | 130.4 | 46.02 | 1 | 60 | 0 | 40 | | | 3 |
| 78 | 82 | 106 | E | 130.1 | 96.77 | 1 | 60 | 0 | 40 | E106K | 0 | 4 |
| 474 | 478 | 502 | T | 125.0 | 35 | 1 | 60 | 1 | 40 | | | 1 |
| 320 | 324 | 348 | D | 120.3 | 58.69 | 1 | 80 | 1 | 60 | | | 3 |
| 375 | 379 | 403 | P | 119.4 | 32.33 | 1 | 80 | 1 | 40 | | | 3 |
| 316 | 320 | 344 | A | 119.4 | 64 | 1 | 40 | 0 | 20 | A344T | 1 | 1 |
| 121 | 125 | 149 | T | 115.0 | 35.32 | 1 | 40 | 1 | 20 | | | 1 |
| 266 | 270 | 294 | S | 114.1 | 43.53 | 1 | 40 | 0 | 20 | | | 1 |
| 79 | 83 | 107 | T | 113.8 | 98.21 | 1 | 60 | 1 | 20 | | | 1 |
| 100 | 104 | 128 | Q | 111.0 | 32.1 | 1 | 40 | 2 | 20 | | | 3 |
| 225 | 229 | 253 | A | 109.7 | 36.47 | 1 | 60 | 1 | 40 | | | 1 |
| 364 | 368 | 392 | E | 109.6 | 77.34 | 1 | 60 | 1 | 20 | | | 4 |
| 314 | 318 | 342 | N | 107.1 | 59.91 | 1 | 80 | 1 | 40 | N342K | 0 | 2 |
| 538 | 542 | 566 | E | 105.8 | 96.98 | 1 | 80 | 1 | 60 | | | 4 |

Figure 5D continued

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | Polymorph. | Phenotype Change | Conserved Mutation vs. Cysteine |
|---|---|---|---|---|---|---|---|---|---|---|---|---|
| 72 | 76 | 100 | T | 105.0 | 32.05 | 1 | 40 | 1 | 20 | | | 1 |
| 393 | 397 | 421 | Q | 101.6 | 58.94 | 1 | 40 | 0 | 20 | | | 3 |
| 60 | 40 | 64 | E | 101.3 | 31.14 | 1 | 40 | 1 | 40 | | | 4 |
| 321 | 325 | 349 | V | 100.0 | 50.37 | 1 | 80 | 1 | 40 | | | 3 |
| 386 | 390 | 414 | Q | 96.9 | 52.9 | 1 | 40 | 0 | 20 | | | 3 |
| 574 | 578 | 602 | A | 96.8 | 98.62 | 1 | 20 | 0 | 20 | | | 1 |
| 475 | 479 | 503 | E | 94.2 | 40.83 | 1 | 60 | 1 | 20 | E503K | 0 | 4 |
| 546 | 550 | 574 | D | 94.2 | 80.18 | 1 | 40 | 1 | 20 | D574G, D574A | 0 | 3 |
| 382 | 386 | 410 | N | 94.1 | 42.58 | 1 | 80 | 1 | 40 | | | 2 |
| 573 | 577 | 601 | A | 93.5 | 97.86 | 1 | 60 | 1 | 40 | | | 1 |
| 44 | 48 | 72 | E | 91.0 | 31.25 | 1 | 60 | 1 | 40 | | | 4 |
| 570 | 574 | 598 | K | 90.8 | 99.51 | 1 | 80 | 0 | 40 | K598N | 0 | 4 |
| 317 | 321 | 345 | E | 88.5 | 67.18 | 1 | 80 | 1 | 40 | E345K | 0 | 4 |
| 118 | 122 | 146 | V | 87.7 | 43.96 | 1 | 40 | 0 | 20 | V146E | 0 | 3 |
| 279 | 283 | 307 | L | 87.6 | 36.51 | 1 | 40 | 1 | 20 | | | 4 |
| 34 | 38 | 62 | D | 87.0 | 34.73 | 1 | 60 | 1 | 40 | | | 3 |
| 576 | 580 | 604 | Q | 86.6 | 101.91 | 1 | 60 | 0 | 40 | | | 3 |
| 562 | 566 | 590 | T | 86.3 | 94.83 | 1 | 40 | 1 | 40 | | | 1 |
| 48 | 52 | 76 | T | 86.3 | 35.9 | 1 | 40 | 1 | 20 | | | 1 |
| 351 | 355 | 379 | T | 86.3 | 40.3 | 1 | 80 | 0 | 40 | | | 1 |
| 392 | 396 | 420 | E | 85.9 | 62.51 | 1 | 80 | 1 | 40 | E420K | 0 | 4 |
| 262 | 266 | 290 | E | 83.3 | 41.21 | 1 | 80 | 1 | 40 | | | 4 |
| 569 | 573 | 597 | K | 81.6 | 98.2 | 1 | 80 | 1 | 40 | K597E | 0 | 4 |
| 542 | 546 | 570 | A | 80.6 | 91.51 | 1 | 60 | 1 | 40 | | | 1 |

Figure 6A

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (All Sps. V) | Disulphide Information | (Polymorp.) Phenotype Change | Modification Score |
|---|---|---|---|---|---|---|---|---|---|---|---|---|
| 71 | 75 | 99 | C | 20.7 | 24.72 | 1 | 100 | 0 | 80 | pairs with C91 | | high |
| 87 | 91 | 115 | C | 32.6 | 33.58 | 0 | 100 | 1 | 60 | pairs with C75 | | high |
| 120 | 124 | 148 | C | 3.3 | 34.94 | 1 | 100 | 0 | 60 | pairs with C169 | | high |
| 164 | 168 | 192 | C | 0.0 | 31.68 | 1 | 100 | 1 | 60 | pairs with C177 | | high |
| 165 | 169 | 193 | C | 14.1 | 32.95 | 0 | 100 | 1 | 60 | pairs with C124 | | high |
| 312 | 316 | 340 | C | 23.9 | 62.19 | 1 | 100 | 1 | 80 | pairs with C361 | | high |
| 356 | 360 | 384 | C | 2.2 | 60.95 | 1 | 100 | 1 | 80 | pairs with C369 | | high |
| 357 | 361 | 385 | C | 42.4 | 66.33 | 0 | 100 | 2 | 80 | pairs with C316 | | high |
| 554 | 558 | 582 | C | 1.1 | 76.28 | 1 | 100 | 1 | 80 | pairs with C567 | | high |
| 563 | 567 | 591 | C | 25.0 | 92.56 | 1 | 100 | 1 | 80 | pairs with C558 | | high |

Figure 6B

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (All Sps. V) | Disulphide Information | (Polymorp.) Phenotype Change | Modification Score |
|---|---|---|---|---|---|---|---|---|---|---|---|---|
| 71 | 75 | 99 | C | 20.7 | 24.72 | 1 | 100 | 0 | 80 | pairs with C91 | | high |
| 87 | 91 | 115 | C | 32.6 | 33.58 | 0 | 100 | 1 | 60 | pairs with C75 | | high |
| 120 | 124 | 148 | C | 3.3 | 34.94 | 1 | 100 | 0 | 60 | pairs with C169 | | high |
| 165 | 169 | 193 | C | 14.1 | 32.95 | 0 | 100 | 1 | 60 | pairs with C124 | | high |
| 173 | 177 | 201 | C | 30.4 | 28.29 | 1 | 100 | 1 | 80 | pairs with C168 | (C201F) 2 | medium |
| 312 | 316 | 340 | C | 23.9 | 62.19 | 1 | 100 | 1 | 80 | pairs with C361 | | high |
| 357 | 361 | 385 | C | 42.4 | 66.33 | 0 | 100 | 2 | 80 | pairs with C316 | | high |
| 365 | 369 | 393 | C | 48.9 | 69.93 | 1 | 100 | 1 | 80 | pairs with C360 | | medium |
| 554 | 558 | 582 | C | 1.1 | 76.28 | 1 | 100 | 1 | 80 | pairs with C567 | | high |
| 563 | 567 | 591 | C | 25.0 | 92.56 | 1 | 100 | 1 | 80 | pairs with C558 | | high |

Figure 10

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | (Polymorp.) Phenotype Change | Selection Group | Proximity Group |
|---|---|---|---|---|---|---|---|---|---|---|---|---|
| n/a | 1 | 25 | D | n/a | n/a | 0 | 40 | 0 | 40 | (D25V) 0 | 1 | E |
| n/a | 2 | 26 | A | n/a | n/a | 0 | 40 | 0 | 20 | | 1 | E |
| 71 | 75 | 99 | C | 20.7 | 24.72 | 1 | 100 | 0 | 80 | | 3 | K |
| 75 | 79 | 103 | T | 103.8 | 67.13 | 0 | 40 | 0 | 20 | | 1 | A |
| 78 | 82 | 106 | E | 130.1 | 96.77 | 1 | 60 | 0 | 40 | (E106K) 0 | 2 | F |
| 82 | 86 | 110 | E | 99.4 | 88.78 | 0 | 60 | 0 | 20 | | 1 | A |
| 87 | 91 | 115 | C | 32.6 | 33.58 | 0 | 100 | 1 | 60 | | 3 | K |
| 117 | 121 | 145 | D | 130.4 | 46.02 | 1 | 60 | 0 | 40 | | 2 | H |
| 120 | 124 | 148 | C | 3.3 | 34.94 | 1 | 100 | 0 | 60 | | 3 | L |
| 125 | 129 | 153 | D | 211.6 | 43.69 | 1 | 40 | 0 | 20 | | 2 | H |
| 165 | 169 | 193 | C | 14.1 | 32.95 | 0 | 100 | 1 | 60 | | 3 | L |
| 173 | 177 | 201 | C | 30.4 | 28.29 | 1 | 100 | 1 | 80 | (C201F) 2 | 3 | L |
| 266 | 270 | 294 | S | 114.1 | 43.53 | 1 | 40 | 0 | 20 | | 2 | G |
| 312 | 316 | 340 | C | 23.9 | 62.19 | 1 | 100 | 1 | 80 | | 3 | M |
| 357 | 361 | 385 | C | 42.4 | 66.33 | 0 | 100 | 2 | 80 | | 3 | M |
| 360 | 364 | 388 | A | 164.5 | 80.24 | 0 | 40 | 0 | 20 | | 1 | C |
| 365 | 369 | 393 | C | 48.9 | 69.93 | 1 | 100 | 1 | 80 | | 3 | M |
| 393 | 397 | 421 | Q | 101.6 | 58.94 | 1 | 40 | 0 | 20 | | 2 | J |
| 500 | 504 | 528 | A | 108.1 | 98.55 | 0 | 60 | 0 | 40 | | 1 | D |
| 501 | 505 | 529 | E | 105.8 | 93.84 | 0 | 60 | 0 | 40 | (E529K) 0 | 1 | D |
| 545 | 549 | 573 | D | 146.4 | 84.68 | 1 | 40 | 0 | 20 | | 2 | J |

Figure 10 continued

| Position in 1AO6 | Position in Mature HSA | Position with Leader Sequence | Amino Acid | % SASA | B-Factor | SS | Align 1 (Mamm. W) | Adj. 100%'s (Align 1) | Align 2 (Var. Sps. V) | (Polymorp.) Phenotype Change | Selection Group | Proximity Group |
|---|---|---|---|---|---|---|---|---|---|---|---|---|
| 554 | 558 | 582 | C | 1.1 | 76.28 | 1 | 100 | 1 | 80 | | 3 | N |
| 558 | 562 | 586 | D | 217.4 | 95.72 | 0 | 40 | 0 | 40 | | 1 | B |
| 563 | 567 | 591 | C | 25 | 92.56 | 1 | 100 | 1 | 80 | | 3 | N |
| 574 | 578 | 602 | A | 96.8 | 98.62 | 1 | 20 | 0 | 20 | | 2 | I |
| 577 | 581 | 605 | A | 133.9 | 103.91 | 1 | 40 | 0 | 40 | | 2 | I |
| n/a | 585 | 609 | L | n/a | n/a | 0 | 0 | 0 | 0 | | 1 | D |

Figure 11

| Construct Reference | Mutation | Plasmid Name | Transformant | Yeast Stock Number | Positions Modified in SEQ ID N0.2 | Original Codon | Original Residue | Mutant Codon | Mutant Residue | DNA SEQ ID No. | Protein SEQ ID No. |
|---|---|---|---|---|---|---|---|---|---|---|---|
| TA1 | A2C | pDB4029 | B | 9012 | 4-6 | GCA | A | TGT | C | 5 | 50 |
| TA2 | D1C | pDB4030 | B | 9013 | 1-3 | GAT | D | TGT | C | 6 | 51 |
| TA3 | C75S | pDB4031 | A | 9014 | 223-225 | TGC | C | TCT | S | 7 | 52 |
| TA4 | T79C | pDB4032 | D | 9015 | 235-237 | ACT | T | TGT | C | 8 | 53 |
| TA5 | E82C | pDB4033 | D | 9016 | 244-246 | GAA | E | TGT | C | 9 | 54 |
| TA6 | E86C | pDB4034 | A | 9017 | 256-258 | GAA | E | TGT | C | 10 | 55 |
| TA7 | C124S | pDB4035 | D | 9018 | 370-372 | TGC | C | TCT | S | 11 | 56 |
| TA8 | C168S | pDB4036 | B | 9019 | 502-504 | TGT | C | TCT | S | 12 | 57 |
| TA9 | C169S | pDB4037 | B | 9020 | 505-507 | TGC | C | TCT | S | 13 | 58 |
| TA10 | C91S | pDB4038 | B | 9021 | 271-273 | TGT | C | TCT | S | 14 | 59 |
| TA11 | D121C | pDB4039 | B | 9022 | 361-363 | GAT | D | TGT | C | 15 | 60 |

Figure 11 continued

| Construct Reference | Mutation | Plasmid Name | Transformant | Yeast Stock Number | Positions Modified in SEQ ID NO.2 | Original Codon | Original Residue | Mutant Codon | Mutant Residue | DNA SEQ ID No. | Protein SEQ ID No. |
|---|---|---|---|---|---|---|---|---|---|---|---|
| TA12 | D129C | pDB4040 | C | 9023 | 385-387 | GAC | D | TGT | C | 16 | 61 |
| TA13 | S270C | pDB4041 | D | 9024 | 808-810 | TCG | S | TGT | C | 17 | 62 |
| TA14 | C316A | pDB4042 | B | 9025 | 946-948 | TGC | C | GCT | A | 18 | 63 |
| TA16 | C360S | pDB4044 | B | 9026 | 1078-1080 | TGC | C | TCT | S | 19 | 64 |
| TA17 | C361A | pDB4045 | A | 9027 | 1081-1083 | TGT | C | GCT | A | 20 | 65 |
| TA18 | C361S | pDB4046 | C | 9028 | 1081-1083 | TGT | C | TCT | S | 21 | 66 |
| TA19 | A364C | pDB4047 | D | 9029 | 1090-1092 | GCT | A | TGT | C | 22 | 67 |
| TA20 | Q397C | pDB4048 | A | 9030 | 1189-1191 | CAG | Q | TGT | C | 23 | 68 |
| TA21 | A504C | pDB4049 | A | 9031 | 1510-1512 | GCT | A | TGT | C | 24 | 69 |
| TA22 | A578C | pDB4050 | D | 9032 | 1732-1734 | GCA | A | TGT | C | 25 | 70 |
| TA23 | A581C | pDB4051 | C | 9033 | 1741-1743 | GCT | A | TGT | C | 26 | 71 |
| TA24 | C558S | pDB4052 | D | 9034 | 1672-1674 | TGC | C | TCT | S | 27 | 72 |
| TA25 | C567S | pDB4053 | B | 9035 | 1699-1701 | TGC | C | TCT | S | 28 | 73 |
| TA26 | D549C | pDB4054 | B | 9036 | 1645-1647 | GAT | D | TGT | C | 29 | 74 |
| TA27 | D562C | pDB4055 | B | 9037 | 1684-1686 | GAC | D | TGT | C | 30 | 75 |
| TA28 | E505C | pDB4056 | D | 9038 | 1513-1515 | GAA | E | TGT | C | 31 | 76 |
| TA29 | L585C | pDB4057 | B | 9039 | 1753-1755 | TTA | L | TGT | C | 32 | 77 |
| TA30 | N/A | pDB3927 | A | 9040 | N/A | N/A | N/A | N/A | N/A | 2 | 1 |
| TA31 | N/A | pDB3964 | D | 9041 | N/A | N/A | N/A | N/A | N/A | 4 | 1 |
| TA32 | N/A | pDB2244 | B | 9042 | N/A | N/A | N/A | N/A | N/A | 2 | 1 |

Figure 16

| Construct Reference | Mutation(s) | Plasmid Number | Transformant | Yeast Stock Number | Combination of Single Mutants | Additional Mutations | Positions Modified in SEQ ID NO. 2 | Original Codon | Mutant Codon(s) | DNA SEQ ID No. | Protein SEQ ID No. |
|---|---|---|---|---|---|---|---|---|---|---|---|
| TA33 | A2C, L585C | pDB4058 | C | 9116 | SEQ ID 5 SEQ ID 33 | N/A | N/A | N/A | N/A | 33 | 78 |
| TA34 | A2C, A504C | pDB4059 | B | 9117 | SEQ ID 5 SEQ ID 25 | N/A | N/A | N/A | N/A | 34 | 79 |
| TA35 | A2C, A364C, D562C | pDB4060 | B | 9118 | SEQ ID 5 SEQ ID 23 SEQ ID 31 | N/A | N/A | N/A | N/A | 35 | 80 |
| TA36 | A2C, C34A, A364C, D562C | pDB4061 | A | 9119 | SEQ ID 5 SEQ ID 23 SEQ ID 31 | C34A | 100-102 | TGT | GCT | 36 | 81 |
| TA38 | A2C, A364C, D562C, L585C | pDB4062 | C | 9130 | SEQ ID 5 SEQ ID 23 SEQ ID 31 SEQ ID 33 | N/A | N/A | N/A | N/A | 37 | 82 |
| TA39 | C34A, A504C, E505C | pDB4063 | C | 9120 | SEQ ID 25 SEQ ID 32 | C34A | 100-102 | TGT | GCT | 38 | 83 |
| TA41 | S270C, A581C | pDB4064 | A | 9121 | SEQ ID 17 SEQ ID 27 | N/A | N/A | N/A | N/A | 39 | 84 |
| TA43 | D129C, S270C, A581C | pDB4065 | A | 9122 | SEQ ID 16 SEQ ID 17 SEQ ID 27 | N/A | N/A | N/A | N/A | 40 | 85 |
| TA46 | C169S, C316A | pDB4066 | A | 9123 | SEQ ID 13 SEQ ID 18 | N/A | N/A | N/A | N/A | 41 | 86 |
| TA47 | D129C, C360S, L585C | pDB4067 | B | 9124 | SEQ ID 16 SEQ ID 20 | N/A | N/A | N/A | N/A | 42 | 87 |

Figure 16 continued

| Construct Reference | Mutation(s) | Plasmid Number | Transformant | Yeast Stock Number | Combination of Single Mutants | Additional Mutation(s) | | | | DNA SEQ ID No. | Protein SEQ ID No. |
|---|---|---|---|---|---|---|---|---|---|---|---|
| | | | | | | Additional Mutations | Positions Modified in SEQ ID NO. 2 | Original Codon | Mutant Codon(s) | | |
| | | | | | SEQ ID 33 | | | | | | |
| TA51 | A2C, rHA-Cys | pDB4068 | A | 9125 | SEQ ID 5 | -Cys | Addition before 1756 | N/A | TGT | 43 | 88 |
| TA57 | A2C, G584_L585insC | pDB4069 | C | 9126 | SEQ ID 5 | G584_L585insC | Addition before 1753 | N/A | TGT | 44 | 89 |
| TA60 | A2C, C316del | pDB4070 | A | 9127 | SEQ ID 5 | C316del | 946-948 (deletion) | TGC | N/A | 45 | 90 |
| TA63 | H39C, C253P | pDB4071 | A | 9128 | N/A | H39C, C253P | 115-117, 757-759 | CAT, TGT | TGT, CCA | 46 | 91 |
| TA64 | C177F | pDB4072 | C | 9129 | N/A | C177F | 529-531 | TGC | TTT | 47 | 92 |
| TA65 | Cys-rHA-Ala-Cys | 4073 | D | 9131 | N/A | Cys-and -Ala-Cys | Additions before 1 and 1756 | N/A | TGT, GCTTGT | 48 | 93 |

Figure 18

| Protein | Construct Reference | SEQ ID No. | Fermentation Yield (g/L supernatant) | Colour Intensity after DTNB Treatment |
|---|---|---|---|---|
| Negative Control (Transferrin) | N/A | N/A | N/A | - |
| Positive Control (rHA, Human Albumin, Recombumin®) | N/A | 50 | N/A | + |
| rHA (A2C, L585C) | TA33 | 80 | 2.8 | ++++ |
| rHA (A2C, A364C, D562C) | TA35 | 82 | 1.1 | ++++ |
| rHA (A2C, A364C, D562C, L585C) | TA38 | 84 | 1.3 | ++++ |
| rHA (D129C, C360S, L585C) | TA47 | 89 | 1.6 | ++++ |
| A2C, rHA-Cys | TA51 | 90 | 2.9 | ++++ |

SEQUENCE LISTING

<160> NUMBER OF SEQ ID NOS: 138

<210> SEQ ID NO 1
<211> LENGTH: 585
<212> TYPE: PRT
<213> ORGANISM: Homo sapiens
<220> FEATURE:
<221> NAME/KEY: MISC_FEATURE
<222> LOCATION: (1)..(585)
<223> OTHER INFORMATION: Human serum albumin (mature protein)

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 2
<211> LENGTH: 1758
<212> TYPE: DNA
<213> ORGANISM: Artificial Sequence
<220> FEATURE:
<223> OTHER INFORMATION: Polynucleotide coding sequence (not codon
      optimised) for human serum albumin

<400> SEQUENCE: 2
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttca taccctttttt ggagacaaat tatgcacagt tgcaactctt     240
cgtgaaacct atggtgaaat ggctgactgc tgtgcaaaac aagaacctga gaaaatgaa      300 tgcttcttgc aacacaaaga tgacaaccca aacctccccc gattggtgag accagaggtt     360
gatgtgatgt gcactgcttt tcatgacaat gaagagacat tttgaaaaaa atacttatat     420
gaaattgcca agacatccc ttactttat gccccggaac tccttttctt tgctaaaagg      480
tataaagctg ctttttacaga atgttgccaa gctgctgata agctgcctg cctgttgcca     540 aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660

```
cagagatttc ccaaagctga gtttgcagaa gtttccaagt tagtgacaga tcttaccaaa      720
gtccacacgg aatgctgcca tggagatctg cttgaatgtg ctgatgacag ggcggacctt      780
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg cagatcctca tgaatgctat gccaaagtgt tcgatgaatt taaacctctt     1140
gtggaagagc tcagaattt aatcaaacaa aattgtgagc tttttgagca gcttggagag      1200
tacaaattcc agaatgcgct attagttcgt tacaccaaga aagtacccca agtgtcaact     1260
ccaactcttg tagaggtctc aagaaaccta ggaaaagtgg gcagcaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca ggcgaccatg cttttcagct ctggaagtcg atgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caaggcaaca     1620 aaagagcaac tgaaagctgt tatggatgat ttcgcagctt ttgtagagaa gtgctgcaag     1680
gctgacgata aggagacctg ctttgccgag gagggtaaaa aacttgttgc tgcaagtcaa     1740
gctgccttag gcttataa                                                   1758

<210> SEQ ID NO 3
<211> LENGTH: 1758
<212> TYPE: DNA
<213> ORGANISM: Artificial Sequence
<220> FEATURE:
<223> OTHER INFORMATION: Polynucleotide coding sequence (codon optimised
      for expression in yeast) for human serum albumin

<400> SEQUENCE: 3
gacgctcaca agtccgaagt cgctcacaga ttcaaggact tgggtgaaga aaacttcaag       60
gctttggtct tgatcgcttt cgctcaatac ttgcaacaat gtccattcga agatcacgtc      120
aagttggtca acgaagttac cgaattcgct aagacttgtg ttgctgacga atctgctgaa      180
aactgtgaca gtccttgca caccttgttc ggtgataagt tgtgtactgt tgctaccttg      240
agagaaacct acggtgaaat ggctgactgt tgtgctaagc aagaaccaga agaaacgaa       300 tgtttcttgc aacacaagga cgacaaccca aacttgccaa gattggttag accagaagtt      360
gacgtcatgt gtactgcttt ccacgacaac gaagaaacct tcttgaagaa gtacttgtac      420
gaaattgcta agacacccc atacttctac gctccagaat gttgttctt cgctaagaga      480 tacaaggctc tttcaccga atgttgtcaa gctgctgata ggctgcttg tttgttgcca       540 aagttggatg aattgagaga cgaaggtaag gcttcttccg ctaagcaaag attgaagtgt      600
gcttccttgc aaaagttcgg tgaaagagct ttcaaggctt gggctgtcgc tagattgtct      660
caaagattcc caaaggctga attcgctgaa gtttctaagt tggttactga cttgactaag      720
gttcacactg aatgttgtca cggtgacttg ttggaatgtg ctgatgacag agctgacttg      780
gctaagtaca tctgtgaaaa ccaagactct atctcttcca gttgaagga atgttgtgaa      840 aagccattgt tggaaaagtc tcactgtatt gctgaagttg aaaacgatga aatgccagct      900
```

```
gacttgccat ctttggctgc tgacttcgtt gaatctaagg acgtttgtaa gaactacgct      960
gaagctaagg acgtcttctt gggtatgttc ttgtacgaat acgctagaag acacccagac     1020
tactccgttg tcttgttgtt gagattggct aagacctacg aaactacctt ggaaaagtgt     1080
tgtgctgctg ctgacccaca cgaatgttac gctaaggttt tcgatgaatt caagccattg     1140
gtcgaagaac cacaaaactt gatcaagcaa aactgtgaat tgttcgaaca attgggtgaa     1200
tacaagttcc aaaacgcttt gttggttaga tacactaaga aggtcccaca agtctccacc     1260
ccaactttgg ttgaagtctc tagaaacttg ggtaaggtcg ttctaagtg ttgtaagcac      1320 ccagaagcta agagaatgcc atgtgctgaa gattacttgt ccgtcgtttt gaaccaattg     1380
tgtgttttgc acgaaaagac cccagtctct gatagagtca ccaagtgttg tactgaatct     1440
ttggttaaca aagaccatg tttctctgct ttggaagtcg acgaaactta cgttccaaag      1500
gaattcaacg ctgaaacttt caccttccac gctgatatct gtaccttgtc cgaaaaggaa     1560
agacaaatta gaagcaaac tgctttggtt gaattggtca agcacaagcc aaaggctact      1620
aaggaacaat tgaaggctgt catggatgat ttcgctgctt tcgttgaaaa gtgttgtaag     1680
gctgatgata aggaaacttg tttcgctgaa gaaggtaaga agttggtcgc tgcttcccaa     1740
gctgctttgg gtttgtaa                                                   1758
```

<210> SEQ ID NO 4
<211> LENGTH: 1758
<212> TYPE: DNA
<213> ORGANISM: Artificial Sequence
<220> FEATURE:
<223> OTHER INFORMATION: HA mutated to introduce restriction enzyme
      sites

<400> SEQUENCE: 4

```
gatgcacaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtccgcggaa      180
aattgtgaca aatcacttca tacccttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttgtgaaaaa atactatat       420 gaaattgcca aagacatcc ttactttat gccccggaac tccttttctt tgctaaaagg       480
tataaagctg cttttacaga atgttgccaa gctgctgata agctgcctg cctgttgcca      540 aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag gcggaccttt      780
gccaagtata tctgtgaaa tcaagattcg atctccagta aactgaagga atgctgtgaa       840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg ctgatcctca tgaatgctat gccaaagtgt tcgatgaatt taaacctctt     1140
```

-continued

```
gtggaagagc ctcagaattt aatcaaacaa aattgtgagc tttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc aaggcaaca     1620 aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gcttataa                                                  1758
```

<210> SEQ ID NO 5
<211> LENGTH: 1758
<212> TYPE: DNA
<213> ORGANISM: Artificial sequence
<220> FEATURE:
<223> OTHER INFORMATION: TA1: HA with A2C

<400> SEQUENCE: 5

```
gattgtcaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtccgcggaa     180
aattgtgaca atcacttca tacccttttt ggagacaaat tatgcacagt tgcaactctt     240
cgtgaaacct atggtgaaat ggctgactgc tgtgcaaaac aagaacctga gaaaatgaa     300 tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca agacatcc ttactttat gccccggaac tccttttctt tgctaaaagg       480
tataaagctg cttttacaga atgttgccaa gctgctgata agctgcctg cctgttgcca     540 aagctcgatg aacttcggga tgaagggaag gctagctctg ccaaacagag actcaagtgt     600
gccagtctcc aaaaatttgg agaaagagct ttcaaagcat gggcagtagc tcgcctgagc     660
cagagatttc ccaaagctga gtttgcagaa gttttccaagt tagtgacaga tcttaccaaa    720
gtccacacgg aatgctgcca tggagatctg ctcgagtgtg ctgatgacag gcggaccttt    780
gccaagtata tctgtgaaaa tcaagattcg atctccagta aactgaagga atgctgtgaa    840
aaacctctgt tggaaaaatc ccactgcatt gccgaagtgg aaaatgatga atgcctgct     900 gacttgcctt cattagctgc tgattttgtt gaaagtaagg atgtttgcaa aaactatgct    960
gaggcaaagg atgtcttcct gggcatgttt ttgtatgaat atgcaagaag gcatcctgat    1020
tactctgtcg tgctgctgct gagacttgcc aagacatatg aaaccactct agaaagtgc    1080 tgtgccgctg ctgatcctca tgaatgctat gccaaagtgt tcgatgaatt taaacctctt   1140
gtggaagagc ctcagaattt aatcaaacaa aattgtgagc tttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
```

| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag agggtaaaa aacttgttgc tgcaagtcaa | 1740 |
| gctgccttag gcttataa | 1758 |

<210> SEQ ID NO 6
<211> LENGTH: 1758
<212> TYPE: DNA
<213> ORGANISM: Artificial sequence
<220> FEATURE:
<223> OTHER INFORMATION: TA2: HA with D1C

<400> SEQUENCE: 6

| tgtgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca atcacttca tacccttttt ggagacaaat tatgcacagt tgcaactctt | 240 |
| cgtgaaacct atggtgaaat ggctgactgc tgtgcaaaac aagaacctga gaaaatgaa | 300 |
| tgcttcttgc aacacaaaga tgacaaccca aacctccccc gattggtgag accagaggtt | 360 |
| gatgtgatgt gcactgcttt tcatgacaat gaagagacat ttttgaaaaa atacttatat | 420 |
| gaaattgcca gaagacatcc ttacttttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag gctagctctg ccaaacagag actcaagtgt | 600 |
| gccagtctcc aaaaatttgg agaaagagct tcaaagcat gggcagtagc tcgcctgagc | 660 |
| cagagatttc caaagctga gtttgcagaa gtttccaagt tagtgacaga tcttaccaaa | 720 |
| gtccacacgg aatgctgcca tggagatctg ctcgagtgtg ctgatgacag gcggaccttt | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga atgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |
| gtggaagagc ctcagaattt aatcaaacaa aattgtgagc tttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gatccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |

```
gctgacgata aggagacctg ctttgccgag gagggtaaaa aacttgttgc tgcaagtcaa   1740
gctgccttag gcttataa                                                 1758

<210> SEQ ID NO 7
<211> LENGTH: 1758
<212> TYPE: DNA
<213> ORGANISM: Artificial sequence
<220> FEATURE:
<223> OTHER INFORMATION: TA3: HA with C75S

<400> SEQUENCE: 7
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca atcacttca tacccttttt ggagacaaat tatctacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca aagacatcc ttactttat gccccggaac tccttttctt tgctaaaagg    480
tataaagctg cttttacaga atgttgccaa gctgctgata agctgcctg cctgttgcca    540 aagctcgatg aacttcggga tgaagggaag ctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag gcggaccttt    780
gccaagtata tctgtgaaaa tcaagattcg atctccagta aactgaagga atgctgtgaa    840
aaacctctgt tggaaaaatc ccactgcatt gccgaagtgg aaaatgatga tgctgctgct    900
gacttgccct tcattagctg ctgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gatccaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc aaggcaaca    1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttataa                                                 1758

<210> SEQ ID NO 8
<211> LENGTH: 1758
<212> TYPE: DNA
<213> ORGANISM: Artificial sequence
```

<220> FEATURE:
<223> OTHER INFORMATION: TA4: HA with T79C

<400> SEQUENCE: 8

| | | | | | |
|---|---|---|---|---|---|
| gatgcacaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |
| aaattagtga | atgaagtaac | tgaatttgca | aaaacatgtg | ttgctgatga | gtccgcggaa | 180 |
| aattgtgaca | aatcacttca | tacccttttt | ggagacaaat | tatgcacagt | tgcatgtctt | 240 |
| cgtgaaacct | atggtgaaat | ggctgactgc | tgtgcaaaac | aagaacctga | gagaaatgaa | 300 |
| tgcttcttgc | aacacaaaga | tgacaaccca | aacctccccc | gattggtgag | accagaggtt | 360 |
| gatgtgatgt | gcactgcttt | tcatgacaat | gaagagacat | ttttgaaaaa | atacttatat | 420 |
| gaaattgcca | agacatcc | ttactttat | gccccggaac | tccttttctt | tgctaaaagg | 480 |
| tataaagctg | cttttacaga | atgttgccaa | gctgctgata | aagctgcctg | cctgttgcca | 540 |
| aagctcgatg | aacttcggga | tgaagggaag | gctagctctg | ccaaacagag | actcaagtgt | 600 |
| gccagtctcc | aaaaatttgg | agaaagagct | ttcaaagcat | gggcagtagc | tcgcctgagc | 660 |
| cagagatttc | ccaaagctga | gtttgcagaa | gtttccaagt | tagtgacaga | tcttaccaaa | 720 |
| gtccacacgg | aatgctgcca | tggagatctg | ctcgagtgtg | ctgatgacag | ggcggacctt | 780 |
| gccaagtata | tctgtgaaaa | tcaagattcg | atctccagta | aactgaagga | atgctgtgaa | 840 |
| aaacctctgt | ggaaaaatc | ccactgcatt | gccgaagtgg | aaaatgatga | gatgcctgct | 900 |
| gacttgcctt | cattagctgc | tgattttgtt | gaaagtaagg | atgtttgcaa | aaactatgct | 960 |
| gaggcaaagg | atgtcttcct | gggcatgttt | ttgtatgaat | atgcaagaag | gcatcctgat | 1020 |
| tactctgtcg | tgctgctgct | gagacttgcc | aagacatatg | aaaccactct | agaaagtgc | 1080 |
| tgtgccgctg | ctgatcctca | tgaatgctat | gccaaagtgt | tcgatgaatt | taaacctctt | 1140 |
| gtggaagagc | ctcagaattt | aatcaaacaa | aattgtgagc | tttttgagca | gcttggagag | 1200 |
| tacaaattcc | agaatgcgct | attagttcgt | tacaccaaga | aagtacccca | agtgtcaact | 1260 |
| ccaactcttg | tagaggtctc | aagaaaccta | ggaaaagtgg | gatccaaatg | ttgtaaacat | 1320 |
| cctgaagcaa | aaagaatgcc | ctgtgcagaa | gactatctat | ccgtggtcct | gaaccagtta | 1380 |
| tgtgtgttgc | atgagaaaac | gccagtaagt | gacagagtca | ccaaatgctg | cacagaatcc | 1440 |
| ttggtgaaca | ggcgaccatg | cttttcagct | ctggaagtcg | acgaaacata | cgttcccaaa | 1500 |
| gagtttaatg | ctgaaacatt | caccttccat | gcagatatat | gcacactttc | tgagaaggag | 1560 |
| agacaaatca | agaaacaaac | tgcacttgtt | gagctcgtga | aacacaagcc | caaggcaaca | 1620 |
| aaagagcaac | tgaaagctgt | tatggatgat | ttcgcagctt | ttgtagagaa | gtgctgcaag | 1680 |
| gctgacgata | aggagacctg | ctttgccgag | gagggtaaaa | aacttgttgc | tgcaagtcaa | 1740 |
| gctgccttag | gcttataa | | | | | 1758 |

<210> SEQ ID NO 9
<211> LENGTH: 1758
<212> TYPE: DNA
<213> ORGANISM: Artificial sequence
<220> FEATURE:
<223> OTHER INFORMATION: TA5: HA with E82C

<400> SEQUENCE: 9

| | | | | | |
|---|---|---|---|---|---|
| gatgcacaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |

```
aaattagtga atgaagtaac tgaatttgca aaaacatgtg ttgctgatga gtccgcggaa      180
aattgtgaca aatcacttca taccctttttt ggagacaaat tatgcacagt tgcaactctt      240
cgttgtacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttactttat gccccggaac tccttttctt tgctaaaagg       480
tataaagctg cttttacaga atgttgccaa gctgctgata aagctgcctg cctgttgcca      540
aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag ggcggacctt      780
gccaagtata tctgtgaaaa tcaagattcg atctccagta aactgaagga atgctgtgaa      840
aaacctctgt ggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg ctgatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga agtaccccca agtgtcaact     1260
ccaactcttg tagaggtctc aagaaaccta ggaaaagtgg atccaaatg ttgtaaacat     1320 cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca ggcgaccatg cttttcagct ctggaagtcg acgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caaggcaaca     1620 aaagagcaac tgaaagctgt tatggatgat ttcgcagctt ttgtagagaa gtgctgcaag     1680
gctgacgata aggagacctg cttttgccga g agggtaaaa aacttgttgc tgcaagtcaa     1740
gctgccttag gcttataa                                                    1758

<210> SEQ ID NO 10
<211> LENGTH: 1758
<212> TYPE: DNA
<213> ORGANISM: Artificial sequence
<220> FEATURE:
<223> OTHER INFORMATION: TA6: HA with E86C

<400> SEQUENCE: 10
gatgcacaca agagtgaggt tgctcatcgg tttaaagatt gggagaaga aaattttcaaa       60 gccttggtgt tgattgcctt gctcagtat cttcagcagt gtccatttga agatcatgta      120
aaattagtga atgaagtaac tgaatttgca aaaacatgtg ttgctgatga gtccgcggaa     180
aattgtgaca aatcacttca taccctttttt ggagacaaat tatgcacagt tgcaactctt     240
cgtgaaacct atggttgtat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
```

```
gaaattgcca agaagacatcc ttacttttat gccccggaac tccttttctt tgctaaaagg      480
tataaagctg cttttacaga atgttgccaa gctgctgata aagctgcctg cctgttgcca      540
aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag gcggaccctt      780
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg ctgatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga aagtacccca agtgtcaact     1260
ccaactcttg tagaggtctc aagaaaccta ggaaaagtgg gatccaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca gcgaccatg cttttcagct ctggaagtcg acgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caaggcaaca     1620 aaagagcaac tgaaagctgt tatggatgat ttcgcagctt ttgtagagaa gtgctgcaag     1680
gctgacgata aggagacctg ctttgccgag gagggtaaaa aacttgttgc tgcaagtcaa     1740
gctgccttag gcttataa                                                  1758

<210> SEQ ID NO 11
<211> LENGTH: 1758
<212> TYPE: DNA
<213> ORGANISM: Artificial sequence
<220> FEATURE:
<223> OTHER INFORMATION: TA7: HA with C124S

<400> SEQUENCE: 11
gatgcacaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtccgcggaa      180
aattgtgaca atcacttca taccctttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt ctactgcttt tcatgacaat gaagagacat ttttgaaaaa atacttatat      420
gaaattgcca agaagacatcc ttacttttat gccccggaac tccttttctt tgctaaaagg      480
tataaagctg cttttacaga atgttgccaa gctgctgata aagctgcctg cctgttgcca      540
aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
```

```
cagagatttc ccaaagctga gtttgcagaa gtttccaagt tagtgacaga tcttaccaaa    720
gtccacacgg aatgctgcca tggagatctg ctcgagtgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc tttttgagca gcttggagag   1200
tacaaattcc agaatgcgct attagttcgt tacaccaaga aagtaccccca agtgtcaact   1260 ccaactcttg tagaggtctc aagaaaccta ggaaaagtgg gatccaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caggcaaca    1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttataa                                                1758

<210> SEQ ID NO 12
<211> LENGTH: 1758
<212> TYPE: DNA
<213> ORGANISM: Artificial sequence
<220> FEATURE:
<223> OTHER INFORMATION: TA8: HA with C168S

<400> SEQUENCE: 12
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca atcacttca tacccttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca acctccccc gattggtgag accagaggtt    360
gatgtgatgt gcactgcttt tcatgacaat gaagagacat tttgaaaaaa atacttatat    420
gaaattgcca aagacatcc ttactttat gccccggaac tcctttctt tgctaaaagg    480 tataaagctg cttttacaga atcttgccaa gctgctgata agctgcctg cctgttgcca    540 aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
```

```
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg ctgatcctca tgaatgctat gccaaagtgt tcgatgaatt taaacctctt    1140
gtggaagagc ctcagaattt aatcaaacaa aattgtgagc tttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg ctgaaacatt caccttccat gcagatatat gcacactttc tgagaaggag    1560
agacaaatca gaaacaaac  tgcacttgtt gagctcgtga acacaagcc  caaggcaaca    1620 aaagagcaac tgaaagctgt tatgatgat  ttcgcagctt ttgtagagaa gtgctgcaag    1680
gctgacgata aggagacctg cttttgccgag gagggtaaaa aacttgttgc tgcaagtcaa    1740
gctgccttag gcttataa                                                 1758

<210> SEQ ID NO 13
<211> LENGTH: 1758
<212> TYPE: DNA
<213> ORGANISM: Artificial sequence
<220> FEATURE:
<223> OTHER INFORMATION: TA9: HA with C169S

<400> SEQUENCE: 13
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtccgcggaa     180
aattgtgaca aatcacttca taccctttt  ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat tttgaaaaa atacttatat     420 gaaattgcca aagacatcc ttacttttat gccccgaac  tccttttctt tgctaaaagg     480
tataaagctg cttttacaga atgttctcaa gctgctgata agctgcctg  cctgttgcca     540 aagctcgatg aacttcggga tgaagggaag ctagctctg  ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg ctcgagtgtg ctgatgacag gcggacctt      780 gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg ctgatcctca tgaatgctat gccaaagtgt tcgatgaatt taaacctctt    1140
gtggaagagc ctcagaattt aatcaaacaa aattgtgagc tttttgagca gcttggagag    1200
```

| | |
|---|---|
| tacaaattcc agaatgcgct attagttcgt tacaccaaga agtaccccca agtgtcaact | 1260 |
| ccaactcttg tagaggtctc aagaaaccta ggaaaagtgg gatccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa aacttgttgc tgcaagtcaa | 1740 |
| gctgccttag gcttataa | 1758 |

<210> SEQ ID NO 14
<211> LENGTH: 1758
<212> TYPE: DNA
<213> ORGANISM: Artificial sequence
<220> FEATURE:
<223> OTHER INFORMATION: TA10: HA with C91S

<400> SEQUENCE: 14

| | |
|---|---|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca aatcacttca tacccttttt ggagacaaat tatgcacagt tgcaactctt | 240 |
| cgtgaaacct atggtgaaat ggctgactgc tctgcaaaac aagaacctga gagaaatgaa | 300 |
| tgcttcttgc aacacaaaga tgacaaccca aacctccccc gattggtgag accagaggtt | 360 |
| gatgtgatgt gcactgcttt tcatgacaat gaagagacat ttttgaaaaa atacttatat | 420 |
| gaaattgcca aagacatcc ttactttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag ctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag ggcggacctt | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |
| gtggaagagc ctcagaattt aatcaaacaa aattgtgagc ttttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gatccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |

```
gagtttaatg ctgaaacatt caccttccat gcagatatat gcacactttc tgagaaggag    1560
agacaaatca agaaacaaac tgcacttgtt gagctcgtga acacaagcc caaggcaaca     1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttataa                                                  1758
```

<210> SEQ ID NO 15
<211> LENGTH: 1758
<212> TYPE: DNA
<213> ORGANISM: Artificial sequence
<220> FEATURE:
<223> OTHER INFORMATION: TA11: HA with D121C

<400> SEQUENCE: 15

```
gatgcacaca agagtgaggt tgctcatcgg tttaaagatt tgggagaaga aaatttcaaa    60
gccttggtgt tgattgcctt tgctcagtat cttcagcagt gtccatttga agatcatgta   120
aaattagtga atgaagtaac tgaatttgca aaaacatgtg ttgctgatga gtccgcggaa   180
aattgtgaca aatcacttca tacccttttt ggagacaaat tatgcacagt tgcaactctt   240
cgtgaaacct atggtgaaat ggctgactgc tgtgcaaaac aagaacctga gaaaatgaa    300 tgcttcttgc aacacaaaga tgacaaccca aacctccccc gattggtgag ccagagggtt   360
tgtgtgatgt gcactgcttt tcatgacaat gaagagacat ttttgaaaaa atacttatat   420
gaaattgcca aagacatcc ttacttttat gcccccggaac tccttttctt tgctaaaagg   480
tataaagctg cttttacaga atgttgccaa gctgctgata agctgcctg cctgttgcca   540 aagctcgatg aacttcggga tgaagggaag gctagctctg ccaaacagag actcaagtgt   600
gccagtctcc aaaaatttgg agaaagagct ttcaaagcat gggcagtagc tcgcctgagc   660
cagagatttc ccaaagctga gtttgcagaa gtttccaagt tagtgacaga tcttaccaaa   720
gtccacacgg aatgctgcca tggagatctg ctcgagtgtg ctgatgacag gcggaccttt   780
gccaagtata tctgtgaaaa tcaagattcg atctccagta aactgaagga atgctgtgaa    840
aaacctctgt ggaaaaatc ccactgcatt gccgaagtgg aaaatgatga gatgcctgct   900 gacttgccttt cattagctgc tgattttgtt gaaagtaagg atgtttgcaa aaactatgct  960
gaggcaaagg atgtcttcct gggcatgttt ttgtatgaat atgcaagaag gcatcctgat 1020
tactctgtcg tgctgctgct gagacttgcc aagacatatg aaaccactct agaagagtgc 1080
tgtgccgctg ctgatcctca tgaatgctat gccaagtgt tcgatgaatt taaacctctt   1140
gtggaagagc ctcagaattt aatcaaacaa aattgtgagc tttttgagca gcttggagag 1200
tacaaattcc agaatgcgct attagttcgt tacaccaaga agtacccca agtgtcaact 1260 ccaactcttg tagaggtctc aagaaaccta ggaaaagtgg atccaaatg ttgtaaacat  1320 cctgaagcaa aaagaatgcc ctgtgcagaa gactatctat ccgtggtcct gaaccagtta 1380
tgtgtgttgc atgagaaaac gccagtaagt gacagagtca ccaaatgctg cacagaatcc   1440
ttggtgaaca gcgaccatg cttttcagct ctggaagtcg acgaaacata cgttcccaaa  1500
gagtttaatg ctgaaacatt caccttccat gcagatatat gcacactttc tgagaaggag  1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag  1680
gctgacgata aggagacctg ctttgccgag gagggtaaaa aacttgttgc tgcaagtcaa  1740
```
gctgccttag gcttataa                                                 1758

<210> SEQ ID NO 16
<211> LENGTH: 1758
<212> TYPE: DNA
<213> ORGANISM: Artificial sequence
<220> FEATURE:
<223> OTHER INFORMATION: TA12: HA with D129C

<400> SEQUENCE: 16

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtccgcggaa     180
aattgtgaca atcacttca taccctttttt ggagacaaat tatgcacagt tgcaactctt     240
cgtgaaacct atggtgaaat ggctgactgc tgtgcaaaac aagaacctga gaaaatgaa      300
tgcttcttgc aacacaaaga tgacaaccca aacctccccc gattggtgag accagaggtt     360
gatgtgatgt gcactgcttt tcattgtaat gaagagacat ttttgaaaaa atacttatat     420
gaaattgcca aagacatcc ttactttat gccccggaac tccttttctt tgctaaaagg      480
tataaagctg cttttacaga atgttgccaa gctgctgata agctgcctg cctgttgcca      540
aagctcgatg aacttcggga tgaagggaag gctagctctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg ctcgagtgtg ctgatgacag gcggaccttt     780
gccaagtata tctgtgaaaaa tcaagattcg atctccagta aactgaagga atgctgtgaa     840
aaacctctgt ggaaaaaatc ccactgcatt gccgaagtgg aaaatgatga atgcctgct      900
gacttgcctt cattagctgc tgatttttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg ctgatcctca tgaatgctat gccaaagtgt tcgatgaatt taaacctctt    1140
gtggaagagc tcagaatttt aatcaaacaa aattgtgagc tttttgagca gcttggagag    1200
tacaaattcc agaatgcgct attagttcgt tacaccaaga agtaccccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg ctttttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620
aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gcttataa                                                 1758
```

<210> SEQ ID NO 17
<211> LENGTH: 1758
<212> TYPE: DNA
<213> ORGANISM: Artificial sequence
<220> FEATURE:
<223> OTHER INFORMATION: TA13: HA with S270C

<400> SEQUENCE: 17

```
gatgcacaca agagtgaggt tgctcatcgg tttaaagatt tgggagaaga aaatttcaaa        60
gccttggtgt tgattgcctt tgctcagtat cttcagcagt gtccatttga agatcatgta       120
aaattagtga atgaagtaac tgaatttgca aaaacatgtg ttgctgatga gtccgcggaa       180
aattgtgaca aatcacttca tacccttttt ggagacaaat tatgcacagt tgcaactctt       240
cgtgaaacct atggtgaaat ggctgactgc tgtgcaaaac aagaacctga gagaaatgaa       300
tgcttcttgc aacacaaaga tgacaaccca aacctccccc gattggtgag accagaggtt       360
gatgtgatgt gcactgcttt tcatgacaat gaagagacat ttttgaaaaa atacttatat       420
gaaattgcca aagacatcc ttactttat gcccggaac tccttttctt tgctaaaagg       480
tataaagctg cttttacaga atgttgccaa gctgctgata agctgcctg cctgttgcca       540
aagctcgatg aacttcggga tgaagggaag gctagctctg ccaaacagag actcaagtgt       600
gccagtctcc aaaaatttgg agaaagagct ttcaaagcat gggcagtagc tcgcctgagc       660
cagagatttc ccaaagctga gtttgcagaa gtttccaagt tagtgacaga tcttaccaaa       720
gtccacacgg aatgctgcca tggagatctg ctcgagtgtg ctgatgacag gcggaccttt       780
gccaagtata tctgtgaaaa tcaagattgt atctccagta aactgaagga atgctgtgaa       840
aaacctctgt tggaaaaatc ccactgcatt gccgaagtgg aaaatgatga atgcctgct       900
gacttgcctt cattagctgc tgattttgtt gaaagtaagg atgtttgcaa aaactatgct       960
gaggcaaagg atgtcttcct gggcatgttt ttgtatgaat atgcaagaag gcatcctgat      1020
tactctgtcg tgctgctgct gagacttgcc aagacatatg aaaccactct agagaagtgc      1080
tgtgccgctg ctgatcctca tgaatgctat gccaaagtgt tcgatgaatt taaacctctt      1140
gtggaagagc tcagaatttt aatcaaacaa aattgtgagc ttttgagca gcttggagag      1200
tacaaattcc agaatgcgct attagttcgt tacaccaaga aagtacccca agtgtcaact      1260
ccaactcttg tagaggtctc aagaaaccta ggaaaagtgg gatccaaatg ttgtaaacat      1320
cctgaagcaa aaagaatgcc ctgtgcagaa gactatctat ccgtggtcct gaaccagtta      1380
tgtgtgttgc atgagaaaac gccagtaagt gacagagtca ccaaatgctg cacagaatcc      1440
ttggtgaaca gcgaccatg cttttcagct ctggaagtcg acgaaacata cgttcccaaa      1500
gagtttaatg ctgaaacatt caccttccat gcagatatat gcacactttc tgagaaggag      1560
agacaaatca gaaacaaac tgcacttgtt gagctcgtga acacaagcc caaggcaaca      1620
aaagagcaac tgaaagctgt tatggatgat ttcgcagctt ttgtagagaa gtgctgcaag      1680
gctgacgata aggagacctg ctttgccgag gagggtaaaa aacttgttgc tgcaagtcaa      1740
gctgccttag gcttataa                                                   1758
```

<210> SEQ ID NO 18
<211> LENGTH: 1758
<212> TYPE: DNA
<213> ORGANISM: Artificial sequence
<220> FEATURE:
<223> OTHER INFORMATION: TA14:HA with C316A

<400> SEQUENCE: 18

```
gatgcacaca agagtgaggt tgctcatcgg tttaaagatt tgggagaaga aaatttcaaa        60
gccttggtgt tgattgcctt tgctcagtat cttcagcagt gtccatttga agatcatgta       120
aaattagtga atgaagtaac tgaatttgca aaaacatgtg ttgctgatga gtccgcggaa       180
```

```
aattgtgaca aatcacttca tacccttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca acctccccc gattggtgag accagaggtt    360
gatgtgatgt gcactgcttt tcatgacaat gaagagacat ttttgaaaaa atacttatat    420
gaaattgcca gaagacatcc ttactttat gccccggaac tccttttctt tgctaaaagg    480
tataaagctg cttttacaga atgttgccaa gctgctgata agctgcctg cctgttgcca    540
aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag gcggaccttt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgttgctaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gatccaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca   1620
aaagagcaac tgaaagctgt tatggatgat ttcgcagctt ttgtagagaa gtgctgcaag   1680
gctgacgata aggagacctg cttttgccga gagggtaaaa aacttgttgc tgcaagtcaa   1740
gctgccttag gcttataa                                                 1758
```

<210> SEQ ID NO 19
<211> LENGTH: 1758
<212> TYPE: DNA
<213> ORGANISM: Artificial sequence
<220> FEATURE:
<223> OTHER INFORMATION: TA16: HA with C360S

<400> SEQUENCE: 19

```
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca aatcacttca tacccttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca acctccccc gattggtgag accagaggtt    360
gatgtgatgt gcactgcttt tcatgacaat gaagagacat ttttgaaaaa atacttatat    420
gaaattgcca gaagacatcc ttactttat gccccggaac tccttttctt tgctaaaagg    480
```

```
tataaagctg cttttacaga atgttgccaa gctgctgata aagctgcctg cctgttgcca    540
aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag ggcggacctt    780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtct   1080
tgtgccgctg ctgatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gatccaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca agaaacaaac tgcacttgtt gagctcgtga aacacaagcc caaggcaaca   1620
aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttataa                                                 1758
```

```
<210> SEQ ID NO 20
<211> LENGTH: 1758
<212> TYPE: DNA
<213> ORGANISM: Artificial sequence
<220> FEATURE:
<223> OTHER INFORMATION: TA17: HA with C361A

<400> SEQUENCE: 20
```

```
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca aatcacttca tacccttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat tttgaaaaa atacttatat     420 gaaattgcca gaagacatcc ttacttttat gccccggaac tccttttctt tgctaaaagg    480
tataaagctg cttttacaga atgttgccaa gctgctgata aagctgcctg cctgttgcca    540
aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
```

| | |
|---|---|
| gtccacacgg aatgctgcca tggagatctg ctcgagtgtg ctgatgacag ggcgg

| | |
|---|---|
| tactctgtcg tgctgctgct gagacttgcc aagacatatg aaaccactct agagaagtgc | 1080 |
| tctgccgctg ctgatcctca tgaatgctat gccaaagtgt tcgatgaatt taaacctctt | 1140 |
| gtggaagagc ctcagaattt aatcaaacaa aattgtgagc tttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gatccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa aacttgttgc tgcaagtcaa | 1740 |
| gctgccttag gcttataa | 1758 |

<210> SEQ ID NO 22
<211> LENGTH: 1758
<212> TYPE: DNA
<213> ORGANISM: Artificial sequence
<220> FEATURE:
<223> OTHER INFORMATION: TA19: HA with A364C

<400> SEQUENCE: 22

| | |
|---|---|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca aatcacttca tacccttttt ggagacaaat tatgcacagt tgcaactctt | 240 |
| cgtgaaacct atggtgaaat ggctgactgc tgtgcaaaac aagaacctga gagaaatgaa | 300 |
| tgcttcttgc aacacaaaga tgacaaccca aacctccccc gattggtgag accagaggtt | 360 |
| gatgtgatgt gcactgcttt tcatgacaat gaagagacat ttttgaaaaa atacttatat | 420 |
| gaaattgcca agacatcc ttactttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag gctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag gcggaccctt | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctt gtgatcctca tgaatgctat gccaaagtgt tcgatgaatt taaacctctt | 1140 |
| gtggaagagc ctcagaattt aatcaaacaa aattgtgagc tttttgagca gcttggagag | 1200 |
| tacaaattcc agaatgcgct attagttcgt tacaccaaga agtaccccca agtgtcaact | 1260 |

```
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620 aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gcttataa                                                  1758
```

<210> SEQ ID NO 23
<211> LENGTH: 1758
<212> TYPE: DNA
<213> ORGANISM: Artificial sequence
<220> FEATURE:
<223> OTHER INFORMATION: TA20: HA with Q397C

<400> SEQUENCE: 23

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca aatcacttca tacccttttt ggagacaaat tatgcacagt tgcaactctt    240
cgtgaaacct atggtgaaat ggctgactgc tgtgcaaaac aagaacctga gaaaatgaa    300 tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca aagacatcc ttacttttat gccccggaac tccttttctt tgctaaaagg    480
tataaagctg cttttacaga atgttgccaa gctgctgata agctgcctg cctgttgcca    540 aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag gcggaccttt    780
gccaagtata tctgtgaaaa tcaagattcg atctccagta aactgaagga atgctgtgaa    840
aaacctctgt tggaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc ttttgagtg tcttggagag   1200 tacaaattcc agaatgcgct attagttcgt tacaccaaga agtaccccca gtgtcaact   1260 ccaactcttg tagaggtctc aagaaaccta ggaaaagtgg gatccaaatg ttgtaaacat   1320
cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
```

```
agacaaatca agaaacaaac tgcacttgtt gagctcgtga acacaagcc caaggcaaca    1620 aaagagcaac tgaaagctgt tatggatgat ttcgcagctt ttgtagagaa gtgctgcaag   1680
gctgacgata aggagacctg ctttgccgag gagggtaaaa aacttgttgc tgcaagtcaa   1740
gctgccttag gcttataa                                                 1758
```

<210> SEQ ID NO 24
<211> LENGTH: 1758
<212> TYPE: DNA
<213> ORGANISM: Artificial sequence
<220> FEATURE:
<223> OTHER INFORMATION: TA21: HA with A504C

<400> SEQUENCE: 24

```
gatgcacaca agagtgaggt tgctcatcgg tttaaagatt tgggagaaga aaatttcaaa    60
gccttggtgt tgattgcctt tgctcagtat cttcagcagt gtccatttga agatcatgta   120
aaattagtga atgaagtaac tgaatttgca aaaacatgtg ttgctgatga gtccgcggaa   180
aattgtgaca atcacttcca tacccttttt ggagacaaat tatgcacagt tgcaactctt   240
cgtgaaacct atggtgaaat ggctgactgc tgtgcaaaac aagaacctga gaaaatgaa    300 tgcttcttgc aacacaaaga tgacaaccca acctcccccc gattggtgag accagaggtt   360
gatgtgatgt gcactgcttt tcatgacaat aagagacat ttttgaaaaa atacttatat   420
gaaattgcca aagacatcc ttactttat gccccggaac tccttttctt tgctaaaagg    480
tataaagctg cttttacaga atgttgccaa gctgctgata agctgcctg cctgttgcca   540 aagctcgatg aacttcggga tgaagggaag gctagctctg ccaaacagag actcaagtgt   600
gccagtctcc aaaaatttgg agaaagagct ttcaaagcat gggcagtagc tcgcctgagc   660
cagagatttc ccaaagctga gtttgcagaa gttttccaagt tagtgacaga tcttaccaaa   720
gtccacacgg aatgctgcca tggagatctg ctcgagtgtg ctgatgacag gcggaccttt   780
gccaagtata tctgtgaaaa tcaagattcg atctccagta aactgaagga tgctgtgaa    840 aaacctctgt tggaaaaatc ccactgcatt gccgaagtgg aaaatgatga gatgcctgct   900
gacttgcctt cattagctgc tgattttgtt gaaagtaagg atgtttgcaa aaactatgct   960
gaggcaaagg atgtcttcct gggcatgttt ttgtatgaat atgcaagaag gcatcctgat  1020
tactctgtcg tgctgctgct gagacttgcc aagacatatg aaaccactct agagaagtgc  1080
tgtgccgctg ctgatcctca tgaatgctat gccaaagtgt tcgatgaatt taaacctctt  1140
gtggaagagc tcagaatttt aatcaaacaa aattgtgagc ttttttgagca gcttggagag  1200 tacaaattcc agaatgcgct attagttcgt tacaccaaga aagtacccca agtgtcaact  1260
ccaactcttg tagaggtctc aagaaaccta ggaaagtgg atccaaatg ttgtaaacat   1320 cctgaagcaa aaagaatgcc ctgtgcagaa gactatctat ccgtggtcct gaaccagtta  1380
tgtgtgttgc atgagaaaac gccagtaagt gacagagtca ccaaatgctg cacagaatcc  1440
ttggtgaaca ggcgaccatg cttttcagct ctggaagtcg acgaaacata cgttcccaaa  1500
gagtttaatt gtgaaacatt caccttccat gcagatatat gcacactttc tgagaaggag  1560
agacaaatca gaaacaaac tgcacttgtt gagctcgtga acacaagcc caaggcaaca   1620 aaagagcaac tgaaagctgt tatggatgat ttcgcagctt ttgtagagaa gtgctgcaag  1680
gctgacgata aggagacctg ctttgccgag gagggtaaaa aacttgttgc tgcaagtcaa  1740
gctgccttag gcttataa                                                1758
```

<210> SEQ ID NO 25
<211> LENGTH: 1758
<212> TYPE: DNA
<213> ORGANISM: Artificial sequence
<220> FEATURE:
<223> OTHER INFORMATION: TA22: HA with A578C

<400> SEQUENCE: 25

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtccgcggaa     180
aattgtgaca aatcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttactttat gccccggaac tccttttctt tgctaaaagg     480
tataaagctg cttttacaga atgttgccaa gctgctgata agctgcctg cctgttgcca     540
aagctcgatg aacttcggga tgaagggaag ctagctctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg ctcgagtgtg ctgatgacag ggcggacctt     780
gccaagtata tctgtgaaaa tcaagattcg atctccagta aactgaagga atgctgtgaa     840
aaacctctgt tggaaaaatc ccactgcatt gccgaagtgg aaaatgatga tgccttgct     900
gacttgcctt cattagctgc tgattttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg ctgatcctca tgaatgctat gccaaagtgt tcgatgaatt taaacctctt    1140
gtggaagagc tcagaatttt aatcaaacaa aattgtgagc tttttgagca gcttggagag    1200
tacaaattcc agaatgcgct attagttcgt tacaccaaga aagtacccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg ctttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620
aaagagcaac tgaaagctgt tatggatgat ttcgcagctt ttgtagagaa gtgctgcaag    1680
gctgacgata aggagacctg ctttgccgag gagggtaaaa aacttgttgc ttgtagtcaa    1740
gctgccttag gcttataa                                                  1758
```

<210> SEQ ID NO 26
<211> LENGTH: 1758
<212> TYPE: DNA
<213> ORGANISM: Artificial sequence
<220> FEATURE:
<223> OTHER INFORMATION: TA23: HA with A581C

<400> SEQUENCE: 26

```
gatgcacaca agagtgaggt tgctcatcgg tttaaagatt tgggagaaga aaatttcaaa

```
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttacttttat gccccggaac tccttttctt tgctaaaagg       480
tataaagctg cttttacaga atgttgccaa gctgctgata aagctgcctg cctgttgcca      540
aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag ggcggacctt      780
gccaagtata tctgtgaaaa tcaagattcg atctccagta aactgaagga atgctgtgaa      840
aaacctctgt ggaaaaatc ccactgcatt gccgaagtgg aaaatgatga gatgcctgct       900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg ctgatcctca tgaatgctat gccaaagtgt tcgatgaatt taaacctctt     1140
gtggaagagc tcagaatttt aatcaaacaa aattgtgagc tttttgagca gcttggagag     1200
tacaaattcc agaatgcgct attagttcgt tacaccaaga aagtacccca agtgtcaact     1260
ccaactcttg tagaggtctc aagaaaccta ggaaaagtgg atccaaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca gccgaccatg cttttcagct ctggaagtcg acgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caaggcaaca      1620 aaagagcaac tgaaagctgt tatggatgat ttcgcagctt ttgtagagaa gtcttgcaag     1680
gctgacgata aggagacctg ctttgccgag gagggtaaaa aacttgttgc tgcaagtcaa     1740
gctgccttag gcttataa                                                  1758

<210> SEQ ID NO 28
<211> LENGTH: 1758
<212> TYPE: DNA
<213> ORGANISM: Artificial sequence
<220> FEATURE:
<223> OTHER INFORMATION: TA25: HA with C567S

<400> SEQUENCE: 28
gatgcacaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtccgcggaa      180
aattgtgaca atcacttca taccctttt ggagacaaat tatgcacagt tgcaactctt        240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttacttttat gccccggaac tccttttctt tgctaaaagg       480
tataaagctg cttttacaga atgttgccaa gctgctgata aagctgcctg cctgttgcca      540
```

```
aagctcgatg aacttcggga tgaagggaag gctagctctg ccaaacagag act

| | |
|---|---|
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgatttttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |
| gtggaagagc ctcagaattt aatcaaacaa aattgtgagc ttttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gatccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca gccgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatgtgtgat ttcgcagctt ttgtagagaa gtgctgcaag | 1680 |
| gctgacgata aggagacctg ctttgccgag gagggtaaaa aacttgttgc tgcaagtcaa | 1740 |
| gctgccttag gcttataa | 1758 |

<210> SEQ ID NO 30
<211> LENGTH: 1758
<212> TYPE: DNA
<213> ORGANISM: Artificial sequence
<220> FEATURE:
<223> OTHER INFORMATION: TA27: HA with D562C

<400> SEQUENCE: 30

| | |
|---|---|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca atcacttcta taccctttttt ggagacaaat tatgcacagt tgcaactctt | 240 |
| cgtgaaacct atggtgaaat ggctgactgc tgtgcaaaac aagaacctga gagaaatgaa | 300 |
| tgcttcttgc aacacaaaga tgacaaccca acctcccccc gattggtgag accagaggtt | 360 |
| gatgtgatgt gcactgcttt tcatgacaat gaagagacat ttttgaaaaa atacttatat | 420 |
| gaaattgcca agacatcc ttactttttat gccccggaac tcctttttctt tgctaaaagg | 480 |
| tataaagctg cttttacaga atgttgccaa gctgctgata agctgcctg cctgttgcca | 540 |
| aagctcgatg aacttcggga tgaagggaag gctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag ggcggacctt | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgatttttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |

```
tgtgccgctg ctgatcctca tgaatgctat gccaaagtgt tcgatgaatt taaacctctt    1140
gtggaagagc ctcagaattt aatcaaacaa aattgtgagc ttttgagca gcttggagag    1200 tacaaattcc agaatgcgct attagttcgt tacaccaaga agtaccccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620 aaagagcaac tgaaagctgt tatggatgat ttcgcagctt ttgtagagaa gtgctgcaag    1680
gcttgtgata aggagacctg ctttgccgag gagggtaaaa aacttgttgc tgcaagtcaa    1740
gctgccttag gcttataa                                                  1758

<210> SEQ ID NO 31
<211> LENGTH: 1758
<212> TYPE: DNA
<213> ORGANISM: Artificial sequence
<220> FEATURE:
<223> OTHER INFORMATION: TA28: HA with E505C

<400> SEQUENCE: 31
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtccgcggaa     180
aattgtgaca aatcacttca tacccttttt ggagacaaat tatgcacagt tgcaactctt     240
cgtgaaacct atggtgaaat ggctgactgc tgtgcaaaac aagaacctga gaaaatgaa     300 tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttacttttat gccccggaac tccttttctt tgctaaaagg     480
tataaagctg cttttacaga atgttgccaa gctgctgata agctgcctg cctgttgcca     540 aagctcgatg aacttcggga tgaagggaag ctagctctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg ctcgagtgtg ctgatgacag gcgggacctt     780
gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc ctcagaattt aatcaaacaa aattgtgagc ttttgagca gcttggagag    1200 tacaaattcc agaatgcgct attagttcgt tacaccaaga agtaccccca agtgtcaact   1260
ccaactcttg tagaggtctc aagaaaccta ggaaaagtgg gatccaaatg ttgtaaacat   1320
```

```
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg cttgtacatt caccttccat gcagatatat gcacactttc tgagaaggag    1560
agacaaatca agaaacaaac tgcacttgtt gagctcgtga acacaagcc  caaggcaaca    1620 aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
gctgccttag gcttataa                                                  1758

<210> SEQ ID NO 32
<211> LENGTH: 1758
<212> TYPE: DNA
<213> ORGANISM: Artificial sequence
<220> FEATURE:
<223> OTHER INFORMATION: TA29: HA with L585C

<400> SEQUENCE: 32
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca atcacttcca tacccttttt ggagacaaat tatgcacagt tgcaactctt    240
cgtgaaacct atggtgaaat ggctgactgc tgtgcaaaac aagaacctga gagaatgaa     300 tgcttcttgc aacacaaaga tgacaaccca aacctccccc gattggtgag accagaggtt    360
gatgtgatgt gcactgcttt tcatgacaat aagagacat ttttgaaaaa atacttatat    420
gaaattgcca aagacatcc ttactttat gccccgaac tccttttctt tgctaaaagg      480
tataaagctg cttttacaga atgttgccaa gctgctgata agctgcctg cctgttgcca   540 aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag ggcggacctt    780
gccaagtata tctgtgaaaa tcaagattcg atctccagta aactgaagga tgctgtgaa    840 aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc ttttgagca gcttggagag    1200 tacaaattcc agaatgcgct attagttcgt tacaccaaga agtaccccca gtgtcaact    1260 ccaactcttg tagaggtctc aagaaaccta ggaaaagtgg atccaaatg ttgtaaacat    1320 cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca agaaacaaac tgcacttgtt gagctcgtga acacaagcc  caaggcaaca   1620
```

| aaagagcaac tgaaagctgt tatggatgat ttcgcagctt ttgtagagaa gtgctgcaag | 1680 |
| gctgacgata aggagacctg ctttgccgag gagggtaaaa acttgttgc tgcaagtcaa | 1740 |
| gctgccttag gctgttaa | 1758 |

<210> SEQ ID NO 33
<211> LENGTH: 1758
<212> TYPE: DNA
<213> ORGANISM: Artificial sequence
<220> FEATURE:
<223> OTHER INFORMATION: TA33: HA with A2C and L585C

<400> SEQUENCE: 33

| gattgtcaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca aatcacttca tacccttttt ggagacaaat tatgcacagt tgcaactctt | 240 |
| cgtgaaacct atggtgaaat ggctgactgc tgtgcaaaac aagaacctga gaaaatgaa | 300 |
| tgcttcttgc aacacaaaga tgacaaccca accctcccc gattggtgag ccagagggtt | 360 |
| gatgtgatgt gcactgcttt tcatgacaat gaagagacat ttttgaaaaa atacttatat | 420 |
| gaaattgcca aagacatcc ttactttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag gctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag ggcggacctt | 780 |
| gccaagtata tctgtgaaaa tcaagattcg atctccagta aactgaagga tgctgtgaa | 840 |
| aaacctctgt tggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agaagaagtgc | 1080 |
| tgtgccgctg ctgatcctca tgaatgctat gccaaagtgt tcgatgaatt taaacctctt | 1140 |
| gtggaagagc tcagaatttt aatcaaacaa aattgtgagc tttttgagca gcttggagag | 1200 |
| tacaaattcc agaatgcgct attagttcgt tacaccaaga aagtacccca agtgtcaact | 1260 |
| ccaactcttg tagaggtctc aagaaaccta ggaaaagtgg gatccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa acttgttgc tgcaagtcaa | 1740 |
| gctgccttag gctgttaa | 1758 |

<210> SEQ ID NO 34

<211> LENGTH: 1758
<212> TYPE: DNA
<213> ORGANISM: Artificial sequence
<220> FEATURE:
<223> OTHER INFORMATION: TA34: HA with A2C and A504C

<400> SEQUENCE: 34

| | | | | | |
|---|---|---|---|---|---|
| gattgtcaca | agagtgaggt | tgctcatcgg | tttaaagatt | tgggagaaga | aaatttcaaa | 60 |
| gccttggtgt | tgattgcctt | tgctcagtat | cttcagcagt | gtccatttga | agatcatgta | 120 |
| aaattagtga | atgaagtaac | tgaatttgca | aaacatgtg | ttgctgatga | gtccgcggaa | 180 |
| aattgtgaca | atcacttca | tacccttttt | ggagacaaat | tatgcacagt | tgcaactctt | 240 |
| cgtgaaacct | atggtgaaat | ggctgactgc | tgtgcaaaac | aagaacctga | gagaaatgaa | 300 |
| tgcttcttgc | aacacaaaga | tgacaaccca | aacctcccc | gattggtgag | accagaggtt | 360 |
| gatgtgatgt | gcactgcttt | tcatgacaat | gaagagacat | ttttgaaaaa | atacttatat | 420 |
| gaaattgcca | aagacatcc | ttactttat | gccccggaac | tccttttctt | tgctaaaagg | 480 |
| tataaagctg | cttttacaga | atgttgccaa | gctgctgata | aagctgcctg | cctgttgcca | 540 |
| aagctcgatg | aacttcggga | tgaagggaag | gctagctctg | ccaaacagag | actcaagtgt | 600 |
| gccagtctcc | aaaaatttgg | agaaagagct | ttcaaagcat | gggcagtagc | tcgcctgagc | 660 |
| cagagatttc | ccaaagctga | gtttgcagaa | gtttccaagt | tagtgacaga | tcttaccaaa | 720 |
| gtccacacgg | aatgctgcca | tggagatctg | ctcgagtgtg | ctgatgacag | gcggacctt | 780 |
| gccaagtata | tctgtgaaaa | tcaagattcg | atctccagta | aactgaagga | atgctgtgaa | 840 |
| aaacctctgt | tggaaaaatc | ccactgcatt | gccgaagtgg | aaaatgatga | gatgcctgct | 900 |
| gacttgcctt | cattagctgc | tgattttgtt | gaaagtaagg | atgtttgcaa | aaactatgct | 960 |
| gaggcaaagg | atgtcttcct | gggcatgttt | ttgtatgaat | atgcaagaag | gcatcctgat | 1020 |
| tactctgtcg | tgctgctgct | gagacttgcc | aagacatatg | aaaccactct | agagaagtgc | 1080 |
| tgtgccgctg | ctgatcctca | tgaatgctat | gccaaagtgt | tcgatgaatt | taaacctctt | 1140 |
| gtggaagagc | ctcagaattt | aatcaaacaa | aattgtgagc | ttttttgagca | gcttggagag | 1200 |
| tacaaattcc | agaatgcgct | attagttcgt | tacaccaaga | aagtacccca | agtgtcaact | 1260 |
| ccaactcttg | tagaggtctc | aagaaaccta | ggaaaagtgg | gatccaaatg | ttgtaaacat | 1320 |
| cctgaagcaa | aaagaatgcc | ctgtgcagaa | gactatctat | ccgtggtcct | gaaccagtta | 1380 |
| tgtgtgttgc | atgagaaaac | gccagtaagt | gacagagtca | ccaaatgctg | cacagaatcc | 1440 |
| ttggtgaaca | ggcgaccatg | cttttcagct | ctggaagtcg | acgaaacata | cgttcccaaa | 1500 |
| gagtttaatt | gtgaaacatt | caccttccat | gcagatatat | gcacactttc | tgagaaggag | 1560 |
| agacaaatca | agaacaaac | tgcacttgtt | gagctcgtga | acacaagcc | caaggcaaca | 1620 |
| aaagagcaac | tgaaagctgt | tatggatgat | ttcgcagctt | ttgtagagaa | gtgctgcaag | 1680 |
| gctgacgata | aggagacctg | ctttgccgag | gagggtaaaa | aacttgttgc | tgcaagtcaa | 1740 |
| gctgccttag | gcttataa | | | | | 1758 |

<210> SEQ ID NO 35
<211> LENGTH: 1758
<212> TYPE: DNA
<213> ORGANISM: Artificial sequence
<220> FEATURE:
<223> OTHER INFORMATION: TA35: HA with A2C, A364C and D562C

<400> SEQUENCE: 35

| | | | | | |
|---|---|---|---|---|---|
| gattgtcaca | agagtgaggt | tgctcatcgg | tttaaagatt | tgggagaaga | aaatttcaaa | 60 |

```
gccttggtgt tgattgcctt tgctcagtat cttcagcagt gtccatttga agatcatgta      120
aaattagtga atgaagtaac tgaatttgca aaaacatgtg ttgctgatga gtccgcggaa      180
aattgtgaca aatcacttca taccctttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttactttat gccccggaac tccttttctt tgctaaaagg      480
tataaagctg cttttacaga atgttgccaa gctgctgata agctgcctg cctgttgcca      540 aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag gcggaccttt     780
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctt gtgatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga agtaccccca agtgtcaact     1260
ccaactcttg tagaggtctc aagaaaccta ggaaaagtgg gatccaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca gcgaccatg cttttcagct ctggaagtcg acgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caggcaaca     1620 aaagagcaac tgaaagctgt tatggatgat ttcgcagctt ttgtagagaa gtgctgcaag     1680
gcttgtgata ggagacctg ctttgccgag gagggtaaaa aacttgttgc tgcaagtcaa     1740
gctgccttag gcttataa                                                   1758

<210> SEQ ID NO 36
<211> LENGTH: 1758
<212> TYPE: DNA
<213> ORGANISM: Artificial sequence
<220> FEATURE:
<223> OTHER INFORMATION: TA36: HA with A2C, C34A, A364C and D562C

<400> SEQUENCE: 36
gattgtcaca agagtgaggt tgctcatcgg tttaaagatt tgggagaaga aaatttcaaa       60
gccttggtgt tgattgcctt tgctcagtat cttcagcagg ctccatttga agatcatgta      120
aaattagtga atgaagtaac tgaatttgca aaaacatgtg ttgctgatga gtccgcggaa      180
aattgtgaca aatcacttca taccctttt ggagacaaat tatgcacagt tgcaactctt      240
cgtgaaacct atggtgaaat ggctgactgc tgtgcaaaac aagaacctga gagaaatgaa      300
```

```
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca gaagacatcc ttacttttat gccccggaac tccttttctt tgctaaaagg    480
tataaagctg cttttacaga atgttgccaa gctgctgata agctgcctg cctgttgcca     540 aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag gcggacctt     780 gccaagtata tctgtgaaaa tcaagattcg atctccagta aactgaagga atgctgtgaa    840
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctt gtgatcctca tgaatgctat gccaaagtgt tcgatgaatt taaacctctt   1140
gtggaagagc ctcagaattt aatcaaacaa aattgtgagc tttttgagca gcttggagag   1200
tacaaattcc agaatgcgct attagttcgt tacaccaaga agtacccca agtgtcaact    1260 ccaactcttg tagaggtctc aagaaaccta ggaaaagtgg atccaaatg ttgtaaacat     1320 cctgaagcaa aaagaatgcc ctgtgcagaa gactatctat ccgtggtcct gaaccagtta   1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca    1620 aaagagcaac tgaaagctgt tatggatgat ttcgcagctt ttgtagagaa gtgctgcaag   1680
gcttgtgata aggagacctg ctttgccgag agggtaaaa acttgttgc tgcaagtcaa     1740 gctgccttag gcttataa                                                  1758

<210> SEQ ID NO 37
<211> LENGTH: 1758
<212> TYPE: DNA
<213> ORGANISM: Artificial sequence
<220> FEATURE:
<223> OTHER INFORMATION: TA38: HA withA2C, A364C, D562C and L585C

<400> SEQUENCE: 37
gattgtcaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca aatcacttca taccttttt ggagacaaat tatgcacagt tgcaactctt     240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca gaagacatcc ttacttttat gccccggaac tccttttctt tgctaaaagg    480
tataaagctg cttttacaga atgttgccaa gctgctgata agctgcctg cctgttgcca     540 aagctcgatg aacttcggga tgaagggaag gctagctctg ccaaacagag actcaagtgt    600
```

```
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag gcggaccttt      780
gccaagtata tctgtgaaaa tcaagattcg atctccagta aactgaagga atgctgtgaa      840
aaacctctgt tggaaaaatc ccactgcatt gccgaagtgg aaaatgatga gatgcctgct      900
gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctt gtgatcctca tgaatgctat gccaaagtgt tcgatgaatt taaacctctt     1140
gtggaagagc tcagaatttt aatcaaacaa aattgtgagc tttttgagca gcttggagag     1200
tacaaattcc agaatgcgct attagttcgt tacaccaaga aagtaccccca agtgtcaact     1260 ccaactcttg tagaggtctc aagaaaccta ggaaaagtgg gatccaaatg ttgtaaacat     1320
cctgaagcaa aagaatgcc ctgtgcagaa gactatctat ccgtggtcct gaaccagtta      1380
tgtgtgttgc atgagaaaac gccagtaagt gacagagtca ccaaatgctg cacagaatcc     1440
ttggtgaaca ggcgaccatg cttttcagct ctggaagtcg acgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caaggcaaca      1620 aaagagcaac tgaaagctgt tatggatgat ttcgcagctt ttgtagagaa gtgctgcaag     1680
gcttgtgata aggagacctg cttgccgag gagggtaaaa aacttgttgc tgcaagtcaa      1740
gctgccttag gctgttaa                                                    1758

<210> SEQ ID NO 38
<211> LENGTH: 1758
<212> TYPE: DNA
<213> ORGANISM: Artificial sequence
<220> FEATURE:
<223> OTHER INFORMATION: TA39: HA with C34A, A504C and E505C.

<400> SEQUENCE: 38
gatgcacaca agagtgaggt tgctcatcgg tttaaagatt gggagaaga aaatttcaaa       60 gccttggtgt tgattgcctt tgctcagtat cttcagcagg ctccatttga agatcatgta     120
aaattagtga atgaagtaac tgaatttgca aaaacatgtg ttgctgatga gtccgcggaa     180
aattgtgaca atcacttcca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttacttttat gccccggaac tccttttctt tgctaaaagg      480
tataaagctg cttttacaga atgttgccaa gctgctgata agctgcctg cctgttgcca      540 aagctcgatg aacttcggga tgaagggaag ctagctctg ccaaacagag actcaagtgt      600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg ctcgagtgtg ctgatgacag gcggaccttt     780
gccaagtata tctgtgaaaa tcaagattcg atctccagta aactgaagga atgctgtgaa     840
```

| aaacctctgt tggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |
| gtggaagagc ctcagaattt aatcaaacaa aattgtgagc tttttgagca gcttggagag | 1200 |
| tacaaattcc agaatgcgct attagttcgt tacaccaaga aagtacccca agtgtcaact | 1260 |
| ccaactcttg tagaggtctc aagaaaccta ggaaaagtgg gatccaaatg ttgtaaacat | 1320 |
| cctgaagcaa aagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatt gttgtacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa acttgttgc tgcaagtcaa | 1740 |
| gctgccttag gcttataa | 1758 |

<210> SEQ ID NO 39
<211> LENGTH: 1758
<212> TYPE: DNA
<213> ORGANISM: Artificial sequence
<220> FEATURE:
<223> OTHER INFORMATION: TA41: HA with S270C and A581C

<400> SEQUENCE: 39

| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca aatcacttca tacccttttt ggagacaaat tatgcacagt tgcaactctt | 240 |
| cgtgaaacct atggtgaaat ggctgactgc tgtgcaaaac aagaacctga gagaaatgaa | 300 |
| tgcttcttgc aacacaaaga tgacaaccca aacctccccc gattggtgag accagaggtt | 360 |
| gatgtgatgt gcactgcttt tcatgacaat gaagagacat ttttgaaaaa atacttatat | 420 |
| gaaattgcca aagacatcc ttacttttat gccccggaac tccttttctt tgctaaaagg | 480 |
| tataaagctg cttttacaga atgttgccaa gctgctgata agctgcctg cctgttgcca | 540 |
| aagctcgatg aacttcggga tgaagggaag ctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag gcggaccctt | 780 |
| gccaagtata tctgtgaaaa tcaagattgt atctccagta aactgaagga atgctgtgaa | 840 |
| aaacctctgt ggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |

```
gtggaagagc tcagaattt aatcaaacaa aattgtgagc ttttgagca gcttggagag    1200 tacaaattcc agaatgcgct attagttcgt tacaccaaga agtacccca agtgtcaact    1260 ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620 aaagagcaac tgaaagctgt tatggatgat ttcgcagctt ttgtagagaa gtgctgcaag    1680
gctgacgata aggagacctg ctttgccgag gagggtaaaa aacttgttgc tgcaagtcaa    1740
tgtgccttag gcttataa                                                1758

<210> SEQ ID NO 40
<211> LENGTH: 1758
<212> TYPE: DNA
<213> ORGANISM: Artificial sequence
<220> FEATURE:
<223> OTHER INFORMATION: TA43: HA with D129C, S270C and A581C

<400> SEQUENCE: 40
gatgcacaca agagtgaggt tgctcatcgg tttaaagatt tgggagaaga aaatttcaaa     60
gccttggtgt tgattgcctt tgctcagtat cttcagcagt gtccatttga agatcatgta    120
aaattagtga atgaagtaac tgaatttgca aaaacatgtg ttgctgatga gtccgcggaa    180
aattgtgaca atccacttca tacccttttt ggagacaaat tatgcacagt tgcaactctt    240
cgtgaaacct atggtgaaat ggctgactgc tgtgcaaaac aagaacctga gagaaatgaa    300
tgcttcttgc aacacaaaga tgacaaccca aacctccccc gattggtgag accagaggtt    360
gatgtgatgt gcactgcttt tcattgtaat gaagagacat ttttgaaaaa atacttatat    420
gaaattgcca agacatcc ttactttat gcccgggaac tccttttctt tgctaaaagg    480
tataaagctg ctttacaga atgttgccaa gctgctgata agctgcctg cctgttgcca    540 aagctcgatg aacttcggga tgaagggaag gctagctctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg ctcgagtgtg ctgatgacag gcggaccctt    780
gccaagtata tctgtgaaaa tcaagattgt atctccagta aactgaagga atgctgtgaa    840
aaacctctgt ggaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg ctgatcctca tgaatgctat gccaaagtgt tcgatgaatt taaacctctt    1140
gtggaagagc tcagaattt aatcaaacaa aattgtgagc ttttgagca gcttggagag    1200 tacaaattcc agaatgcgct attagttcgt tacaccaaga agtacccca agtgtcaact    1260 ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
```

| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa aacttgttgc tgcaagtcaa | 1740 |
| tgtgccttag gcttataa | 1758 |

<210> SEQ ID NO 41
<211> LENGTH: 1758
<212> TYPE: DNA
<213> ORGANISM: Artificial sequence
<220> FEATURE:
<223> OTHER INFORMATION: TA46: HA with C169S

<400> SEQUENCE: 41

| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca aatcacttca tacccttttt ggagacaaat tatgcacagt tgcaactctt | 240 |
| cgtgaaacct atggtgaaat ggctgactgc tgtgcaaaac aagaacctga gaaaatgaa | 300 |
| tgcttcttgc aacacaaaga tgacaaccca aacctccccc gattggtgag accagaggtt | 360 |
| gatgtgatgt gcactgcttt tcatgacaat gaagagacat tttgaaaaa atacttatat | 420 |
| gaaattgcca gaagacatcc ttactttat gccccggaac tccttttctt tgctaaaagg | 480 |
| tataaagctg cttttacaga atgttctcaa gctgctgata agctgcctg cctgttgcca | 540 |
| aagctcgatg aacttcggga tgaagggaag gctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag gcggaccctt | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgattttgtt gaaagtaagg atgttgctaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |
| gtggaagagc ctcagaattt aatcaaacaa aattgtgagc ttttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg gatccaaatg ttgtaaacat | 1320 |
| cctgaagcaa aagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |

```
<210> SEQ ID NO 42
<211> LENGTH: 1758
<212> TYPE: DNA
<213> ORGANISM: Artificial sequence
<220> FEATURE:
<223> OTHER INFORMATION: TA47: HA with D129C, C360S and L585C

<400> SEQUENCE: 42
```

| | |
|---|---:|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca atcacttca tacccttttt ggagacaaat tatgcacagt tgcaactctt | 240 |
| cgtgaaacct atggtgaaat ggctgactgc tgtgcaaaac aagaacctga gagaaatgaa | 300 |
| tgcttcttgc aacacaaaga tgacaaccca aacctccccc gattggtgag accagaggtt | 360 |
| gatgtgatgt gcactgcttt tcattgtaat gaagagacat ttttgaaaaa atacttatat | 420 |
| gaaattgcca agacatcc ttactttat gccccggaac tccttttctt tgctaaaagg | 480 |
| tataagctg cttttacaga atgttgccaa gctgctgata agctgcctg cctgttgcca | 540 |
| aagctcgatg aacttcggga tgaagggaag gctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag gcggaccct | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtct | 1080 |
| tgtgccgctg ctgatcctca tgaatgctat gccaaagtgt tcgatgaatt taaacctctt | 1140 |
| gtggaagagc tcagaattt aatcaaacaa aattgtgagc ttttgagca gcttggagag | 1200 |
| tacaaattcc agaatgcgct attagttcgt tacaccaaga agtaccccca agtgtcaact | 1260 |
| ccaactcttg tagaggtctc aagaaaccta ggaaaagtgg atccaaatg ttgtaaacat | 1320 |
| cctgaagcaa aaagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa aacttgttgc tgcaagtcaa | 1740 |
| gctgccttag gctgttaa | 1758 |

```
<210> SEQ ID NO 43
<211> LENGTH: 1761
<212> TYPE: DNA
```

<213> ORGANISM: Artificial sequence
<220> FEATURE:
<223> OTHER INFORMATION: TA51: HA with A2C and a cysteine immediately before the stop codon

<400> SEQUENCE: 43

```
gattgtcaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtccgcggaa     180
aattgtgaca aatcacttca taccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttactttta gccccggaac tccttttctt tgctaaaagg     480
tataaagctg cttttacaga atgttgccaa gctgctgata agctgcctg cctgttgcca     540
aagctcgatg aacttcggga tgaagggaag gctagctctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg ctcgagtgtg ctgatgacag gcggaccttg     780
gccaagtata tctgtgaaaa tcaagattcg atctccagta aactgaagga atgctgtgaa     840
aaacctctgt tggaaaaatc ccactgcatt gccgaagtgg aaaatgatga atgcctgct     900
gacttgcctt cattagctgc tgattttgtt gaaagtaagg atgtttgcaa aactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg ctgatcctca tgaatgctat gccaaagtgt tcgatgaatt taaacctctt    1140
gtggaagagc ctcagaattt aatcaaacaa aattgtgagc ttttttgagca gcttggagag    1200
tacaaattcc agaatgcgct attagttcgt tacaccaaga aagtaccca agtgtcaact    1260
ccaactcttg tagaggtctc aagaaaccta ggaaaagtgg gatccaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg acgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caggcaaca    1620
aaagagcaac tgaaagctgt tatggatgat ttcgcagctt ttgtagagaa gtgctgcaag    1680
gctgacgata aggagaacctg cttttgccgag gagggtaaaa aacttgttgc tgcaagtcaa    1740
gctgccttag gcttatgtta a                                              1761
```

<210> SEQ ID NO 44
<211> LENGTH: 1761
<212> TYPE: DNA
<213> ORGANISM: Artificial sequence
<220> FEATURE:
<223> OTHER INFORMATION: TA57: HA with A2C and a Cys insertion between G584 and L585

<400> SEQUENCE: 44

```
gattgtcaca agagtgaggt tgctcatcgg tttaaagatt tgggagaaga aaatttcaaa      60
```

```
gccttggtgt tgattgcctt tgctcagtat cttcagcagt gtccatttga agatcatgta      120
aaattagtga atgaagtaac tgaatttgca aaaacatgtg ttgctgatga gtccgcggaa      180
aattgtgaca aatcacttca tacccttttt ggagacaaat tatgcacagt tgcaactctt      240
cgtgaaacct atggtgaaat ggctgactgc tgtgcaaaac aagaacctga gagaaatgaa      300
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca aagacatcc ttactttat gccccggaac tccttttctt tgctaaaagg       480
tataaagctg cttttacaga atgttgccaa gctgctgata agctgcctg cctgttgcca      540 aagctcgatg aacttcggga tgaagggaag gctagctctg ccaaacagag actcaagtgt      600
gccagtctcc aaaaatttgg agaaagagct ttcaaagcat gggcagtagc tcgcctgagc      660
cagagatttc ccaaagctga gtttgcagaa gtttccaagt tagtgacaga tcttaccaaa      720
gtccacacgg aatgctgcca tggagatctg ctcgagtgtg ctgatgacag gcggaccttt     780
gccaagtata tctgtgaaaa tcaagattcg atctccagta aactgaagga atgctgtgaa      840
aaacctctgt tggaaaaatc ccactgcatt gccgaagtgg aaaatgatga atgcctgct      900 gacttgcctt cattagctgc tgattttgtt gaaagtaagg atgtttgcaa aaactatgct      960
gaggcaaagg atgtcttcct gggcatgttt ttgtatgaat atgcaagaag gcatcctgat     1020
tactctgtcg tgctgctgct gagacttgcc aagacatatg aaaccactct agagaagtgc     1080
tgtgccgctg ctgatcctca tgaatgctat gccaaagtgt tcgatgaatt taaacctctt     1140
gtggaagagc ctcagaattt aatcaaacaa aattgtgagc tttttgagca gcttggagag     1200
tacaaattcc agaatgcgct attagttcgt tacaccaaga aagtaccccca agtgtcaact     1260 ccaactcttg tagaggtctc aagaaaccta ggaaaagtgg gatccaaatg ttgtaaacat     1320
cctgaagcaa aaagaatgcc ctgtgcagaa gactatctat ccgtggtcct gaaccagtta     1380
tgtgtgttgc atgagaaaac gccagtaagt gacagagtca ccaaatgctg cacagaatcc     1440
ttggtgaaca ggcgaccatg cttttcagct ctggaagtcg acgaaacata cgttcccaaa     1500
gagtttaatg ctgaaacatt caccttccat gcagatatat gcacactttc tgagaaggag     1560
agacaaatca gaaacaaac tgcacttgtt gagctcgtga acacaagcc caaggcaaca     1620 aaagagcaac tgaaagctgt tatggatgat ttcgcagctt ttgtagagaa gtgctgcaag     1680
gctgacgata ggagacctg ctttgccgag gagggtaaaa aacttgttgc tgcaagtcaa     1740
gctgccttag ctgtttata a                                              1761
```

<210> SEQ ID NO 45
<211> LENGTH: 1755
<212> TYPE: DNA
<213> ORGANISM: Artificial sequence
<220> FEATURE:
<223> OTHER INFORMATION: TA60: HA with A2C deltion of C316

<400> SEQUENCE: 45

```
gattgtcaca agagtgaggt tgctcatcgg tttaaagatt tgggagaaga aaatttcaaa       60
gccttggtgt tgattgcctt tgctcagtat cttcagcagt gtccatttga agatcatgta      120
aaattagtga atgaagtaac tgaatttgca aaaacatgtg ttgctgatga gtccgcggaa      180
aattgtgaca aatcacttca tacccttttt ggagacaaat tatgcacagt tgcaactctt      240
cgtgaaacct atggtgaaat ggctgactgc tgtgcaaaac aagaacctga gagaaatgaa      300
```

```
tgcttcttgc aacacaaaga tgacaaccca aacctccccc gattggtgag accagaggtt      360
gatgtgatgt gcactgcttt tcatgacaat gaagagacat ttttgaaaaa atacttatat      420
gaaattgcca gaagacatcc ttactttat gccccggaac tccttttctt tgctaaaagg      480
tataaagctg cttttacaga atgttgccaa gctgctgata agctgcctg cctgttgcca       540 aagctcgatg aacttcggga tgaagggaag gctagctctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa      720
gtccacacgg aatgctgcca tggagatctg ctcgagtgtg ctgatgacag gcggacctt      780 gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgttaaaaa ctatgctgag     960
gcaaaggatg tcttcctggg catgtttttg tatgaatatg caagaaggca tcctgattac    1020
tctgtcgtgc tgctgctgag acttgccaag acatatgaaa ccactctaga gaagtgctgt    1080
gccgctgctg atcctcatga atgctatgcc aaagtgttcg atgaatttaa acctcttgtg    1140
gaagagcctc agaattaat caaacaaat tgtgagcttt ttgagcagct tggagagtac      1200
aaattccaga atgcgctatt agttcgttac accaagaaag taccccaagt gtcaactcca    1260
actcttgtag aggtctcaag aaacctagga aaagtgggat ccaaatgttg taaacatcct    1320
gaagcaaaaa gaatgccctg tgcagaagac tatctatccg tggtcctgaa ccagttatgt    1380
gtgttgcatg agaaaacgcc agtaagtgac agagtcacca aatgctgcac agaatccttg   1440
gtgaacaggc gaccatgctt ttcagctctg gaagtcgacg aaacatacgt tcccaaagag    1500
tttaatgctg aaacattcac cttccatgca gatatatgca cactttctga aaggagaga    1560 caaatcaaga acaaactgc acttgttgag ctcgtgaaac acaagcccaa ggcaacaaaa    1620
gagcaactga agctgttat ggatgatttc gcagcttttg tagagaagtg ctgcaaggct    1680
gacgataagg agacctgctt tgccgaggag ggtaaaaaac ttgttgctgc aagtcaagct   1740
gccttaggct tataa                                                     1755

<210> SEQ ID NO 46
<211> LENGTH: 1758
<212> TYPE: DNA
<213> ORGANISM: Artificial sequence
<220> FEATURE:
<223> OTHER INFORMATION: TA63: HA with H39C and C253P

<400> SEQUENCE: 46
gatgcacaca agagtgaggt tgctcatcgg tttaaagatt tgggagaaga aaatttcaaa       60
gccttggtgt tgattgcctt tgctcagtat cttcagcagt gtccatttga agattgtgta     120
aaattagtga atgaagtaac tgaatttgca aaaacatgtg ttgctgatga gtccgcggaa    180
aattgtgaca atcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca gaagacatcc ttactttat gccccggaac tccttttctt tgctaaaagg      480
tataaagctg cttttacaga atgttgccaa gctgctgata agctgcctg cctgttgcca      540 aagctcgatg aacttcggga tgaagggaag gctagctctg ccaaacagag actcaagtgt    600
```

| | |
|---|---|
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagccag ctgatgacag ggcggacctt | 780 |
| gccaagtata tctgtgaaaa tcaagattcg atctccagta aactgaagga atgctgtgaa | 840 |
| aaacctctgt tggaaaaatc ccactgcatt gccgaagtgg aaaatgatga gatgcctgct | 900 |
| gacttgcctt cattagctgc tgattttgtt gaaagtaagg atgtttgcaa aaactatgct | 960 |
| gaggcaaagg atgtcttcct gggcatgttt ttgtatgaat atgcaagaag gcatcctgat | 1020 |
| tactctgtcg tgctgctgct gagacttgcc aagacatatg aaaccactct agagaagtgc | 1080 |
| tgtgccgctg ctgatcctca tgaatgctat gccaaagtgt tcgatgaatt taaacctctt | 1140 |
| gtggaagagc ctcagaattt aatcaaacaa aattgtgagc tttttgagca gcttggagag | 1200 |
| tacaaattcc agaatgcgct attagttcgt tacaccaaga aagtacccca agtgtcaact | 1260 |
| ccaactcttg tagaggtctc aagaaaccta ggaaaagtgg gatccaaatg ttgtaaacat | 1320 |
| cctgaagcaa aagaatgcc ctgtgcagaa gactatctat ccgtggtcct gaaccagtta | 1380 |
| tgtgtgttgc atgagaaaac gccagtaagt gacagagtca ccaaatgctg cacagaatcc | 1440 |
| ttggtgaaca ggcgaccatg cttttcagct ctggaagtcg acgaaacata cgttcccaaa | 1500 |
| gagtttaatg ctgaaacatt caccttccat gcagatatat gcacactttc tgagaaggag | 1560 |
| agacaaatca gaaacaaac tgcacttgtt gagctcgtga acacaagcc caaggcaaca | 1620 |
| aaagagcaac tgaaagctgt tatggatgat ttcgcagctt ttgtagagaa gtgctgcaag | 1680 |
| gctgacgata aggagacctg ctttgccgag gagggtaaaa acttgttgc tgcaagtcaa | 1740 |
| gctgccttag gcttataa | 1758 |

<210> SEQ ID NO 47
<211> LENGTH: 1758
<212> TYPE: DNA
<213> ORGANISM: Artificial sequence
<220> FEATURE:
<223> OTHER INFORMATION: TA64: HA with C177F

<400> SEQUENCE: 47

| | |
|---|---|
| gatgcacaca agagtgaggt tgctcatcgg tttaaagatt tgggagaaga aaatttcaaa | 60 |
| gccttggtgt tgattgcctt tgctcagtat cttcagcagt gtccatttga agatcatgta | 120 |
| aaattagtga atgaagtaac tgaatttgca aaaacatgtg ttgctgatga gtccgcggaa | 180 |
| aattgtgaca atcacttca tacccttttt ggagacaaat tatgcacagt tgcaactctt | 240 |
| cgtgaaacct atggtgaaat ggctgactgc tgtgcaaaac aagaacctga gagaatgaa | 300 |
| tgcttcttgc aacacaaaga tgacaaccca aacctcccc gattggtgag accagaggtt | 360 |
| gatgtgatgt gcactgcttt tcatgacaat gaagagacat ttttgaaaaa atacttatat | 420 |
| gaaattgcca aagacatcc ttacttttat gccccggaac tccttttctt tgctaaaagg | 480 |
| tataaagctg cttttacaga atgttgccaa gctgctgata agctgccctt tctgttgcca | 540 |
| aagctcgatg aacttcggga tgaagggaag gctagctctg ccaaacagag actcaagtgt | 600 |
| gccagtctcc aaaaatttgg agaaagagct ttcaaagcat gggcagtagc tcgcctgagc | 660 |
| cagagatttc ccaaagctga gtttgcagaa gtttccaagt tagtgacaga tcttaccaaa | 720 |
| gtccacacgg aatgctgcca tggagatctg ctcgagtgtg ctgatgacag ggcggacctt | 780 |
| gccaagtata tctgtgaaaa tcaagattcg atctccagta aactgaagga atgctgtgaa | 840 |

```
aaacctctgt tggaaaaatc ccactgcatt gccgaagtgg aaaatgatga gatgcctgct    900
gacttgcctt cattagctgc tgattttgtt gaaagtaagg atgtttgcaa aaactatgct    960
gaggcaaagg atgtcttcct gggcatgttt ttgtatgaat atgcaagaag gcatcctgat   1020
tactctgtcg tgctgctgct gagacttgcc aagacatatg aaaccactct agagaagtgc   1080
tgtgccgctg ctgatcctca tgaatgctat gccaaagtgt tcgatgaatt taaacctctt   1140
gtggaagagc tcagaatttt aatcaaacaa aattgtgagc ttttttgagca gcttggagag   1200
tacaaattcc agaatgcgct attagttcgt tacaccaaga aagtacccca agtgtcaact   1260
ccaactcttg tagaggtctc aagaaaccta ggaaaagtgg gatccaaatg ttgtaaacat   1320
cctgaagcaa aagaatgcc ctgtgcagaa gactatctat ccgtggtcct gaaccagtta    1380
tgtgtgttgc atgagaaaac gccagtaagt gacagagtca ccaaatgctg cacagaatcc   1440
ttggtgaaca ggcgaccatg cttttcagct ctggaagtcg acgaaacata cgttcccaaa   1500
gagtttaatg ctgaaacatt caccttccat gcagatatat gcacactttc tgagaaggag   1560
agacaaatca gaaacaaac tgcacttgtt gagctcgtga acacaagcc caaggcaaca    1620
aaagagcaac tgaaagctgt tatggatgat ttcgcagctt ttgtagagaa gtgctgcaag   1680
gctgacgata aggagcctg ctttgccgag gagggtaaaa aacttgttgc tgcaagtcaa    1740
gctgccttag gcttataa                                                 1758
```

<210> SEQ ID NO 48
<211> LENGTH: 1767
<212> TYPE: DNA
<213> ORGANISM: Artificial sequence
<220> FEATURE:
<223> OTHER INFORMATION: TA65: HA with a Cys at the N-terminus and an Ala-Cys extension at the C-terminus

<400> SEQUENCE: 48

```
tgtgatgcac acaagagtga ggttgctcat cggtttaaag atttgggaga agaaaatttc     60
aaagccttgg tgttgattgc ctttgctcag tatcttcagc agtgtccatt tgaagatcat    120
gtaaaattag tgaatgaagt aactgaattt gcaaaaacat gtgttgctga tgagtccgcg    180
gaaaattgtg acaaatcact tcatacccctt tttggagaca aattatgcac agttgcaact    240
cttcgtgaaa cctatggtga aatggctgac tgctgtgcaa acaagaacc tgagagaaat    300
gaatgcttct tgcaacacaa agatgacaac ccaaacctcc cccgattggt gagaccagag   360
gttgatgtga tgtgcactgc ttttcatgac aatgaagaga catttttgaa aaaatactta   420
tatgaaattg ccagaagaca tccttacttt tatgccccgg aactcctttt ctttgctaaa   480
aggtataaag ctgcttttac agaatgttgc caagctgctg ataaagctgc ctgcctgttg   540
ccaaagctcg atgaacttcg ggatgaaggg aaggctagct ctgccaaaca gagactcaag   600
tgtgccagtc tccaaaaatt tggagaaaga gctttcaaag catgggcagt agctcgcctg   660
agccagagat ttcccaaagc tgagtttgca gaagtttcca gttagtgac agatcttacc    720
aaagtccaca cggaatgctg ccatggagat ctgctcgagt gtgctgatga cagggcggac   780
cttgccaagt atatctgtga aaatcaagat tcgatctcca gtaaactgaa ggaatgctgt   840
gaaaaacctc tgttggaaaa atcccactgc attgccgaag tggaaaatga tgagatgcct   900
gctgacttgc cttcattagc tgctgatttt gttgaaagta aggatgtttg caaaaactat    960
gctgaggcaa aggatgtctt cctgggcatg ttttttgtatg aatatgcaag aaggcatcct  1020
gattactctg tcgtgctgct gctgagactt gccaagacat atgaaaccac tctagagaag  1080
```

```
tgctgtgccg ctgctgatcc tcatgaatgc tatgccaaag tgttcgatga atttaaacct    1140
cttgtggaag agcctcagaa tttaatcaaa caaaattgtg agcttttga gcagcttgga    1200 gagtacaaat tccagaatgc gctattagtt cgttacacca agaaagtacc ccaagtgtca    1260
actccaactc ttgtagaggt ctcaagaaac ctaggaaaag tgggatccaa atgttgtaaa    1320
catcctgaag caaaaagaat gccctgtgca gaagactatc tatccgtggt cctgaaccag    1380
ttatgtgtgt tgcatgagaa aacgccagta agtgacagag tcaccaaatg ctgcacagaa    1440
tccttggtga acaggcgacc atgctttca gctctggaag tcgacgaaac atacgttccc    1500
aaagagttta atgctgaaac attccccttc catgcagata tatgcacact ttctgagaag    1560
gagagacaaa tcaagaaaca aactgcactt gttgagctcg tgaaacacaa gcccaaggca    1620 acaaagagc aactgaaagc tgttatggat gatttcgcag cttttgtaga gaagtgctgc    1680
aaggctgacg ataaggagac ctgctttgcc gaggagggta aaaaacttgt tgctgcaagt    1740
caagctgcct taggcttagc ttgttaa    1767
```

<210> SEQ ID NO 49
<211> LENGTH: 609
<212> TYPE: PRT
<213> ORGANISM: Artificial Sequence
<220> FEATURE:
<223> OTHER INFORMATION: HA with fusion leader sequence

<400> SEQUENCE: 49

```
Met Lys Trp Val Ser Phe Ile Ser Leu Leu Phe Leu Phe Ser Ser Ala
1               5                   10                  15

Tyr Ser Arg Ser Leu Asp Lys Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240
```

```
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
            260                 265                 270
Asp Leu Leu Glu Cys Ala Asp Asp Arg Ala Asp Leu Ala Lys Tyr Ile
        275                 280                 285
Cys Glu Asn Gln Asp Ser Ile Ser Ser Lys Leu Lys Glu Cys Cys Glu
    290                 295                 300
Lys Pro Leu Leu Glu Lys Ser His Cys Ile Ala Glu Val Glu Asn Asp
305                 310                 315                 320
Glu Met Pro Ala Asp Leu Pro Ser Leu Ala Ala Asp Phe Val Glu Ser
                325                 330                 335
Lys Asp Val Cys Lys Asn Tyr Ala Glu Ala Lys Asp Val Phe Leu Gly
            340                 345                 350
Met Phe Leu Tyr Glu Tyr Ala Arg Arg His Pro Asp Tyr Ser Val Val
        355                 360                 365
Leu Leu Leu Arg Leu Ala Lys Thr Tyr Glu Thr Thr Leu Glu Lys Cys
    370                 375                 380
Cys Ala Ala Ala Asp Pro His Glu Cys Tyr Ala Lys Val Phe Asp Glu
385                 390                 395                 400
Phe Lys Pro Leu Val Glu Glu Pro Gln Asn Leu Ile Lys Gln Asn Cys
                405                 410                 415
Glu Leu Phe Glu Gln Leu Gly Glu Tyr Lys Phe Gln Asn Ala Leu Leu
            420                 425                 430
Val Arg Tyr Thr Lys Lys Val Pro Gln Val Ser Thr Pro Thr Leu Val
        435                 440                 445
Glu Val Ser Arg Asn Leu Gly Lys Val Gly Ser Lys Cys Cys Lys His
    450                 455                 460
Pro Glu Ala Lys Arg Met Pro Cys Ala Glu Asp Tyr Leu Ser Val Val
465                 470                 475                 480
Leu Asn Gln Leu Cys Val Leu His Glu Lys Thr Pro Val Ser Asp Arg
                485                 490                 495
Val Thr Lys Cys Cys Thr Glu Ser Leu Val Asn Arg Arg Pro Cys Phe
            500                 505                 510
Ser Ala Leu Glu Val Asp Glu Thr Tyr Val Pro Lys Glu Phe Asn Ala
        515                 520                 525
Glu Thr Phe Thr Phe His Ala Asp Ile Cys Thr Leu Ser Glu Lys Glu
    530                 535                 540
Arg Gln Ile Lys Lys Gln Thr Ala Leu Val Glu Leu Val Lys His Lys
545                 550                 555                 560
Pro Lys Ala Thr Lys Glu Gln Leu Lys Ala Val Met Asp Asp Phe Ala
                565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
        595                 600                 605
Leu

<210> SEQ ID NO 50
<211> LENGTH: 585
<212> TYPE: PRT
<213> ORGANISM: Artificial sequence
<220> FEATURE:
<223> OTHER INFORMATION: TA1: HA with A2C
```

-continued

```
<400> SEQUENCE: 50

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
    115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
    275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
    355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 51
<211> LENGTH: 585
<212> TYPE: PRT
<213> ORGANISM: Artificial sequence
<220> FEATURE:
<223> OTHER INFORMATION: TA2: HA with D1C

<400> SEQUENCE: 51

Cys Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

```
Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 52
<211> LENGTH: 585
```

<212> TYPE: PRT
<213> ORGANISM: Artificial sequence
<220> FEATURE:
<223> OTHER INFORMATION: TA3: HA with C75S

<400> SEQUENCE: 52

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Ser Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380
```

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
            565                 570                 575

Ala Ala Ser Gln Ala Ala Leu Gly Leu
            580                 585

<210> SEQ ID NO 53
<211> LENGTH: 585
<212> TYPE: PRT
<213> ORGANISM: Artificial sequence
<220> FEATURE:
<223> OTHER INFORMATION: TA4: HA with T79C

<400> SEQUENCE: 53

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln

```
Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
```

-continued

```
              580                 585

<210> SEQ ID NO 54
<211> LENGTH: 585
<212> TYPE: PRT
<213> ORGANISM: Artificial sequence
<220> FEATURE:
<223> OTHER INFORMATION: TA5: HA with E82C

<400> SEQUENCE: 54

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Cys Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
```

355                 360                 365
Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 55
<211> LENGTH: 585
<212> TYPE: PRT
<213> ORGANISM: Artificial sequence
<220> FEATURE:
<223> OTHER INFORMATION: TA6: HA with E86C

<400> SEQUENCE: 55

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

G

```
            130                 135                 140
Arg His Pro Tyr Phe Tyr Ala Pro Glu Leu Leu Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560
```

```
Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 56
<211> LENGTH: 585
<212> TYPE: PRT
<213> ORGANISM: Artificial sequence
<220> FEATURE:
<223> OTHER INFORMATION: TA7: HA with C124S

<400> SEQUENCE: 56

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Ser Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335
```

```
Arg His Pro Asp Tyr Ser Val Val Leu Leu Arg Leu Ala Lys Thr
                340             345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 57
<211> LENGTH: 585
<212> TYPE: PRT
<213> ORGANISM: Artificial sequence
<220> FEATURE:
<223> OTHER INFORMATION: TA8: HA with C168S

<400> SEQUENCE: 57

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

```
Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Ser Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525
```

```
Leu Val Glu Leu Val Lys His Lys Pro Lys Ala Thr Lys Glu Gln Leu
        530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
                580                 585

<210> SEQ ID NO 58
<211> LENGTH: 585
<212> TYPE: PRT
<213> ORGANISM: Artificial sequence
<220> FEATURE:
<223> OTHER INFORMATION: TA9: HA with C169S

<400> SEQUENCE: 58

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
    115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Ser Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
    195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
    275                 280                 285
Cys Ile Ala Glu Val Glu Asn Asp Glu Met Pro Ala Asp Leu Pro Ser
290                 295                 300
```

-continued

```
Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
        340                 345                 350

Tyr Glu Thr Thr Leu Glu Lys Cys Cys Ala Ala Ala Asp Pro His Glu
    355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
        580                 585

<210> SEQ ID NO 59
<211> LENGTH: 585
<212> TYPE: PRT
<213> ORGANISM: Artificial sequence
<220> FEATURE:
<223> OTHER INFORMATION: TA10: HA with C91S

<400> SEQUENCE: 59

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Ser Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
```

```
            500                 505                 510
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 60
<211> LENGTH: 585
<212> TYPE: PRT
<213> ORGANISM: Artificial sequence
<220> FEATURE:
<223> OTHER INFORMATION: TA11: HA with D121C

<400> SEQUENCE: 60

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Cys Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
```

```
            275                 280                 285
Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 61
<211> LENGTH: 585
<212> TYPE: PRT
<213> ORGANISM: Artificial sequence
<220> FEATURE:
<223> OTHER INFORMATION: TA12: HA with D129C

<400> SEQUENCE: 61

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys P

```
                 50                   55                  60
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Cys Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
                290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
                450                 455                 460

Glu Lys Thr Pro Val Ser Asp Arg Val Thr Lys Cys Cys Thr Glu Ser
465                 470                 475                 480
```

```
Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 62
<211> LENGTH: 585
<212> TYPE: PRT
<213> ORGANISM: Artificial sequence
<220> FEATURE:
<223> OTHER INFORMATION: TA13: HA with S270C

<400> SEQUENCE: 62

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

Arg Ala Asp Leu Ala Lys Tyr Ile Cys Glu Asn Gln Asp Cys Ile Ser
                260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
    515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
        580                 585

<210> SEQ ID NO 63
<211> LENGTH: 585
<212> TYPE: PRT
<213> ORGANISM: Artificial sequence
<220> FEATURE:
<223> OTHER INFORMATION: TA14: HA with C316A

<400> SEQUENCE: 63

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

-continued

```
Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
             115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                    165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Ala Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445
```

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 64
<211> LENGTH: 585
<212> TYPE: PRT
<213> ORGANISM: Artificial sequence
<220> FEATURE:
<223> OTHER INFORMATION: TA16: HA with C360S

<400> SEQUENCE: 64

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Ser Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 65
<211> LENGTH: 585
<212> TYPE: PRT
<213> ORGANISM: Artificial sequence
<220> FEATURE:
<223> OTHER INFORMATION: TA17: HA with C361A

<400> SEQUENCE: 65
```

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
```

```
                420             425             430
Val Gly Ser Lys Cys Cys Lys His Pro Glu Ala Lys Arg Met Pro Cys
            435             440             445

Ala Glu Asp Tyr Leu Ser Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
            515             520             525

Leu Val Glu Leu Val Lys His Lys Pro Lys Ala Thr Lys Glu Gln Leu
        530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585

<210> SEQ ID NO 66
<211> LENGTH: 585
<212> TYPE: PRT
<213> ORGANISM: Artificial sequence
<220> FEATURE:
<223> OTHER INFORMATION: TA18: HA with C361S

<400> SEQUENCE: 66

Asp Ala His Lys Ser Glu Val Ala His Arg Phe Lys Asp Leu Gly Glu
1               5               10              15

Glu Asn Phe Lys Ala Leu Val Leu Ile Ala Phe Ala Gln Tyr Leu Gln
            20              25              30

Gln Cys Pro Phe Glu Asp His Val Lys Leu Val Asn Glu Val Thr Glu
        35              40              45

Phe Ala Lys Thr Cys Val Ala Asp Glu Ser Ala Glu Asn Cys Asp Lys
    50              55              60

Ser Leu His Thr Leu Phe Gly Asp Lys Leu Cys Thr Val Ala Thr Leu
65              70              75              80

Arg Glu Thr Tyr Gly Glu Met Ala Asp Cys Cys Ala Lys Gln Glu Pro
            85              90              95

Glu Arg Asn Glu Cys Phe Leu Gln His Lys Asp Asp Asn Pro Asn Leu
        100             105             110

Pro Arg Leu Val Arg Pro Glu Val Asp Val Met Cys Thr Ala Phe His
    115             120             125

Asp Asn Glu Glu Thr Phe Leu Lys Lys Tyr Leu Tyr Glu Ile Ala Arg
130             135             140

Arg His Pro Tyr Phe Tyr Ala Pro Glu Leu Leu Phe Phe Ala Lys Arg
145             150             155             160

Tyr Lys Ala Ala Phe Thr Glu Cys Cys Gln Ala Ala Asp Lys Ala Ala
            165             170             175

Cys Leu Leu Pro Lys Leu Asp Glu Leu Arg Asp Glu Gly Lys Ala Ser
        180             185             190

Ser Ala Lys Gln Arg Leu Lys Cys Ala Ser Leu Gln Lys Phe Gly Glu
```

```
            195                 200                 205
Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Ser Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 67
<211> LENGTH: 585
<212> TYPE: PRT
<213> ORGANISM: Artificial sequence
```

<220> FEATURE:
<223> OTHER INFORMATION: TA19: HA with A364C

<400> SEQUENCE: 67

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Cys Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400
```

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 68
<211> LENGTH: 585
<212> TYPE: PRT
<213> ORGANISM: Artificial sequence
<220> FEATURE:
<223> OTHER INFORMATION: TA20: HA with Q397C

<400> SEQUENCE: 68

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Cys Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

```
<210> SEQ ID NO 69
<211> LENGTH: 585
<212> TYPE: PRT
<213> ORGANISM: Artificial sequence
<220> FEATURE:
<223> OTHER INFORMATION: TA21: HA with A504C

<400> SEQUENCE: 69
```

| | | | | | | | | | | | | | | |
|---|---|---|---|---|---|---|---|---|---|---|---|---|---|---|
|Asp|Ala|His|Lys|Ser|Glu|Val|Ala|His|Arg|Phe|Lys|Asp|Leu|Gly|Glu|
|1| | |  |5| | | | |10| | | | |15| |

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Cys Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 70
<211> LENGTH: 585
<212> TYPE: PRT
<213> ORGANISM: Artificial sequence
<220> FEATURE:
<223> OTHER INFORMATION: TA22: HA with A578C

<400> SEQUENCE: 70

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

-continued

```
Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
```

-continued

```
                565                 570                 575

Ala Cys Ser Gln Ala Ala Leu Gly Leu
            580                 585

<210> SEQ ID NO 71
<211> LENGTH: 585
<212> TYPE: PRT
<213> ORGANISM: Artificial sequence
<220> FEATURE:
<223> OTHER INFORMATION: TA23: HA with A581C

<400> SEQUENCE: 71

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
```

```
                    340                 345                 350
Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Cys Ala Leu Gly Leu
        580                 585

<210> SEQ ID NO 72
<211> LENGTH: 585
<212> TYPE: PRT
<213> ORGANISM: Artificial sequence
<220> FEATURE:
<223> OTHER INFORMATION: TA24: HA with C558S

<400> SEQUENCE: 72

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
```

```
              115                 120                 125
Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540
```

```
Lys Ala Val Met Asp Asp Phe Ala Ala Phe Val Glu Lys Ser Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 73
<211> LENGTH: 585
<212> TYPE: PRT
<213> ORGANISM: Artificial sequence
<220> FEATURE:
<223> OTHER INFORMATION: TA25: HA with C567S

<400> SEQUENCE: 73

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320
```

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Ser Phe Ala Glu Glu Gly Lys Lys Leu Val
                565                 570                 575

Ala Ala Ser Gln Ala Ala Leu Gly Leu
            580                 585

<210> SEQ ID NO 74
<211> LENGTH: 585
<212> TYPE: PRT
<213> ORGANISM: Artificial sequence
<220> FEATURE:
<223> OTHER INFORMATION: TA26: HA with D549C

<400> SEQUENCE: 74

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

-continued

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

```
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Cys Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 75
<211> LENGTH: 585
<212> TYPE: PRT
<213> ORGANISM: Artificial sequence
<220> FEATURE:
<223> OTHER INFORMATION: TA27: HA with D562C

<400> SEQUENCE: 75

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
                450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
                530                 535                 540

Lys Ala Val Met Asp Asp Phe Ala Ala Phe Val Glu Lys Cys Cys Lys
545                 550                 555                 560

Ala Cys Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 76
<211> LENGTH: 585
<212> TYPE: PRT
<213> ORGANISM: Artificial sequence
<220> FEATURE:
<223> OTHER INFORMATION: TA28: HA with E505C

<400> SEQUENCE: 76

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
                35                  40                  45

Phe Ala Lys Thr Cys Val Ala Asp Glu Ser Ala Glu Asn Cys Asp Lys
50                  55                  60

-continued

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
```

-continued

```
                485                 490                 495
Tyr Val Pro Lys Glu Phe Asn Ala Cys Thr Phe Thr Phe His Ala Asp
            500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 77
<211> LENGTH: 585
<212> TYPE: PRT
<213> ORGANISM: Artificial sequence
<220> FEATURE:
<223> OTHER INFORMATION: TA29: HA with L585C

<400> SEQUENCE: 77

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
        50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
```

```
            260                 265                 270
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Cys
            580                 585

<210> SEQ ID NO 78
<211> LENGTH: 585
<212> TYPE: PRT
<213> ORGANISM: Artificial sequence
<220> FEATURE:
<223> OTHER INFORMATION: TA33: HA with A2C and L585C

<400> SEQUENCE: 78

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
```

```
                35                  40                  45
Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Cys
        580                 585

<210> SEQ ID NO 79
<211> LENGTH: 585
<212> TYPE: PRT
<213> ORGANISM: Artificial sequence
<220> FEATURE:
<223> OTHER INFORMATION: TA34: HA with A2C and A504C

<400> SEQUENCE: 79

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240
```

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Cys Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 80
<211> LENGTH: 585
<212> TYPE: PRT
<213> ORGANISM: Artificial sequence
<220> FEATURE:
<223> OTHER INFORMATION: TA35: HA with A2C, A364C and D562C

<400> SEQUENCE: 80

Asp Cys His Lys Ser Glu Val Ala His Arg Phe Lys Asp Leu Gly Glu
1               5                   10                  15

```
Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Cys Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430
```

```
Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Cys Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 81
<211> LENGTH: 585
<212> TYPE: PRT
<213> ORGANISM: Artificial sequence
<220> FEATURE:
<223> OTHER INFORMATION: TA36: HA with A2C, A364C and D562C

<400> SEQUENCE: 81

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205
```

```
Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Cys Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                500                 505                 510

Ile Cys Thr Leu Ser Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Cys Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 82
<211> LENGTH: 585
<212> TYPE: PRT
<213> ORGANISM: Artificial sequence
<220> FEATURE:
<223> OTHER INFORMATION: TA38: HA with A2C, A364C, D562C and L585C
```

<400> SEQUENCE: 82

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Cys Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro

-continued

```
                405                 410                 415
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Cys Asp Lys Glu Thr Cys Phe Ala Glu Glu Gly Lys Lys Leu Val
                565                 570                 575

Ala Ala Ser Gln Ala Ala Leu Gly Cys
            580                 585
```

<210> SEQ ID NO 83
<211> LENGTH: 585
<212> TYPE: PRT
<213> ORGANISM: Artificial sequence
<220> FEATURE:
<223> OTHER INFORMATION: TA39: HA with C34A, A504C and E505C.

<400> SEQUENCE: 83

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ala Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
```

```
                180             185              190
Ser Ala Lys Gln Arg Leu Lys Cys Ala Ser Leu Gln Lys Phe Gly Glu
            195                 200             205
Arg Ala Phe Lys Ala Trp Ala Val Ala Arg Leu Ser Gln Arg Phe Pro
            210                 215             220
Lys Ala Glu Phe Ala Glu Val Ser Lys Leu Val Thr Asp Leu Thr Lys
225             230                 235                     240
Val His Thr Glu Cys Cys His Gly Asp Leu Leu Glu Cys Ala Asp Asp
                245                 250             255
Arg Ala Asp Leu Ala Lys Tyr Ile Cys Glu Asn Gln Asp Ser Ile Ser
            260                 265             270
Ser Lys Leu Lys Glu Cys Cys Glu Lys Pro Leu Leu Glu Lys Ser His
            275                 280             285
Cys Ile Ala Glu Val Glu Asn Asp Glu Met Pro Ala Asp Leu Pro Ser
            290                 295             300
Leu Ala Ala Asp Phe Val Glu Ser Lys Asp Val Cys Lys Asn Tyr Ala
305             310                 315                     320
Glu Ala Lys Asp Val Phe Leu Gly Met Phe Leu Tyr Glu Tyr Ala Arg
                325                 330             335
Arg His Pro Asp Tyr Ser Val Val Leu Leu Leu Arg Leu Ala Lys Thr
            340                 345             350
Tyr Glu Thr Thr Leu Glu Lys Cys Cys Ala Ala Ala Asp Pro His Glu
            355                 360             365
Cys Tyr Ala Lys Val Phe Asp Glu Phe Lys Pro Leu Val Glu Glu Pro
            370                 375             380
Gln Asn Leu Ile Lys Gln Asn Cys Glu Leu Phe Glu Gln Leu Gly Glu
385             390                 395                     400
Tyr Lys Phe Gln Asn Ala Leu Leu Val Arg Tyr Thr Lys Lys Val Pro
                405                 410             415
Gln Val Ser Thr Pro Thr Leu Val Glu Val Ser Arg Asn Leu Gly Lys
            420                 425             430
Val Gly Ser Lys Cys Cys Lys His Pro Glu Ala Lys Arg Met Pro Cys
            435                 440             445
Ala Glu Asp Tyr Leu Ser Val Val Leu Asn Gln Leu Cys Val Leu His
            450                 455             460
Glu Lys Thr Pro Val Ser Asp Arg Val Thr Lys Cys Cys Thr Glu Ser
465             470                 475                     480
Leu Val Asn Arg Arg Pro Cys Phe Ser Ala Leu Glu Val Asp Glu Thr
                485                 490             495
Tyr Val Pro Lys Glu Phe Asn Cys Cys Thr Phe Thr Phe His Ala Asp
                500             505             510
Ile Cys Thr Leu Ser Glu Lys Glu Arg Gln Ile Lys Lys Gln Thr Ala
            515                 520             525
Leu Val Glu Leu Val Lys His Lys Pro Lys Ala Thr Lys Glu Gln Leu
            530                 535             540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570             575
Ala Ala Ser Gln Ala Ala Leu Gly Leu
            580             585

<210> SEQ ID NO 84
```

-continued

```
<211> LENGTH: 585
<212> TYPE: PRT
<213> ORGANISM: Artificial sequence
<220> FEATURE:
<223> OTHER INFORMATION: TA41: HA with S270C and A581C

<400> SEQUENCE: 84

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Cys Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380
```

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Cys Ala Leu Gly Leu
            580                 585

<210> SEQ ID NO 85
<211> LENGTH: 585
<212> TYPE: PRT
<213> ORGANISM: Artificial sequence
<220> FEATURE:
<223> OTHER INFORMATION: TA43: HA with D129C, S270C and A581C

<400> SEQUENCE: 85

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Cys Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

```
Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Cys Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575
```

Ala Ala Ser Gln Cys Ala Leu Gly Leu
        580                 585

<210> SEQ ID NO 86
<211> LENGTH: 585
<212> TYPE: PRT
<213> ORGANISM: Artificial sequence
<220> FEATURE:
<223> OTHER INFORMATION: TA46: HA with C169S

<400> SEQUENCE: 86

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Ser Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Ala Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

```
Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Lys His Pro Glu Ala Lys Arg Met Pro Cys
    435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 87
<211> LENGTH: 585
<212> TYPE: PRT
<213> ORGANISM: Artificial sequence
<220> FEATURE:
<223> OTHER INFORMATION: TA47: HA with D129C and L585C

<400> SEQUENCE: 87

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln

```
Cys Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Ser Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
```

-continued

```
                545                 550                 555                 560
            Ala Asp Asp Lys Glu Thr Cys Phe Ala Glu Glu Gly Lys Lys Leu Val
                            565                 570                 575

Ala Ala Ser Gln Ala Ala Leu Gly Cys
                            580                 585

<210> SEQ ID NO 88
<211> LENGTH: 586
<212> TYPE: PRT
<213> ORGANISM: Artificial sequence
<220> FEATURE:
<223> OTHER INFORMATION: TA51: HA with A2C and a cysteine immediately
      before the stop codon

<400> SEQUENCE: 88

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320
```

```
Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Cys
            580                 585

<210> SEQ ID NO 89
<211> LENGTH: 586
<212> TYPE: PRT
<213> ORGANISM: Artificial sequence
<220> FEATURE:
<223> OTHER INFORMATION: TA57: HA with A2C and an insertion between G584
      and L585

<400> SEQUENCE: 89

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

-continued

```
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Cys Leu
            580                 585

<210> SEQ ID NO 90
<211> LENGTH: 584
<212> TYPE: PRT
<213> ORGANISM: Artificial sequence
<220> FEATURE:
<223> OTHER INFORMATION: TA60: HA with A2C and deletion of C316

<400> SEQUENCE: 90

Asp Cys His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

```
Cys Ile Ala Glu Val Glu Asn Asp Glu Met Pro Ala Asp Leu Pro Ser
    290                 295                 300

Leu Ala Ala Asp Phe Val Glu Ser Lys Asp Val Lys Asn Tyr Ala Glu
305                 310                 315                 320

Ala Lys Asp Val Phe Leu Gly Met Phe Leu Tyr Glu Tyr Ala Arg Arg
                325                 330                 335

His Pro Asp Tyr Ser Val Val Leu Leu Leu Arg Leu Ala Lys Thr Tyr
            340                 345                 350

Glu Thr Thr Leu Glu Lys Cys Cys Ala Ala Ala Asp Pro His Glu Cys
        355                 360                 365

Tyr Ala Lys Val Phe Asp Glu Phe Lys Pro Leu Val Glu Glu Pro Gln
    370                 375                 380

Asn Leu Ile Lys Gln Asn Cys Glu Leu Phe Glu Gln Leu Gly Glu Tyr
385                 390                 395                 400

Lys Phe Gln Asn Ala Leu Leu Val Arg Tyr Thr Lys Lys Val Pro Gln
                405                 410                 415

Val Ser Thr Pro Thr Leu Val Glu Val Ser Arg Asn Leu Gly Lys Val
            420                 425                 430

Gly Ser Lys Cys Cys Lys His Pro Glu Ala Lys Arg Met Pro Cys Ala
        435                 440                 445

Glu Asp Tyr Leu Ser Val Val Leu Asn Gln Leu Cys Val Leu His Glu
    450                 455                 460

Lys Thr Pro Val Ser Asp Arg Val Thr Lys Cys Cys Thr Glu Ser Leu
465                 470                 475                 480

Val Asn Arg Arg Pro Cys Phe Ser Ala Leu Glu Val Asp Glu Thr Tyr
                485                 490                 495

Val Pro Lys Glu Phe Asn Ala Glu Thr Phe Thr Phe His Ala Asp Ile
            500                 505                 510

Cys Thr Leu Ser Glu Lys Glu Arg Gln Ile Lys Lys Gln Thr Ala Leu
        515                 520                 525

Val Glu Leu Val Lys His Lys Pro Lys Ala Thr Lys Glu Gln Leu Lys
    530                 535                 540

Ala Val Met Asp Asp Phe Ala Ala Phe Val Glu Lys Cys Cys Lys Ala
545                 550                 555                 560

Asp Asp Lys Glu Thr Cys Phe Ala Glu Glu Gly Lys Lys Leu Val Ala
                565                 570                 575

Ala Ser Gln Ala Ala Leu Gly Leu
            580

<210> SEQ ID NO 91
<211> LENGTH: 585
<212> TYPE: PRT
<213> ORGANISM: Artificial sequence
<220> FEATURE:
<223> OTHER INFORMATION: TA63: HA with H39C and C253P

<400> SEQUENCE: 91

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Gl

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Pro Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
```

```
                    485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
                515                 520                 525
Leu Val Glu Leu Val Lys His Lys Pro Lys Ala Thr Lys Glu Gln Leu
                530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
                580                 585

<210> SEQ ID NO 92
<211> LENGTH: 585
<212> TYPE: PRT
<213> ORGANISM: Artificial sequence
<220> FEATURE:
<223> OTHER INFORMATION: TA64: HA with C177F

<400> SEQUENCE: 92

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
                35                  40                  45
Phe Ala Lys Thr Cys Val Ala Asp Glu

```
            260                 265                 270
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 93
<211> LENGTH: 588
<212> TYPE: PRT
<213> ORGANISM: Artificial sequence
<220> FEATURE:
<223> OTHER INFORMATION: TA65: HA with a Cys at the N-terminus and an
      Ala-Cys extension at the C-terminus of HA

<400> SEQUENCE: 93

Cys Asp Ala His Lys Ser Glu Val Ala His Arg Phe Lys Asp Leu Gly
1               5                   10                  15

Glu Glu Asn Phe Lys Ala Leu Val Leu Ile Ala Phe Ala Gln Tyr Leu
            20                  25                  30
```

| | | | | | | | | | | | |
|---|---|---|---|---|---|---|---|---|---|---|---|
|Gln|Gln|Cys|Pro|Phe|Glu|Asp|His|Val|Lys|Leu|Val|Asn|Glu|Val|Thr|

Gln Gln Cys Pro Phe Glu Asp His Val Lys Leu Val Asn Glu Val Thr
              35                  40                  45

Glu Phe Ala Lys Thr Cys Val Ala Asp Glu Ser Ala Glu Asn Cys Asp
 50                  55                  60

Lys Ser Leu His Thr Leu Phe Gly Asp Lys Leu Cys Thr Val Ala Thr
 65                  70                  75                  80

Leu Arg Glu Thr Tyr Gly Glu Met Ala Asp Cys Cys Ala Lys Gln Glu
                 85                  90                  95

Pro Glu Arg Asn Glu Cys Phe Leu Gln His Lys Asp Asp Asn Pro Asn
             100                 105                 110

Leu Pro Arg Leu Val Arg Pro Glu Val Asp Val Met Cys Thr Ala Phe
             115                 120                 125

His Asp Asn Glu Glu Thr Phe Leu Lys Lys Tyr Leu Tyr Glu Ile Ala
 130                 135                 140

Arg Arg His Pro Tyr Phe Tyr Ala Pro Glu Leu Leu Phe Phe Ala Lys
145                 150                 155                 160

Arg Tyr Lys Ala Ala Phe Thr Glu Cys Cys Gln Ala Ala Asp Lys Ala
                 165                 170                 175

Ala Cys Leu Leu Pro Lys Leu Asp Glu Leu Arg Asp Glu Gly Lys Ala
             180                 185                 190

Ser Ser Ala Lys Gln Arg Leu Lys Cys Ala Ser Leu Gln Lys Phe Gly
             195                 200                 205

Glu Arg Ala Phe Lys Ala Trp Ala Val Ala Arg Leu Ser Gln Arg Phe
             210                 215                 220

Pro Lys Ala Glu Phe Ala Glu Val Ser Lys Leu Val Thr Asp Leu Thr
225                 230                 235                 240

Lys Val His Thr Glu Cys Cys His Gly Asp Leu Leu Glu Cys Ala Asp
                 245                 250                 255

Asp Arg Ala Asp Leu Ala Lys Tyr Ile Cys Glu Asn Gln Asp Ser Ile
             260                 265                 270

Ser Ser Lys Leu Lys Glu Cys Cys Glu Lys Pro Leu Leu Glu Lys Ser
             275                 280                 285

His Cys Ile Ala Glu Val Glu Asn Asp Glu Met Pro Ala Asp Leu Pro
 290                 295                 300

Ser Leu Ala Ala Asp Phe Val Glu Ser Lys Asp Val Cys Lys Asn Tyr
305                 310                 315                 320

Ala Glu Ala Lys Asp Val Phe Leu Gly Met Phe Leu Tyr Glu Tyr Ala
                 325                 330                 335

Arg Arg His Pro Asp Tyr Ser Val Val Leu Leu Leu Arg Leu Ala Lys
             340                 345                 350

Thr Tyr Glu Thr Thr Leu Glu Lys Cys Cys Ala Ala Ala Asp Pro His
             355                 360                 365

Glu Cys Tyr Ala Lys Val Phe Asp Glu Phe Lys Pro Leu Val Glu Glu
             370                 375                 380

Pro Gln Asn Leu Ile Lys Gln Asn Cys Glu Leu Phe Glu Gln Leu Gly
385                 390                 395                 400

Glu Tyr Lys Phe Gln Asn Ala Leu Leu Val Arg Tyr Thr Lys Lys Val
                 405                 410                 415

Pro Gln Val Ser Thr Pro Thr Leu Val Glu Val Ser Arg Asn Leu Gly
             420                 425                 430

Lys Val Gly Ser Lys Cys Cys Lys His Pro Glu Ala Lys Arg Met Pro
             435                 440                 445

Cys Ala Glu Asp Tyr Leu Ser Val Val Leu Asn Gln Leu Cys Val Leu

-continued

```
                450                 455                 460
His Glu Lys Thr Pro Val Ser Asp Arg Val Thr Lys Cys Cys Thr Glu
465                 470                 475                 480

Ser Leu Val Asn Arg Arg Pro Cys Phe Ser Ala Leu Glu Val Asp Glu
                485                 490                 495

Thr Tyr Val Pro Lys Glu Phe Asn Ala Glu Thr Phe Thr Phe His Ala
                500                 505                 510

Asp Ile Cys Thr Leu Ser Glu Lys Glu Arg Gln Ile Lys Lys Gln Thr
            515                 520                 525

Ala Leu Val Glu Leu Val Lys His Lys Pro Lys Ala Thr Lys Glu Gln
            530                 535                 540

Leu Lys Ala Val Met Asp Asp Phe Ala Ala Phe Val Glu Lys Cys Cys
545                 550                 555                 560

Lys Ala Asp Asp Lys Glu Thr Cys Phe Ala Glu Glu Gly Lys Lys Leu
                565                 570                 575

Val Ala Ala Ser Gln Ala Ala Leu Gly Leu Ala Cys
            580                 585
```

<210> SEQ ID NO 94
<211> LENGTH: 607
<212> TYPE: PRT
<213> ORGANISM: Bos taurus

<400> SEQUENCE: 94

```
Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240
```

```
Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
        435                 440                 445

Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 95
<211> LENGTH: 608
<212> TYPE: PRT
<213> ORGANISM: Felis catus

<400> SEQUENCE: 95

Met Lys Trp Val Thr Phe Ile Ser Leu Leu Leu Leu Phe Ser Ser Ala
1               5                   10                  15
```

-continued

```
Tyr Ser Arg Gly Val Thr Arg Arg Glu Ala His Gln Ser Glu Ile Ala
             20                  25                  30

His Arg Phe Asn Asp Leu Gly Glu Glu His Phe Arg Gly Leu Val Leu
         35                  40                  45

Val Ala Phe Ser Gln Tyr Leu Gln Gln Cys Pro Phe Glu Asp His Val
 50                  55                  60

Lys Leu Val Asn Glu Val Thr Glu Phe Ala Lys Gly Cys Val Ala Asp
 65                  70                  75                  80

Gln Ser Ala Ala Asn Cys Glu Lys Ser Leu His Glu Leu Leu Gly Asp
                 85                  90                  95

Lys Leu Cys Thr Val Ala Ser Leu Arg Asp Lys Tyr Gly Glu Met Ala
             100                 105                 110

Asp Cys Cys Glu Lys Lys Glu Pro Glu Arg Asn Glu Cys Phe Leu Gln
         115                 120                 125

His Lys Asp Asp Asn Pro Gly Phe Gly Gln Leu Val Thr Pro Glu Ala
130                 135                 140

Asp Ala Met Cys Thr Ala Phe His Glu Asn Glu Gln Arg Phe Leu Gly
145                 150                 155                 160

Lys Tyr Leu Tyr Glu Ile Ala Arg Arg His Pro Tyr Phe Tyr Ala Pro
                 165                 170                 175

Glu Leu Leu Tyr Tyr Ala Glu Glu Tyr Lys Gly Val Phe Thr Glu Cys
             180                 185                 190

Cys Glu Ala Ala Asp Lys Ala Ala Cys Leu Thr Pro Lys Val Asp Ala
         195                 200                 205

Leu Arg Glu Lys Val Leu Ala Ser Ser Ala Lys Glu Arg Leu Lys Cys
210                 215                 220

Ala Ser Leu Gln Lys Phe Gly Glu Arg Ala Phe Lys Ala Trp Ser Val
225                 230                 235                 240

Ala Arg Leu Ser Gln Lys Phe Pro Lys Ala Glu Phe Ala Glu Ile Ser
                 245                 250                 255

Lys Leu Val Thr Asp Leu Ala Lys Ile His Lys Glu Cys Cys His Gly
             260                 265                 270

Asp Leu Leu Glu Cys Ala Asp Asp Arg Ala Asp Leu Ala Lys Tyr Ile
         275                 280                 285

Cys Glu Asn Gln Asp Ser Ile Ser Thr Lys Leu Lys Glu Cys Cys Gly
290                 295                 300

Lys Pro Val Leu Glu Lys Ser His Cys Ile Ser Glu Val Glu Arg Asp
305                 310                 315                 320

Glu Leu Pro Ala Asp Leu Pro Pro Leu Ala Val Asp Phe Val Glu Asp
                 325                 330                 335

Lys Glu Val Cys Lys Asn Tyr Gln Glu Ala Lys Asp Val Phe Leu Gly
             340                 345                 350

Thr Phe Leu Tyr Glu Tyr Ser Arg Arg His Pro Glu Tyr Ser Val Ser
         355                 360                 365

Leu Leu Leu Arg Leu Ala Lys Glu Tyr Glu Ala Thr Leu Glu Lys Cys
370                 375                 380

Cys Ala Thr Asp Asp Pro Pro Ala Cys Tyr Ala His Val Phe Asp Glu
385                 390                 395                 400

Phe Lys Pro Leu Val Glu Pro His Asn Leu Val Lys Thr Asn Cys
                 405                 410                 415

Glu Leu Phe Glu Lys Leu Gly Glu Tyr Gly Phe Gln Asn Ala Leu Leu
             420                 425                 430
```

Val Arg Tyr Thr Lys Lys Val Pro Gln Val Ser Pro Thr Leu Val
                435                 440                 445

Glu Val Ser Arg Ser Leu Gly Lys Val Gly Ser Lys Cys Cys Thr His
450                 455                 460

Pro Glu Ala Glu Arg Leu Ser Cys Ala Glu Asp Tyr Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Thr Glu Ser Leu Val Asn Arg Arg Pro Cys Phe
                500                 505                 510

Ser Ala Leu Gln Val Asp Glu Thr Tyr Val Pro Lys Glu Phe Ser Ala
                515                 520                 525

Glu Thr Phe Thr Phe His Ala Asp Leu Cys Thr Leu Pro Glu Ala Glu
                530                 535                 540

Lys Gln Ile Lys Lys Gln Ser Ala Leu Val Glu Leu Lys His Lys
545                 550                 555                 560

Pro Lys Ala Thr Glu Glu Gln Leu Lys Thr Val Met Gly Asp Phe Gly
                565                 570                 575

Ser Phe Val Asp Lys Cys Cys Ala Ala Glu Asp Lys Glu Ala Cys Phe
                580                 585                 590

Ala Glu Glu Gly Pro Lys Leu Val Ala Ala Gln Ala Ala Leu Ala
                595                 600                 605

<210> SEQ ID NO 96
<211> LENGTH: 608
<212> TYPE: PRT
<213> ORGANISM: Canis lupus familaris

<400> SEQUENCE: 96

Met Lys Trp Val Thr Phe Ile Ser Leu Phe Phe Leu Phe Ser Ser Ala
1                   5                   10                  15

Tyr Ser Arg Gly Leu Val Arg Arg Glu Ala Tyr Lys Ser Glu Ile Ala
                20                  25                  30

His Arg Tyr Asn Asp Leu Gly Glu Glu His Phe Arg Gly Leu Val Leu
                35                  40                  45

Val Ala Phe Ser Gln Tyr Leu Gln Gln Cys Pro Phe Glu Asp His Val
50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
                85                  90                  95

Lys Leu Cys Thr Val Ala Ser Leu Arg Asp Lys Tyr Gly Asp Met Ala
                100                 105                 110

Asp Cys Cys Glu Lys Gln Glu Pro Asp Arg Asn Glu Cys Phe Leu Ala
                115                 120                 125

His Lys Asp Asp Asn Pro Gly Phe Pro Pro Leu Val Ala Pro Glu Pro
130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Gln Gln Tyr Lys Gly Val Phe Ala Glu Cys
                180                 185                 190

Cys Gln Ala Ala Asp Lys Ala Ala Cys Leu Gly Pro Lys Ile Glu Ala
                195                 200                 205

```
Leu Arg Glu Lys Val Leu Leu Ser Ser Ala Lys Glu Arg Phe Lys Cys
    210                 215                 220

Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
                245                 250                 255

Lys Val Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Thr Lys Leu Lys Glu Cys Cys Asp
    290                 295                 300

Lys Pro Val Leu Glu Lys Ser Gln Cys Leu Ala Glu Val Glu Arg Asp
305                 310                 315                 320

Glu Leu Pro Gly Asp Leu Pro Ser Leu Ala Ala Asp Phe Val Glu Asp
                325                 330                 335

Lys Glu Val Cys Lys Asn Tyr Gln Glu Ala Lys Asp Val Phe Leu Gly
            340                 345                 350

Thr Phe Leu Tyr Glu Tyr Ala Arg Arg His Pro Glu Tyr Ser Val Ser
        355                 360                 365

Leu Leu Leu Arg Leu Ala Lys Glu Tyr Glu Ala Thr Leu Glu Lys Cys
    370                 375                 380

Cys Ala Thr Asp Asp Pro Pro Thr Cys Tyr Ala Lys Val Leu Asp Glu
385                 390                 395                 400

Phe Lys Pro Leu Val Asp Glu Pro Gln Asn Leu Val Lys Thr Asn Cys
                405                 410                 415

Glu Leu Phe Glu Lys Leu Gly Glu Tyr Gly Phe Gln Asn Ala Leu Leu
            420                 425                 430

Val Arg Tyr Thr Lys Lys Ala Pro Gln Val Ser Thr Pro Thr Leu Val
        435                 440                 445

Glu Val Ser Arg Lys Leu Gly Lys Val Gly Thr Lys Cys Cys Lys Lys
    450                 455                 460

Pro Glu Ser Glu Arg Met Ser Cys Ala Glu Asp Phe Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Ser Glu Ser Leu Val Asn Arg Arg Pro Cys Phe
            500                 505                 510

Ser Gly Leu Glu Val Asp Glu Thr Tyr Val Pro Lys Glu Phe Asn Ala
        515                 520                 525

Glu Thr Phe Thr Phe His Ala Asp Leu Cys Thr Leu Pro Glu Ala Glu
    530                 535                 540

Lys Gln Val Lys Lys Gln Thr Ala Leu Val Glu Leu Leu Lys His Lys
545                 550                 555                 560

Pro Lys Ala Thr Asp Glu Gln Leu Lys Thr Val Met Gly Asp Phe Gly
                565                 570                 575

Ala Phe Val Glu Lys Cys Cys Ala Ala Glu Asn Lys Glu Gly Cys Phe
            580                 585                 590

Ser Glu Glu Gly Pro Lys Leu Val Ala Ala Gln Ala Ala Leu Val
        595                 600                 605

<210> SEQ ID NO 97
<211> LENGTH: 607
```

```
<212> TYPE: PRT
<213> ORGANISM: Equus asinus

<400> SEQUENCE: 97
```

| | | | | | | | | | | | | | | |
|---|---|---|---|---|---|---|---|---|---|---|---|---|---|---|
| Met | Lys | Trp | Val | Thr | Phe | Val | Ser | Leu | Leu | Phe | Leu | Phe | Ser | Ser | Ala |
| 1 | | | | 5 | | | | | 10 | | | | | 15 | |

Met Lys Trp Val Thr Phe Val Ser Leu Leu Phe Leu Phe Ser Ser Ala
1               5                   10                  15

Tyr Phe Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
            35                  40              45

Val Ala Phe Ser Gln Tyr Leu Gln Gln Cys Pro Phe Glu Asp His Val
50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
                100                 105                 110

Asp Cys Cys Glu Lys Gln Glu Pro Glu Arg Asn Glu Cys Phe Leu Thr
                115                 120                 125

His Lys Asp Asp His Pro Asn Leu Pro Lys Leu Lys Pro Glu Pro Asp
            130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
                180                 185                 190

Pro Ala Asp Asp Lys Ala Gly Cys Leu Ile Pro Lys Leu Asp Ala Leu
            195                 200                 205

Lys Glu Arg Ile Leu Leu Ser Ser Ala Lys Glu Arg Leu Lys Cys Ser
            210                 215                 220

Ser Phe Gln Lys Phe Gly Glu Arg Ala Phe Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
                260                 265                 270

Leu Leu Glu Cys Ala Asp Asp Arg Ala Asp Leu Thr Lys Tyr Ile Cys
            275                 280                 285

Glu His Gln Asp Ser Ile Ser Gly Lys Leu Lys Ala Cys Cys Asp Lys
            290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
                340                 345                 350

Phe Leu Tyr Glu Tyr Ser Arg Arg His Pro Asp Tyr Ser Val Ser Leu
            355                 360                 365

Leu Leu Arg Ile Ala Lys Thr Tyr Glu Ala Thr Leu Glu Lys Cys Cys
            370                 375                 380

Ala Glu Ala Asp Pro Pro Ala Cys Tyr Ala Thr Val Phe Asp Gln Phe
385                 390                 395                 400

-continued

Thr Pro Leu Val Glu Glu Pro Lys Ser Leu Val Lys Asn Cys Asp
            405                 410                 415

Leu Phe Glu Glu Val Gly Glu Tyr Asp Phe Gln Asn Ala Leu Ile Val
        420                 425                 430

Arg Tyr Thr Lys Lys Ala Pro Gln Val Ser Thr Pro Thr Leu Val Glu
            435                 440                 445

Ile Gly Arg Thr Leu Gly Lys Val Gly Ser Arg Cys Cys Lys Leu Pro
    450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
            500                 505                 510

Ala Leu Glu Leu Asp Glu Gly Tyr Ile Pro Lys Glu Phe Lys Ala Glu
        515                 520                 525

Thr Phe Thr Phe His Ala Asp Ile Cys Thr Leu Pro Glu Asp Glu Lys
    530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575

Phe Val Ala Lys Cys Cys Gly Ala Glu Asp Lys Glu Ala Cys Phe Ala
            580                 585                 590

Glu Glu Gly Pro Lys Leu Val Ala Ser Ser Gln Leu Ala Leu Ala
        595                 600                 605

<210> SEQ ID NO 98
<211> LENGTH: 609
<212> TYPE: PRT
<213> ORGANISM: Meriones unguiculatus

<400> SEQUENCE: 98

Met Lys Trp Val Thr Phe Leu Leu Leu Leu Phe Val Ser Gly Ser Ala
1               5                   10                  15

Phe Ser Arg Gly Val Phe Arg Arg Asp Ala Ala His Lys Ser Glu Ile
            20                  25                  30

Ala His Arg Tyr Lys Asp Leu Gly Glu Lys Tyr Phe Lys Gly Leu Val
        35                  40                  45

Leu Tyr Thr Phe Ser Gln Tyr Leu Gln Lys Cys Ser Tyr Glu Glu His
    50                  55                  60

Val Lys Leu Val Arg Glu Val Thr Asp Phe Ala Ser Asn Cys Ala Lys
65                  70                  75                  80

Asp Glu Ser Ala Glu Asn Cys Asp Lys Ser Leu His Thr Leu Phe Gly
                85                  90                  95

Asp Lys Leu Cys Ser Leu Pro Asn Phe Gly Lys Tyr Ala Glu Met
            100                 105                 110

Ala Asp Cys Cys Ala Lys Gln Glu Pro Glu Arg Asn Glu Cys Phe Leu
        115                 120                 125

Gln His Lys Asp Asp Asn Pro Gln Leu Pro Pro Phe Lys Arg Ala Glu
    130                 135                 140

Pro Asp Ala Met Cys Thr Ala Phe Gln Glu Asn Ala Glu Ala Phe Met
145                 150                 155                 160

Gly His Tyr Leu His Glu Val Ala Arg Arg His Pro Tyr Phe Tyr Gly

```
            165                 170                 175
Pro Glu Leu Leu Tyr Leu Ala Asp Lys Tyr Thr Ala Val Leu Thr Glu
            180                 185                 190

Cys Cys Ala Ala Asp Asp Lys Gly Ala Cys Leu Thr Pro Lys Leu Asp
            195                 200                 205

Ala Leu Lys Glu Lys Ala Leu Val Ser Ala Val Arg Gln Arg Leu Lys
            210                 215                 220

Cys Ser Ser Met Lys Lys Phe Gly Glu Arg Ala Phe Lys Ala Trp Ala
225                 230                 235                 240

Val Ala Arg Met Ser Gln Thr Phe Pro Asn Ala Asp Phe Ala Glu Ile
                245                 250                 255

Thr Lys Leu Ala Thr Asp Leu Thr Lys Val Thr Gln Glu Cys Cys His
            260                 265                 270

Gly Asp Leu Leu Glu Cys Ala Asp Asp Arg Ala Glu Leu Ala Lys Tyr
            275                 280                 285

Met Cys Glu Asn Gln Ala Ser Ile Ser Ser Lys Leu Gln Ala Cys Cys
            290                 295                 300

Asp Lys Glu Met Leu Gln Lys Ser Gln Cys Leu Ala Glu Val Glu His
305                 310                 315                 320

Asp Asp Met Pro Ala Asp Leu Pro Ala Leu Thr Ala Asp Phe Val Glu
                325                 330                 335

Asp Lys Asp Val Cys Lys Asn Tyr Ala Glu Ala Lys Asp Val Phe Leu
            340                 345                 350

Gly Thr Phe Leu Tyr Glu Tyr Ser Arg Arg His Pro Glu Tyr Ser Val
            355                 360                 365

Ser Leu Leu Leu Arg Leu Ala Lys Lys Tyr Glu Ala Thr Leu Glu Lys
            370                 375                 380

Cys Cys Ala Glu Ala Asp Pro His Ala Cys Tyr Gly His Val Phe Asp
385                 390                 395                 400

Glu Phe Lys Pro Leu Val Glu Glu Pro Gln Asn Leu Val Lys Ser Asn
                405                 410                 415

Cys Glu Leu Tyr Glu Lys Leu Gly Glu Tyr Gly Phe Gln Asn Ala Val
            420                 425                 430

Leu Val Arg Tyr Thr Lys Lys Ala Pro Gln Val Ser Thr Pro Thr Leu
            435                 440                 445

Val Glu Ala Ala Arg Ser Leu Gly Arg Val Gly Thr His Cys Cys Ala
450                 455                 460

Leu Pro Glu Lys Lys Arg Leu Pro Cys Val Glu Asp Tyr Leu Ser Ala
465                 470                 475                 480

Ile Leu Asn Arg Val Cys Leu Leu His Glu Lys Thr Pro Val Ser Glu
                485                 490                 495

Gln Val Thr Lys Cys Cys Ser Gly Ser Leu Val Glu Arg Arg Pro Cys
            500                 505                 510

Phe Ser Ala Leu Pro Val Asp Glu Thr Tyr Val Pro Lys Glu Phe Lys
            515                 520                 525

Ala Glu Thr Phe Thr Phe His Ala Asn Ile Cys Thr Leu Pro Glu Lys
            530                 535                 540

Glu Lys Gln Met Glu Lys Gln Thr Ala Leu Ala Glu Leu Val Lys His
545                 550                 555                 560

Lys Pro Gln Ala Thr Glu Glu Gln Leu Lys Lys Val Met Gly Asp Phe
                565                 570                 575

Ala Glu Phe Leu Glu Lys Cys Cys Lys Gln Glu Asp Lys Glu Ala Cys
            580                 585                 590
```

```
Phe Ser Thr Glu Gly Pro Lys Leu Val Ala Glu Ser Gln Lys Ala Leu
        595                 600                 605
Ala
```

```
<210> SEQ ID NO 99
<211> LENGTH: 583
<212> TYPE: PRT
<213> ORGANISM: Capra hircus

<400> SEQUENCE: 99
```

```
Asp Thr His Lys Ser Glu Ile Ala His Arg Phe Asn Asp Leu Gly Glu
1               5                   10                  15

Glu Asn Phe Gln Gly Leu Val Leu Ile Ala Phe Ser Gln Tyr Leu Gln
            20                  25                  30

Gln Cys Pro Phe Asp Glu His Val Lys Leu Val Lys Glu Leu Thr Glu
        35                  40                  45

Phe Ala Lys Thr Cys Val Ala Asp Glu Ser His Ala Gly Cys Asp Lys
    50                  55                  60

Ser Leu His Thr Leu Phe Gly Asp Glu Leu Cys Lys Val Ala Thr Leu
65                  70                  75                  80

Arg Glu Thr Tyr Gly Asp Met Ala Asp Cys Cys Glu Lys Gln Glu Pro
                85                  90                  95

Glu Arg Asn Glu Cys Phe Leu Lys His Lys Asp Asp Ser Pro Asp Leu
            100                 105                 110

Pro Lys Leu Lys Pro Glu Pro Asp Thr Leu Cys Ala Glu Phe Lys Ala
        115                 120                 125

Asp Glu Lys Lys Phe Trp Gly Lys Tyr Leu Tyr Glu Val Ala Arg Arg
    130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Ala Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
    210                 215                 220

Ala Asp Phe Thr Asp Val Thr Lys Ile Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp His Gln Asp Thr Leu Ser Ser
            260                 265                 270

Lys Leu Lys Glu Cys Cys Asp Lys Pro Val Leu Glu Lys Ser His Cys
        275                 280                 285

Ile Ala Glu Ile Asp Lys Asp Ala Val Pro Glu Asn Leu Pro Pro Leu
    290                 295                 300

Thr Ala Asp Phe Ala Glu Asp Lys Glu Val Cys Lys Asn Tyr Gln Glu
305                 310                 315                 320

Ala Lys Asp Val Phe Leu Gly Ser Phe Leu Tyr Glu Tyr Ser Arg Arg
                325                 330                 335

His Pro Glu Tyr Ala Val Ser Val Leu Leu Arg Leu Ala Lys Glu Tyr
            340                 345                 350
```

```
Glu Ala Thr Leu Glu Asp Cys Cys Ala Lys Glu Asp Pro His Ala Cys
            355                 360                 365

Tyr Ala Thr Val Phe Asp Lys Leu Lys His Leu Val Asp Glu Pro Gln
            370                 375                 380

Asn Leu Ile Lys Lys Asn Cys Glu Leu Phe Glu Lys His Gly Glu Tyr
385                 390                 395                 400

Gly Phe Gln Asn Ala Leu Ile Val Arg Tyr Thr Arg Lys Ala Pro Gln
                405                 410                 415

Val Ser Thr Pro Thr Leu Val Glu Ile Ser Arg Ser Leu Gly Lys Val
            420                 425                 430

Gly Thr Lys Cys Cys Ala Lys Pro Glu Ser Glu Arg Met Pro Cys Thr
            435                 440                 445

Glu Asp Tyr Leu Ser Leu Ile Leu Asn Arg Leu Cys Val Leu His Glu
            450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Asp Leu Thr Leu Asp Glu Thr Tyr
                485                 490                 495

Val Pro Lys Pro Phe Asp Gly Asp Ser Phe Thr Phe His Ala Asp Ile
            500                 505                 510

Cys Thr Leu Pro Asp Thr Glu Lys Gln Ile Lys Lys Gln Thr Ala Leu
            515                 520                 525

Val Glu Leu Leu Lys His Lys Pro Lys Ala Thr Asp Glu Gln Leu Lys
            530                 535                 540

Thr Val Met Glu Asn Phe Val Ala Phe Val Asp Lys Cys Cys Ala Ala
545                 550                 555                 560

Asp Asp Lys Glu Gly Cys Phe Leu Leu Glu Gly Pro Lys Leu Val Ala
                565                 570                 575

Ser Thr Gln Ala Ala Leu Ala
            580

<210> SEQ ID NO 100
<211> LENGTH: 608
<212> TYPE: PRT
<213> ORGANISM: Cavia porcellus

<400> SEQUENCE: 100

Met Lys Trp Val Thr Phe Ile Ser Leu Leu Phe Leu Phe Ser Ser Val
1               5                   10                  15

Tyr Ser Arg Gly Val Phe Arg Arg Glu Ala His Lys Ser Glu Ile Ala
                20                  25                  30

His Arg Phe Asn Asp Leu Gly Glu Gly His Phe Lys Gly Leu Val Leu
            35                  40                  45

Ile Thr Leu Ser Gln His Leu Gln Lys Ser Pro Phe Glu Glu His Val
        50                  55                  60

Lys Leu Val Asn Glu Val Thr Asp Phe Ala Lys Ala Cys Val Ala Asp
65                  70                  75                  80

Glu Ser Ala Gln Asn Cys Gly Lys Ala Ile Ala Thr Leu Phe Gly Asp
                85                  90                  95

Lys Val Cys Ala Ile Pro Ser Leu Arg Glu Thr Tyr Gly Glu Leu Ala
            100                 105                 110

Asp Cys Cys Ala Lys Glu Asp Pro Asp Arg Val Glu Cys Phe Leu Gln
            115                 120                 125

His Lys Asp Asp Asn Pro Asn Leu Pro Pro Phe Glu Arg Pro Glu Pro
```

```
            130                 135                 140
Glu Ala Leu Cys Thr Ala Phe Lys Glu Asn Asn Asp Arg Phe Ile Gly
145                 150                 155                 160

His Tyr Leu Tyr Glu Val Ser Arg Arg His Pro Tyr Phe Tyr Ala Pro
                    165                 170                 175

Glu Leu Leu Tyr Tyr Ala Glu Lys Tyr Lys Asn Ala Leu Thr Glu Cys
                180                 185                 190

Cys Glu Ala Ala Asp Lys Ala Ala Cys Leu Thr Pro Lys Leu Asp Ala
                195                 200                 205

Ile Lys Glu Lys Ala Leu Val Ser Ser Ala Gln Gln Arg Leu Lys Cys
210                 215                 220

Ala Ser Leu Gln Lys Phe Gly Glu Arg Ala Phe Lys Ala Trp Ser Val
225                 230                 235                 240

Ala Arg Leu Ser Gln Lys Phe Pro Lys Ala Glu Phe Ala Glu Ile Ser
                245                 250                 255

Thr Ile Val Thr Ser Leu Thr Lys Val Thr Lys Glu Cys Cys His Gly
                260                 265                 270

Asp Leu Leu Glu Cys Ala Asp Asp Arg Gln Glu Leu Ala Lys Tyr Met
                275                 280                 285

Cys Glu His Gln Asp Ser Ile Ser Ser Lys Leu Lys Glu Cys Cys Val
                290                 295                 300

Lys Pro Thr Leu Gln Lys Ala His Cys Ile Leu Glu Ile Gln Arg Asp
305                 310                 315                 320

Glu Leu Pro Thr Glu Leu Pro Asp Leu Ala Val Asp Phe Val Glu Asp
                325                 330                 335

Lys Glu Val Cys Lys Asn Phe Ala Glu Ala Lys Asp Val Phe Leu Gly
                340                 345                 350

Thr Phe Leu Tyr Glu Tyr Ser Arg Arg His Pro Glu Tyr Ser Ile Gly
                355                 360                 365

Met Leu Leu Arg Ile Ala Lys Gly Tyr Glu Ala Lys Leu Glu Lys Cys
                370                 375                 380

Cys Ala Glu Ala Asp Pro His Ala Cys Tyr Ala Lys Val Phe Asp Glu
385                 390                 395                 400

Leu Gln Pro Leu Ile Asp Glu Pro Lys Lys Leu Val Gln Gln Asn Cys
                405                 410                 415

Glu Leu Phe Asp Lys Leu Gly Tyr Gly Phe Gln Asn Ala Leu Ala
                420                 425                 430

Val Arg Tyr Thr Gln Lys Ala Pro Gln Val Ser Thr Pro Thr Leu Val
                435                 440                 445

Glu Tyr Ala Arg Lys Leu Gly Ser Val Gly Thr Lys Cys Cys Ser Leu
450                 455                 460

Pro Glu Thr Glu Arg Leu Ser Cys Thr Glu Asn Tyr Leu Ala Leu Ile
465                 470                 475                 480

Leu Asn Arg Leu Cys Ile Leu His Glu Lys Thr Pro Val Ser Glu Arg
                485                 490                 495

Val Thr Lys Cys Cys Thr Glu Ser Leu Val Asn Arg Arg Pro Cys Phe
                500                 505                 510

Ser Ala Leu His Val Asp Glu Thr Tyr Val Pro Lys Pro Phe His Ala
                515                 520                 525

Asp Ser Phe Thr Phe His Ala Asp Ile Cys Thr Leu Pro Glu Lys Glu
                530                 535                 540

Lys Gln Val Lys Gln Met Ala Leu Val Glu Leu Val Lys His Lys
545                 550                 555                 560
```

-continued

```
Pro Lys Ala Ser Glu Glu Gln Met Lys Thr Val Met Gly Asp Phe Ala
                565                 570                 575

Ala Phe Leu Lys Lys Cys Cys Asp Ala Asp Asn Lys Glu Ala Cys Phe
            580                 585                 590

Thr Glu Asp Gly Pro Lys Leu Val Ala Lys Cys Gln Ala Thr Leu Ala
        595                 600                 605

<210> SEQ ID NO 101
<211> LENGTH: 607
<212> TYPE: PRT
<213> ORGANISM: Equus caballus

<400> SEQUENCE: 101

Met Lys Trp Val Thr Phe Val Ser Leu Leu Phe Leu Phe Ser Ser Ala
1               5                   10                  15

Tyr Ser Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Leu Ala Cys Leu Ile Pro Lys Leu Asp Ala Leu
        195                 200                 205

Lys Glu Arg Ile Leu Leu Ser Ser Ala Lys Glu Arg Leu Lys Cys Ser
    210                 215                 220

Ser Phe Gln Asn Phe Gly Glu Arg Ala Val Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
```

```
                        325                 330                 335
Glu Ile Cys Lys His Tyr Lys Asp Ala Lys Asp Val Phe Leu Gly Thr
                340                 345                 350
Phe Leu Tyr Glu Tyr Ser Arg Arg His Pro Asp Tyr Ser Val Ser Leu
            355                 360                 365
Leu Leu Arg Ile Ala Lys Thr Tyr Glu Ala Thr Leu Glu Lys Cys Cys
        370                 375                 380
Ala Glu Ala Asp Pro Pro Ala Cys Tyr Arg Thr Val Phe Asp Gln Phe
385                 390                 395                 400
Thr Pro Leu Val Glu Glu Pro Lys Ser Leu Val Lys Lys Asn Cys Asp
                405                 410                 415
Leu Phe Glu Glu Val Gly Glu Tyr Asp Phe Gln Asn Ala Leu Ile Val
                420                 425                 430
Arg Tyr Thr Lys Lys Ala Pro Gln Val Ser Thr Pro Thr Leu Val Glu
            435                 440                 445
Ile Gly Arg Thr Leu Gly Lys Val Gly Ser Arg Cys Cys Lys Leu Pro
        450                 455                 460
Glu Ser Glu Arg Leu Pro Cys Ser Glu Asn His Leu Ala Leu Ala Leu
465                 470                 475                 480
Asn Arg Leu Cys Val Leu His Glu Lys Thr Pro Val Ser Glu Lys Ile
                485                 490                 495
Thr Lys Cys Cys Thr Asp Ser Leu Ala Glu Arg Arg Pro Cys Phe Ser
                500                 505                 510
Ala Leu Glu Leu Asp Glu Gly Tyr Val Pro Lys Glu Phe Lys Ala Glu
            515                 520                 525
Thr Phe Thr Phe His Ala Asp Ile Cys Thr Leu Pro Glu Asp Glu Lys
        530                 535                 540
Gln Ile Lys Lys Gln Ser Ala Leu Ala Glu Leu Val Lys His Lys Pro
545                 550                 555                 560
Lys Ala Thr Lys Glu Gln Leu Lys Thr Val Leu Gly Asn Phe Ser Ala
                565                 570                 575
Phe Val Ala Lys Cys Cys Gly Arg Glu Asp Lys Glu Ala Cys Phe Ala
                580                 585                 590
Glu Glu Gly Pro Lys Leu Val Ala Ser Ser Gln Leu Ala Leu Ala
            595                 600                 605

<210> SEQ ID NO 102
<211> LENGTH: 609
<212> TYPE: PRT
<213> ORGANISM: Homo sapiens

<400> SEQUENCE: 102

Met Lys Trp Val Thr Phe Ile Ser Leu Leu Phe Leu Phe Ser Ser Ala
1               5                   10                  15
Tyr Ser Arg Gly Val Phe Arg Arg Asp Ala His Lys Ser Glu Val Ala
                20                  25                  30
His Arg Phe Lys Asp Leu Gly Glu Glu Asn Phe Lys Ala Leu Val Leu
            35                  40                  45
Ile Ala Phe Ala Gln Tyr Leu Gln Gln Cys Pro Phe Glu Asp His Val
        50                  55                  60
Lys Leu Val Asn Glu Val Thr Glu Phe Ala Lys Thr Cys Val Ala Asp
65                  70                  75                  80
Glu Ser Ala Glu Asn Cys Asp Lys Ser Leu His Thr Leu Phe Gly Asp
                85                  90                  95
```

```
Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Arg Leu Val Arg Pro Glu Val
        130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
```

```
            515                 520                 525
Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 103
<211> LENGTH: 600
<212> TYPE: PRT
<213> ORGANISM: Macca mulatta

<400> SEQUENCE: 103

Leu Leu Phe Leu Phe Ser Ser Ala Tyr Ser Arg Gly Val Phe Arg Arg
1               5                   10                  15

Asp Thr His Lys Ser Glu Val Ala His Arg Phe Lys Asp Leu Gly Glu
                20                  25                  30

Glu His Phe Lys Gly Leu Val Leu Val Ala Phe Ser Gln Tyr Leu Gln
                35                  40                  45

Gln Cys Pro Phe Glu His Val Lys Leu Val Asn Glu Val Thr Glu
    50                  55                  60

Phe Ala Lys Thr Cys Val Ala Asp Glu Ser Ala Glu Asn Cys Asp Lys
65                  70                  75                  80

Ser Leu His Thr Leu Phe Gly Asp Lys Leu Cys Thr Val Ala Thr Leu
                85                  90                  95

Arg Glu Thr Tyr Gly Glu Met Ala Asp Cys Cys Ala Lys Gln Glu Pro
                100                 105                 110

Glu Arg Asn Glu Cys Phe Leu Gln His Lys Asp Asp Asn Pro Asn Leu
                115                 120                 125

Pro Pro Leu Val Arg Pro Glu Val Asp Val Met Cys Thr Ala Phe His
                130                 135                 140

Asp Asn Glu Ala Thr Phe Leu Lys Lys Tyr Leu Tyr Glu Val Ala Arg
145                 150                 155                 160

Arg His Pro Tyr Phe Tyr Ala Pro Glu Leu Leu Phe Phe Ala Ala Arg
                165                 170                 175

Tyr Lys Ala Ala Phe Ala Glu Cys Cys Gln Ala Ala Asp Lys Ala Ala
                180                 185                 190

Cys Leu Leu Pro Lys Leu Asp Glu Leu Arg Asp Glu Gly Lys Ala Ser
                195                 200                 205

Ser Ala Lys Gln Arg Leu Lys Cys Ala Ser Leu Gln Lys Phe Gly Asp
    210                 215                 220

Arg Ala Phe Lys Ala Trp Ala Val Ala Arg Leu Ser Gln Lys Phe Pro
225                 230                 235                 240

Lys Ala Glu Phe Ala Glu Val Ser Lys Leu Val Thr Asp Leu Thr Lys
                245                 250                 255

Val His Thr Glu Cys Cys His Gly Asp Leu Leu Glu Cys Ala Asp Asp
                260                 265                 270

Arg Ala Asp Leu Ala Lys Tyr Met Cys Glu Asn Gln Asp Ser Ile Ser
```

```
            275                 280                 285
Ser Lys Leu Lys Glu Cys Cys Asp Lys Pro Leu Leu Glu Lys Ser His
    290                 295                 300

Cys Leu Ala Glu Val Glu Asn Asp Glu Met Pro Ala Asp Leu Pro Ser
305                 310                 315                 320

Leu Ala Ala Asp Tyr Val Glu Ser Lys Asp Val Cys Lys Asn Tyr Ala
                325                 330                 335

Glu Ala Lys Asp Val Phe Leu Gly Met Phe Leu Tyr Tyr Ala Arg
            340                 345                 350

Arg His Pro Asp Tyr Ser Val Met Leu Leu Arg Leu Ala Lys Ala
            355                 360                 365

Tyr Glu Ala Thr Leu Glu Lys Cys Cys Ala Ala Ala Asp Pro His Glu
    370                 375                 380

Cys Tyr Ala Lys Val Phe Asp Glu Phe Gln Pro Leu Val Glu Glu Pro
385                 390                 395                 400

Gln Asn Leu Val Lys Gln Asn Cys Glu Leu Phe Glu Gln Leu Gly Glu
                405                 410                 415

Tyr Lys Phe Gln Asn Ala Leu Leu Val Arg Tyr Thr Lys Lys Val Pro
            420                 425                 430

Gln Val Ser Thr Pro Thr Leu Val Glu Val Ser Arg Asn Leu Gly Lys
    435                 440                 445

Val Gly Ala Lys Cys Cys Lys Leu Pro Glu Ala Lys Arg Met Pro Cys
450                 455                 460

Ala Glu Asp Tyr Leu Ser Val Val Leu Asn Arg Leu Cys Val Leu His
465                 470                 475                 480

Glu Lys Thr Pro Val Ser Glu Lys Val Thr Lys Cys Cys Thr Glu Ser
                485                 490                 495

Leu Val Asn Arg Arg Pro Cys Phe Ser Ala Leu Glu Leu Asp Glu Ala
            500                 505                 510

Tyr Val Pro Lys Ala Phe Asn Ala Glu Thr Phe Thr Phe His Ala Asp
    515                 520                 525

Met Cys Thr Leu Ser Glu Lys Glu Lys Gln Val Lys Lys Gln Thr Ala
530                 535                 540

Leu Val Glu Leu Val Lys His Lys Pro Lys Ala Thr Lys Glu Gln Leu
545                 550                 555                 560

Lys Gly Val Met Asp Asn Phe Ala Ala Phe Val Glu Lys Cys Cys Lys
                565                 570                 575

Ala Asp Asp Lys Glu Ala Cys Phe Ala Glu Glu Gly Pro Lys Phe Val
            580                 585                 590

Ala Ala Ser Gln Ala Ala Leu Ala
            595                 600

<210> SEQ ID NO 104
<211> LENGTH: 608
<212> TYPE: PRT
<213> ORGANISM: Mus musculus

<400> SEQUENCE: 104

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45
```

-continued

```
Ile Ala Phe Ser Gln Tyr Leu Gln Lys Cys Ser Tyr Asp Glu His Ala
 50                  55                  60
Lys Leu Val Gln Glu Val Thr Asp Phe Ala Lys Thr Cys Val Ala Asp
 65                  70                  75                  80
Glu Ser Ala Ala Asn Cys Asp Lys Ser Leu His Thr Leu Phe Gly Asp
                 85                  90                  95
Lys Leu Cys Ala Ile Pro Asn Leu Arg Glu Asn Tyr Gly Glu Leu Ala
            100                 105                 110
Asp Cys Cys Thr Lys Gln Glu Pro Glu Arg Asn Glu Cys Phe Leu Gln
            115                 120                 125
His Lys Asp Asp Asn Pro Ser Leu Pro Pro Phe Glu Arg Pro Glu Ala
130                 135                 140
Glu Ala Met Cys Thr Ser Phe Lys Glu Asn Pro Thr Thr Phe Met Gly
145                 150                 155                 160
His Tyr Leu His Glu Val Ala Arg Arg His Pro Tyr Phe Tyr Ala Pro
                165                 170                 175
Glu Leu Leu Tyr Tyr Ala Glu Gln Tyr Asn Glu Ile Leu Thr Gln Cys
            180                 185                 190
Cys Ala Glu Ala Asp Lys Glu Ser Cys Leu Thr Pro Lys Leu Asp Gly
            195                 200                 205
Val Lys Glu Lys Ala Leu Val Ser Ser Val Arg Gln Arg Met Lys Cys
210                 215                 220
Ser Ser Met Gln Lys Phe Gly Glu Arg Ala Phe Lys Ala Trp Ala Val
225                 230                 235                 240
Ala Arg Leu Ser Gln Thr Phe Pro Asn Ala Asp Phe Ala Glu Ile Thr
                245                 250                 255
Lys Leu Ala Thr Asp Leu Thr Lys Val Asn Lys Glu Cys Cys His Gly
            260                 265                 270
Asp Leu Leu Glu Cys Ala Asp Asp Arg Ala Glu Leu Ala Lys Tyr Met
            275                 280                 285
Cys Glu Asn Gln Ala Thr Ile Ser Ser Lys Leu Gln Thr Cys Cys Asp
            290                 295                 300
Lys Pro Leu Leu Lys Lys Ala His Cys Leu Ser Glu Val Glu His Asp
305                 310                 315                 320
Thr Met Pro Ala Asp Leu Pro Ala Ile Ala Ala Asp Phe Val Glu Asp
                325                 330                 335
Gln Glu Val Cys Lys Asn Tyr Ala Glu Ala Lys Asp Val Phe Leu Gly
            340                 345                 350
Thr Phe Leu Tyr Glu Tyr Ser Arg Arg His Pro Asp Tyr Ser Val Ser
            355                 360                 365
Leu Leu Leu Arg Leu Ala Lys Lys Tyr Glu Ala Thr Leu Glu Lys Cys
370                 375                 380
Cys Ala Glu Ala Asn Pro Pro Ala Cys Tyr Gly Thr Val Leu Ala Glu
385                 390                 395                 400
Phe Gln Pro Leu Val Glu Glu Pro Lys Asn Leu Val Lys Thr Asn Cys
                405                 410                 415
Asp Leu Tyr Glu Lys Leu Gly Glu Tyr Gly Phe Gln Asn Ala Ile Leu
            420                 425                 430
Val Arg Tyr Thr Gln Lys Ala Pro Gln Val Ser Thr Pro Thr Leu Val
            435                 440                 445
Glu Ala Ala Arg Asn Leu Gly Arg Val Gly Thr Lys Cys Cys Thr Leu
450                 455                 460
Pro Glu Asp Gln Arg Leu Pro Cys Val Glu Asp Tyr Leu Ser Ala Ile
```

```
                465                 470                 475                 480
Leu Asn Arg Val Cys Leu Leu His Glu Lys Thr Pro Val Ser Glu His
                    485                 490                 495

Val Thr Lys Cys Cys Ser Gly Ser Leu Val Glu Arg Arg Pro Cys Phe
                500                 505                 510

Ser Ala Leu Thr Val Asp Glu Thr Tyr Val Pro Lys Glu Phe Lys Ala
                515                 520                 525

Glu Thr Phe Thr Phe His Ser Asp Ile Cys Thr Leu Pro Lys Glu
                530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
                580                 585                 590

Ser Thr Glu Gly Pro Asn Leu Val Thr Arg Cys Lys Asp Ala Leu Ala
                595                 600                 605

<210> SEQ ID NO 105
<211> LENGTH: 607
<212> TYPE: PRT
<213> ORGANISM: Sus scrofa

<400> SEQUENCE: 105

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
                20                  25                  30

His Arg Phe Lys Asp Leu Gly Glu Gln Tyr Phe Lys Gly Leu Val Leu
            35                  40                  45

Ile Ala Phe Ser Gln His Leu Gln Gln Cys Pro Tyr Glu Glu His Val
        50                  55                  60

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Glu Pro Glu Arg Asn Glu Cys Phe Leu Gln
        115                 120                 125

His Lys Asn Asp Asn Pro Asp Ile Pro Lys Leu Lys Pro Asp Pro Val
130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205

Arg Glu Lys Val Leu Thr Ser Ala Ala Lys Gln Arg Leu Lys Cys Ala
    210                 215                 220

Ser Ile Gln Lys Phe Gly Glu Arg Ala Phe Lys Ala Trp Ser Leu Ala
225                 230                 235                 240
```

```
Arg Leu Ser Gln Arg Phe Pro Lys Ala Asp Phe Thr Glu Ile Ser Lys
                245                 250                 255

Ile Val Thr Asp Leu Ala Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Thr Ile Ser Thr Lys Leu Lys Glu Cys Cys Asp Lys
    290                 295                 300

Pro Leu Leu Glu Lys Ser His Cys Ile Ala Glu Ala Lys Arg Asp Glu
305                 310                 315                 320

Leu Pro Ala Asp Leu Asn Pro Leu Glu His Asp Phe Val Glu Asp Lys
                325                 330                 335

Glu Val Cys Lys Asn Tyr Lys Glu Ala Lys His Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Ile Tyr Glu Ala Thr Leu Glu Asp Cys Cys
    370                 375                 380

Ala Lys Glu Asp Pro Pro Ala Cys Tyr Ala Thr Val Phe Asp Lys Phe
385                 390                 395                 400

Gln Pro Leu Val Asp Glu Pro Lys Asn Leu Ile Lys Gln Asn Cys Glu
                405                 410                 415

Leu Phe Glu Lys Leu Gly Glu Tyr Gly Phe Gln Asn Ala Leu Ile Val
            420                 425                 430

Arg Tyr Thr Lys Lys Val Pro Gln Val Ser Thr Pro Thr Leu Val Glu
        435                 440                 445

Val Ala Arg Lys Leu Gly Leu Val Gly Ser Arg Cys Cys Lys Arg Pro
    450                 455                 460

Glu Glu Glu Arg Leu Ser Cys Ala Glu Asp Tyr Leu Ser Leu Val Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Lys Pro Lys Glu Phe Val Glu Gly
        515                 520                 525

Thr Phe Thr Phe His Ala Asp Leu Cys Thr Leu Pro Glu Asp Glu Lys
    530                 535                 540

Gln Ile Lys Lys Gln Thr Ala Leu Val Glu Leu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
            580                 585                 590

Val Glu Gly Pro Lys Phe Val Ile Glu Ile Arg Gly Ile Leu Ala
        595                 600                 605

<210> SEQ ID NO 106
<211> LENGTH: 608
<212> TYPE: PRT
<213> ORGANISM: Oryctolagus cuniculus

<400> SEQUENCE: 106

Met Lys Trp Val Thr Phe Ile Ser Leu Leu Phe Leu Phe Ser Ser Ala
1               5                   10                  15
```

```
Tyr Ser Arg Gly Val Phe Arg Arg Glu Ala His Lys Ser Glu Ile Ala
            20                  25                  30

His Arg Phe Asn Asp Val Gly Glu Glu His Phe Ile Gly Leu Val Leu
            35                  40                  45

Ile Thr Phe Ser Gln Tyr Leu Gln Lys Cys Pro Tyr Glu Glu His Ala
 50                  55                  60

Lys Leu Val Lys Glu Val Thr Asp Leu Ala Lys Ala Cys Val Ala Asp
 65                  70                  75                  80

Glu Ser Ala Ala Asn Cys Asp Lys Ser Leu His Asp Ile Phe Gly Asp
                 85                  90                  95

Lys Ile Cys Ala Leu Pro Ser Leu Arg Asp Thr Tyr Gly Asp Val Ala
            100                 105                 110

Asp Cys Cys Glu Lys Lys Glu Pro Glu Arg Asn Glu Cys Phe Leu His
            115                 120                 125

His Lys Asp Asp Lys Pro Asp Leu Pro Pro Phe Ala Arg Pro Glu Ala
130                 135                 140

Asp Val Leu Cys Lys Ala Phe His Asp Glu Lys Ala Phe Phe Gly
145                 150                 155                 160

His Tyr Leu Tyr Glu Val Ala Arg Arg His Pro Tyr Phe Tyr Ala Pro
                165                 170                 175

Glu Leu Leu Tyr Tyr Ala Gln Lys Tyr Lys Ala Ile Leu Thr Glu Cys
            180                 185                 190

Cys Glu Ala Ala Asp Lys Gly Ala Cys Leu Thr Pro Lys Leu Asp Ala
            195                 200                 205

Leu Glu Gly Lys Ser Leu Ile Ser Ala Ala Gln Glu Arg Leu Arg Cys
            210                 215                 220

Ala Ser Ile Gln Lys Phe Gly Asp Arg Ala Tyr Lys Ala Trp Ala Leu
225                 230                 235                 240

Val Arg Leu Ser Gln Arg Phe Pro Lys Ala Asp Phe Thr Asp Ile Ser
                245                 250                 255

Lys Ile Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
            275                 280                 285

Cys Glu His Gln Glu Thr Ile Ser Ser His Leu Lys Glu Cys Cys Asp
290                 295                 300

Lys Pro Ile Leu Glu Lys Ala His Cys Ile Tyr Gly Leu His Asn Asp
305                 310                 315                 320

Glu Thr Pro Ala Gly Leu Pro Ala Val Ala Glu Phe Val Glu Asp
                325                 330                 335

Lys Asp Val Cys Lys Asn Tyr Gln Glu Ala Lys Asp Leu Phe Leu Gly
            340                 345                 350

Lys Phe Leu Tyr Glu Tyr Ser Arg Arg His Pro Asp Tyr Ser Val Val
            355                 360                 365

Leu Leu Leu Arg Leu Gly Lys Ala Tyr Glu Ala Thr Leu Lys Lys Cys
            370                 375                 380

Cys Ala Thr Asp Asp Pro His Ala Cys Tyr Ala Lys Val Leu Asp Glu
385                 390                 395                 400

Phe Gln Pro Leu Val Asp Glu Pro Lys Asn Leu Val Lys Gln Asn Cys
                405                 410                 415

Glu Leu Tyr Glu Gln Leu Gly Asp Tyr Asn Phe Gln Asn Ala Leu Leu
            420                 425                 430
```

```
Val Arg Tyr Thr Lys Lys Val Pro Gln Val Ser Pro Thr Leu Val
            435                 440                 445

Glu Ile Ser Arg Ser Leu Gly Lys Val Gly Ser Lys Cys Cys Lys His
450                 455                 460

Pro Glu Ala Glu Arg Leu Pro Cys Val Glu Asp Tyr Leu Ser Val Val
465                 470                 475                 480

Leu Asn Arg Leu Cys Val Leu His Glu Lys Thr Pro Val Ser Glu Lys
                485                 490                 495

Val Thr Lys Cys Cys Ser Glu Ser Leu Val Asp Arg Arg Pro Cys Phe
            500                 505                 510

Ser Ala Leu Gly Pro Asp Glu Thr Tyr Val Pro Lys Glu Phe Asn Ala
            515                 520                 525

Glu Thr Phe Thr Phe His Ala Asp Ile Cys Thr Leu Pro Glu Thr Glu
            530                 535                 540

Arg Lys Ile Lys Lys Gln Thr Ala Leu Val Glu Leu Val Lys His Lys
545                 550                 555                 560

Pro His Ala Thr Asn Asp Gln Leu Lys Thr Val Val Gly Glu Phe Thr
                565                 570                 575

Ala Leu Leu Asp Lys Cys Cys Ser Ala Glu Asp Lys Glu Ala Cys Phe
            580                 585                 590

Ala Val Glu Gly Pro Lys Leu Val Glu Ser Ser Lys Ala Thr Leu Gly
            595                 600                 605

<210> SEQ ID NO 107
<211> LENGTH: 608
<212> TYPE: PRT
<213> ORGANISM: Rattus norvegicus

<400> SEQUENCE: 107

Met Lys Trp Val Thr Phe Leu Leu Leu Leu Phe Ile Ser Gly Ser Ala
1               5                   10                  15

Phe Ser Arg Gly Val Phe Arg Arg Glu Ala His Lys Ser Glu Ile Ala
                20                  25                  30

His Arg Phe Lys Asp Leu Gly Glu Gln His Phe Lys Gly Leu Val Leu
            35                  40                  45

Ile Ala Phe Ser Gln Tyr Leu Gln Lys Cys Pro Tyr Glu Glu His Ile
50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
            100                 105                 110

Asp Cys Cys Ala Lys Gln Glu Pro Glu Arg Asn Glu Cys Phe Leu Gln
            115                 120                 125

His Lys Asp Asp Asn Pro Asn Leu Pro Pro Phe Gln Arg Pro Glu Ala
            130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
            180                 185                 190

Cys Thr Glu Ser Asp Lys Ala Ala Cys Leu Thr Pro Lys Leu Asp Ala
            195                 200                 205
```

Val Lys Glu Lys Ala Leu Val Ala Ala Val Arg Gln Arg Met Lys Cys
210                 215                 220

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
                245                 250                 255

Lys Leu Ala Thr Asp Val Thr Lys Ile Asn Lys Glu Cys Cys His Gly
                260                 265                 270

Asp Leu Leu Glu Cys Ala Asp Asp Arg Ala Glu Leu Ala Lys Tyr Met
                275                 280                 285

Cys Glu Asn Gln Ala Thr Ile Ser Ser Lys Leu Gln Ala Cys Cys Asp
290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
                340                 345                 350

Thr Phe Leu Tyr Glu Tyr Ser Arg Arg His Pro Asp Tyr Ser Val Ser
                355                 360                 365

Leu Leu Leu Arg Leu Ala Lys Lys Tyr Glu Ala Thr Leu Glu Lys Cys
370                 375                 380

Cys Ala Glu Gly Asp Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Glu Leu Tyr Glu Lys Leu Gly Glu Tyr Gly Phe Gln Asn Ala Val Leu
                420                 425                 430

Val Arg Tyr Thr Gln Lys Ala Pro Gln Val Ser Thr Pro Thr Leu Val
                435                 440                 445

Glu Ala Ala Arg Asn Leu Gly Arg Val Gly Thr Lys Cys Cys Thr Leu
450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
                500                 505                 510

Ser Ala Leu Thr Val Asp Glu Thr Tyr Val Pro Lys Glu Phe Lys Ala
                515                 520                 525

Glu Thr Phe Thr Phe His Ser Asp Ile Cys Thr Leu Pro Asp Lys Glu
                530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
                580                 585                 590

Ala Thr Glu Gly Pro Asn Leu Val Ala Arg Ser Lys Glu Ala Leu Ala
                595                 600                 605

<210> SEQ ID NO 108
<211> LENGTH: 607

```
<212> TYPE: PRT
<213> ORGANISM: Ovis aries

<400> SEQUENCE: 108

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Asn Asp Leu Gly Glu Glu Asn Phe Gln Gly Leu Val Leu
        35                  40                  45

Ile Ala Phe Ser Gln Tyr Leu Gln Gln Cys Pro Phe Asp Glu His Val
    50                  55                  60

Lys Leu Val Lys Glu Leu Thr Glu Phe Ala Lys Thr Cys Val Ala Asp
65                  70                  75                  80

Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
            100                 105                 110

Asp Cys Cys Glu Lys Gln Glu Pro Glu Arg Asn Glu Cys Phe Leu Asn
        115                 120                 125

His Lys Asp Asp Ser Pro Asp Leu Pro Lys Leu Lys Pro Glu Pro Asp
    130                 135                 140

Thr Leu Cys Ala Glu Phe Lys Ala Asp Glu Lys Lys Phe Trp Gly Lys
145                 150                 155                 160

Tyr Leu Tyr Glu Val Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Asp Ala Met
        195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Asp Phe Thr Asp Val Thr Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp His Gln Asp Ala Leu Ser Ser Lys Leu Lys Glu Cys Cys Asp Lys
    290                 295                 300

Pro Val Leu Glu Lys Ser His Cys Ile Ala Glu Val Asp Lys Asp Ala
305                 310                 315                 320

Val Pro Glu Asn Leu Pro Pro Leu Thr Ala Asp Phe Ala Glu Asp Lys
                325                 330                 335

Glu Val Cys Lys Asn Tyr Gln Glu Ala Lys Asp Val Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Asp Cys Cys
    370                 375                 380

Ala Lys Glu Asp Pro His Ala Cys Tyr Ala Thr Val Phe Asp Lys Leu
385                 390                 395                 400
```

```
Lys His Leu Val Asp Glu Pro Gln Asn Leu Ile Lys Asn Cys Glu
            405                 410                 415

Leu Phe Glu Lys His Gly Glu Tyr Gly Phe Gln Asn Ala Leu Ile Val
            420                 425                 430

Arg Tyr Thr Arg Lys Ala Pro Gln Val Ser Thr Pro Thr Leu Val Glu
            435                 440                 445

Ile Ser Arg Ser Leu Gly Lys Val Gly Thr Lys Cys Cys Ala Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
            500                 505                 510

Asp Leu Thr Leu Asp Glu Thr Tyr Val Pro Lys Pro Phe Asp Glu Lys
            515                 520                 525

Phe Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Asp Glu Gln Leu Lys Thr Val Met Glu Asn Phe Val Ala
            565                 570                 575

Phe Val Asp Lys Cys Cys Ala Ala Asp Asp Lys Glu Gly Cys Phe Val
            580                 585                 590

Leu Glu Gly Pro Lys Leu Val Ala Ser Thr Gln Ala Ala Leu Ala
            595                 600                 605

<210> SEQ ID NO 109
<211> LENGTH: 609
<212> TYPE: PRT
<213> ORGANISM: Homo sapiens

<400> SEQUENCE: 109

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
            85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
```

```
                165                 170                 175
Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590
```

```
Ala Glu Glu Gly Lys Lys Leu Val Ala Ala Ser Gln Ala Ala Leu Gly
            595                 600                 605

Leu

<210> SEQ ID NO 110
<211> LENGTH: 609
<212> TYPE: PRT
<213> ORGANISM: Pongo abelii

<400> SEQUENCE: 110

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Lys Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Val Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Leu Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350
```

```
Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Glu Leu Leu
        420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
    450                 455                 460

Pro Glu Pro Lys Arg Met Pro Cys Ala Glu Asp Tyr Leu Ser Val Val
465                 470                 475                 480

Leu Asn Gln Leu Cys Val Leu His Glu Lys Thr Pro Val Ser Glu Arg
            485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Asp Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Thr Val Met Glu Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
    595                 600                 605

Leu

<210> SEQ ID NO 111
<211> LENGTH: 615
<212> TYPE: PRT
<213> ORGANISM: Gallus gallus

<400> SEQUENCE: 111

Met Lys Trp Val Thr Leu Ile Ser Phe Ile Phe Leu Phe Ser Ala
1               5                   10                  15

Thr Ser Arg Asn Leu Gln Arg Phe Ala Arg Asp Ala Glu His Lys Ser
            20                  25                  30

Glu Ile Ala His Arg Tyr Asn Asp Leu Lys Glu Glu Thr Phe Lys Ala
        35                  40                  45

Val Ala Met Ile Thr Phe Ala Gln Tyr Leu Gln Arg Cys Ser Tyr Glu
    50                  55                  60

Gly Leu Ser Lys Leu Val Lys Asp Val Val Asp Leu Ala Gln Lys Cys
65                  70                  75                  80

Val Ala Asn Glu Asp Ala Pro Glu Cys Ser Lys Pro Leu Pro Ser Ile
            85                  90                  95

Ile Leu Asp Glu Ile Cys Gln Val Glu Lys Leu Arg Asp Ser Tyr Gly
            100                 105                 110
```

```
Ala Met Ala Asp Cys Cys Ser Lys Ala Asp Pro Glu Arg Asn Glu Cys
        115                 120                 125

Phe Leu Ser Phe Lys Val Ser Gln Pro Asp Phe Val Gln Pro Tyr Gln
130                 135                 140

Arg Pro Ala Ser Asp Val Ile Cys Gln Glu Tyr Gln Asp Asn Arg Val
145                 150                 155                 160

Ser Phe Leu Gly His Phe Ile Tyr Ser Val Ala Arg Arg His Pro Phe
                165                 170                 175

Leu Tyr Ala Pro Ala Ile Leu Ser Phe Ala Val Asp Phe Glu His Ala
                180                 185                 190

Leu Gln Ser Cys Cys Lys Glu Ser Asp Val Gly Ala Cys Leu Asp Thr
                195                 200                 205

Lys Glu Ile Val Met Arg Glu Lys Ala Lys Gly Val Ser Val Lys Gln
        210                 215                 220

Gln Tyr Phe Cys Gly Ile Leu Lys Gln Phe Gly Asp Arg Val Phe Gln
225                 230                 235                 240

Ala Arg Gln Leu Ile Tyr Leu Ser Gln Lys Tyr Pro Lys Ala Pro Phe
                245                 250                 255

Ser Glu Val Ser Lys Phe Val His Asp Ser Ile Gly Val His Lys Glu
                260                 265                 270

Cys Cys Glu Gly Asp Met Val Glu Cys Met Asp Asp Met Ala Arg Met
        275                 280                 285

Met Ser Asn Leu Cys Ser Gln Gln Asp Val Phe Ser Gly Lys Ile Lys
        290                 295                 300

Asp Cys Cys Glu Lys Pro Ile Val Glu Arg Ser Gln Cys Ile Met Glu
305                 310                 315                 320

Ala Glu Phe Asp Glu Lys Pro Ala Asp Leu Pro Ser Leu Val Glu Lys
                325                 330                 335

Tyr Ile Glu Asp Lys Glu Val Cys Lys Ser Phe Glu Ala Gly His Asp
                340                 345                 350

Ala Phe Met Ala Glu Phe Val Tyr Glu Tyr Ser Arg Arg His Pro Glu
                355                 360                 365

Phe Ser Ile Gln Leu Ile Met Arg Ile Ala Lys Gly Tyr Glu Ser Leu
        370                 375                 380

Leu Glu Lys Cys Cys Lys Thr Asp Asn Pro Ala Glu Cys Tyr Ala Asn
385                 390                 395                 400

Ala Gln Glu Gln Leu Asn Gln His Ile Lys Glu Thr Gln Asp Val Val
                405                 410                 415

Lys Thr Asn Cys Asp Leu Leu His Asp His Gly Glu Ala Asp Phe Leu
                420                 425                 430

Lys Ser Ile Leu Ile Arg Tyr Thr Lys Lys Met Pro Gln Val Pro Thr
                435                 440                 445

Asp Leu Leu Leu Glu Thr Gly Lys Lys Met Thr Thr Ile Gly Thr Lys
450                 455                 460

Cys Cys Gln Leu Gly Glu Asp Arg Arg Met Ala Cys Ser Glu Gly Tyr
465                 470                 475                 480

Leu Ser Ile Val Ile His Asp Thr Cys Arg Lys Gln Glu Thr Thr Pro
                485                 490                 495

Ile Asn Asp Asn Val Ser Gln Cys Cys Ser Gln Leu Tyr Ala Asn Arg
                500                 505                 510

Arg Pro Cys Phe Thr Ala Met Gly Val Asp Thr Lys Tyr Val Pro Pro
        515                 520                 525
```

```
Pro Phe Asn Pro Asp Met Phe Ser Phe Asp Glu Lys Leu Cys Ser Ala
    530                 535                 540

Pro Ala Glu Glu Arg Glu Val Gly Gln Met Lys Leu Leu Ile Asn Leu
545                 550                 555                 560

Ile Lys Arg Lys Pro Gln Met Thr Glu Gln Ile Lys Thr Ile Ala
                565                 570                 575

Asp Gly Phe Thr Ala Met Val Asp Lys Cys Cys Lys Gln Ser Asp Ile
            580                 585                 590

Asn Thr Cys Phe Gly Glu Gly Ala Asn Leu Ile Val Gln Ser Arg
        595                 600                 605

Ala Thr Leu Gly Ile Gly Ala
    610                 615

<210> SEQ ID NO 112
<211> LENGTH: 386
<212> TYPE: PRT
<213> ORGANISM: Gallus gallus

<400> SEQUENCE: 112

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
        50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
                100                 105                 110

Pro Ile Leu Pro Glu Tyr Leu Gln Cys Val Lys Glu Leu Tyr Arg Gly
            115                 120                 125

Gly Leu Glu Pro Ile Asn Phe Gln Thr Ala Ala Asp Gln Ala Arg Glu
        130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285
```

```
Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala His Ala Glu Ile Asn
            325                 330                 335

Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 113
<211> LENGTH: 386
<212> TYPE: PRT
<213> ORGANISM: Maleagris gallopavo

<400> SEQUENCE: 113

Met Gly Ser Ile Gly Ala Val Ser Met Glu Phe Cys Phe Asp Val Phe
1               5                   10                  15

Lys Glu Leu Lys Val His His Ala Asn Glu Asn Ile Phe Tyr Ser Pro
                20                  25                  30

Phe Thr Ile Ile Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
50                  55                  60

Gly Phe Gly Asp Ser Val Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Thr Tyr
            100                 105                 110

Pro Ile Leu Pro Glu Tyr Leu Gln Cys Val Lys Glu Leu Tyr Arg Gly
            115                 120                 125

Gly Leu Glu Ser Ile Asn Phe Gln Thr Ala Ala Asp Gln Ala Arg Gly
    130                 135                 140

Leu Ile Asn Ser Trp Val Glu Ser Gln Thr Asn Gly Met Ile Lys Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Ile Pro Phe Arg Val Thr Glu Gln Glu Ser Lys Pro
        195                 200                 205

Val Gln Met Met Tyr Gln Ile Gly Leu Phe Lys Val Ala Ser Met Ala
    210                 215                 220

Ser Glu Lys Met Lys Ile Leu Glu Leu Pro Phe Ala Ser Gly Thr Met
225                 230                 235                 240

Ser Met Trp Val Leu Leu Pro Asp Glu Val Ser Gly Leu Glu Gln Leu
                245                 250                 255

Glu Thr Thr Ile Ser Phe Glu Lys Met Thr Glu Trp Ile Ser Ser Asn
```

```
                260                 265                 270
Ile Met Glu Glu Arg Arg Ile Lys Val Tyr Leu Pro Arg Met Lys Met
            275                 280                 285

Glu Glu Lys Tyr Asn Leu Thr Ser Val Leu Met Ala Met Gly Ile Thr
            290                 295                 300

Asp Leu Phe Ser Ser Ser Ala Asn Leu Ser Gly Ile Ser Ser Ala Gly
305                 310                 315                 320

Ser Leu Lys Ile Ser Gln Ala Ala His Ala Tyr Ala Glu Ile Tyr
                325                 330                 335

Glu Ala Gly Arg Glu Val Ile Gly Ser Ala Glu Ala Gly Ala Asp Ala
                340                 345                 350

Thr Ser Val Ser Glu Glu Phe Arg Val Asp His Pro Phe Leu Tyr Cys
            355                 360                 365

Ile Lys His Asn Leu Thr Asn Ser Ile Leu Phe Phe Gly Arg Cys Ile
            370                 375                 380

Ser Pro
385

<210> SEQ ID NO 114
<211> LENGTH: 551
<212> TYPE: PRT
<213> ORGANISM: Petromyzon marinus

<400> SEQUENCE: 114

Thr Met Gly Asp Cys Cys Gly Lys Glu Asn Ala Ala Gly Cys Leu Leu
1               5                   10                  15

His His Arg Tyr Leu Phe Gln Asp Glu Leu Cys Glu Gly Val Ser Ser
                20                  25                  30

Ile Pro Ser Ala Ala Ser Cys Cys Ser Leu Ala Asn Glu Glu Asp Arg
            35                  40                  45

Ala Asp Cys Leu Val Ser Leu Arg Gly Asn Leu Ser Ile His Ser Val
50                  55                  60

Pro Leu Ala Pro Ala Ser Gln Leu Cys His Asp Arg Arg Trp Lys Ser
65                  70                  75                  80

His Glu Ser Phe Ala Ser Leu Leu Trp Glu Phe Gly Arg His Pro
                85                  90                  95

Arg Ala Ala Asp Ser Gln Val Glu Glu Leu Ala Glu Arg Phe Ser Lys
            100                 105                 110

Ile Gly Asp Ala Cys Cys Asp Leu Ala Asp Glu Lys Glu Cys Ile Thr
            115                 120                 125

Arg Gly Arg Glu Ala Ile His Gln Glu Val Ser Ala Ala Tyr Ala Asp
130                 135                 140

Ala Ala Gln Leu Cys Ser Ser Leu Gln Ala Leu Gly Ala Gln Lys Phe
145                 150                 155                 160

Leu Gly Arg Met Val Leu Val Phe Ser Gln Arg Ala Pro Asn Ala Thr
                165                 170                 175

Phe Asp Gln Ile Ser Lys Leu Ser His Arg Phe His Ser Tyr Ala Gln
            180                 185                 190

Thr Cys Cys Gly Glu Gly Trp Ser Pro Gly Cys Phe Ala Glu Gln Arg
            195                 200                 205

His Leu Ile His Asp Glu Met Cys His Asp Met Glu Ala Leu Ser Arg
        210                 215                 220

Val Pro Ala Met Ala Lys Cys Cys Gln Ile Ser Gly Ser Ala Arg Ala
225                 230                 235                 240
```

```
Lys Cys Met Glu Thr Ile Pro Arg Gly Lys Pro Val Leu Asp Val Ala
                245                 250                 255

Leu Ala Arg Phe Asp Gly His Lys Val Cys Gln Met Asn Ala Glu Ala
            260                 265                 270

Pro Gln Glu Leu Leu Gly Arg Met Leu Tyr Glu Phe Gly Arg Arg His
        275                 280                 285

Thr Asp Ala Ser Val Gly Glu Ala Lys Lys Ile Ile Thr Glu Trp Met
    290                 295                 300

Asp Gly Val Lys Asp Cys Cys Ala Gly Asn His Ser Glu Glu Gln Ala
305                 310                 315                 320

Cys Leu Val Ser Lys Lys Ala Ala Ile Ser Val Lys Ile Gly Glu Glu
                325                 330                 335

Gln Ala Lys Ser His Lys Ile Cys Glu Gln Leu Gln Lys Asp Gly His
            340                 345                 350

Glu Val Phe Glu Glu Met Val Leu Ile Asp Phe Ala Ile Glu Ala Arg
        355                 360                 365

Thr Leu Ser Leu Asp Lys Val Val Glu Phe Ala His Arg Tyr Thr His
    370                 375                 380

His Ala Ile Arg Cys Cys Ala His Gln Ala His Cys Leu Leu Asp Glu
385                 390                 395                 400

Asn Leu His Leu Phe Ser Ser Leu Cys Ser Asp Leu Ser Tyr Leu Ala
                405                 410                 415

Ala His Asp Gly Tyr Arg Lys Cys Cys Arg Leu Ala Pro Ser Glu Ala
            420                 425                 430

Val Ser Cys His Val Glu His Glu Arg Ala His Glu Ala Glu Arg Ala
        435                 440                 445

Thr Glu Glu Val Glu Asn His Gly Lys Glu Arg Val Glu His Gln Ala
    450                 455                 460

Lys Val Glu Ala Val Glu Ala Val Ala Pro Phe Ala Glu Glu Gly
465                 470                 475                 480

Ala Ala Arg Ser Cys Leu Arg Phe Arg Gln Leu Pro Gly Lys Tyr Leu
                485                 490                 495

Gln Arg Leu Leu Tyr Lys Ala Ala His Gln Ala Pro Ala Gly Val Asp
            500                 505                 510

His Ser Arg Ile Arg Leu Gln Val His His Phe Val Glu Val Thr Ala
        515                 520                 525

Lys Cys Cys Arg Ala Tyr Asp Lys Ser Glu Cys Phe Ser His Glu Ile
    530                 535                 540

Lys Glu Met Lys Asn Ser Pro
545                 550

<210> SEQ ID NO 115
<211> LENGTH: 1423
<212> TYPE: PRT
<213> ORGANISM: Petromyzon marinus

<400> SEQUENCE: 115

Met Gly Lys Ala Met Leu Lys Leu Cys Ile Thr Leu Met Val Leu Val
1               5                   10                  15

Phe Ser Gly Thr Ala Glu Ser Lys Gly Val Met Arg Arg Glu Asp Glu
            20                  25                  30

Ser Phe Pro His Leu Lys Ser Arg Leu Cys Gly Gly Leu Asn Gly Leu
        35                  40                  45

Gly Glu Asp Ala Tyr Arg Ser His Cys Val Val Tyr Tyr Thr Lys Arg
    50                  55                  60
```

```
Met Gly Val Val Ser Leu Asp His Val Glu Glu Leu Ala Asn His Cys
 65                  70                  75                  80

Leu Arg Ile Val Lys Gln Cys Cys Ala Glu Gly Ala Ala Asp Asp Cys
             85                  90                  95

Leu Gln Thr Glu Leu Ala Ala Val Gln Glu Gln Val Cys Thr Arg Met
            100                 105                 110

Ser Glu Ala Lys Asp Val Pro Leu Val Gly Arg Cys Cys Ala Leu Ala
            115                 120                 125

Gly Ser Glu Arg His Asp Cys Phe His His Ala Gly Val Ala Glu
            130                 135                 140

Gly Glu Gly Ala Trp Pro His Ala Leu Pro Val Thr Ser Pro Pro Glu
145                 150                 155                 160

Tyr Asp Ser Val Thr Val Cys Ala Leu His Ala Thr Ala Asn Ala Arg
                165                 170                 175

Leu Tyr Asp Thr Leu Leu Trp Glu Phe Ser Arg Arg Tyr Pro Ser Ala
            180                 185                 190

Ser Asp Ser His Leu Ile Ala Leu Ala Asn Glu Phe Ile Thr Gly Leu
            195                 200                 205

Thr Thr Cys Cys Leu Val Glu Glu His Gly Ala Cys Leu Ala Thr
210                 215                 220

Leu Arg Glu Asp Phe Lys His Lys Leu Thr Glu Ala Ser His Lys Ser
225                 230                 235                 240

Gln Asn Leu Cys Lys Ala Leu Lys Ser Leu Gly Lys Glu Lys Phe Glu
                245                 250                 255

Asp Arg Ile Ile Val Arg Phe Thr Gln Arg Ala Pro Gln Ala Pro Phe
            260                 265                 270

Glu Leu Ile Gln Lys Leu Ala His Arg Phe Glu Val Leu Ala Glu Lys
            275                 280                 285

Cys Cys Glu Leu Gly His Ser Asp Arg Cys Leu Val Glu Glu Arg Tyr
            290                 295                 300

Thr Val Asp Asp Glu Leu Cys Leu Glu Gln Ser Phe Val Ala Thr Cys
305                 310                 315                 320

Pro Arg Leu Ser Ser Cys Cys Ser Leu Ser Gly Ser Ser Arg Ala Gln
                325                 330                 335

Cys Leu Glu Thr Val Pro Val Leu Glu Thr Ser Asp Lys Ala Ser Pro
            340                 345                 350

Ala Thr Pro Thr Leu Pro Ile Ser Glu Gln Cys Thr Leu Trp Ala Gly
            355                 360                 365

Lys Pro Val Glu Phe His Lys Arg Val Val Trp Gln Ile Ser His Arg
370                 375                 380

Tyr Pro Thr Thr Gly Val Ala Gln Val Glu Ala Leu Ala His Tyr
385                 390                 395                 400

Leu Glu His Leu Thr Ile Cys Cys Ala Ser Glu Asp Lys Asp Thr Cys
                405                 410                 415

Ile Ala Thr Glu Val Ala Glu Phe Lys Ser Glu Val Glu Lys Val His
            420                 425                 430

Thr Lys Ser Asp Trp Trp Cys Arg Met Ser Asp Leu Leu Gly Thr Asp
            435                 440                 445

Arg Phe Asn Leu Leu Ile Val Thr Tyr Ser Gln Arg Val Pro Gln
    450                 455                 460

Ala Thr Phe Glu Gln Val Glu Glu Ile Ser His His Phe Ala Leu Ile
465                 470                 475                 480
```

```
Thr Arg Lys Cys Cys Ser His Arg Lys Asn Gly Ser Cys Phe Leu Glu
                485                 490                 495

Glu Arg Tyr Ala Leu His Asp Ala Ile Cys Arg Asp Glu Ala Trp Leu
            500                 505                 510

Ser Gly Leu Ala Glu Val Ser Arg Cys Cys Ala Met Asp Gly Arg Ala
        515                 520                 525

Arg Ile Leu Cys Phe Asp Glu Leu Ser Ser His Leu Asn Ala Ser Val
    530                 535                 540

Glu Glu Arg Pro Glu Leu Cys Ser Thr Ser Leu Cys Ser Lys Tyr His
545                 550                 555                 560

Asp Leu Gly Phe Glu Phe Lys Gln Arg Val Ala Tyr Gly Phe Gly Gln
                565                 570                 575

Arg Phe Pro Lys Ala Ala Met Gly Gln Met Arg Asp Leu Ile Ser Lys
            580                 585                 590

Tyr Leu Ala Met Val Gln Arg Cys Cys Asp Ala Met Ser Asp Phe Lys
        595                 600                 605

Met Asp Val Glu Glu Val Glu Leu Arg Ala His Arg Leu Cys Leu Asp
    610                 615                 620

Ala His Gln Leu Gly Glu Glu Lys Leu Ala Asp Arg Ile Met Ile Gly
625                 630                 635                 640

Leu Ala Gln Arg Ile Ser Val Ala Ser Phe Val Asn Ile Ser Ser Val
                645                 650                 655

Ala Leu His Phe Ala Gln Ser Val Ile Lys Cys Cys Asp Ala Asp His
            660                 665                 670

Glu Lys Thr Cys Phe Met Glu Gln Glu Phe Ala Leu Glu Asp Gln Val
        675                 680                 685

Cys Ser Asp Ser Glu Ala Leu Ser His Ile Pro Ser Val Ser Arg Cys
    690                 695                 700

Cys Glu Leu His Pro Phe Asp Arg Ser Val Cys Phe His Ser Leu Arg
705                 710                 715                 720

Ser Thr Gln Ala Ser Thr Leu Ala Ser Thr His Val Ala Val Gly Lys
                725                 730                 735

Asp Asp Ser Leu Pro Gly His Val Glu Glu Cys Gln Ala Phe Ala Ser
            740                 745                 750

Gly Asn His Ser Leu Thr Asp Gln Val Met Phe Glu Phe Ala Arg Arg
        755                 760                 765

His Pro Arg Ala Ser Val Ser Gln Val Glu Ser Leu Ala Arg Leu Tyr
    770                 775                 780

Ser Glu Leu Ala Arg Ala Cys Cys Ala Leu Thr Asp Ala Asp Gln Glu
785                 790                 795                 800

Ser Cys Leu His Thr Ala Arg Ser Gln Ala Arg Gln Glu Ala Leu Lys
                805                 810                 815

Ser Leu Gln Arg Ser Glu Arg Ile Cys Asn Thr Leu Ser Ala Ile Gly
            820                 825                 830

Lys Glu Lys Phe Glu Asp Arg Ile Val Ile Ala Leu Ser Gln Lys Ala
        835                 840                 845

Thr Asp Ala Ser Phe Glu Gln Ile Leu Glu Ile Ala Asn Arg Met Ser
    850                 855                 860

Arg Gly Leu Ala Arg Cys Cys Glu Gln Gly Asn Asn Val Gly Cys Leu
865                 870                 875                 880

Met Asp His Arg His Ala Leu His Glu Ala Ile Cys Ser Thr Pro Asp
                885                 890                 895

Gly Ser Leu Pro Gln Ser Val Ala Ala Cys Cys Asn Thr Ser Asn Thr
```

-continued

```
                900               905                 910
Ser Thr Thr Thr Ser Thr Thr Thr Ser Thr Thr Ser Thr Thr Thr
            915                 920                 925
Ser Thr Thr Thr Ser Thr Thr Ser Thr Thr Ala Ala Glu Ile Arg
            930                 935             940
Asp Ser Cys Phe Asp Asn Leu Gln Ala Asn Val Ser Arg Ala His Ala
945                 950                 955                 960
Pro Phe Tyr Ser Asn Ser Gln Leu Cys Leu Met Lys Leu Arg Thr Pro
                965                 970                 975
His Arg Phe Leu Glu Arg Phe Leu Trp Glu Phe Gly Arg Arg His Pro
            980                 985                 990
Gln Ala Ala Leu Ser Gln Val Glu Glu Leu Ala Glu Met Tyr Val Lys
            995                 1000                1005
Met Thr Asp Ser Cys Cys Gly Lys Leu His Ser Lys Ser Cys Phe
        1010                1015                1020
Thr Glu Gln Arg His Thr Ile His Met Glu Ile Arg His Ala Tyr
        1025                1030                1035
Ala Glu Val Gln His Ile Cys Gly Ser Leu His Ser Arg Gly Glu
        1040                1045                1050
Glu Thr Phe Ile Gln Arg Glu Val Thr Leu Leu Ser Gln Lys Ala
        1055                1060                1065
Pro Asn Ala Ser Phe Glu Lys Val Ser Gln Leu Ala Arg His Phe
        1070                1075                1080
Leu Ser Leu Ala Lys Lys Cys Cys Ala Pro Asp His Ala Ala Gly
        1085                1090                1095
Cys Phe Leu Glu Glu Pro Tyr Ala Ile His Asp Glu Val Cys Arg
        1100                1105                1110
Asp Asp Glu Val Val Asp Gln Val Gly Gly Leu Ala Thr Cys Cys
        1115                1120                1125
Arg Met Ser Gly Thr Ser Arg Ala Lys Cys Leu Ala Gln Leu Pro
        1130                1135                1140
Arg Asp Leu Gly Arg His Gly Asn Arg Glu Thr Pro Glu Phe Asp
        1145                1150                1155
Glu Leu Lys Ile Cys Glu Leu Arg Arg Asp Asn Pro Ala Val Leu
        1160                1165                1170
Met Glu Lys Ile Leu Tyr Glu Phe Gly Arg Arg His Ser Asp Ser
        1175                1180                1185
Ala Val Ser Glu Val Lys Asn Phe Ala Gln Lys Phe Ser His Ser
        1190                1195                1200
Val Thr Glu Cys Cys Thr Ser Glu Lys Thr His Glu Cys Phe Val
        1205                1210                1215
Glu Lys Arg Ala Ala Ile Glu Lys Val Ile Lys Asp Glu Glu Ala
        1220                1225                1230
Lys Gly Asn Leu Thr Cys Gln Arg Leu Lys Ala Gln Gly Val Glu
        1235                1240                1245
His Phe Glu Gln Leu Val Ile Leu Asn Phe Ala Arg Ala Ala Lys
        1250                1255                1260
Ser Leu Pro Met Glu Lys Val Val Glu Phe Ala His Arg Phe Thr
        1265                1270                1275
Arg Ile Ala Gly Gln Cys Cys Glu His Asp Thr His Cys Leu Ile
        1280                1285                1290
Asp Glu Ser Phe His Leu His Ala Glu Met Cys Gly Asp His Gly
        1295                1300                1305
```

```
Tyr Ile Met Ala His Pro Gly Val Ala Asn Cys Cys Lys Ser Asp
    1310                1315                1320

Val Ser Glu Gln Gly Thr Cys Phe Lys Ile His Glu Asp Val His
    1325                1330                1335

His Ala Glu Glu Ile Leu Ser Lys Asp Val Ser Pro Ala His Pro
    1340                1345                1350

Thr Ala Glu Arg Val Cys Leu Arg Tyr Arg Gln Phe Pro Glu Lys
    1355                1360                1365

Phe Ile Asn Leu Ala Leu Phe Glu Leu Val His Arg Leu Pro Leu
    1370                1375                1380

Leu Glu Ser Ser Val Leu Arg Arg Lys Ala Leu Ala Tyr Thr Gly
    1385                1390                1395

Phe Thr Asp Asp Cys Cys Arg Ala Val Asp Lys Thr Ala Cys Phe
    1400                1405                1410

Thr Glu Lys Leu Glu Ala Ile Lys Ser Ser
    1415                1420

<210> SEQ ID NO 116
<211> LENGTH: 382
<212> TYPE: PRT
<213> ORGANISM: Rana catesbeiana

<400> SEQUENCE: 116

Lys Cys Arg Ile Ile Arg Glu Phe Pro Asp Ile Val Phe Lys Gly Leu
1               5                   10                  15

Thr Leu Val Gln Val Ser Gln Lys Phe Gly Lys Ala Gly Phe Glu Asp
                20                  25                  30

Val Lys Lys Val Thr Glu Glu Ile Val His Leu Asn Glu Asp Cys Cys
            35                  40                  45

Lys Gly Asp Ala Val Glu Cys Met Met Glu Arg Met Glu Ala Thr Asp
    50                  55                  60

His Ile Cys Glu Ala Lys Asp Lys Leu Ser Ser Lys Leu Ala Asp Cys
65                  70                  75                  80

Cys Ala Lys Ser Ile Leu Glu Arg Thr Pro Cys Leu Leu Ala Leu Pro
                85                  90                  95

Asn Asp Glu Ser Asp Leu Ser Lys Glu Leu Lys Asn Tyr Tyr Glu Asp
                100                 105                 110

Glu Arg Val Cys Glu Asn Tyr Lys Lys Asp Lys Leu Leu Phe Leu Ala
            115                 120                 125

His Phe Thr His Asp Tyr Ala Arg Ser His Gln Glu Ser Ser Pro Gln
    130                 135                 140

Ser Cys Leu Arg Val Ser Lys Gly Phe Glu Gly Leu Leu Glu Lys Cys
145                 150                 155                 160

Cys Ala Ser Glu Asn His Ala Glu Cys Leu Lys Gln Ala Pro Ile Leu
                165                 170                 175

Leu Glu Ala Ala Leu Lys Glu Ile Glu Glu Leu Arg Lys Gln Asn Cys
                180                 185                 190

Gly Ala Leu Gln Leu Leu Gly Phe Arg Asp Tyr Asn Ile Gln Leu Leu
            195                 200                 205

Phe Arg Tyr Phe Phe Lys Met Pro Gln Val Thr Ala Pro Thr Leu Val
    210                 215                 220

Glu Leu Ala Gly Arg Met Thr Lys Val Ala Val Tyr Cys Cys Gly Leu
225                 230                 235                 240

Ala Glu Asn Lys Gln Gln Thr Cys Ala Glu Glu Lys Leu Asp Ile Leu
```

```
                245                 250                 255
Leu Gly Glu Met Cys Glu Lys Glu Lys His Thr Phe Val Asn Asp Asn
            260                 265                 270

Val Arg His Cys Cys Val Asp Ser Tyr Ala Asn Arg Lys Cys Phe
            275                 280             285

Thr Asp Leu Gln Arg Tyr Pro Asn Tyr Val Ala Pro Lys Trp Asp Glu
            290                 295                 300

Ser Lys Leu His Phe Asn Glu Asp Leu Cys Lys Gly Ser Glu Asp Asp
305                 310                 315                 320

Gln Ile Lys Lys Leu Glu Val Leu Val Glu Tyr Met Lys Met Lys
                325                 330                 335

Pro Asp Cys Gly Pro Glu Lys Leu Lys Glu Val Val Glu Ala Phe Arg
            340                 345                 350

Lys Ile Asp Ile Lys Cys Cys Ala Ala Glu Asp His Gln Lys Cys Phe
            355                 360                 365

Asp Asp Glu Lys Ala Gly Leu Leu Gln Ile Ile Glu Ala His
            370                 375                 380

<210> SEQ ID NO 117
<211> LENGTH: 603
<212> TYPE: PRT
<213> ORGANISM: Rana shqiperica

<400> SEQUENCE: 117

Lys Trp Ala Thr Leu Ile Cys Leu Phe Ile Leu Ser Ile Thr Thr Glu
1               5                   10                  15

Ser Arg His Leu Gln Lys Arg His His Glu Gly His Pro Arg Ile Ile
            20                  25                  30

Asn Asp Ile Val Lys Ala Val Gly Lys Pro Ala Val Glu Lys Leu Val
            35                  40                  45

Leu Val Met Val Ala Gln Asp Phe Glu Lys Cys Ser Leu Asp Glu His
        50                  55                  60

Leu Lys Val Gln Ala Lys Ile Ile Glu Ala Val Asp Asn Cys Glu Lys
65                  70                  75                  80

His Pro Glu Glu Ala Glu Cys Lys Lys Pro Ala Ile Glu Leu Tyr His
                85                  90                  95

Asp Ile Val Cys Lys Glu Glu Asp Ile Asp Gln Leu Tyr Pro Trp Thr
            100                 105                 110

Thr Glu Cys Cys Gly Lys Ala Glu Ala Glu Arg Thr Lys Cys Phe Tyr
        115                 120                 125

Glu His Arg Glu Val Arg Val Glu Glu Tyr Lys Ile Pro Asn Ile Glu
    130                 135                 140

Glu Ser Cys Lys Glu His Lys Glu His Pro Gln Arg Ala Phe Ser Tyr
145                 150                 155                 160

Tyr Leu Ser Asn Ile Ala Lys Arg His Ser Lys Leu Tyr Pro Pro Ala
                165                 170                 175

Val Leu Gly Phe Ala Ile Gln Tyr Asn Glu Ile Thr Thr Glu Cys Cys
            180                 185                 190

Ala Ala Glu Asp Lys Ala Lys Cys Phe Gly Glu Arg Met Pro Gln Val
        195                 200                 205

Lys Lys Leu Thr Asn Tyr Leu Glu Asp Lys His Lys Gln Lys Cys Arg
    210                 215                 220

Val Leu Lys Glu Phe Pro Glu Arg Val Ser Gln Ala Leu Thr Leu Val
225                 230                 235                 240
```

```
Gln Val Ser Gln Arg Phe Gly Asn Ala Lys Tyr Asp Asp Val Glu Lys
            245                 250                 255

Val Thr Ile Glu Ile Ala His Leu Asn Glu Asp Cys Cys Lys Gly Asp
        260                 265                 270

Ala Val Glu Cys Met Ile Glu Arg Met Glu Ala Thr Glu His Ile Cys
        275                 280                 285

Leu Ala Lys Glu Lys Leu Ser Ser Lys Leu Ser Asp Cys Cys Ala Lys
        290                 295                 300

Gly Val Leu Glu Arg Thr Pro Cys Ile Leu Ala Leu Pro Asn Glu Glu
305                 310                 315                 320

Pro Asp Leu Pro Ile Glu Leu Lys Glu Tyr Tyr Glu Asp Glu His Val
                325                 330                 335

Cys Glu Asn Tyr Gln Lys Asp Lys Arg Lys Tyr Leu Ala His Phe Thr
                340                 345                 350

His Asp Tyr Ser Arg Ser His Gln Glu Ser Ser Pro Gln Ser Cys Leu
            355                 360                 365

Arg Val Ser Arg Gly Phe Glu Met Leu Leu Glu Lys Cys Cys Ala Ser
        370                 375                 380

Ala Asn Ser Ala Glu Cys Leu Lys Asp Ala Pro Lys Leu Leu Glu Ala
385                 390                 395                 400

Ala Leu Lys Glu Asn Glu Glu Ile Ser Lys Gln Asn Cys Gly Ala Leu
                405                 410                 415

Glu Lys Leu Gly Phe Asn Asp Phe Tyr Ile Gln Leu Leu Val Arg Tyr
                420                 425                 430

Phe Gly Lys Met Pro Gln Val Thr Ala Gln Thr Leu Val Glu Leu Thr
            435                 440                 445

Gly Arg Met Ala Lys Ile Gly Val Tyr Cys Cys Gly Leu Pro Asp Asn
450                 455                 460

Lys Lys Gln Pro Cys Ala Glu Glu Lys Leu Asp Ile Leu Leu Gly Glu
465                 470                 475                 480

Met Cys Glu Arg Glu Lys Lys Thr Phe Ile Asn Asp Asn Val His His
                485                 490                 495

Cys Cys Val Asp Ser Tyr Ala Asn Arg Arg Pro Cys Phe Thr Lys Leu
                500                 505                 510

Gly Pro Tyr Ala Asn Tyr Glu Ala Pro Val Trp Asp Glu Ser Lys Leu
            515                 520                 525

His Phe Thr Ala Asp Met Cys Lys Gly Ser Ala Asp Asp Gln Leu Lys
            530                 535                 540

Thr Lys Leu Val Leu Leu Val Glu Phe Leu Lys Met Lys Pro Thr Cys
545                 550                 555                 560

Gly Lys Glu Lys Leu Thr Glu Val Ile Glu Ser Phe Arg Lys Thr Val
                565                 570                 575

Val Glu Cys Cys Ala Ala Glu Asn Gln Gln Ala Cys Phe Asp Glu Lys
                580                 585                 590

Lys Gly Gly Leu His Glu Ile Ile Lys Asp His
            595                 600

<210> SEQ ID NO 118
<211> LENGTH: 608
<212> TYPE: PRT
<213> ORGANISM: Xenopus laevis

<400> SEQUENCE: 118

Met Lys Trp Ile Thr Leu Ile Cys Leu Leu Ile Ser Ser Thr Leu Ile
1               5                   10                  15
```

-continued

```
Glu Ser Arg Ile Ile Phe Lys Arg Asp Thr Asp Val Asp His His Lys
             20                  25                  30

His Ile Ala Asp Met Tyr Asn Leu Leu Thr Glu Arg Thr Phe Lys Gly
         35                  40                  45

Leu Thr Leu Ala Ile Val Ser Gln Asn Leu Gln Lys Cys Ser Leu Glu
 50                  55                  60

Glu Leu Ser Lys Leu Val Asn Glu Ile Asn Asp Phe Ala Lys Ser Cys
65                  70                  75                  80

Thr Gly Asn Asp Lys Thr Pro Glu Cys Glu Lys Pro Ile Gly Thr Leu
                 85                  90                  95

Phe Tyr Asp Lys Leu Cys Ala Asp Pro Lys Val Gly Val Asn Tyr Glu
            100                 105                 110

Trp Ser Lys Glu Cys Cys Ser Lys Gln Asp Pro Glu Arg Ala Gln Cys
        115                 120                 125

Phe Arg Ala His Arg Val Phe Glu His Asn Pro Val Arg Pro Lys Pro
    130                 135                 140

Glu Glu Thr Cys Ala Leu Phe Lys Glu His Pro Asp Asp Leu Leu Ser
145                 150                 155                 160

Ala Phe Ile His Glu Glu Ala Arg Asn His Pro Asp Leu Tyr Pro Pro
                165                 170                 175

Ala Val Leu Leu Leu Thr Gln Gln Tyr Gly Lys Leu Val Glu His Cys
            180                 185                 190

Cys Glu Glu Glu Asp Lys Asp Lys Cys Phe Ala Glu Lys Met Lys Glu
        195                 200                 205

Leu Met Lys His Ser His Ser Ile Glu Asp Lys Gln Lys His Phe Cys
    210                 215                 220

Trp Ile Val Asn Asn Tyr Pro Glu Arg Val Ile Lys Ala Leu Asn Leu
225                 230                 235                 240

Ala Arg Val Ser His Arg Tyr Pro Lys Pro Asp Phe Lys Leu Ala His
                245                 250                 255

Lys Phe Thr Glu Glu Thr Thr His Phe Ile Lys Asp Cys Cys His Gly
            260                 265                 270

Asp Met Phe Glu Cys Met Thr Glu Arg Leu Glu Leu Ser Glu His Thr
        275                 280                 285

Cys Gln His Lys Asp Glu Leu Ser Thr Lys Leu Glu Lys Cys Cys Asn
    290                 295                 300

Leu Pro Leu Leu Glu Arg Thr Tyr Cys Ile Val Thr Leu Glu Asn Asp
305                 310                 315                 320

Asp Val Pro Ala Glu Leu Ser Lys Pro Ile Thr Glu Phe Thr Glu Asp
                325                 330                 335

Pro His Val Cys Glu Lys Tyr Ala Glu Asn Lys Glu Ser Phe Leu Glu
            340                 345                 350

Arg Ile Ser Pro Trp Gln Ser Gln Glu Thr Pro Glu Leu Ser Glu Gln
        355                 360                 365

Phe Leu Leu Gln Ser Ala Lys Glu Tyr Glu Ser Leu Leu Asn Lys Cys
    370                 375                 380

Cys Phe Ser Asp Asn Pro Pro Glu Cys Tyr Lys Asp Gly Ala Asp Arg
385                 390                 395                 400

Phe Met Asn Glu Ala Lys Glu Arg Phe Ala Tyr Leu Lys Gln Asn Cys
                405                 410                 415

Asp Ile Leu His Glu His Gly Glu Tyr Leu Phe Glu Asn Glu Leu Leu
            420                 425                 430
```

```
Ile Arg Tyr Thr Lys Lys Met Pro Gln Val Ser Asp Glu Thr Leu Ile
            435                 440                 445

Gly Ile Ala His Gln Met Ala Asp Ile Gly Glu His Cys Cys Ala Val
    450                 455                 460

Pro Glu Asn Gln Arg Met Pro Cys Ala Glu Gly Asp Leu Thr Ile Leu
465                 470                 475                 480

Ile Gly Lys Met Cys Glu Arg Gln Lys Lys Thr Phe Ile Asn Asn His
                485                 490                 495

Val Ala His Cys Cys Thr Asp Ser Tyr Ser Gly Met Arg Ser Cys Phe
            500                 505                 510

Thr Ala Leu Gly Pro Asp Glu Asp Tyr Val Pro Pro Val Thr Asp
            515                 520                 525

Asp Thr Phe His Phe Asp Asp Lys Ile Cys Thr Ala Asn Asp Lys Glu
            530                 535                 540

Lys Gln His Ile Lys Gln Lys Phe Leu Val Lys Leu Ile Lys Val Ser
545                 550                 555                 560

Pro Lys Leu Glu Lys Asn His Ile Asp Glu Trp Leu Leu Glu Phe Leu
                565                 570                 575

Lys Met Val Gln Lys Cys Cys Thr Ala Asp Glu His Gln Pro Cys Phe
            580                 585                 590

Asp Thr Glu Lys Pro Val Leu Ile Glu His Cys Gln Lys Leu His Pro
            595                 600                 605

<210> SEQ ID NO 119
<211> LENGTH: 572
<212> TYPE: PRT
<213> ORGANISM: Xenopus (Silwana) tropicalis

<400> SEQUENCE: 119

Met Asn Ala Leu Met Arg Arg Ala Cys Cys Gly Ala Leu Phe Pro Leu
1               5                   10                  15

Ser Phe Arg Leu Ala Ala Leu Ser Pro Met Lys Gly Ala Ser Asn Phe
            20                  25                  30

Ser Cys Gly Asn Val Cys Ala Ser Pro Ala Gly Cys Trp Ala Pro Pro
        35                  40                  45

Ser Gly His Asp Thr Gly Ile Lys Val Tyr Asn Ser Leu Thr Arg Arg
    50                  55                  60

Lys Asp Pro Leu Ile Leu Ala Asp Pro Thr Val Ala Thr Trp Tyr Ser
65                  70                  75                  80

Cys Gly Pro Thr Val Tyr Asp His Ala His Leu Gly His Ala Cys Ser
                85                  90                  95

Tyr Val Arg Phe Asp Ile Ile Arg Arg Ile Leu Leu Lys Val Phe Gly
            100                 105                 110

Ile Asp Thr Val Val Met Val Thr Asp Ile Asp Lys Ile
            115                 120                 125

Ile Lys Arg Ala Lys Glu Leu Asn Ile Ser Pro Val Ala Leu Ala Arg
        130                 135                 140

Thr Tyr Glu Gln Asp Phe Lys Gln Asp Met Thr Ala Leu Lys Val Leu
145                 150                 155                 160

Pro Pro Thr Val Tyr Met Arg Val Thr Glu Asn Ile Pro Gln Ile Ile
                165                 170                 175

Ser Phe Ile Glu His Ile Ile Ala Asn Gly Tyr Ala Tyr Ala Thr Ser
            180                 185                 190

Gln Gly Asn Val Tyr Phe Asp Val Gln Ser Ile Gly Glu Arg Tyr Gly
        195                 200                 205
```

Lys Phe Asn Asp Ser Phe Ser Asp Thr Ala Ser Glu Ser Ala Ser Gln
210                 215                 220

Asp Lys Arg His Ile Arg Asp Phe Ala Leu Trp Lys Thr Ser Lys Pro
225                 230                 235                 240

Glu Glu Pro Tyr Trp Ala Ser Pro Trp Gly Lys Gly Arg Pro Gly Trp
            245                 250                 255

His Ile Glu Cys Ser Thr Ile Ala Ser Ser Val Phe Gly Lys His Leu
            260                 265                 270

Asp Ile His Thr Gly Gly Ile Asp Leu Ala Phe Pro His His Glu Asn
        275                 280                 285

Glu Ile Ala Gln Cys Glu Ala Tyr His Gln Ser Thr Gln Trp Gly Asn
        290                 295                 300

Tyr Phe Leu His Thr Gly His Leu His Leu Lys Gly Asn Glu Glu Lys
305                 310                 315                 320

Met Ser Lys Ser Leu Arg Asn Tyr Leu Thr Val Lys Glu Phe Leu Lys
            325                 330                 335

Ser Phe Ser Pro Asp Gln Phe Arg Met Phe Cys Leu Arg Ser Lys Tyr
            340                 345                 350

Lys Ser Ala Val Glu Tyr Ser Asn Gly Ser Met His Asp Ala Val Asn
        355                 360                 365

Thr Leu His Thr Ile Ser Ser Phe Val Asp Asp Ala Lys Ala Tyr Met
        370                 375                 380

Lys Gly Gln Leu Ile Cys Gln Pro Val Gln Glu Ala Leu Leu Trp Gln
385                 390                 395                 400

Arg Leu Asn Glu Thr Lys Val Asn Val Lys Ala Ala Phe Ser Asp Asp
            405                 410                 415

Phe Asp Thr Pro Arg Ala Val Asp Ala Val Met Asp Leu Ile His His
            420                 425                 430

Gly Asn Arg Gln Leu Lys Ala Val Ser Lys Glu Ser Asn Ser Pro Arg
        435                 440                 445

Ser Ser Val Val Tyr Gly Ala Met Ile Ser Tyr Ile Glu Gln Phe Leu
450                 455                 460

Glu Ile Leu Gly Ile Ser Leu Ser Gln Asn Gln Val Ala Ala Glu Asp
465                 470                 475                 480

Arg His Ser Ala Val Leu Phe Asn Val Val Glu Glu Met Ile Ser Phe
            485                 490                 495

Arg Ser Lys Val Arg Asn Tyr Ala Leu Ala Ala Asp Glu Ser Pro Asn
            500                 505                 510

Ala Ile Gly Gln Glu Glu Lys Gln Gln Tyr Lys Glu Arg Arg Arg Gln
        515                 520                 525

Leu Leu Leu Glu Arg Glu Pro Leu Leu Gln Ala Cys Asp Ile Met Arg
530                 535                 540

Gln His Leu Ala Val Tyr Gly Ile Asn Val Lys Asp Arg Gly Asn Thr
545                 550                 555                 560

Ser Thr Trp Glu Leu Leu Asp Arg Lys Glu Glu Thr
            565                 570

<210> SEQ ID NO 120
<211> LENGTH: 626
<212> TYPE: PRT
<213> ORGANISM: Ambystoma maculatum

<400> SEQUENCE: 120

Met Lys Trp Ala Thr Leu Ile Ser Ile Val Ile Val Leu Ser Cys Thr

-continued

```
1               5                   10                  15
Glu Ser Arg Ile Leu Asn Lys Arg His His Glu Gly His Val Asp
                20                  25                  30
Asn Pro Pro His Leu Ile Gly Asp Leu Ile Pro Met Ile Gly Val Asp
                35                  40                  45
Asn Ser Lys Gly Leu Val Leu Ala Ala Val Ser Gln Met Leu Pro Leu
50                  55                  60
Cys Pro Tyr Glu His Leu Gln Arg Val Glu Asp Val Met Gln Ile
65                  70                  75                  80
Ala Asp Leu Cys Ala Lys Gly Ala Arg His Ala Asn Cys Ala Lys Ser
                85                  90                  95
Pro Met Thr Ile Ile Leu Asp Glu Leu Cys Lys Lys Pro Glu Asn Ala
                100                 105                 110
Glu Lys Tyr Pro Phe His Gln Glu Cys Cys Lys Lys Glu Asp Pro Glu
                115                 120                 125
Arg His Lys Cys Phe Val Glu His Lys Met Ala Asn His Glu Glu Leu
                130                 135                 140
Thr Lys Tyr Val Arg Pro Ala Pro Glu Gln Ile Cys Lys Asp His Ala
145                 150                 155                 160
Glu Asn Arg Gly Pro Leu Leu Ala Arg Tyr Ile Phe Met Leu Ala Ile
                165                 170                 175
Gly His Pro His Met Tyr Ile Pro Ala Ile Leu Gly Phe Ala Gln Arg
                180                 185                 190
Phe Asp Gly Ile Val Ser His Cys Cys Lys Asp Val Glu Thr Ala Gly
                195                 200                 205
Gln Cys Phe Asn Asp Lys Met Pro Glu His Lys Gln Glu Val Glu Tyr
                210                 215                 220
Val Cys Ala Leu Gln Lys His Asn Cys Tyr Ile Leu Gln Asp Phe Lys
225                 230                 235                 240
Glu Arg Ala Leu Thr Ala Tyr Lys Ala Val Gln Ala Ser Gln Lys Phe
                245                 250                 255
Pro Leu Ala Ser Phe Glu Asn Val Gln Ile Ile Val Pro Asp Thr Val
                260                 265                 270
His Leu His Gln Thr Cys Cys Gly Gly Asp Met Met Ala Cys Met Leu
                275                 280                 285
Glu Arg Met Lys Leu Thr Ala Lys Ile Cys Glu Lys Lys Asp Glu Leu
                290                 295                 300
Ala Thr His Leu Lys Glu Cys Cys Asp Lys Pro Leu Leu Glu Arg Ser
305                 310                 315                 320
Ala Cys Ile Ile Arg Leu Pro Asn Asp Gln Lys Pro Ala Asp Leu Ser
                325                 330                 335
Pro Lys Val Pro His Tyr Ile Asp Pro Glu Val Cys Lys Leu Tyr
                340                 345                 350
Thr Glu Gly Gly Asp Thr Phe Met Gly Arg Phe Leu Tyr Glu Cys Ala
                355                 360                 365
Arg Arg His Gln Asp Tyr Ser Pro Glu Met Leu Leu Arg Met Gly Ser
                370                 375                 380
Gly Tyr Glu Glu Phe Leu Lys Lys Cys Cys Ala Ala Glu Gly His Asn
385                 390                 395                 400
Glu Cys Leu Ala Lys Thr Glu Glu Ser Leu Lys Lys Glu Ile Glu Ser
                405                 410                 415
Ser Val Thr Leu Leu Lys Thr Asn Cys Gly Ala Leu Asp Lys Leu Lys
                420                 425                 430
```

```
Ser Tyr Leu Phe Gln Asn Leu Leu Ile Phe Lys Tyr Val Ala Arg Met
            435                 440                 445

Pro Ala Leu Ser Glu Gln Ser Leu Leu Arg Ile Thr Lys Ser Met Thr
450                 455                 460

Thr Ile Gly Glu Lys Cys Cys His Arg Pro Glu Asp Gln Gln Met Thr
465                 470                 475                 480

Cys Ser Glu Gly Gly Leu Gly Ile Val Phe Gly Gln Ile Cys Met Lys
                485                 490                 495

Gln Lys Thr Thr Pro Val Asn Glu Lys Val Ala Gln Cys Cys Ser His
            500                 505                 510

Ser Leu Ser Ser Gln Thr Pro Cys Phe Ser Ala Leu Pro Val Asp Glu
            515                 520                 525

Thr Tyr Val Pro Pro Leu Ser Val Ala Ser Phe Asn Phe Asn Asp
530                 535                 540

Glu Leu Cys Thr Thr Ser Glu Pro Glu Gln Gln Ser Lys Lys Gln Val
545                 550                 555                 560

Phe Leu Ile Arg Leu Met Lys Gln Tyr Pro His Met Thr Asp Glu Gln
                565                 570                 575

Leu Lys Thr Cys Val Val Asn Phe Val Pro Met Val Asp Gln Cys Cys
            580                 585                 590

Lys Ala Asp Asn His Asn Glu Cys Phe Ala Leu Glu Gly Ala Lys Leu
            595                 600                 605

Ile Asp Ala Cys Lys Ala Ile Leu Ala Val His Pro Ala Val Glu Val
            610                 615                 620

Ser Val
625

<210> SEQ ID NO 121
<211> LENGTH: 608
<212> TYPE: PRT
<213> ORGANISM: Salmo salar

<400> SEQUENCE: 121

Met Gln Trp Leu Ser Val Cys Ser Leu Leu Val Leu Leu Ser Val Leu
1               5                   10                  15

Ser Arg Ser Gln Ala Gln Asn Gln Ile Cys Thr Ile Phe Thr Glu Ala
            20                  25                  30

Lys Glu Asp Gly Phe Lys Ser Leu Ile Leu Val Gly Leu Ala Gln Asn
            35                  40                  45

Leu Pro Asp Ser Thr Leu Gly Asp Leu Val Pro Leu Ile Ala Glu Ala
50                  55                  60

Leu Ala Met Gly Val Lys Cys Cys Ser Asp Thr Pro Pro Glu Asp Cys
65                  70                  75                  80

Glu Arg Asp Val Ala Asp Leu Phe Gln Ser Ala Val Cys Ser Ser Glu
                85                  90                  95

Thr Leu Val Glu Lys Asn Asp Leu Lys Met Cys Cys Glu Lys Thr Ala
            100                 105                 110

Ala Glu Arg Thr His Cys Phe Val Asp His Lys Ala Lys Ile Pro Arg
            115                 120                 125

Asp Leu Ser Leu Lys Ala Glu Leu Pro Ala Ala Asp Gln Cys Glu Asp
            130                 135                 140

Phe Lys Lys Asp His Lys Ala Phe Val Gly Arg Phe Ile Phe Lys Phe
145                 150                 155                 160

Ser Lys Ser Asn Pro Met Leu Pro Pro His Val Val Leu Ala Ile Ala
```

-continued

```
                165                 170                 175
Lys Gly Tyr Gly Glu Val Leu Thr Thr Cys Cys Gly Glu Ala Glu Ala
            180                 185                 190

Gln Thr Cys Phe Asp Thr Lys Lys Ala Thr Phe Gln His Ala Val Met
            195                 200                 205

Lys Arg Val Ala Glu Leu Arg Ser Leu Cys Ile Val His Lys Lys Tyr
            210                 215                 220

Gly Asp Arg Val Val Lys Ala Lys Lys Leu Val Gln Tyr Ser Gln Lys
225                 230                 235                 240

Met Pro Gln Ala Ser Phe Gln Glu Met Gly Gly Met Val Asp Lys Ile
                245                 250                 255

Val Ala Thr Val Ala Pro Cys Cys Ser Gly Asp Met Val Thr Cys Met
                260                 265                 270

Lys Glu Arg Lys Thr Leu Val Asp Glu Val Cys Ala Asp Glu Ser Val
            275                 280                 285

Leu Ser Arg Ala Ala Gly Leu Ser Ala Cys Cys Lys Glu Asp Ala Val
            290                 295                 300

His Arg Gly Ser Cys Val Glu Ala Met Lys Pro Asp Pro Lys Pro Asp
305                 310                 315                 320

Gly Leu Ser Glu His Tyr Asp Ile His Ala Asp Ile Ala Ala Val Cys
                325                 330                 335

Gln Thr Phe Thr Lys Thr Pro Asp Val Ala Met Gly Lys Leu Val Tyr
                340                 345                 350

Glu Ile Ser Val Arg His Pro Glu Ser Ser Gln Gln Val Ile Leu Arg
            355                 360                 365

Phe Ala Lys Glu Ala Glu Gln Ala Leu Leu Gln Cys Cys Asp Met Glu
            370                 375                 380

Asp His Ala Glu Cys Val Lys Thr Ala Leu Ala Gly Ser Asp Ile Asp
385                 390                 395                 400

Lys Lys Ile Thr Asp Glu Thr Asp Tyr Tyr Lys Lys Met Cys Ala Ala
                405                 410                 415

Glu Ala Ala Val Ser Asp Asp Ser Phe Glu Lys Ser Met Met Val Tyr
            420                 425                 430

Tyr Thr Arg Ile Met Pro Gln Ala Ser Phe Asp Gln Leu His Met Val
            435                 440                 445

Ser Glu Thr Val His Asp Val Leu His Ala Cys Cys Lys Asp Glu Gln
            450                 455                 460

Gly His Phe Val Leu Pro Cys Ala Glu Glu Lys Leu Thr Asp Ala Ile
465                 470                 475                 480

Asp Ala Thr Cys Asp Asp Tyr Asp Pro Ser Ser Ile Asn Pro His Ile
                485                 490                 495

Ala His Cys Cys Asn Gln Ser Tyr Ser Met Arg Arg His Cys Ile Leu
                500                 505                 510

Ala Ile Gln Pro Asp Thr Glu Phe Thr Pro Pro Glu Leu Asp Ala Ser
            515                 520                 525

Ser Phe His Met Gly Pro Glu Leu Cys Thr Lys Asp Ser Lys Asp Leu
            530                 535                 540

Leu Leu Ser Gly Lys Lys Leu Leu Tyr Gly Val Val Arg His Lys Thr
545                 550                 555                 560

Thr Ile Thr Glu Asp His Leu Lys Thr Ile Ser Thr Lys Tyr His Thr
                565                 570                 575

Met Lys Glu Lys Cys Cys Ala Ala Glu Asp Gln Ala Ala Cys Phe Thr
            580                 585                 590
```

Glu Glu Ala Pro Lys Leu Val Ser Glu Ser Ala Glu Leu Val Lys Val
            595                 600                 605

<210> SEQ ID NO 122
<211> LENGTH: 527
<212> TYPE: PRT
<213> ORGANISM: Sphenodon punctatus

<400> SEQUENCE: 122

Glu Asp Pro Thr Cys Leu Lys Ser Leu Asp Thr Ile Phe Leu Asp Glu
1               5                   10                  15

Ile Cys His Glu Glu Gly Phe Ala Ala Lys Tyr Asp Leu Ala Ala Cys
            20                  25                  30

Cys Ala Lys Ala Glu Val Glu Arg Lys Glu Cys Leu Leu Ala His Lys
        35                  40                  45

Asn Ala Thr Pro Gly Phe Ile Pro Ala Phe Gln Arg Pro Gly Ile Glu
    50                  55                  60

Val Ser Cys Lys Leu Tyr Gln Asp Asp Arg Leu Thr Leu Leu Gly Asn
65                  70                  75                  80

Tyr Ile Tyr Glu Val Ala Arg Arg His Pro Tyr Leu Gln Val Pro Pro
                85                  90                  95

Val Phe Ala Thr Ala Ser Leu Tyr Asp Glu Ala Leu Lys Thr Cys Cys
            100                 105                 110

Gln Thr Ala Asp Lys Ala Thr Cys Phe His Pro Arg Ile Pro Pro Leu
        115                 120                 125

Ile Glu Tyr Leu Lys Met Ser Asn Gly Ile Gln Glu Asn Thr Cys Gly
    130                 135                 140

Ile Leu Lys Lys Phe Gly Glu Arg Thr Leu Lys Ala Thr Lys Leu Val
145                 150                 155                 160

Gln Met Ser Gln Lys Phe Pro Lys Ala Asp Phe Ala Thr Ile Asn Lys
                165                 170                 175

Leu Val Glu Asp Ile Thr His Met His Thr Glu Cys Cys Arg Gly Asp
            180                 185                 190

Thr Leu Glu Cys Leu Arg Asp Arg Glu Ala Leu Thr Glu Tyr Thr Cys
        195                 200                 205

Ser His Lys Asp Ala Ile Ser Ser Lys Leu Pro Thr Cys Cys Glu Lys
    210                 215                 220

Ser Val Leu Glu Arg Gly Glu Cys Ile Val Arg Leu Glu Asn Asp Asp
225                 230                 235                 240

Lys Pro Ala Asp Leu Ser Glu Arg Ile Ala Glu Tyr Ile Glu Asp Pro
                245                 250                 255

His Val Cys Asp His Leu Ala Lys Glu Gln Asp Ala Phe Leu Ala Lys
            260                 265                 270

Phe Leu Tyr Glu Tyr Ser Arg Arg His Pro Glu Leu Ser Thr Gln Ile
        275                 280                 285

Leu Leu Gly Val Gly Lys Gly Tyr Gln Glu Leu Leu Glu Arg Cys Cys
    290                 295                 300

Lys Thr Asp Asn Pro Pro Glu Cys Tyr Gly Gln Ala Glu Ala Asp Leu
305                 310                 315                 320

Lys Lys His Ile Ala Gln Phe Gln Glu Leu Val Gln Asn Cys Asp
                325                 330                 335

Leu Tyr Asn Thr Leu Gly Gly Tyr Leu Phe His Asn Ala Leu Leu Ile
            340                 345                 350

Arg Tyr Thr Lys Arg Met Pro Gln Leu Thr Ser Glu Glu Leu Ile Phe

```
            355                 360                 365
Tyr Thr Arg Ile Thr Lys Ala Ala Ser Arg Cys Cys Glu Val Ser Val
    370                 375                 380

Asp Lys Lys Leu Pro Cys Thr Glu Gly Tyr Val Asp Phe Val Leu Gly
385                 390                 395                 400

Gln Ile Cys Gln Arg His Gln Arg Ser Ser Ile Asn Val Asn Val Cys
                405                 410                 415

Gln Cys Cys Ser Asn Ser Tyr Ala Leu Arg Ser Leu Cys Ile Thr Ser
            420                 425                 430

Leu Gly Gly Asp Glu Lys Phe Val Pro Ile Glu Phe Ser Ala Asp Leu
        435                 440                 445

Phe Thr Phe His Glu Asp Leu Cys His Ala Ala Gln Asp Lys Leu Gln
    450                 455                 460

Glu Arg Lys Gln Gln Met Ile Val Asn Leu Val Lys His Lys Pro Asn
465                 470                 475                 480

Ile Thr Lys Glu Gln Leu Gln Thr Val Phe Gly Gly Phe Thr Lys Met
                485                 490                 495

Thr Glu Lys Cys Cys Lys Ala Glu Asp His Glu Ala Cys Phe Gly Glu
            500                 505                 510

Glu Gly Pro Lys Leu Val Ala Glu Ser Gln Thr Ala Leu Ala Ala
        515                 520                 525

<210> SEQ ID NO 123
<211> LENGTH: 101
<212> TYPE: PRT
<213> ORGANISM: Neoceratodus forsteri
<220> FEATURE:
<221> NAME/KEY: misc_feature
<222> LOCATION: (79)..(79)
<223> OTHER INFORMATION: Xaa can be any naturally occurring amino acid

<400> SEQUENCE: 123

Asp Ala Glu His Lys Ser Asn Ile Cys Lys His Phe Gln Val Val Gly
1               5                   10                  15

Glu Glu Lys Phe Lys Asn Ile Ile Leu Val Thr Gln Asp Gly His Gly
            20                  25                  30

Pro Phe Ile Gln Val Ser Lys Glu Glu Gln Cys Lys His Tyr Ala Glu
        35                  40                  45

Asn Arg Val Pro Tyr Met Gly Asn Phe Ile Tyr Thr Ala Ala Lys Arg
    50                  55                  60

His Pro Asp Leu Pro Ala Thr Glu Val Leu Ile Tyr Ala Phe Xaa Tyr
65                  70                  75                  80

Glu Ser Gly Ala Val Leu Val Ser Tyr Pro Glu Met Val Gly Cys Cys
                85                  90                  95

Pro Pro Asp Val Leu
            100

<210> SEQ ID NO 124
<211> LENGTH: 614
<212> TYPE: PRT
<213> ORGANISM: Naja kaouthia

<400> SEQUENCE: 124

Met Lys Trp Val Ile Phe Ile Ser Leu Leu Cys Leu Val Ser Phe Ala
1               5                   10                  15

Glu Val Lys Asn Leu Pro Arg Arg Tyr Arg His Val Asp Asp Gln His
            20                  25                  30
```

```
Ser Thr Ile Arg Leu Ala Ser Gln Ile Ser Ala Thr Asp Phe Gly Ala
            35                  40                  45

Ile Thr Leu Thr Leu Val Thr Gln Thr Val Pro Asn Ala Thr Leu Glu
 50                  55                  60

Asp Leu Lys Lys Leu Ser Ala Glu Ile Ile Glu Leu His Lys Lys Cys
 65                  70                  75                  80

Val Ala Ser Glu Phe Ser Asp Pro Pro Cys Thr Lys Pro Leu Gly Ile
                 85                  90                  95

Val Phe Leu Asp Val Leu Cys His Asn Glu Glu Phe Ser Asn Lys Tyr
            100                 105                 110

Gly Ile Asn Asp Cys Cys Ala Lys Ala Asp Pro Asp Arg Asn Glu Cys
            115                 120                 125

Val Leu Ser His Lys Thr Ser Ser Thr Gly Thr Ile Ser Pro Phe Val
130                 135                 140

His Pro Asn Ala Glu Glu Ala Cys Gln Ala Phe Gln Asn Asp Arg Asp
145                 150                 155                 160

Ser Val Leu Ala Gln Tyr Ile Phe Glu Leu Ser Arg Arg Tyr Pro Thr
            165                 170                 175

Ala Leu Ser Val Val Ile Leu Glu Ser Thr Lys Thr Tyr Lys Lys Ile
                180                 185                 190

Leu Glu Thr Cys Cys Ala Glu Ala Asp Lys Asp Ala Cys Ile His Glu
            195                 200                 205

Lys Ala Thr Glu Ala Lys Lys Lys Phe Arg Glu Ile Met Glu Glu Gln
210                 215                 220

Glu Tyr Thr Cys Tyr Asn Leu Lys Lys Tyr Gly Lys Asp Lys Leu Tyr
225                 230                 235                 240

Ala Leu Lys Phe Ile Glu Thr His Glu Lys Phe Val Asn Ala Lys Leu
            245                 250                 255

Glu Thr Ile Thr Gly Ile Ala Glu Phe Val His Ile Tyr Glu Glu
            260                 265                 270

Ile Cys Met Gly Asp Ser Val Asp Val Leu Val Asp Arg Ala Ala Leu
            275                 280                 285

Ser Gln Tyr Val Cys Glu His Lys Asp Ala Ile Ser Ser Asn Val Gly
290                 295                 300

His Cys Cys Glu Lys Pro Leu Val Glu Arg Pro Asn Cys Leu Ala Thr
305                 310                 315                 320

Leu Ala Asn Asp Ala Arg Ser Pro Asp Leu Pro Pro Ser Glu Glu
                325                 330                 335

Ile Leu Lys Glu Thr Glu Ala Cys Thr Thr Tyr Thr Glu Gln Arg Glu
            340                 345                 350

Asn Tyr Lys Glu Ser Phe Leu Phe Thr Leu Thr Arg Asn His Pro Glu
            355                 360                 365

Leu Ser Lys Leu Ile Asp Leu Glu Ile Leu Tyr Lys Tyr Glu Lys Leu
370                 375                 380

Leu Glu Glu Cys Cys Gln Ser Glu His His Val Gln Cys Leu His Gly
385                 390                 395                 400

Gly Glu Gln Val Phe Lys Leu Tyr Ile Thr Lys Ile Asn Glu Val Val
                405                 410                 415

Lys Ser Asn Cys Asp Ser Tyr Lys Glu Leu Gly Asp Tyr Phe Phe Thr
            420                 425                 430

Asn Glu Phe Leu Val Lys Tyr Ser Arg Met Met Pro Gln Ala Pro Thr
            435                 440                 445

Ser Phe Leu Ile Glu Leu Thr Glu Lys Val Gly Lys Val Ala Glu Lys
```

```
        450                 455                 460
Cys Cys Asn Leu Asp Ser Asn His Gln Val Ser Cys Ala Leu Glu Asn
465                 470                 475                 480

Thr Asp Lys Val Met Gly Ser Ile Cys Lys Tyr His Asn Lys His Phe
                485                 490                 495

Ile Asn Asp Gln Ile Cys His Cys Asn Ser Ser Phe Ile Ser Arg
                500                 505                 510

Trp Glu Cys Ile Ser Asn Leu Gly Pro Asp Leu Ser Phe Val Pro Pro
                515                 520                 525

Thr Phe Asn Pro Lys Thr Met Asp Asn Pro Glu Lys Leu Cys Ser Thr
            530                 535                 540

Ser Glu Asp Thr Val Gln Lys Ser Lys Lys Gly Leu Leu Ser Glu Leu
545                 550                 555                 560

Val Lys Ser Lys Pro Asn Ile Ser Glu Glu Leu Ala Ala Thr Ile
                565                 570                 575

Leu Thr Phe Arg Glu Ile Gln Lys Leu Cys Cys Glu Ala Glu Asn Lys
                580                 585                 590

Lys Glu Cys Phe Asp Lys Lys Gly Gln Glu Met Val Glu His Leu Gln
            595                 600                 605

Asn Gly Pro Thr Thr Glu
            610

<210> SEQ ID NO 125
<211> LENGTH: 608
<212> TYPE: PRT
<213> ORGANISM: Schistosoma mansoni

<400> SEQUENCE: 125

Met Lys Trp Val Thr Phe Leu Leu Leu Leu Phe Val Ser Asp Ser Ala
1               5                   10                  15

Phe Ser Arg Gly Leu Phe Arg Arg Asp Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Phe Leu Gln Lys Cys Pro Tyr Glu Glu His Val
    50                  55                  60

Lys Leu Val Asn Glu Val Thr Asp Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Ala Ile Pro Thr Leu Arg Asp Ser Tyr Gly Glu Leu Ala
            100                 105                 110

Asp Cys Cys Ala Lys Lys Glu Pro Glu Arg Asn Glu Cys Phe Leu Lys
        115                 120                 125

His Lys Asp Asp His Pro Asn Leu Pro Pro Phe Val Arg Pro Asp Ala
    130                 135                 140

Glu Ala Met Cys Thr Ser Phe Gln Glu Asn Ala Val Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Ser Ala Ile Met Thr Glu Cys
            180                 185                 190

Cys Gly Glu Ala Asp Lys Ala Ala Cys Ile Thr Pro Lys Leu Asp Ala
        195                 200                 205
```

-continued

Leu Lys Glu Lys Ala Leu Ala Ser Ser Val Asn Gln Arg Leu Lys Cys
210                 215                 220

Ser Ser Leu Gln Arg Phe Gly Gln Arg Ala Phe Lys Ala Trp Ala Val
225                 230                 235                 240

Ala Arg Met Ser Gln Lys Phe Pro Lys Ala Asp Phe Ala Glu Ile Thr
            245                 250                 255

Lys Leu Ala Thr Asp Leu Thr Lys Leu Thr Glu Glu Cys Cys His Gly
            260                 265                 270

Asp Leu Leu Glu Cys Ala Asp Asp Arg Ala Glu Leu Ala Lys Tyr Met
        275                 280                 285

Cys Glu Asn Gln Ala Ser Ile Ser Ser Lys Leu Gln Ala Cys Cys Asp
290                 295                 300

Lys Pro Val Leu Lys Lys Ser His Cys Leu Ser Glu Val Glu Asn Asp
305                 310                 315                 320

Asp Leu Pro Ala Asp Leu Pro Ser Leu Ala Ala Asp Phe Val Glu Asp
            325                 330                 335

Lys Glu Val Cys Lys Asn Tyr Ala Glu Ala Lys Asp Val Phe Leu Gly
            340                 345                 350

Thr Phe Leu Tyr Glu Tyr Ala Arg Arg His Pro Asp Tyr Ser Val Ala
        355                 360                 365

Leu Leu Leu Arg Leu Ala Lys Lys Tyr Glu Ala Thr Leu Glu Lys Cys
370                 375                 380

Cys Ala Glu Ala Asp Pro Ser Ala Cys Tyr Gly Lys Val Leu Asp Glu
385                 390                 395                 400

Phe Gln Pro Leu Val Glu Glu Pro Lys Asn Leu Val Lys Ala Asn Cys
            405                 410                 415

Glu Leu Phe Glu Lys Leu Gly Glu Tyr Gly Phe Gln Asn Ala Leu Ile
            420                 425                 430

Val Arg Tyr Thr Gln Lys Ala Pro Gln Val Ser Thr Pro Thr Leu Val
        435                 440                 445

Glu Ala Ala Arg Asn Leu Gly Lys Val Gly Ser Lys Cys Cys Val Leu
450                 455                 460

Pro Glu Ala Gln Arg Leu Pro Cys Val Glu Asp Tyr Ile Ser Ala Ile
465                 470                 475                 480

Leu Asn Arg Val Cys Val Leu His Glu Lys Thr Pro Val Ser Glu Gln
            485                 490                 495

Val Thr Lys Cys Cys Thr Gly Ser Val Val Glu Arg Arg Pro Cys Phe
            500                 505                 510

Ser Ala Leu Pro Val Asp Glu Thr Tyr Val Pro Lys Glu Phe Lys Ala
        515                 520                 525

Glu Thr Phe Thr Phe His Ala Asp Ile Cys Ser Leu Pro Glu Lys Glu
530                 535                 540

Lys Gln Met Lys Lys Gln Ala Ala Leu Val Glu Leu Val Lys His Lys
545                 550                 555                 560

Pro Lys Ala Thr Gly Pro Gln Leu Arg Thr Val Leu Gly Glu Phe Thr
            565                 570                 575

Ala Phe Leu Asp Lys Cys Cys Lys Ala Glu Asp Lys Glu Ala Cys Phe
            580                 585                 590

Ser Glu Asp Gly Pro Lys Leu Val Ala Ser Ser Gln Ala Ala Leu Ala
        595                 600                 605

<210> SEQ ID NO 126
<211> LENGTH: 14
<212> TYPE: DNA

```
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 126
gagtcagctg aaaa                                                       14

<210> SEQ ID NO 127
<211> LENGTH: 14
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 127
gagtccgcgg aaaa                                                       14

<210> SEQ ID NO 128
<211> LENGTH: 14
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 128
aaggcttcgt ctgc                                                       14

<210> SEQ ID NO 129
<211> LENGTH: 14
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 129
aaggctagct ctgc                                                       14

<210> SEQ ID NO 130
<211> LENGTH: 15
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 130
tctgcttgaa tgtgc                                                      15

<210> SEQ ID NO 131
<211> LENGTH: 15
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 131
tctgctcgag tgtgc                                                      15

<210> SEQ ID NO 132
<211> LENGTH: 13
<212> TYPE: DNA
<213> ORGANISM: Artificial Sequence
```

```
<220> FEATURE:
<223> OTHER INFORMATION: Fragment of nucleic acid encoding albumin to
      introduce restriction site into SEQ ID NO: 2

<400> SEQUENCE: 132
gtgggcagca aat                                                           13

<210> SEQ ID NO 133
<211> LENGTH: 13
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 133
gtgggatcca aat                                                           13

<210> SEQ ID NO 134
<211> LENGTH: 14
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 134
ggaagtcgat gaaa                                                          14

<210> SEQ ID NO 135
<211> LENGTH: 14
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 135
ggaagtcgac gaaa                                                          14

<210> SEQ ID NO 136
<211> LENGTH: 39
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 136
cgctagcctc gaggtttaaa cgctagcgag ctcggatcc                               39

<210> SEQ ID NO 137
<211> LENGTH: 47
<212> TYPE: DNA
<213> ORGANISM: Artificial Sequence
<220> FEATURE:
<223> OTHER INFORMATION: Fragment of nucleic acid encoding albumin to
      introduce restriction site into SEQ ID NO: 2

<400> SEQUENCE: 137
catggcgatc ggagctccaa atttgcgatc gctcgagcct aggccgg                      47

<210> SEQ ID NO 138
<211> LENGTH: 608
<212> TYPE: PRT
<213> ORGANISM: Salmo salar
```

```
<400> SEQUENCE: 138

Met Gln Trp Leu Ser Val Cys Ser Leu Leu Val Leu Leu Ser Val Leu
1               5                   10                  15

Ser Arg Ser Gln Ala Gln Asn Gln Ile Cys Thr Ile Phe Thr Glu Ala
            20                  25                  30

Lys Glu Asp Gly Phe Lys Ser Leu Ile Leu Val Gly Leu Ala Gln Asn
        35                  40                  45

Leu Pro Asp Ser Thr Leu Gly Asp Leu Val Pro Leu Ile Ala Glu Ala
    50                  55                  60

Leu Ala Met Gly Val Lys Cys Cys Ser Asp Thr Pro Pro Glu Asp Cys
65                  70                  75                  80

Glu Arg Asp Val Ala Asp Leu Phe Gln Ser Ala Val Cys Ser Ser Glu
                85                  90                  95

Thr Leu Val Glu Lys Asn Asp Leu Lys Met Cys Cys Glu Lys Thr Ala
            100                 105                 110

Ala Glu Arg Thr His Cys Phe Val Asp His Lys Ala Lys Ile Pro Arg
        115                 120                 125

Asp Leu Ser Leu Lys Ala Glu Leu Pro Ala Ala Asp Gln Cys Glu Asp
    130                 135                 140

Phe Lys Lys Asp His Lys Ala Phe Val Gly Arg Phe Ile Phe Lys Phe
145                 150                 155                 160

Ser Lys Ser Asn Pro Met Leu Pro Pro His Val Val Leu Ala Ile Ala
                165                 170                 175

Lys Gly Tyr Gly Glu Val Leu Thr Thr Cys Cys Gly Glu Ala Glu Ala
            180                 185                 190

Gln Thr Cys Phe Asp Thr Lys Lys Ala Thr Phe Gln His Ala Ile Ala
        195                 200                 205

Lys Arg Val Ala Glu Leu Lys Ser Leu Cys Ile Val His Lys Lys Tyr
    210                 215                 220

Gly Asp Arg Val Val Lys Ala Lys Lys Leu Val Gln Tyr Ser Gln Lys
225                 230                 235                 240

Met Pro Gln Ala Ser Phe Gln Glu Met Ala Gly Met Val Asp Lys Ile
                245                 250                 255

Val Ala Thr Val Ala Pro Cys Cys Ser Gly Asp Met Val Thr Cys Met
            260                 265                 270

Lys Glu Arg Lys Thr Leu Val Asp Glu Val Cys Ala Asp Glu Ser Val
        275                 280                 285

Leu Ser Arg Ala Ala Gly Leu Ser Ala Cys Cys Lys Glu Asp Ala Val
    290                 295                 300

His Arg Gly Ser Cys Val Glu Ala Met Lys Pro Asp Pro Lys Pro Asp
305                 310                 315                 320

Gly Leu Ser Glu His Tyr Asp Val His Ala Asp Ile Ala Ala Val Cys
                325                 330                 335

Gln Thr Phe Thr Lys Thr Pro Asp Val Ala Met Gly Lys Leu Val Tyr
            340                 345                 350

Glu Ile Ser Val Arg His Pro Glu Ser Ser Gln Gln Val Ile Leu Arg
        355                 360                 365

Phe Ala Lys Glu Ala Glu Gln Ala Leu Leu Gln Cys Cys Asp Met Glu
    370                 375                 380

Asp His Ala Glu Cys Val Lys Thr Ala Leu Ala Gly Ser Asp Ile Asp
385                 390                 395                 400

Lys Lys Ile Thr Asp Glu Thr Asp Tyr Tyr Lys Lys Met Cys Ala Ala
                405                 410                 415
```

```
Glu Ala Ala Val Ser Asp Asp Asn Phe Glu Lys Ser Met Met Val Tyr
            420             425             430

Tyr Thr Arg Ile Met Pro Gln Ala Ser Phe Asp Gln Leu His Met Val
        435             440             445

Ser Glu Thr Val His Asp Val Leu His Ala Cys Cys Lys Asp Glu Pro
    450             455             460

Gly His Phe Val Leu Pro Cys Ala Glu Glu Lys Leu Thr Asp Ala Ile
465             470             475                         480

Asp Ala Thr Cys Asp Asp Tyr Asp Pro Ser Ser Ile Asn Pro His Ile
            485             490                     495

Ala His Cys Cys Asn Gln Ser Tyr Ser Met Arg Arg His Cys Ile Leu
        500             505             510

Ala Ile Gln Pro Asp Thr Glu Phe Thr Pro Pro Glu Leu Asp Ala Ser
        515             520             525

Ser Phe His Met Gly Pro Glu Leu Cys Thr Lys Asp Ser Lys Asp Leu
    530             535             540

Leu Leu Ser Gly Lys Lys Leu Leu Tyr Gly Val Val Arg His Lys Thr
545             550             555                         560

Thr Ile Thr Glu Asp His Leu Lys Thr Ile Ser Thr Lys Tyr His Thr
            565             570             575

Met Lys Asp Lys Cys Cys Ala Ala Glu Asp Gln Ala Ala Cys Phe Thr
            580             585             590

Glu Glu Ala Pro Lys Leu Val Ser Glu Ser Ala Glu Leu Val Lys Val
            595             600             605
```

ALBUMIN VARIANTS AND CONJUGATES

CROSS-REFERENCE TO RELATED APPLICATIONS

This application is a continuation of U.S. application Ser. No. 15/280,733, filed on Sep. 29, 2016, which is a division of U.S. application Ser. No. 13/201,123, filed on Aug. 11, 2011, now U.S. Pat. No. 9,493,545, which is a 35 U.S.C. 371 national application of PCT/EP2010/051751 filed Feb. 11, 2010, which claims the benefit of priority to European application nos. 09152625.1 and 09152686.3, filed Feb. 11, 2009 and Feb. 12, 2009, respectively, and U.S. provisional application No. 61/154,555, filed Feb. 23, 2009. The contents of each of which are fully incorporated herein by reference.

REFERENCE TO SEQUENCE LISTING

This application contains a Sequence Listing in computer readable form. The sequence listing was created on Mar. 23, 2020, and is entitled 2020-03-23_Sequence_Listing_ALBUM.007C1, and is 511 kb in size. The information in the electronic format of the Sequence Listing is incorporated herein by reference in its entirety.

FIELD OF THE INVENTION

The present invention relates to conjugation competent albumins and albumin-related polypeptides, and their conjugates with at least one moiety, and to polynucleotides encoding them.

BACKGROUND OF THE INVENTION

Serum albumins provide valuable scaffolds to which bioactive molecules may be fused, either through genetic fusions or chemical fusions to improve the properties of the fused molecule(s) (Leger, R. et al. (2004). Bioorg Med Chem Lett 14(17): 4395-8; Thibaudeau, K., et al. (2005). Bioconjug Chem 16(4): 1000-8; Balan, V. et al. (2006). Antivir Ther 11(1): 35-45; EP 0 413 622; WO 90/13653; EP 1 681 304; WO 1997/024445; WO 01/79271). Albumins and albumin particles are also important for carrying and delivering drugs and prodrugs to their sites of action (Kratz (2008) Journal of Controlled Release, 132 (3), p. 171-183). Fusion and particle technologies offer improved dosing regimes due to improved pharmacokinetic properties, such as half-life extension, and may improve bioavailability and protect the fused bioactive molecule from inactivation.

The biochemistry, genetics and medical applications of albumins are well characterized ("All about Albumin", T. Peters Jr., Academic Press N. Y.). Human serum albumin (HSA, also referred to as HA) is the most abundant protein in human plasma at ~60 g/L. The sequence of HSA is provided in SEQ ID NO: 1. Natural variants of HSA occur and a list of know polymorphisms is given in Minchiotti et al. (2008). Hum Mutat 29(8): 1007-16.

The production and purification of recombinant human albumins are well established (WO 95/23857; WO 00/44772; WO 2006/066595; EP 0 305 216; Sleep et al. 1990 Biotechnology (NY). 1990 January; 8(1):42-6)) and include recombinant human albumin for pharmaceutical applications (Bosse et al. (2005). J Clin Pharmacol 45(1): 57-67). The three-dimensional structure of HSA has been elucidated by X-ray crystallography (Carter et al. (1989). Science 244(4909): 1195-8; Sugio et al. (1999). Protein Eng 12(6): 439-46). The HSA polypeptide chain has 35 cysteine residues, which form 17 disulphide bonds and one unpaired (free) cysteine at position 34 of the mature protein (SEQ ID NO: 1). Cysteine-34 has been used to for conjugation of molecules to albumin (Leger et al. (2004) Bioorg Med Chem Lett 14(17): 4395-8; Thibaudeau et al. (2005). Bioconjug Chem 16(4): 1000-8), and provides a precise, well defined site for conjugation. However, conjugation at cysteine-34 provides only one site for attachment of a single moiety thus there is no choice of conjugation site. Also, the provision of a single conjugation sites means that only one moiety can be conjugated to each albumin molecule. What is required is an albumin molecule which provides one or more alternative attachment sites.

SUMMARY OF THE INVENTION

Based on an analysis of the three-dimensional structure of a human serum albumin (HSA), conserved residues within albumin polypeptides and natural polymorphisms thereof, the inventors have designed variant polypeptides (muteins) of albumin which have one or more conjugation competent cysteine residues. The term 'thio-albumin' is used herein to describe an albumin variant which comprises one or more unpaired cysteine residues, particularly an albumin variant in which one or more of the unpaired cysteine residues does not occur in a naturally occurring variant of an albumin. Thus a thio-albumin is a 'conjugation competent albumin'. A thio-albumin may be referred to as a 'cysteine variant of an albumin'.

Throughout this specification, the term 'albumin' includes naturally occurring albumin, albumin-related proteins and variants thereof such as natural and engineered variants. Variants include polymorphisms, fragments such as domains and sub-domains, fragments and/or fusion proteins. The albumin may have at least 40, 50, 60, 70, 80, 90, 95, 96, 97, 98, 99% similarity or identity to SEQ ID NO: 1. Thus a thio-albumin of the invention may be a derivative of, or be based on, any of such albumin.

The unpaired cysteine residues may be provided by insertion, deletion, substitution, addition or extension of an albumin sequence.

The invention also relates to a conjugate comprising at least one, for example 2, 3, 4, 5 or 6, conjugation partners such as bioactive compounds and a polypeptide according to the invention.

The invention also provides a method for designing conjugation-competent albumins.

BRIEF DESCRIPTION OF DRAWINGS

FIG. 1. is a table showing criteria used to select sites in human serum albumin (SEQ ID NO: 1) for amino acid substitutions, insertions and deletions for the generation of conjugation competent cysteines.

FIGS. 5A, 5B, 5C and 5D are tables showing groups of preferred sites in human serum albumin (SEQ ID NO: 1) for amino acid substitutions, insertions and deletions for the generation of one or more conjugation competent cysteine.

FIGS. 6A and 6B are tables showing groups of preferred sites in human serum albumin (SEQ ID NO: 1) for disruption of one or more disulphide bonds for the generation of one or more conjugation competent cysteines.

FIG. 10 is a table showing preferred sites for conjugation grouped according to their relative position on a folded albumin of SEQ ID NO: 1.

FIG. 11 is a table showing mutations (see second column) made to native human serum albumin to generate molecules having a single free thiol group in addition to Cys-34 of native human serum albumin.

FIG. 16 is a table showing mutations (see second column) made to native human serum albumin to generate molecules having one or more free thiol groups in addition to Cys-34 of native human serum albumin and/or having Cys-34 removed.

FIG. 18 is a table showing the fermentation yield and relative level of conjugation to albumin molecules comprising one or more free-thiols.

DETAILED DESCRIPTION OF THE INVENTION

Figure 2:
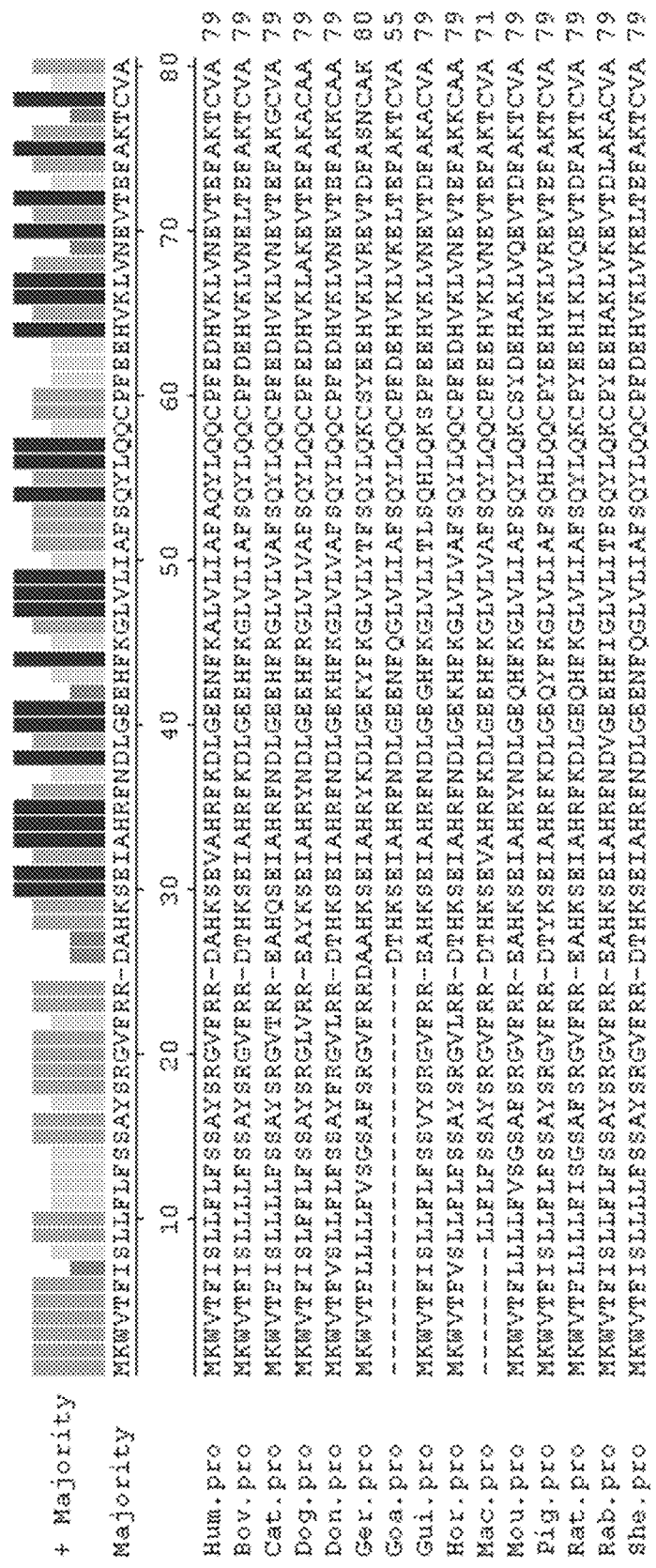
FIG. 2. is an alignment of the amino acid sequence of human serum albumin (SEQ ID NO: 1=Human—P02768.pro) with albumins from fifteen other mammalian species. 'Majority' shows the consensus sequence. '+ Majority' shows the relative homology between all sixteen sequences in bar chart form, where the height of the bar indicates the relative homology at 20, 40, 60, 80 and 100%. The protein sequences include the leader sequence. Hum.pro (SEQ ID NO: 109); Bov.pro (SEQ ID NO: 94); Cat.pro (SEQ ID NO: 95); Dog.pro (SEQ ID NO: 96); Don.pro (SEQ ID NO: 97); Ger.pro (SEQ ID NO: 98); Goa.pro (SEQ ID NO: 99); Gui.pro (SEQ ID NO: 100); Hor.pro (SEQ ID NO: 101); Mac.pro (SEQ ID NO: 103); Mou.pro (SEQ ID NO: 104); Pig.pro (SEQ ID NO: 105); Rat.pro (SEQ ID NO: 107); Rab. pro (SEQ ID NO: 106); and She.pro (SEQ ID NO: 108).
Figure 2:
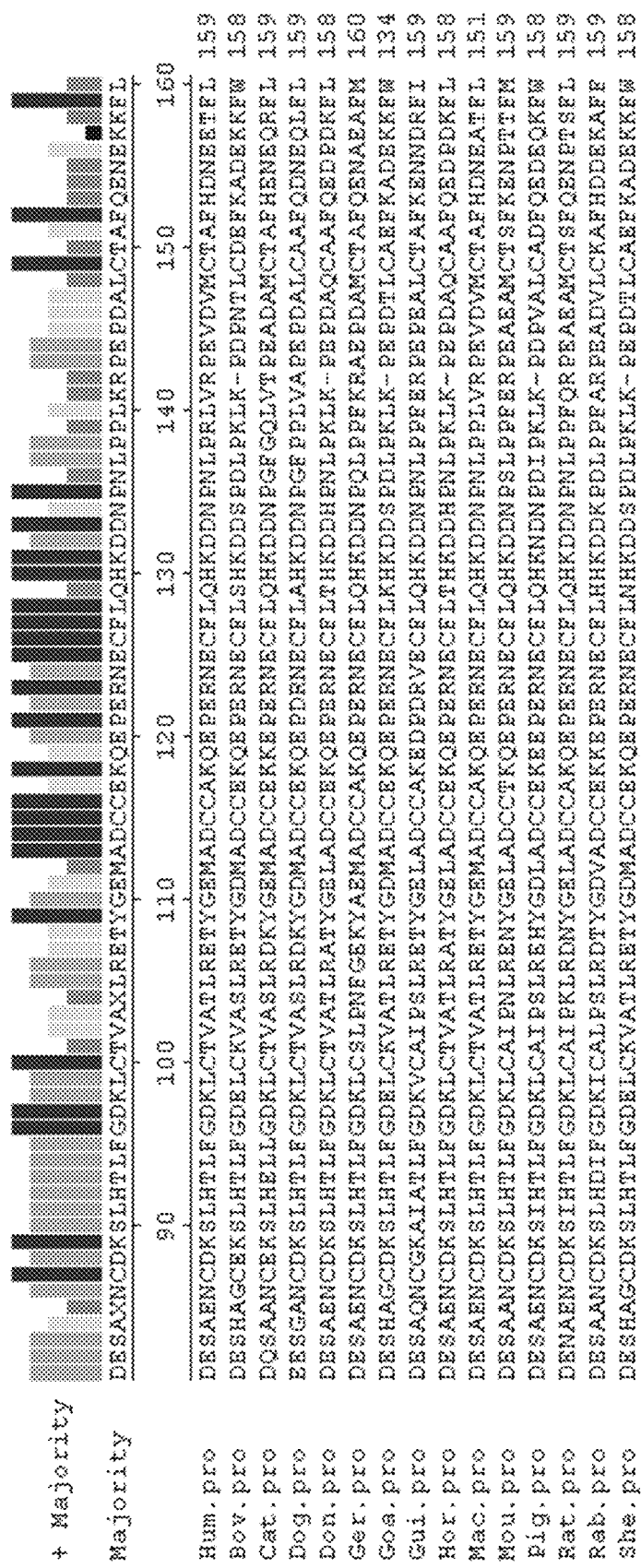
Figure 2:
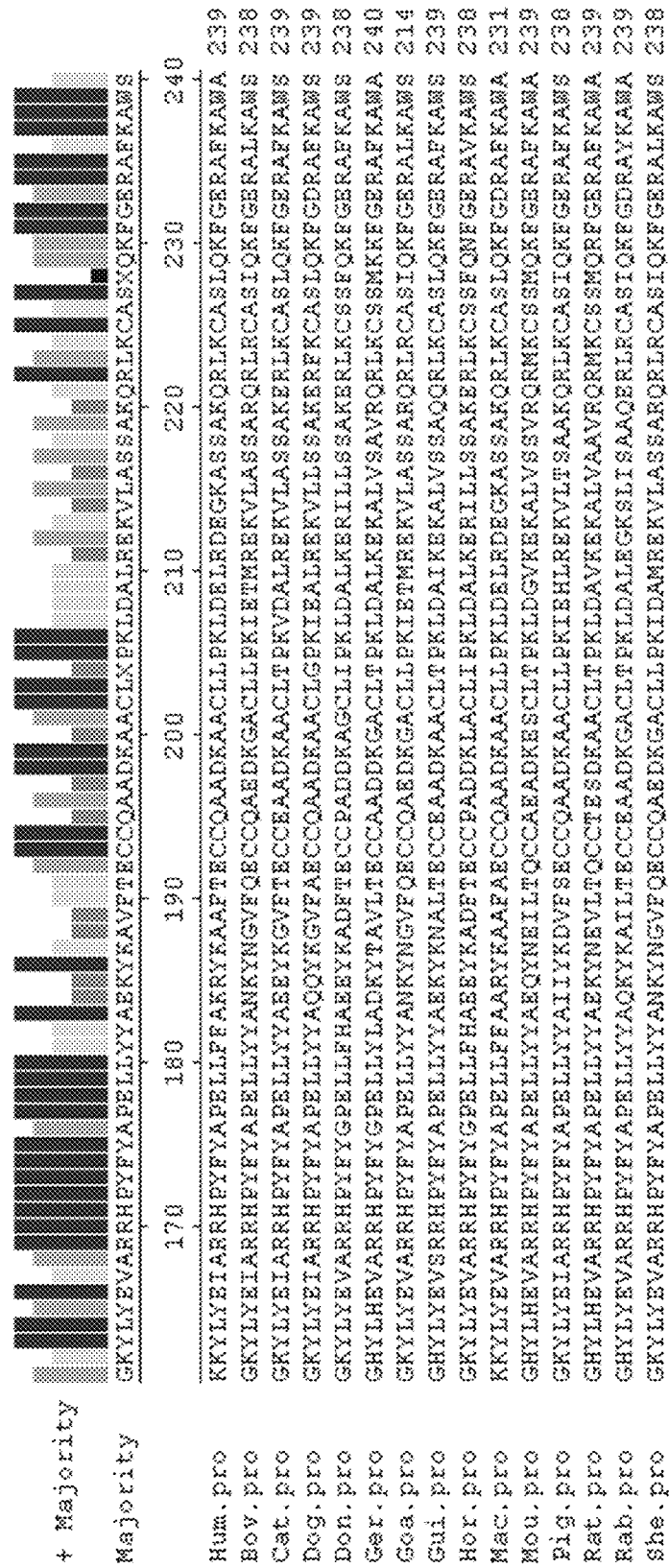
Figure 2:
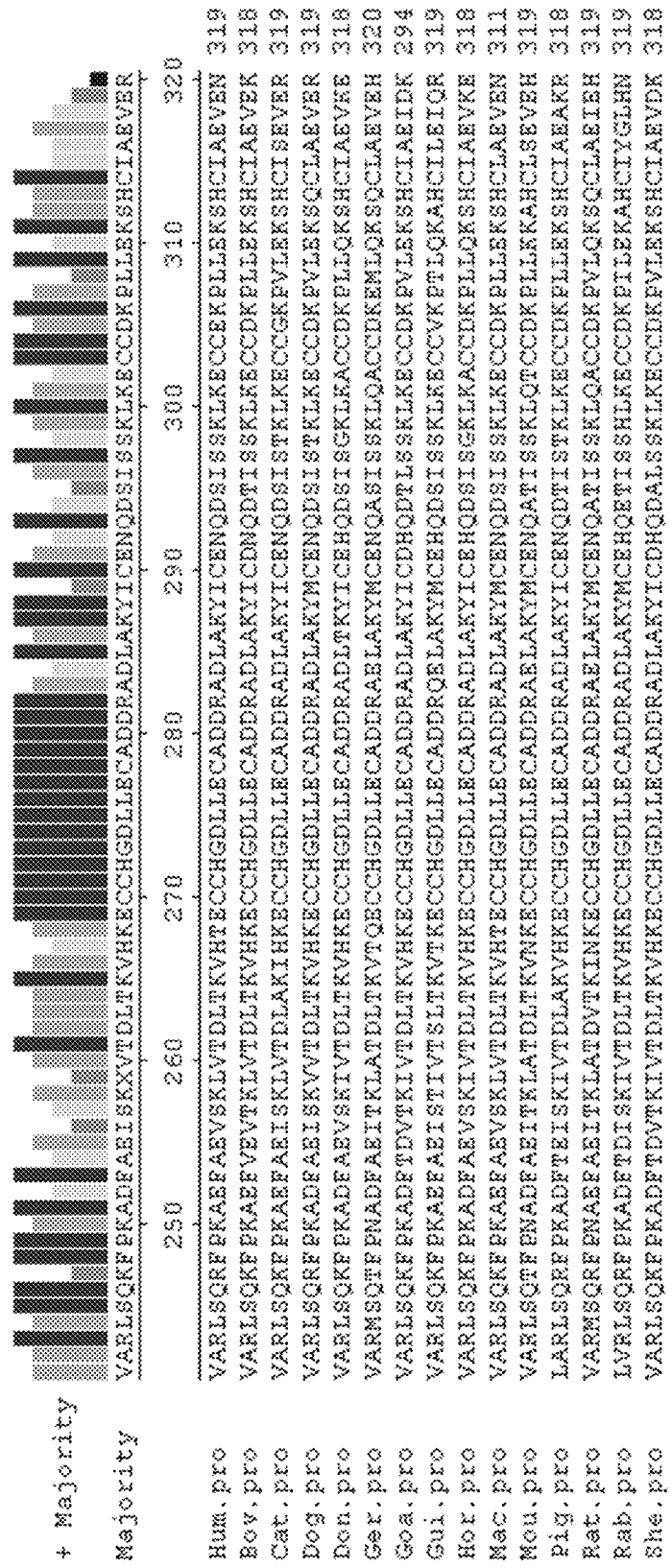
Figure 2:
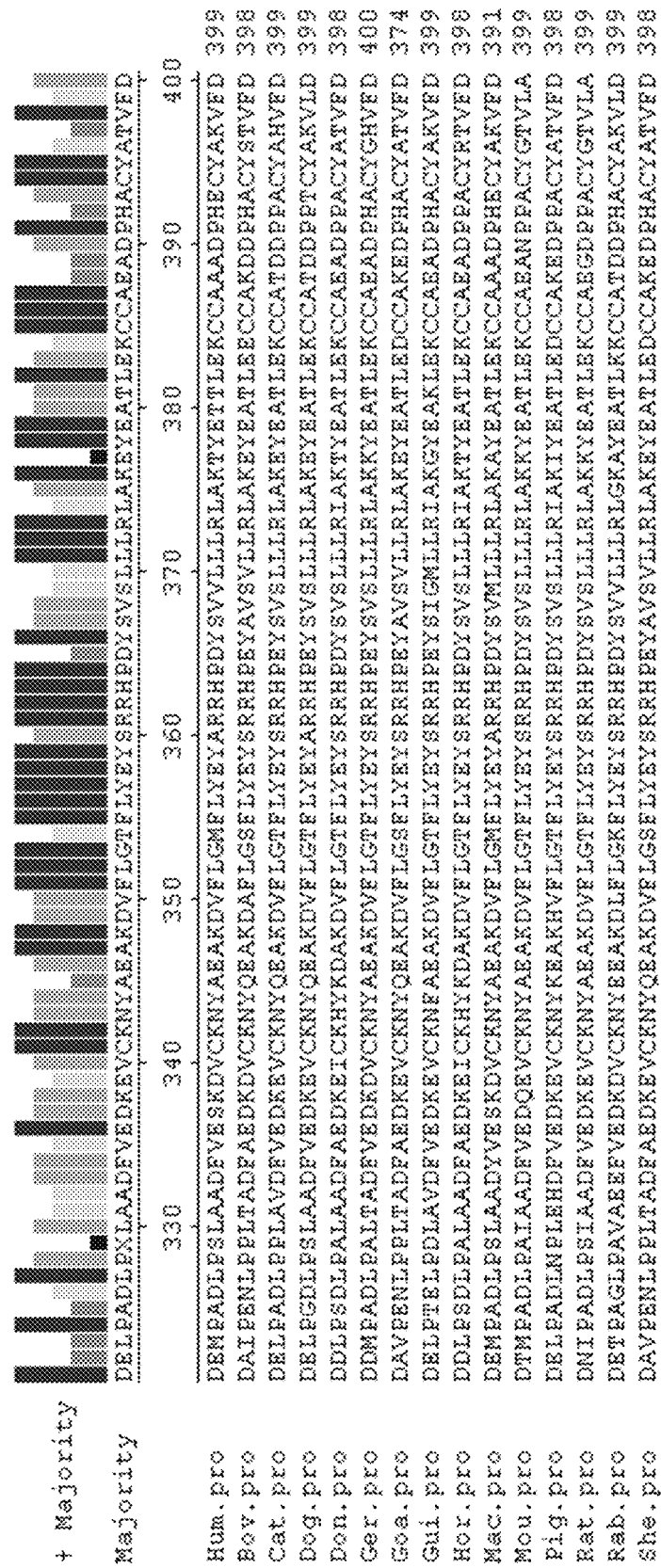
Figure 2:
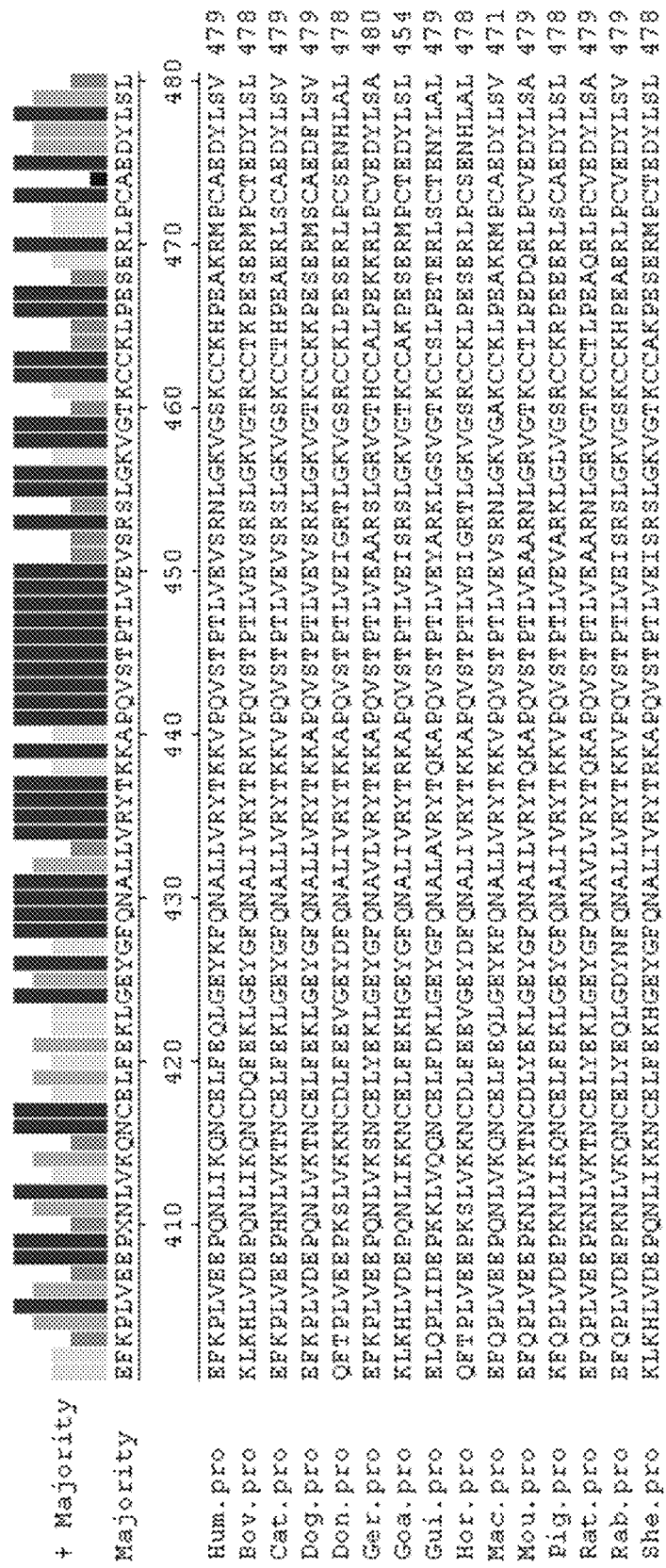
Figure 2:
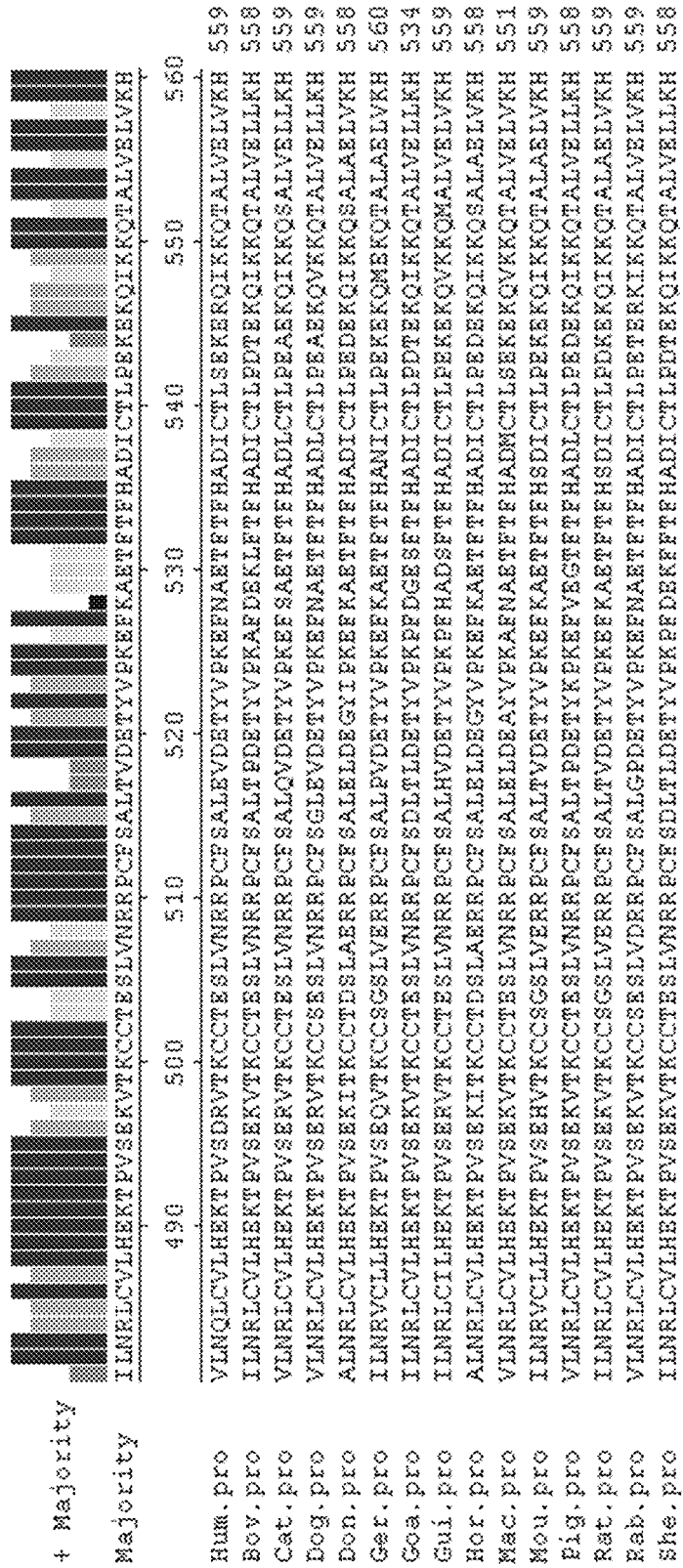
Figure 2:
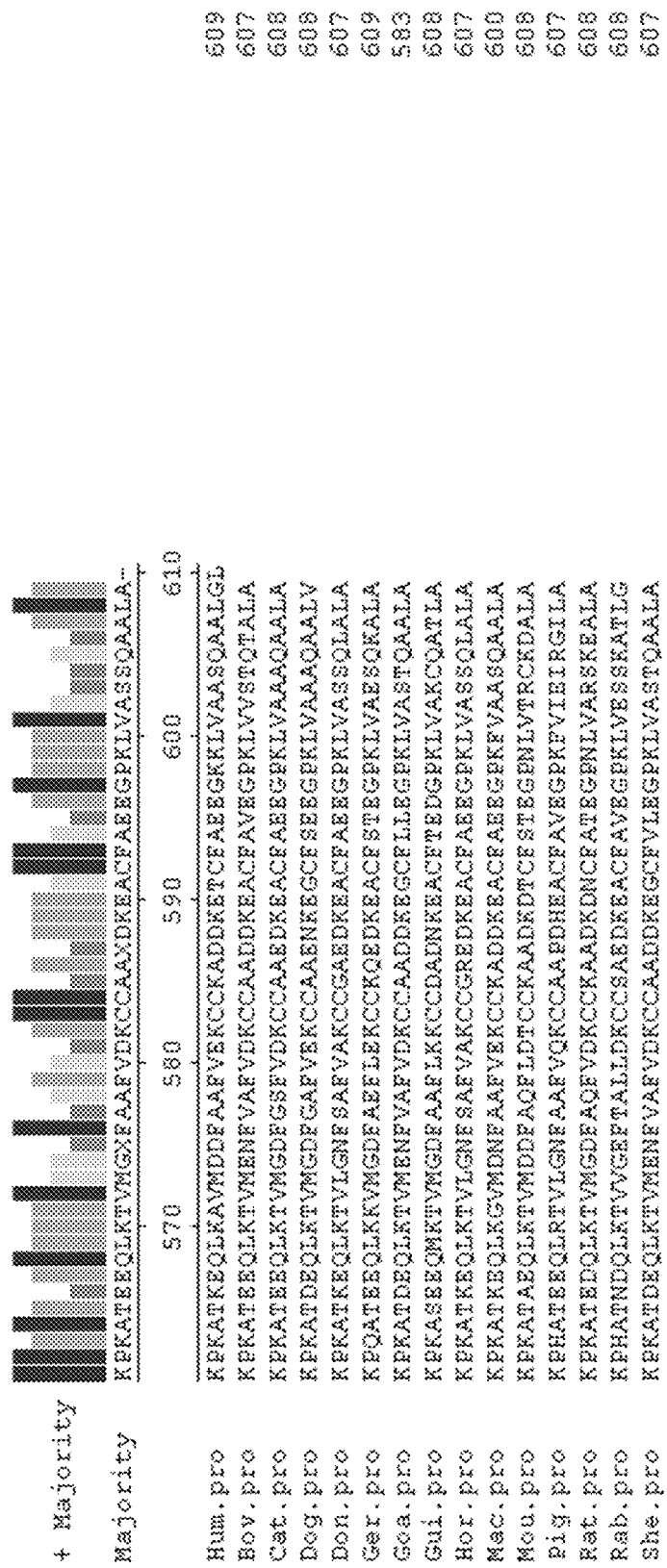

A first aspect of the invention provides a method for designing and/or preparing variant albumins comprising one or more conjugation competent cysteine residues. Therefore, the polypeptide may be considered to be conjugation-competent. Such an albumin may be referred to as a 'thioalbumin' or as a 'cysteine varant' of an albumin. The term 'conjugation competent cysteine' includes a cysteine which has a thiol which is not disulphide bonded to another cysteine and which is, preferably, not blocked from conjugating to another molecule (which may be referred to as a 'conjugation partner') due to unfavorable steric hindrances. That is, preferably the location of the cysteine within or on a folded polypeptide is such that it is available for conjugation.

A number of selection criteria may or may not be used alone or in any combination in order to identify suitable sites for introduction of a conjugation competent cysteine residue. Therefore, the invention provides a method and/or rules for a priori identification of sites of an amino acid sequence of albumin at which a conjugation competent cysteine may be introduced. Such sites may be referred to as 'candidate residues'. The albumin sequence on which the variant albumin is based may be SEQ ID NO: 1 or any other albumin. For example, the variant albumin may be based on an albumin which does or does not have a cysteine at position 34 to the amino acid sequence, or an equivalent position. Cysteine residues may or may not be introduced by one or more of substitution, insertion, deletion, extension and addition. Sites may or may not be selected with reference to a 3-dimensional structure of an albumin or variant thereof. The following criteria may or may not be used to select suitable sites:

(a) Solvent Accessible Surface Area ("Surface Accessibility" (% SASA)).

Preferably the surface accessibility is high. For example, preferably the surface accessibility is at least 60%, more preferably, from 60, 65, 70, 75, 80, 85, 90, 95, 96, 97, 98 or 99% to 65, 70, 75, 80, 85, 90, 95, 96, 97, 98, 99 or 100%. % SASA may be determined as a 'raw score' using the methods described herein or may be calculated relative to the score of the residue which has the maximum surface accessibility in the protein. For example, the albumin of HSA 1AO6 has a maximum surface accessibility of 229.0 and this is the highest scoring residue in HSA. A higher surface accessibility indicates that the residue is on the surface of the protein and is therefore available for binding. Such accessibility may be calculated using a method as described herein.

(b) Presence or Absence of Crystallographic B-Factor(s).

B-factor indicates relative flexibility of an amino acid residue within a 3-dimensional structure. Preferably the B-factor is from at least 30, 40, 50, 60, 70, 80 or 90% to at least 40, 50, 60, 70, 80, 90 or 100% which may or may not be relative to the maximal B-factor score of any amino acid residue within the molecule. For HSA (e.g. 1AO6), preferably the B-factor score is high, for example from at least 30, 40, 50, 60, 70, 80, 90, or 100 to at least 40, 50, 60, 70, 80, 90, 100 or 106 (for example using the B-factor scoring system described herein). Alternatively the B-factor score may be less than or equal to 100, 90, 80, 70, 60, 50, 40, 30, 20, or 10%, as described herein.

The B-Factor (root mean square fluctuations) of the C-alpha carbon atoms during the last nanosecond of the simulation may be calculated using the Gromacs tool "g_rmsf", version 3.3, based on D. van der Spoel, E. Lindahl, B. Hess, G. Groenhof, A. E. Mark and H. J. C. Berendsen: GROMACS: Fast, Flexible and Free, J. Comp. Chem. 26 pp. 1701-1718 (2005).

(c) Presence or Absence of Secondary Structure (SS).

The candidate residue may or may not be located within secondary structure for example H (Helix), B (isolated beta bridge) or E (Extended sheet). Location of the residue outside of secondary structure indicates that the residue is less likely to be important to secondary structure and/or is more likely to be available for binding than a residue located within secondary structure.

(d) Relative Homology with Other Albumins.

Within a given protein sequence, an amino acid residue showing high homology with other similar sequences is likely to indicate such a residue or region is likely to be important to the structure and/or function of the protein. Therefore it is preferred that a candidate residue shows a homology of less than 100% relative to alignment of the albumin in which the residue is located with known albumins (e.g. mammalian albumins such as those shown in FIG. 2 or a combination of mammalian and non-mammalian albumins such as those shown in FIG. 3). A homology of less than 100, 98, 96, 95, 94, 92, 90, 85, 80, 75, 70, 65, 60, 55, 50, 45, 40, 35, 30, 25, 20, 15, 10, 5 is preferred. Homology can be determined using algorithms known in the art such as Clustal, e.g. Clustal W (Thompson et al. (1994). Nucleic Acids Res 22(22): 4673-80) or Clustal V (Higgins, D. G. and P. M. Sharp (1989). "Fast and sensitive multiple sequence alignments on a microcomputer." Comput Appl Biosci 5(2): 151-3.). Lower homology indicates that the residue is not particularly important or critical to the structure and/or function of the protein. Preferably the homology is determined with reference to the sixteen mammalian albumins of FIG. 2 or the thirty three mammalian and non-mammalian albumins of FIG. 3.

(e) Presence or Absence of Adjacent Conserved Residues.

Within an amino acid sequence, each residue has one or two adjacent residues. If a candidate residue is immediately adjacent one or more residues having a low homology, relative to known albumins, this indicates that the candidate residue is unlikely to be particularly important or critical to the structure and/or function of the protein. This is because the candidate residue is likely to be located within a relatively unconserved region of the protein. It is therefore preferred that the candidate residue is not adjacent a residue which has 100% homology relative to alignment of the albumin with known albumins. Homology may be determined as described herein. The candidate residue may be adjacent two residues (i.e. one residue C-terminal relative to the candidate residue and one residue N-terminal relative to the candidate residue) which each have 100% homology relative to alignment of the albumin with known albumins (e.g. FIG. 2 or FIG. 3). It is preferred that the candidate residue is adjacent one or two residues having a homology of less than 100, 98, 96, 95, 94, 92, 90, 85, 80, 75, 70, 65, 60, 55, 50, 45, 40, 35, 30, 25, 20, 15, 10, 5—these levels of homology may be referred to as 'thresholds'. Homology may be determined as described herein. Taking into account the homology threshold, the location of an amino acid relative to a conserved region may be quantified, for example by scoring an amino acid which is not adjacent any amino acid exceeding the homology threshold as 0, scoring an amino acid which is adjacent one amino acid exceeding the threshold as 1 and scoring an amino acid which adjacent two amino acids exceeding the threshold as 2.

(f) Evidence for Polymorphism(s).

A polymorphism is a genetic variation, a polymorphism may or may not cause a phenotypic change to the resultant protein. Preferably the candidate residue is not at a position for which a polymorphism causing a phenotypic change is known. More preferably, the candidate residue is not at a position for which a polymorphism causes, or is known to cause, thermal instability. Polymorphisms known for HSA (SEQ ID NO: 1) are detailed in FIG. 1 and are also discussed in Minchiotti et al. (2008). Hum Mutat 29(8): 1007-16. The presence, absence and/or effect of a polymorphism may be quantified, for example by scoring a known polymorphism that has no phenotypic change as 0, scoring a polymorphism where a phenotypic change is known (but not known to cause thermal instability) as 1 and scoring a polymorphism which is known to cause thermal instability as 2.

(g) Relative Conservation of Candidate Amino Acid and Cysteine.

Figure 4:
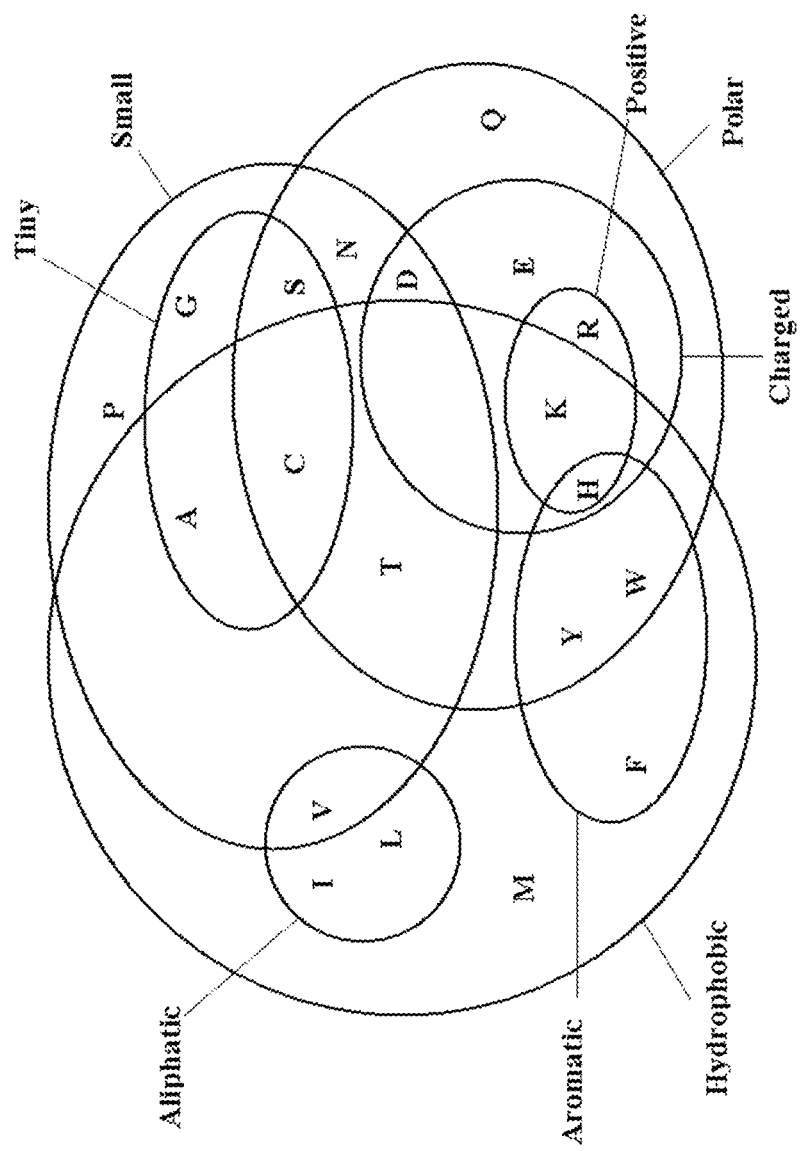
FIG. 4. is a Venn diagram showing the classes of and relationship between twenty amino acids.

Amino acids fall into various well known classes. Therefore, some amino acids are more closely related than others. The introduced cysteine residue may or may not maintain a relatively high level of conservation with the candidate amino acid. FIG. 4 is a Venn diagram which provides one system by which conservation level can be quantified. The scoring system of FIG. 4 uses a scale of 0 to 5 in which substitutions of high conservation have a score of 0, substitutions of low conservation have a score of 5 and substitutions of intermediate conservation have a score of 1, 2, 3 or 4. Preferably substitution of the candidate residue is not an unconserved substitution, that is preferably (using the scoring system of FIG. 4) the candidate residue does not have conservation score (relative to cysteine) of 5. More preferably the candidate residue has a higher conservation relative to cysteine (e.g. a score of 4, 3, 2 and, more preferably, 1). The scoring system is described in the section entitled 'Conservative Substitution' (below).

(h) Expression Level.

The thio-albumin may or may not be capable of being expressed at a level of at least 10, 20, 30, 40, 50, 60, 70, 80, 90 or 100% relative to the expression of an unmodified albumin (such as SEQ ID NO: 1) from a suitable expression system, such as yeast (e.g. *Saccharomyces*, e.g. *S. cerevisiae*) or an *Aspergillus*. Relative expression levels can be determined, for example, by expression of the protein followed by quantification by SDS-PAGE, HPLC or Western Blotting.

(i) Conjugation Competence.

The thio-albumin may or may not have a high level of conjugation competence, for example at least 50, 60, 70, 80, 90, 95 or 100% relative to the conjugation competence of an albumin consisting of SEQ ID NO: 1 having only one conjugation competent cysteine at Cys-34. Conjugation competence may be determined relative to any conjugatable molecule (conjugation partner) of interest, for example a bioactive molecule or a fluorescent dye. Determination may be through mass spectrometry analysis or quantification of the activity of the bioactive compound such as its fluorescence. An advantage of a thio-albumin having a high conjugation competence is that it may allow efficient conjugation of molecules to the thio-albumin. Conjugation competence may be measured with respect to time. Favored thio-albumins may be (a) those which achieve maximal conjugation quickly or (b) slowly.

(j) Activity of Conjugated Compound.

The thio-albumin of the invention may be conjugated to a compound (conjugation partner), for example a bioactive compound, such that the compound has a high level of activity relative to its activity in an unconjugated state. Preferably, the conjugated compound shows at least 1, 10, 20, 40, 50, 60, 70, 80, 80 and most preferably 100% of its activity relative to its unconjugated state. An advantage of a conjugated compound with a high level of activity is that it reduces the quantity of conjugated compound required to achieve a desire effect, e.g. a desired therapeutic effect.

(k) Receptor Binding Capacity of Albumin.

The conjugated- and/or non-conjugated thio-albumin may or may not have a receptor binding activity of at least 10, 20, 30, 40, 50, 60, 70, 80, 90 or 100% of the receptor binding activity of human serum albumin (SEQ ID NO: 1). Alternatively, the conjugated- and/or non-conjugated thio-albumin may or may not have a lower receptor binding activity for example at most 0, 10, 20, 30, 40, 50, 60, 70, 80 or 90% than human serum albumin. Receptor binding activity may be determined by assay, such as in relation to binding to FcRn.

FIG. 1. shows the scores of each amino acid residue of HSA (SEQ ID NO: 1) for each of parameters (a) to (g). For clarity, in vivo, HSA is initially produced as a 609 amino acid protein in which the first twenty four amino acids are a leader sequence. The leader sequence is cleaved off to generate a 585 amino acid mature protein. Throughout this specification, the mature protein is referred to as SEQ ID NO: 1. The structure of HSA model A106 disregards the first four residues and the last three residues of SEQ ID NO: 1 because these are unresolved in the 3D model. Therefore, residue 1 of model A106 is equivalent to residue 5 of SEQ ID NO: 1. Throughout this specification, all residues are cited with reference to SEQ ID NO: 1, unless stated otherwise. The immature sequence of HSA HSA with its natural C-terminal leader sequence) is provided in SEQ ID NO: 102.

The column labels of FIG. 1. are detailed below:

Position in 1AO6: Refers to the amino acid position in the crystal structure of human serum albumin from the RCSD Protein Databank (PDB) with the entry with PDB identity 1AO6 or 1ao6 (Sugio, S., A. Kashima, et al. (1999). Protein Eng 12(6): 439-46). Note that compared to the mature HSA sequence (SEQ ID NO: 1), the 1AO6 structure starts at residue 5S (with the first 4 amino acids absent from the structure) and finishes at 582A of SEQ ID NO: 1 (with the last 3 amino acids absent from the structure). The amino acid positions used herein to describe positions to alter to generate conjugation competent cysteines are referring to the positions in SEQ ID NO: 1, not 1ao6.

Position in Mature HSA: The amino acid position in SEQ ID NO: 1 taken from the 585 residue secreted form of HSA, National Center for Biotechnology Information, ACCESSION: 1AO6_A VERSION GI:3212456 (24 Sep. 2008), Chain A, Crystal Structure Of Human Serum Albumin. (Sugio et al. (1999). Protein Eng 12(6): 439-46).

Position with Leader Sequence: Refers to the position in the unprocessed form of human serum albumin containing the 24 amino acid secretory leader sequence.

Amino Acid: The standard one letter code for each of the 20 amino acids (e.g. A=Ala=Alanine).

% SASA: The solvent accessible surface area calculated for each residue, using the DSSP software described in Kabschand and Sander (1983). Biopolymers 22(12): 2577-637. Each solvent accessible surface area was divided by a standard value for the particular amino acid found in that position and multiplied by 100, thereby obtaining a percentage of the standard value for each residue. The standard solvent accessible surface areas for the 20 different amino acids are defined as (using one-letter codes for the amino acids): A=62, C=92, D=69, E=156, F=123, G=50, H=130, I=84, K=174, L=97, M=103, N=85, P=67, Q=127, R=211, S=64, T=80, V=81, W=126, Y=104).

B-Factor: The crystallographic B-factor value for the C-alpha atom was extracted directly from the PDB file. The B-factor is in column number 11 of the 1ao6 PDB file PDB.

SS (Secondary Structure): The secondary structure determined for each residue using the DSSP software Kabsch and Sander (1983). Biopolymers 22(12): 2577-637. If the secondary structure is defined as H (Helix), B (isolated beta bridge) or E (Extended sheet), the residue is marked '1', otherwise as '0'.

Align 1 (Mamm. W): The homology level for an alignment of various mammalian albumin family proteins with HSA (SEQ ID NO: 1), identified as P02768 compiled using MegAlign program (DNASTAR, Lasergene, version 8.0.2) based on Clustal W; six levels of homology are determined with the highest=100%, decreasing in 20% increments, to the lowest=0% (FIG. 2).

Adj. 100%'s (Align 1): The score according to whether the adjacent residue was highly (100%) conserved when HSA is aligned with the mammalian albumins of FIG. 2. A score of 0 indicates the residue is not adjacent to a residue with 100% homology when HSA is aligned with the mammalian albumins of FIG. 2; a score of 1 indicates that the residue is adjacent to one residue with 100% homology when HSA is aligned with mammalian albumins; a score of 2 indicates that the residue is adjacent to two residue with 100% homology when HSA is aligned with mammalian albumins.

Figure 3:
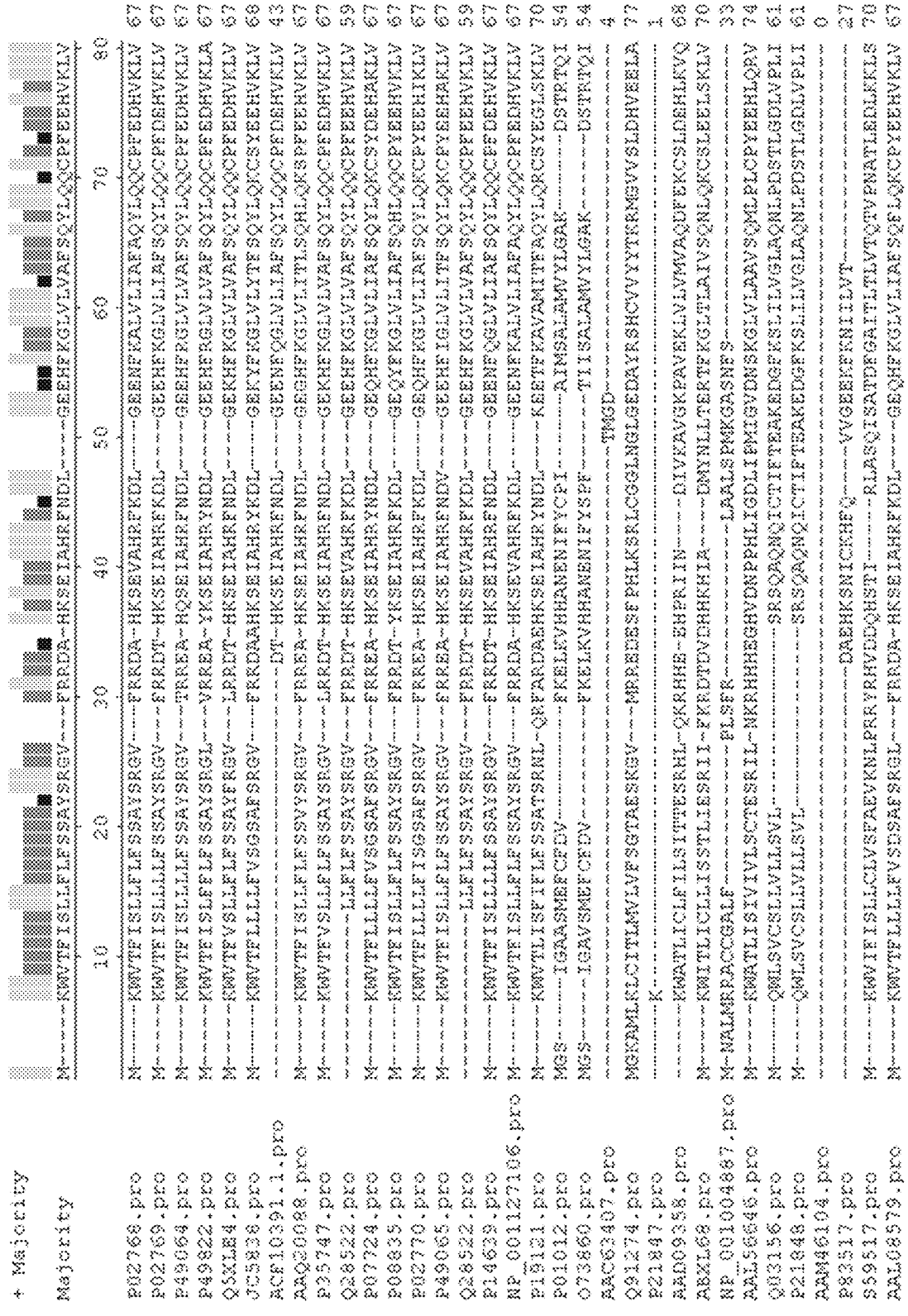
FIG. 3. Is an alignment of the amino acid sequence of human serum albumin (P02768.pro=SEQ ID NO: 109) with albumins from thirty two other species, some of which are mammalian. 'Majority' shows the consensus sequence. '+ Majority' shows the relative homology between all thirty three sequences in bar chart form, where the height of the bar indicates the relative homology at 20, 40, 60, 80 and 100%. The protein sequences include the leader sequence. P02768.pro: human (SEQ ID NO: 109); P02769.pro: bovine (SEQ ID NO: 94); P49064.pro: cat (SEQ ID NO: 95); P49822.pro: dog (SEQ ID NO: 96); Q5XLE4.pro: donkey (SEQ ID NO: 97); JC5838.pro: gerbil (SEQ ID NO: 98); ACF10391,1.pro: goat fragment (SEQ ID NO: 99); AAQ20088.pro: guinea pig (SEQ ID NO: 100); P35747.pro: horse (SEQ ID NO: 101); Q28522.pro: macaque (SEQ ID NO: 103); P07724.pro: mouse (SEQ ID NO: 104); P08835.pro: pig (SEQ ID NO: 105); P02770.pro: rat (SEQ ID NO: 107); P49065.pro: rabbit (SEQ ID NO: 106); Q28522.pro: Rhesus monkey (SEQ ID NO: 103); P14639.pro: sheep (SEQ ID NO: 108); NP_001127106.pro: orangutan (SEQ ID NO: 110); P19121.pro: chicken (SEQ ID NO: 111); P01012.pro: chicken ovalbumin (SEQ ID NO: 112); 073860.pro: turkey ovalbumin (SEQ ID NO: 113); AAC63407.pro: sea lamprey (SEQ ID NO: 114); Q91274.pro: sea lamprey (SEQ ID NO: 115); P21847.pro: bullfrog (SEQ ID NO: 116); AAD09358.pro: Rana shqiperica (SEQ ID NO: 117); ABXL68.pro: *Xenopus* (SEQ ID NO: 118); NP_001004887.pro: *Xenopus* (SEQ ID NO: 119); AAL56646.pro: Spotted Salamander (SEQ ID NO: 120); Q03156.pro: Atlantic salmon (SEQ ID NO: 138); P21848.pro: Atlantic salmon (SEQ ID NO: 121); AAM46104.pro: Sphenodon punctatus (SEQ ID NO: 122); P83517.pro: Australian lungfish (SEQ ID NO: 123); 559517.pro: monocled cobra (SEQ ID NO: 124); AAL08579.pro: *Schistosoma mansoni* (SEQ ID NO: 125).
Figure 3:
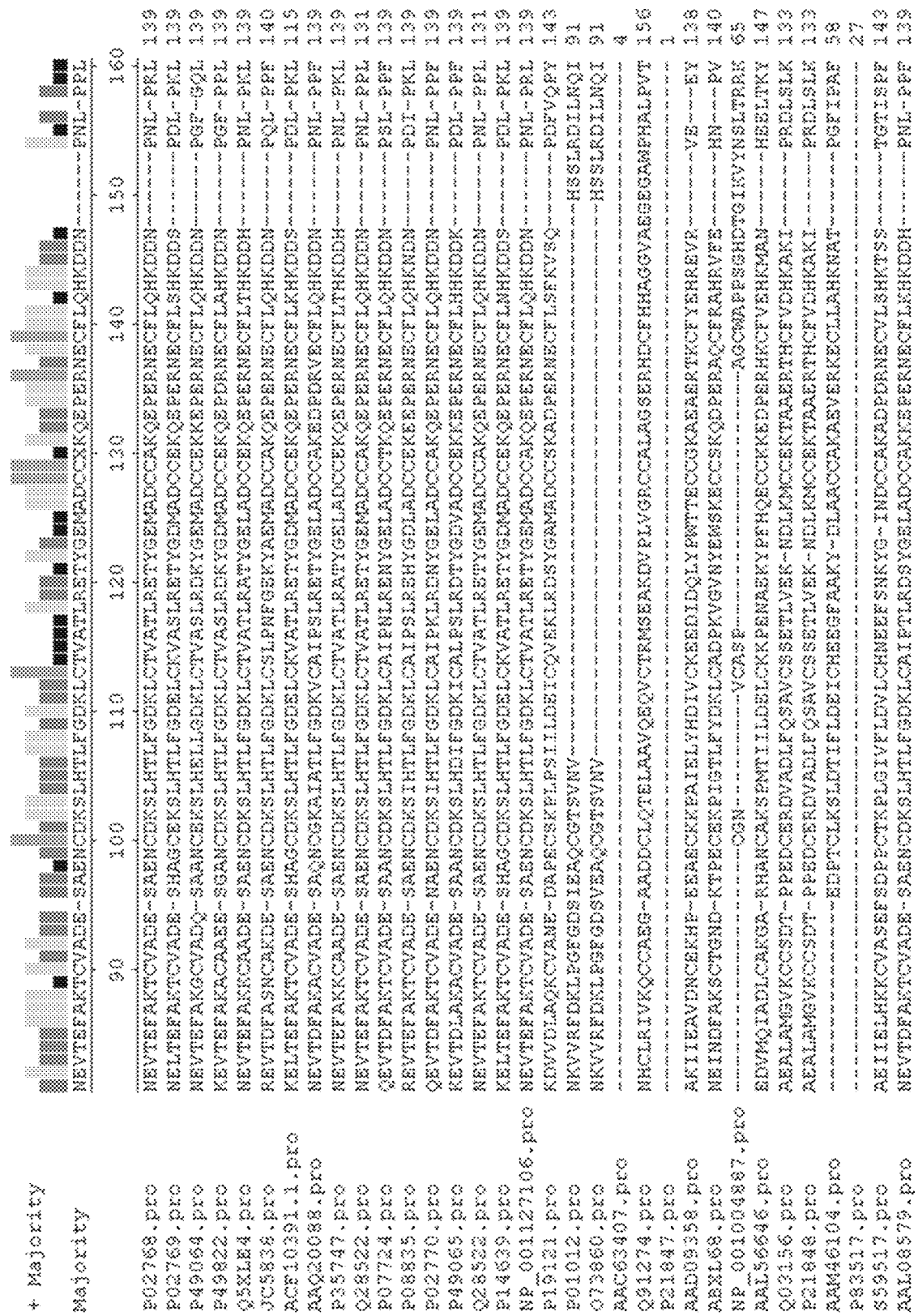
Figure 3:
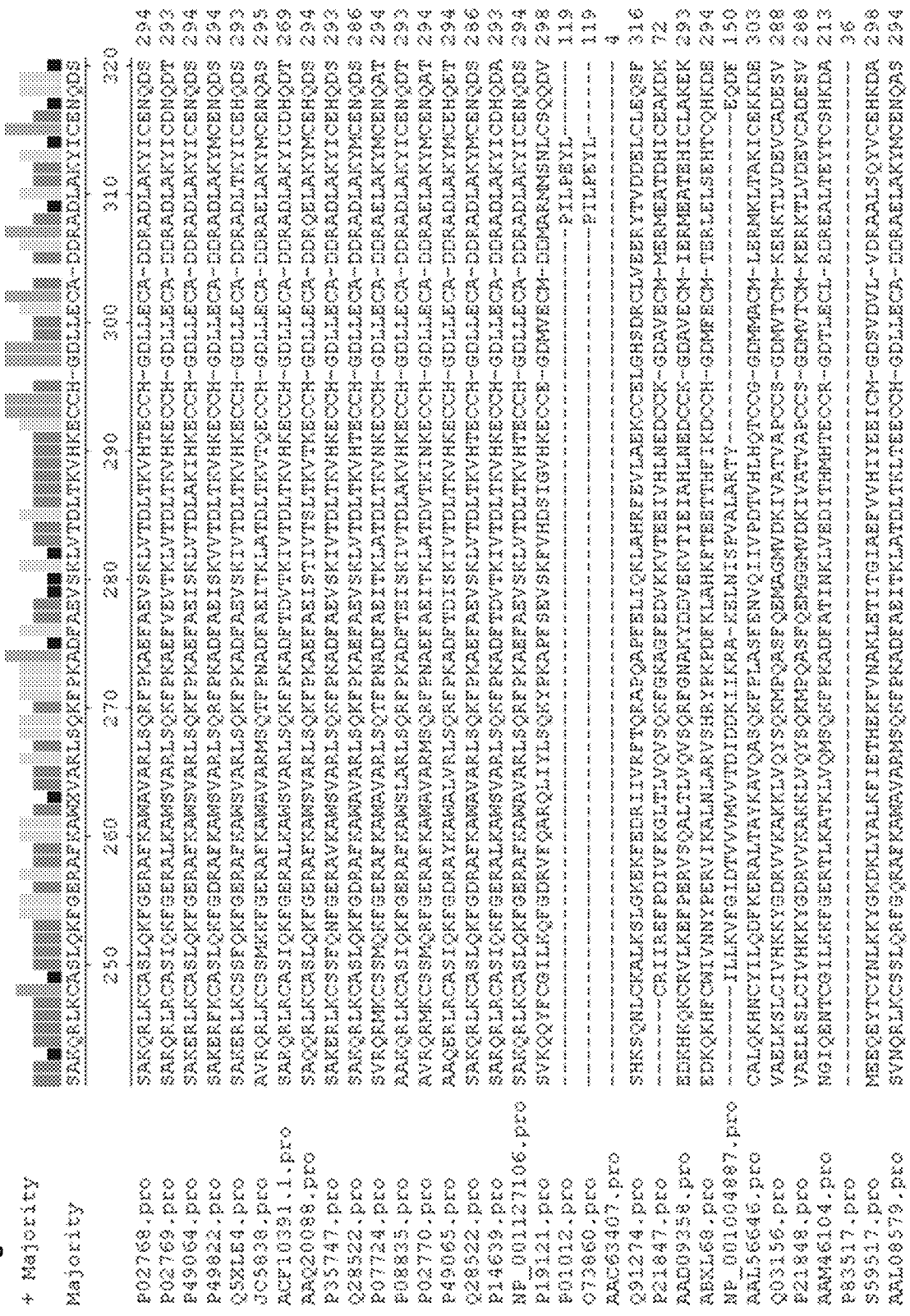
Figure 3:
Figure 3:
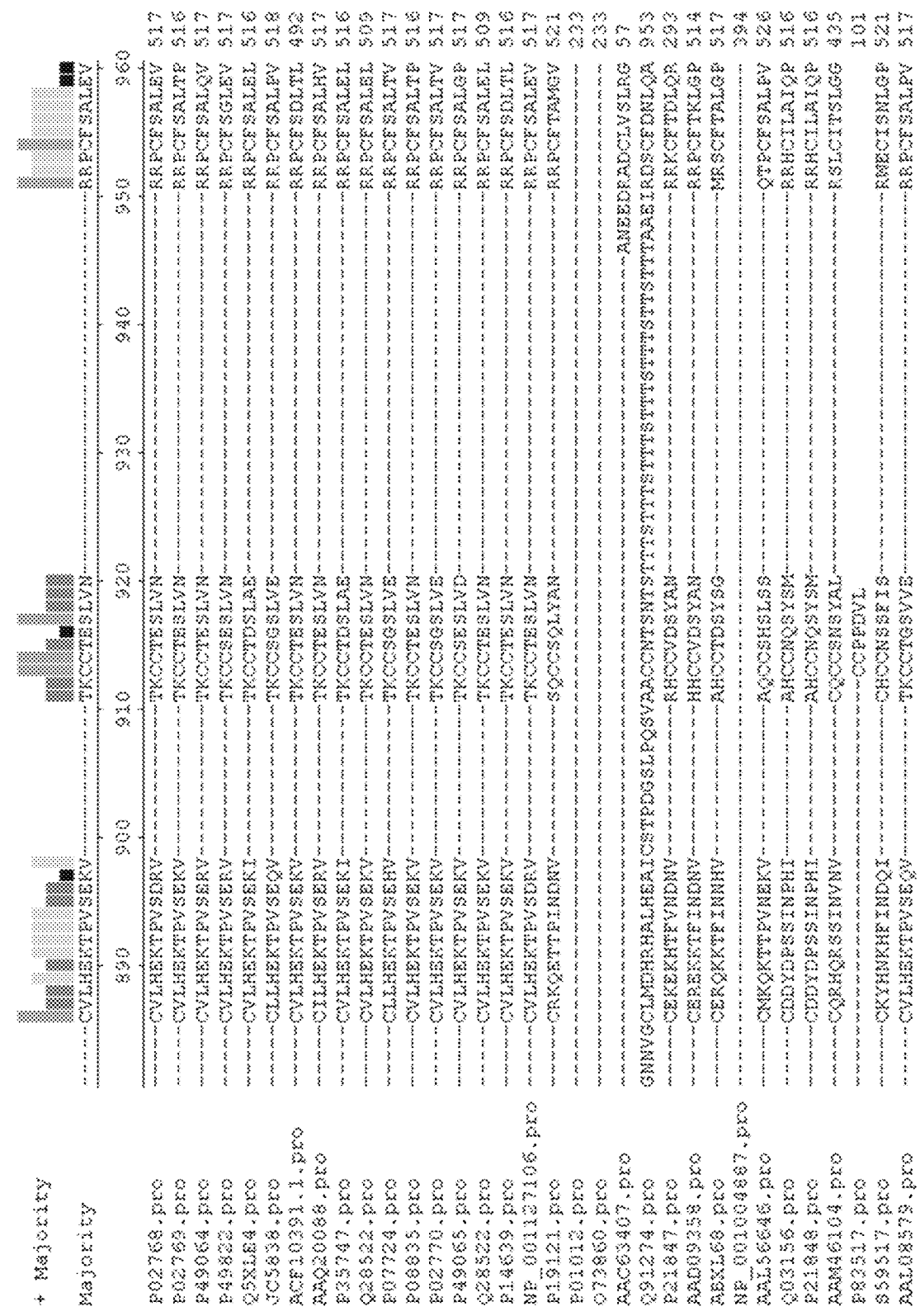
Figure 3:
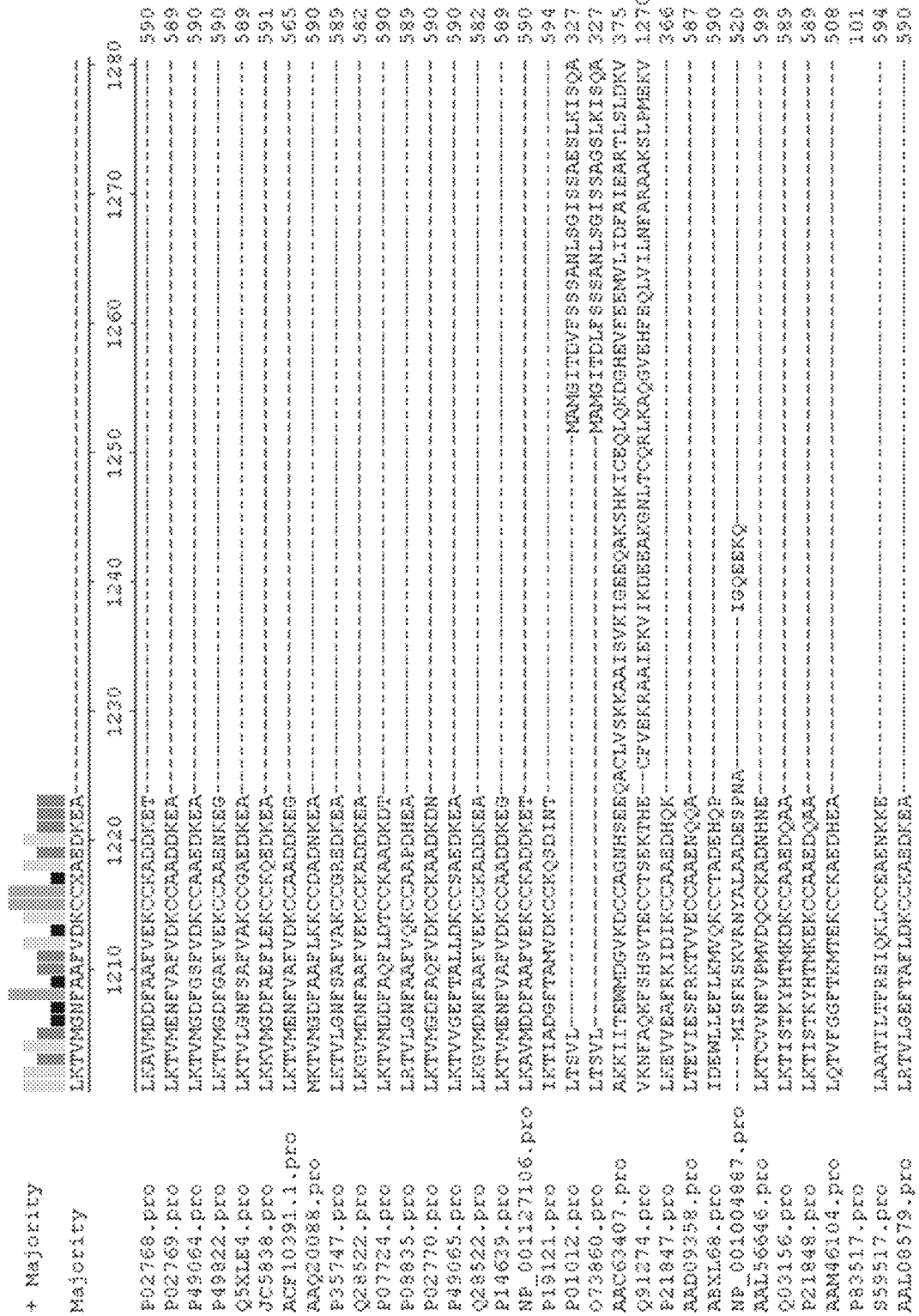

Align 2 (Var. Sps. V): The homology level for an alignment of various albumin family proteins with HSA (SEQ ID NO: 1), identified as P02768 compiled using MegAlign program (DNASTAR, Lasergene, version 8.0.2) based on Clustal V; six levels of homology are determined with the highest=100%, decreasing in 20% increments, to the lowest=0% (FIG. 3).

Polymorph: This identifies whether or not a polymorphism is known at the amino acid residue. Single amino acid polymorphisms of human serum albumin (SEQ ID NO: 1) were taken from Minchiotti et al. (2008). Hum Mutat 29(8): 1007-16, with amino acid positions taken from the unprocessed form of human serum albumin containing the 24 amino acid secretory leader sequence, and described using the standard one letter amino acid code (e.g. D25V refers to an aspartic acid being changed to a valine at position 1 in SEQ ID NO: 1).

Phenotype Change: A score representing the 'severity' of phenotypic change derived from the sources of known phenotypic changes ('Polymorph.', referenced above) where; 0=no known phenotypic change, 1=a phenotypic change has been described for any of the mutations at this position compared to the residue in SEQ ID NO: 1, excluding a change resulting in decreased thermal stability, 2=a mutation at this position in SEQ ID NO: 1 is described as causing reduced thermal stability.

Conserved Mutation vs. Cysteine: A score referring to how well conserved the amino acid is compared to cysteine, as derived from FIG. 4 (described herein), and ranging from 1 to 5 for mutations to cysteine. A score of 1 is assigned to the most conservative changes possible (e.g. alanine to cysteine), and ranging to a score of 5 for the lowest of conservation compared to a cysteine (e.g. histidine to cysteine).

Although the selection criteria can be used in any desired combination, four preferred groups of selection criteria (A, B, C, D) are described, by way of example only, below. Of these (A) and (B) may also be referred to as Selection Groups 1 and 2 (respectively):

(A) A particularly preferred embodiment of the first aspect of the invention provides a method for designing and/or preparing a thio-albumin, the method comprising:

providing a three-dimensional model comprising at least one instance of an albumin sequence (preferably the three dimensional model relates to an amino acid sequence of an albumin and most preferably the amino acid sequence of the albumin sequence is also provided, the amino acid sequence may comprise 1, 2, 3, 4, 5, 6, 7, 8, 9, or 10 amino acids which are not resolved at the C- and/or N-terminus of the three dimensional model, preferably the amino acid sequence is 'full length', i.e. the mature amino acid sequence of the albumin);

selecting a candidate amino acid residue in the albumin sequence which corresponds to the first, second, third, fourth or fifth residue relative to the N- or C-terminus of the albumin sequence (of the model or of the amino acid sequence) or which (preferably in relation to the three dimensional model) fulfils the following conditions: not present within secondary structure; surface accessibility (SASA) of at least 90%; B-factor score of at least 60; less than 80% homology to known mammalian albumins (e.g. FIG. 2); no adjacent residues with 100% homology to known mammalian albumins (e.g. FIG. 2); no polymorphism with a known phenotypic change; and no unconserved amino acid change to cysteine with a score of 5 or above;

substituting one or more of the selected amino acid residues with cysteine or inserting cysteine at the N-side or C-side of the selected residue, optionally making one or more additional alterations to the albumin sequence where each alteration is an amino acid deletion, substitution, extension, addition or insertion; and optionally preparing a polypeptide having the required amino acid sequence.

With reference to model 1A06 and SEQ ID NO: 1, candidate residues identified by selection criteria (A) include L585, D1, A2, D562, A364, A504, E505, T79 and E86 (in descending order of solvent accessibility) and are also shown in FIG. 5A.

(B) Another preferred embodiment of the first aspect of the invention provides a method for designing and/or preparing a thio-albumin, the method comprising:

providing a three-dimensional model comprising at least one instance of an albumin sequence (preferably the three dimensional model relates to an amino acid sequence of an albumin and most preferably the amino acid sequence of the albumin sequence is also provided, the amino acid sequence may comprise 1, 2, 3, 4, 5, 6, 7, 8, 9, or 10 amino acids which are not resolved at the C- and/or N-terminus of the three dimensional model, preferably the amino acid sequence is 'full length', i.e. the mature amino acid sequence of the albumin);

selecting a candidate amino acid residue in the albumin sequence (of the model or of the amino acid sequence) which (preferably in relation to the three dimensional model) fulfils the following conditions: present within secondary structure; surface accessibility of at least 90%; B-factor score of at least 40; less than 80% homology to known mammalian albumins (e.g. FIG. 2); no adjacent residues with 100% homology to known mammalian albumins (e.g. FIG. 2); no polymorphism with a known phenotypic change; and no unconserved amino acid change to cysteine with a score of 5 or above;

substituting one or more of the selected amino acid residues with cysteine or inserting cysteine at the N-side or C-side of the selected residue, optionally making one or more additional alterations to the albumin sequence where each alteration is an amino acid deletion, substitution, extension, addition or insertion; and optionally preparing a polypeptide having the required amino acid sequence.

With reference to model 1A06 and SEQ ID NO: 1, candidate residues identified by selection criteria (B) include D129, D549, A581, D121, E82, S270, Q397 and A578 (in descending order of solvent accessibility) and are also shown in FIG. 5B.

(C) Another preferred embodiment of the first aspect of the invention provides a method for designing and/or preparing a thio-albumin, the method comprising:

providing a three-dimensional model comprising at least one instance of an albumin sequence (preferably the three dimensional model relates to an amino acid sequence of an albumin and most preferably the amino acid sequence of the albumin sequence is also provided, the amino acid sequence may comprise 1, 2, 3, 4, 5, 6, 7, 8, 9, or 10 amino acids which are not resolved at the C- and/or N-terminus of the three dimensional model, preferably the amino acid sequence is 'full length', i.e. the mature amino acid sequence of the albumin);

selecting a candidate amino acid residue in the albumin sequence (of the model or of the amino acid sequence) which (preferably in relation to the three dimensional model) fulfils the following conditions: not present within secondary structure; surface accessibility of at least 80%; B-factor score of at least 50; less than 100% homology to known mammalian albumins (e.g. FIG. 2); less than 80% homology to the various albumins aligned in FIG. 3; no polymorphism known to cause thermal instability; and no unconserved amino acid change to cysteine with a score of 4 or above;

substituting one or more of the selected amino acid residues with cysteine or inserting cysteine at the N-side or C-side of the selected residue;

optionally making one or more additional alterations to the albumin sequence where each alteration is an amino acid deletion, substitution, extension, addition or insertion; and optionally preparing a polypeptide having the required amino acid sequence.

With reference to model 1A06 and SEQ ID NO: 1, candidate residues identified by selection criteria (C) are shown in FIG. 5C.

(D) Another preferred embodiment of the first aspect of the invention provides a method for designing and/or preparing a thio-albumin, the method comprising:

providing a three-dimensional model comprising at least one instance of an albumin sequence (preferably the three dimensional model relates to an amino acid sequence of an albumin and most preferably the amino acid sequence of the albumin sequence is also provided, the amino acid sequence may comprise 1, 2, 3, 4, 5, 6, 7, 8, 9, or 10 amino acids which are not resolved at the C- and/or N-terminus of the three dimensional model);

selecting a candidate amino acid residue in the albumin sequence which (preferably in relation to the three dimensional model) fulfils the following conditions: present within secondary structure; surface accessibility of at least 80%; B-factor score of at least 30; less than 100% homology to known mammalian albumins (e.g. FIG. 2); less than 80% homology to the various albumins aligned in FIG. 3; no polymorphism known to cause thermal instability; and no unconserved amino acid change to cysteine with a score of 4 or above;

substituting one or more of the selected amino acid residues with cysteine or inserting cysteine at the N-side or C-side of the selected residue, optionally making one or more additional alterations to the albumin sequence where each alteration is an amino acid deletion, substitution, extension, addition or insertion; and optionally preparing a polypeptide having the required amino acid sequence.

With reference to model 1A06 and SEQ ID NO: 1, candidate residues identified by selection criteria (D) are shown in FIG. 5D.

Since FIGS. 5A, 5B, 5C and 5D are selections from FIG. 1, the column headings are the same.

A candidate residue may be one or more of the cysteine residues involved in disulphide bonding present in the albumin molecule (in the case of HSA, SEQ ID NO: 1, there are 17 disulphide bonds and therefore 34 cysteines involved in disulphide bonding). Two cysteines which are linked by a disulphide bond may be referred to as 'counterparts'. In order to generate a conjugation competent cysteine, the candidate residue may be deleted or may be substituted with a different amino acid, particularly Ser, Thr, Val or Ala in order to create a free thiol at the partner cysteine. The 34 cysteine residues of SEQ ID NO: 1 which are involved in disulphide bonding are C53, C62, C75, C91, C90, C101, C124, C169, C168, C177, C200, C246, C245, C253, C265, C279, C278, C289, C316, C361, C360, C369, C392, C438, C437, C448, C461, C477, C476, C487, C514, C559, C558 and C567. In relation to the invention, some of these 34 candidate residues are more favored than others.

Cysteine residues were visually inspected using the PyMOL software (Warren L. DeLano "The PyMOL Molecular Graphics System." DeLano Scientific LLC, San Carlos, Calif., USA), and the cysteines in the disulphide bonds were divided into 3 categories:

those that can be replaced, for example, by serine, leaving its counterpart cysteine as a free thiol that has a high probability of being a conjugation site. These correspond to C75, C91, C124, C168, C169, C316, C360, C361, C567, C558.

those that can be replaced by serine, leaving its counterpart as a free thiol that has a medium probability of being a conjugation site. These correspond to C90, C101, C177, C265, C279, C278, C289, C369, C392, C438, C476, C487, C514, C559.

those that can be replaced by serine, leaving its counterpart as a free thiol that has a low probability of being a conjugation site. These correspond to C53, C62, C200, C246, C245, C253, C437, C448, C461, C477.

The judgment is based on surface accessibility and the orientation of the C-alpha—C-beta bond of the potential free thiol relative to the folded polypeptide. Using this judgment each of the cysteine residues of HSA were given a modification score and ranked as high, medium or low.

FIG. 6A, provides a list of all the cysteine residues which have a high modification score (right hand column), indicating that modification of a cysteine residue at this position would result in its counterpart cysteine providing a free thiol that has a high probability of being suitable for use as a conjugation site.

FIG. 6B, provides a list of the counterpart cysteines that that, when unpaired (thus providing a free thiol), have a high probability of being suitable for use as a conjugation site.

The column labels for FIG. 6 are the same for those described for FIG. 1 with the addition of:

Modification Score: defined as 'high', 'medium' or 'low' as described herein.

Disulphide Information: summarises disulphide pairing in SEQ ID NO: 1.

(Polymorp.) Phenotype Change: summarises the columns labelled 'Polymorph.' And 'Phenotype Change' in FIG. 1.

Preferred cysteine residues for modification could be further selected based on the other information provided in FIG. 6A, such as assigned secondary structure, cysteine residues with no adjacent conserved residues (100% amongst mammalian albumins (aligned by Clustal W), no known polymorphisms causing phenotypic changes.

Alternatively cysteine residues for modification could be selected by examining the environment of the cysteine residue (containing a free thiol group) generated by modification of its counterpart cysteine residue provided in FIG. 6A, characteristics such as high % SASA may be preferred (FIG. 6B, fifth column).

For clarity, for albumins other than the human serum albumin of SEQ ID NO: 1, equivalent residues are favored for mutation. Such equivalent residues may or may not have identical residue numbers to those of SEQ ID NO: 1 but would be clearly identifiable by the skilled person, for example with reference to homology alignments with SEQ ID NO: 1 and other albumins such as those of FIG. 2 and/or FIG. 3. For example, in FIG. 2, the residue at positions at 160 of the horizontal 'ruler' are equivalent but have differing residue numbers and, sometimes, are differing amino acids, e.g. L159 in human, W134 in goat fragment, L151 in Macacque and M159 in mouse. It is preferred that, for an alignment such as FIG. 2 or FIG. 3, equivalent residues are within 10, 9, 8, 7, 6, 5, 4, 3, 2 or 1 amino acid of the candidate amino acid of SEQ ID NO: 1. The 'ruler' above the alignment indicates whether an amino acid is within 1 to 10 amino acids of a candidate amino acid of SEQ ID NO: 1.

The selection criteria of Group (A) are more preferable than those of Group (B) which in turn are more preferable than those of Group (C) and in turn are more preferable than those of Group (D).

The method may or may not further comprise determining the receptor binding capacity and/or the conjugation competence of the polypeptide and optionally selecting a polypeptide which does or does not have a receptor binding capacity and/or conjugation competence.

'Preparing' a polypeptide may or may not include expressing the polypeptide in a host cell and/or purifying the polypeptide from the host or host cell media. The method may comprise favoring selection of residues meeting one or all of the following criteria:

residues having high surface accessibility are preferred to those having low surface accessibility;
conservative mutations from another amino acid to cysteine are preferred over non-conservative mutations;

Alternatively, or in addition, selection criteria as detailed throughout this specification may or may not be used to select residues in the method of the first aspect of the invention.

A second aspect of the invention provides a thio-albumin comprising a polypeptide sequence and/or polypeptide designed and/or produced according to the first aspect of the invention.

Preferably the polypeptide is a recombinant polypeptide. Preferably the polypeptide is an isolated and/or purified polypeptide. Preferably the polypeptide is synthetic and/or does not naturally occur in nature.

Specifically, the invention provides a polypeptide which has an amino acid sequence which is at least 60% identical to residues 1 to 585 of SEQ ID NO: 1 or a fragment or fusion thereof, in which:

(a) at a position equivalent to position 34 of SEQ ID NO: 1, there is a conjugation competent cysteine residue; and (b) elsewhere in the polypeptide there is one or more conjugation competent cysteine residues, preferably 2 or more.

In addition the invention provides a conjugation competent polypeptide comprising an amino acid sequence which is at least 60% identical to residues 1 to 585 of SEQ ID NO: 1, or a fragment or fusion thereof, in which:

(a) at a position equivalent to position 34 of SEQ ID NO: 1, there is not a conjugation competent cysteine residue; and (b) elsewhere in the polypeptide there is one or more conjugation competent cysteine residues, preferably 2 or more or 3 or more.

The polypeptide may or may not comprise 3, 4, 5, 6, 7, 8, 9, 10, 11, 12, 13, 14, 15, 16, 17, 18, 19 or 20 conjugation competent cysteine residues.

More specifically, the polypeptide (which may be described in relation to a known albumin sequence such as SEQ ID NO: 1) may or may not comprise one or more of:

(a) substitution of a non-cysteine amino acid with a cysteine at a position corresponding to a position equivalent to any of residues L585, D1, A2, D562, A364, A504, E505, T79, E86, D129, D549, A581, D121, E82, S270, Q397 and A578 of SEQ ID NO: 1;

(b) insertion of a cysteine at a position adjacent the N- or C-side of an amino acid which may or may not correspond to a position equivalent to any of residues L585, D1, A2, D562, A364, A504, E505, T79, E86, D129, D549, A581, D121, E82, S270, Q397 and A578 of SEQ ID NO: 1;

(c) a cysteine with a free thiol group at a position which may or may not correspond to any of C369, C361, C91, C177, C567, C316, C75, C169, C124 and C558 which may or may not be generated by deletion or substitution of C360, C316, C75, C168, C558, C361, C91, C124, C169 and/or C567.

(d) addition of a cysteine to the N-side of the N-terminal residue of an albumin sequence and/or to the C-side of the C-terminal residue of an albumin sequence such that the net result of the substitution, deletion, addition or insertion events of (a), (b), (c) and (d) is that the number of conjugation competent cysteine residues of the polypeptide sequence is increased relative to the polypeptide prior to the substitution, insertion, deletion and addition events. Within (a) to (d), above, the residues all of the residues are preferred. However, within each of (a), (b), (c) and (d), the residues are listed in order of decreasing preference.

A thio-albumin may or may not include a polypeptide where one or more naturally occurring free-thiol group(s), such as cysteine-34 in HSA (SEQ ID NO: 1), is modified to an amino acid which is not cysteine. For example, cysteine may or may not be replaced by an amino acid which has a relatively high conservation score (e.g. 1, 2 or 3 as calculated according to FIG. 4) such as alanine or serine. A thio-albumin may or may not include a polypeptide where one or more naturally occurring free-thiol group(s), such as cysteine-34 in HSA (SEQ ID NO: 1) are present.

As detailed herein, the invention may be achieved by introducing cysteine residues by one or more of extension, addition, insertion, substitution or deletion.

An addition may be made by extension and/or insertion.

For example, one or more conjugation competent cysteines may or may not be created in an albumin by extension; e.g. by adding an extra cysteine residue to the N-terminus or C-terminus of the molecule, which may or may not be added as a single cysteine residue, or as a longer polypeptide which contains one or more conjugation competent cysteines. The cysteine residue(s) may be added immediately adjacent the N- or C-terminus of the albumin. Alternatively, there may be one or more other amino acid residues located between the N- and/or C-terminus of the albumin and the cysteine residue(s). When two or more cysteine residues are added, some or all of the added cysteines may be separated from each other by one or more other amino acids, for example by from 1 to 50 amino acids, such as from 1, 10, 20, 30, or 40 amino acids to from 10, 20, 30, 40, or 50 amino acids. A preferred N-terminal extension is the addition of Cys immediately adjacent the N-terminal of a mature albumin (i.e. albumin cleaved from its leader sequence). For example, for an albumin comprising or consisting of SEQ ID NO: 1, Cys is preferably immediately N-terminal to the first Asp (D1). Such an albumin may be referred to as 'Cys-albumin', e.g. 'Cys-HSA' (where HSA is Human Serum Albumin). Other preferred N-terminal extensions of albumins such as SEQ ID NO: 1 include Cys-Ala-albumin such as Cys-Ala-HSA. A preferred C-terminal extension is the addition of Cys immediately adjacent the C-terminal of an albumin, such as a mature albumin. For example, for an albumin comprising or consisting of SEQ ID NO: 1, Cys is preferably immediately C-terminal to the last Leu (L585) residue. Such an albumin may be referred to as 'albumin-Cys', e.g. HSA-Cys. Other preferred C-terminal extensions of albumins such as SEQ ID NO: 1 include albumin-Ala-Cys, such as HSA-Ala-Cys. Polypeptides suitable for providing extensions, as described above, may be added or inserted to the C- or, N-side of the C- or N-terminal amino acid of the albumin, such as to the C-side of L585 in SEQ ID NO: 1.

The polypeptide may or may not further comprise a further linker to which a conjugation partner, such as a bioactive compound, may be linked. For example a linker may comprise a primary amine such as a lysine.

One or more conjugation competent cysteines may or may not be created in an albumin by insertion; for example by adding one or more additional cysteines without removal of an amino acid residue from the albumin sequence, or by substituting one or more adjacent amino acids with a larger number of residues containing at least one cysteine, thus extending the overall length of the polypeptide. For example, a cysteine residue may be introduced immediately adjacent an albumin residue identified herein. The cysteine residue may be introduced as a single cysteine residue or within a polypeptide. The polypeptide may be from 2 to 50 amino acids long, preferably from 2, 10, 20, 30, or 40 to 10, 20, 30, 40 or 50 amino acids long.

Alternatively, or in addition, the invention includes substitution of one of the cysteine residues in one or more disulphides bond of an albumin with a different amino acid residue, so breaking the disulphide bond to leave an additional free thiol group. For example, a cysteine of one or more of the 17 naturally occurring disulphide bonds of HSA may be substituted to provide a conjugation-competent cysteine. Such a substitution causes the cysteine which has not been substituted to no longer have a disulphide binding partner and therefore provide a free thiol group. Conjugation competent cysteines may be provided from one or more of the naturally occurring disulphide bonds of an albumin such as 1, 2, 3, 4, 5, 6, 7, 8, 9, 10, 11, 12, 13, 14, 15, 16 or 17 of the naturally occurring disulphide bonds of an albumin such as HSA (e.g. SEQ ID NO: 1). For example, one cysteine residue which naturally forms a disulphide bond with another cysteine residue may or may not be substituted with a relatively conserved amino acid residue, particularly Ser, Thr, Val or Ala. With reference to SEQ ID NO: 1, cysteine residues involved in disulphide bonding are C53, C62, C75, C91, C90, C101, C124, C169, C168, C177, C200, C246, C245, C253, C265, C279, C278, C289, C316, C361, C360, C369, C392, C438, C437, C448, C461, C477, C476, C487, C514, C559, C558 and C567. Cysteine residues preferred for modification (i.e. deletion or substitution) may in particular correspond to C360, C316, C75, C168, C558, C361, C91, C124, C169 and/or C567 thus generating a conjugation competent cysteine at one or more of C369, C361, C91, C177, C567, C316, C75, C169, C124 and C558 of SEQ ID NO: 1.

In addition, conjugation competent cysteines may or may not be created in albumin by deletion of one of the cysteines of a disulphide bond in the protein structure, so breaking the disulphide bond to provide an additional free thiol group.

Alternatively, or in addition, one or more of the cysteine residues present in the albumin molecule, but not involved in disulphide bonding (e.g. Cys-34 in the case of SEQ ID NO: 1) may or may not be deleted (i.e. without substitution with a different amino acid) or may or may not be substituted with a different amino acid, particularly Ser, Thr, Val or Ala.

For a polypeptide comprising two or more conjugation competent cysteine residues, when the polypeptide is folded, the conjugation competent cysteine residues may or may not be relatively evenly distributed over the surface of the folded protein. The term 'folded' includes folding of a polypeptide/protein into its natural configuration, for example the most thermodynamically stable folded configuration. An advantage of relatively even distribution is that it allows conjugation of two or more moieties to the thio-albumin without steric hindrance between two or more of the conjugated moieties. This has the advantage of minimising, and optionally eliminating, potential loss of activity due to issues such as steric hindrance between adjacent moieties (conjugation partners) which may be conjugated to the thio-albumin. Such moieties, for example bioactive molecules, may be relatively bulky.

Preferably the two or more conjugation competent cysteines are distributed over the surface of the thio-albumin molecule such that they are spaced as far from each other as possible, for example geometrically possible. Preferably the distance between two or more conjugation competent cysteines is at least 10, 20, 30, 40, 50, 60, 70, or 80 Angstroms. Preferably each conjugation competent cysteine is at least 10, 20, 30, 40, 50, 60, 70, or 80 Angstroms distant from all other conjugation competent cysteines in the molecule. The distance between two conjugation competent cysteines is preferably a distance which is at least 10, 20, 30, 40, 50, 60, 70, 80, 90, or 95% and most preferably 100% of the length of the longest axis of the folded albumin molecule, for example as shown in a model of an albumin. For example, the longest axis of SEQ ID NO: 1 as shown in protein structure 1AO6 is approximately 85 Angstroms. Therefore, it is preferred that the two or more of the cysteine residues are at least 65, 70, 75 or most preferably 80 Angstroms apart. Most preferably each conjugation competent cysteine residue is at a distance of at least 80, 90, or 95% and most preferably 100% of the length of the longest axis of the folded albumin molecule.

Preferably the side chains of conjugation competent cysteines are directed away from each other and/or directed so that a moiety conjugated to the cysteine will be directed away from the centre of the albumin structure. This provides the advantage of preventing interactions between the conjugated moieties and/or the albumin moiety itself.

With reference to an amino acid sequence, candidate amino acid residues may be visually inspected using software such as PyMOL (Warren L. DeLano "The PyMOL Molecular Graphics System" DeLano Scientific LLC, San Carlos, Calif., USA). Candidate amino acids may be divided into categories based on their proximity to other members of that group. For example, candidate amino acids may be divided into 2, 3, 4, 5, 6, 7, 8, 9 or 10 categories. It is preferred that combinations of candidate amino acids are selected from different categories. That is, it is preferred that a thio-albumin contains one or fewer mutations from each category.

With reference to SEQ ID NO: 1, PyMOL was used to analyse the candidate residues of FIGS. 5A and 5B in order to identify particularly favored combinations of cysteine mutations. Such combinations may be used to design a thio-albumin having two or more conjugation competent cysteine residues. Selection Groups 1 and 2 correspond to the selection criteria (A) and (B) (respectively) from FIGS. 5A and 5B of the selection method described herein. Selection Group 3 corresponds to the residues identified in FIG. 6B. Particularly favored residues are given in FIGS. 6A and 6B in which the column headings are the same as those in FIG. 1 with the addition of 'Selection Group' and 'Proximity Group' as described herein.

The results of the analysis are given in FIG. 10 in which column headings are the same as those used in FIG. 1, and FIG. 6 with the addition of:

Proximity Group: allocation of a proximity group as described herein to descrive subsets of sites within HSA (specifically SEQ ID NO: 1).

For example, candidate amino acid residues selected in Selection Group 1 (listed in FIG. 5A) were visually inspected using the PyMOL software, and the amino acids selected were divided into categories based on their proximity to other members of Selection Group 1. Five groups were generated (labeled A to E in FIG. 10 'proximity group', right hand column), four were generated by visual inspection. Group E contains amino acid residues not visible in 1AO6 which are known to be in the N-terminal region. In addition it was observed that cys-34 is present in the proximity group A.

Similarly amino acid residues selected in Selection Group 2 (listed in FIG. 5B) were visually inspected using the PyMOL software, and the amino acids selected were divided into categories based on their proximity to other members of Selection Group 2. Five groups were generated (labeled F-J in FIG. 10 'proximity group', right hand column).

Similarly, the preferred free cysteine residues selected in Selection Group 3 (listed in FIG. 6B), which can be generated by mutations causing disruption of disulphide bonds were visually inspected using the PyMOL software, and the amino acids selected were divided into categories based on their proximity to other members of that group. Four groups were generated (labeled K-N in FIG. 10 'proximity group', right hand column). When referring to the residues of selection group 3, the cited residues are the resultant conjugation competent cysteines (e.g. FIG. 6B). In order to generate such a conjugation competent cysteine it is clear that the counterpart cysteine (e.g. FIG. 6A) in the disulphide bond should be removed for example by deletion or substitution.

When a combination of two or more mutations is desired, amino acid residues which occur in different 'proximity' groups (e.g. with reference to SEQ ID NO: 1) may be preferred over those that occur within the same proximity group. For SEQ ID NO: 1, there are 14 proximity groups (i.e. A to N). It is preferred that, for a thio-albumin having two or more conjugation competent cysteines, there is zero or one conjugation competent cysteine defined from each of the 14 groups. That is, it is preferred that such a thio-albumin does not contain two or more conjugation competent cysteines falling within the same group. A large number of permutations exist which meet this criterion.

For example, for a thio-albumin variant containing two free thiol groups residues based on selection criteria that generated Selection Group 1, then T79+A364, in which one residue is selected from proximity group A to combine with A364 in proximity group C, would be preferred over T79+E86 which both occur in proximity group A.

For combinations including cysteine-34, it is preferred not to select residues from proximity groups A, F or K. That is, it is preferred to select residues from one or more of proximity groups B to E, G to J and L to N.

Examples of preferred mutations selected from within Selection Group 1 may include the following:
 For 2 amino acid residues selected from Selection Group 1; amino acid residues from proximity groups A+C are preferred, such as T79+A364, Similarly, amino acid residues selected from proximity groups C+E, such as A364+D1 are also preferred. Also, amino acid residues from proximity groups D+E, such as L585+A2 or + the C-side of L585+A2, or from G+I, such as S270+A581, are preferred.
 For 3 amino acid residues selected from Selection Group 1; amino acid residues which occur in proximity groups A+C+B are preferred such as T79+A364+D562. Similarly, amino acid residues selected from proximity groups B+C+E, such as D562+A364+A2 or D562+A364+D1, are also preferred.
 For 4 amino acid residues selected from Selection Group 1; amino acid residues which occur in proximity groups A+C+B+D such as such as T79+A364+D562+A504, or alternatively T79+D562+A364+L585 are preferred. Even more preferred are amino acid residues selected from proximity groups A+B+C+E, such as C34+D562+A364+A2 T79+D562+A364+D1.
 For 5 amino acid residues selected from Selection Group 1; amino acid residues which occur in proximity groups A+C+B+D+E such as T79+D562+A364+L585+D1 are preferred. Similarly, E86+D562+A364+A504+A2 are also preferred.
 The above mentioned albumin variants may or may not further comprise a cysteine at Cys34 of SEQ ID NO: 1, or at an equivalent position in another albumin.

Examples of preferred mutations selected from within Selection Group 2 may include the following:
 For 2 amino acid residues selected from Selection Group 2; amino acid residues which occur in proximity groups G+I such as S270+A581 are preferred. Alternatively, amino acid residues which occur in proximity groups G+H such as S270+D129 are preferred.
 For 3 amino acid residues selected from Selection Group 2; amino acid residues which occur in proximity groups G+I+F such as S270+A581+E82 are preferred. Alternatively, amino acid residues which occur in proximity groups G+I+H such as S270+A581+D129 are preferred.
 For 4 amino acid residues selected from Selection Group 2; amino acid residues which occur in proximity groups G+I+F+H such as S270+A581+E82+D129.
 For 5 amino acid residues selected from Selection Group 2; amino acid residues which occur in proximity groups G+I+F+H+J such as S270+A581+E82+D129+Q397 are preferred. However, D549 is not preferred in combination with mutations A578, A581. Also, mutations to D549, A578, A581 or are not preferred in combination with mutation of L585 from Selection Group 1.

Examples of preferred site selected from within Selection Group 3 for the conjugation competent free-thiols may include the following:
 For 2 amino acid residues selected from Selection Group 3; amino acid residues which occur in proximity groups M+L are preferred, such as C369+C177. Similarly, C361+C124 are also preferred.
 More than two mutations disrupting disulphide bonds are less preferred.
 The above mentioned albumin variants may or may not further comprise a cysteine at Cys34 of SEQ ID NO: 1, or at an equivalent position in another albumin.

Combinations of sites from Selection Groups 1, 2 and 3 can also be made, where sites from Selection Group 1 are typically preferred to sites from Selection Group 2, which are typically preferred to sites selected from Selection Group 3.

Examples of sites from Selection Groups 1+2 may include residues from proximity groups C+I, such as A364+A581. Alternatively, residues from proximity groups A+G+I, such as C34+S270+A581, from proximity groups A+H+G+I, such as C34+D129+S270+A581, from proximity groups A+C+I, such as T79+A364+A581, or residues from proximity groups C+I+H such as A364+A581+D129 are also preferred.

Examples of sites from Selection Groups 1+3 may include residues from proximity groups A+L+M, such as C34+

C169+C316, from proximity groups C+L, such as A364+ C177 are preferred. Alternatively, residues from proximity groups B+M, such as D562+C369 are preferred.

Examples of sites from Selection Groups 2+3 may include residues from proximity groups H+M, such as D129+C369 are preferred. Alternatively, residues from proximity groups I+M, such as A581+C369 are preferred.

Examples of sites from Selection Groups 1+2+3 may include residues from proximity groups A+H+M+D, such as C34+D129+C360+L585, from proximity groups B+H+M, such as D562+D129+C369 are preferred.

The above combinations are generally more preferred than combinations of residues from the following sets of proximity groups: (i) A, K and F; (ii) B, D, I, J and N; (iii); C and M; (iv) H and L.

The above albumin variants of the invention may or may not further comprise a cysteine at Cys34 of SEQ ID NO: 1, or at an equivalent position, if based on an albumin other than SEQ ID NO: 1.

A skilled person will appreciate that the sites for introduction of more than one free thiol group (conjugation competent cysteine) have been selected from Selection Groups 1, 2 and 3. However, this approach may also be used to select sites for the introduction of more than one free thiol group from other residues selected from SEQ ID NO: 1, i.e. he could use the disclosed method to generate other useful selection groups.

A preferred thio-albumin comprises SEQ ID NO: 1 with Cys at positions 2 and 585 in addition to the naturally occurring Cys at position 34 (SEQ ID NO: 78, construct 'TA33'). A more preferred thio-albumin comprises SEQ ID NO: 1 with Cys at positions 2, 364, 562, 585 in addition to the naturally occurring Cys at position 34 (SEQ ID NO: 82, construct 'TA38'). Thio-albumins comprising three or four of the Cys at positions 2, 364, 562 and 585 may also be preferred.

The polypeptide may or may not comprise at least one mutation that reduces glycosylation.

A third aspect of the invention provides a polynucleotide which encodes the polypeptide according to the invention. The polynucleotide may or may not be codon-optimised relative to the host from which it is to be expressed. SEQ ID NO: 2 provides the usual coding sequence of HSA (SEQ ID NO: 1). SEQ ID NO: 3 provides a coding sequence of HSA (SEQ ID NO: 1) which is codon-optimised for expression from *S. cerevisiae*. SEQ ID NO: 2 or 3 may be mutated in order to provide a polynucleotide which encodes a polypeptide according to the invention. Preferably the polynucleotide is synthetic and/or recombinant. Preferably the polynucleotide is an isolated polynucleotide. The polynucleotide may encode an HSA with or without a leader sequence. For example, the polynucleotide may encode an HSA with the natural leader sequence of HSA (amino acids 1 to 24 of SEQ ID NO: 102) or an HSA with a fusion leader sequence (amino acids 1 to 24 of SEQ ID NO: 49).

A fourth aspect of the invention provides a plasmid comprising the polynucleotide of the third aspect of the invention. The plasmid may be a 2 micron based plasmid such as those described in WO2005/061719, WO2005/061718 and WO2006/067511 (all incorporated herein by reference). The plasmid may exhibit enhanced chaperone activity, for example through over expression of a chaperone, particularly PDI.

A fifth aspect of the invention provides an expression system such as a host cell comprising a polynucleotide according to the third aspect of the invention and/or a plasmid of the fourth aspect of the invention. Preferably the host cell is a mammalian cell such as a human or bovine cell, or a fungal cell such as a yeast cell. Alternatively, the host cell may be a bacterial cell such as a *Bacillus* or *Escherichia coli* or a viral cell such as Baculovirus or a plant cell such as a rice e.g. *Oryza sativa*. Most preferably, the cell is a yeast cell such as a *Saccharomyces* (e.g. *S. cerevisiae*), a *Pichia* or an *Aspergillus* cell.

A sixth aspect of the invention provides a conjugate which comprises a conjugation partner, such as a bioactive compound, and a polypeptide according to the invention, wherein the conjugation partner is linked to the polypeptide through a conjugation competent cysteine residue of the polypeptide. The conjugation partner may be a therapeutic, diagnostic or imaging compound such as those mentioned herein. The conjugate may comprise 2 or more, for example 2, 3, 4, 5, 6, 7, 8, 9 or 10, conjugation partners which may each be different and/or may be multiple copies of the same compound. Preferably, each conjugation partner is linked to the polypeptide through a conjugation competent cysteine residue of the polypeptide, however conjugation partners may be linked by other means for example by a genetic fusion or covalent bonds to non-cysteine amino acids such as lysine.

A seventh aspect of the invention provides a method of producing a polypeptide of the invention comprising:
(a) culturing a host cell according to the invention under conditions that allow expression of the polypeptide; and
(b) recovering the polypeptide from the host cell and/or from host cell growth medium.

Accordingly, the present invention also provides a method for producing a polypeptide (or protein) of the invention, the method comprising: (a) providing a host cell of the invention comprising a polynucleotide encoding protein product of choice as defined above; and (b) growing the host cell (for example, culturing the host cell in a culture medium); thereby to produce a cell culture or recombinant organism comprising an increased level of the protein product of choice compared to the level of production of the protein product of choice achieved by growing (for example, culturing), under the same conditions, the same host cell that has not been genetically modified to cause over-expression of one or more helper proteins.

The step of growing the host cell may or may not involve allowing a host cell derived from a multicellular organism to be regrown into a multicellular recombinant organism (such as a plant or animal) and, optionally, producing one or more generations of progeny therefrom.

The method may or may not further comprise the step of purifying the thus expressed protein product of choice from the cultured host cell, recombinant organism or culture medium.

The production method may comprise linking a conjugation partner to the polypeptide of the invention through a conjugation competent cysteine residue of the polypeptide. Suitable conjugation methods and conjugation partners are described herein.

An eighth aspect of the invention provides a composition comprising a conjugate according to the invention and at least one pharmaceutically acceptable carrier and/or diluent.

A ninth aspect of the invention provides a method for making a pharmaceutical ingredient and/or a pharmaceutical product comprising making a thio-albumin according to the present invention, optionally conjugating a further molecule to the thio-albumin, optionally formulating the resultant conjugate with a pharmaceutically acceptable diluent and/or carrier and optionally preparing the product in unit dosage form.

A tenth aspect of the invention provides use of a polypeptide according to the invention for the production of a thio-albumin-conjugate.

An eleventh aspect of the invention provides use of a conjugate according to the invention and/or produced by a method according to the invention for treatment of disease, treatment of illness and/or diagnosis.

A twelfth aspect of the invention provides a gel comprising one or more albumins according to the invention. The gel may be formed by any suitable method. For example the gel may be formed by incubating an albumin solution, or suspension, at a suitable temperature e.g. room temperature (15 to 25° C., such as 20° C.) or body temperature (36 to 38° C., preferably 36.9° C.). A gel may be used to coat medical devices, such as a stent. A gel may be used in or on a wound dressing. The albumin may be applied to the medical device or wound dressing before or after it has gelled. The albumin may be applied ex situ or in situ (e.g. applied to a medical device or dressing before, after or during its application on to or insertion into a human or animal body).

The polypeptides and/or conjugates of the invention may be used to prepare nanoparticles which may be used, for example, in angiogenic applications, anti-angiogenic applications and to coat a medical device such as a stent. Nanoparticles are effective at targeting, for example to non tight-junctions, and therefore can be useful for targeting tumors such as cancerous tumors. Nanoparticles can also be useful to target antigen in order to provoke an immune response since nanoparticles are particularly susceptible to engulfment and presentation by phagocytes. The invention provides nanoparticles consisting only of thio-albumin according to the invention which may or may not be conjugated to a moiety (conjugation partner). The invention also provides nanoparticles comprising thio-albumin according to the invention, which may or may not be conjugated to a moiety, and one or more other constituents of a nanoparticle which may or may not be albumin related. In a preferred embodiment, a thio-albumin according to the invention comprises at least two conjugation competent cysteine residues located on the surface of the polypeptide. Such a thio-albumin may be used for the preparation of nanoparticles in which one or more conjugation competent cysteine residues may be used in the formation of a nanoparticle and one or more conjugation competent residue is used for conjugation to a conjugation partner, for example to a bioactive molecule.

The invention relates to all albumins. Whilst preferred residues have been identified in relation to SEQ ID NO: 1, the skilled person would be able to identify equivalent residues in other albumin sequences, such as the albumins disclosed in FIGS. 2 and 3, and understand that mutations of albumins (other than SEQ ID NO: 1) at such equivalent residues are part of the invention. Equivalent residues can be identified by, for example, homology alignment with SEQ ID NO: 1. A residue in an albumin other than SEQ ID NO: 1 may or may not have an identical residue coordinate to its equivalent residue in SEQ ID NO: 1. Thus the invention provides thio-albumins based on any albumin sequence, such as the sequences shown in Table 1 and, more preferably, those shown in FIGS. 2 and/or 3. 'Based on' includes modification of an albumin sequence to introduce one or more additional free-thiols.

Recombinant albumins can offer advantages over animal-derived albumins by having a higher level of conjugation-competent free thiol groups, and can be manufactured without the risk of contamination with pathogenic prions and viruses. An advantage of a thio-albumin conjugate is that the thio-albumin part may be prepared separately to a conjugation partner. Therefore, one batch of thio-albumin may be used to produce many different thio-albumin conjugates. Also, the individual components of the conjugate can be manufactured by different methods and therefore are not restricted to a single method, such as heterologous protein expression in a host cell such as a yeast. Furthermore, a thio-albumin may comprise multiple conjugation sites and therefore a single thio-albumin may be conjugated to more than one type of conjugation partner (e.g. therapeutic agent, diagnostic agent, targeting agent, imaging agent) and/or to multiple copies of one or more types of conjugation partner. The ability to conjugate the thio-albumin to different types of conjugation partners allows the provision of a multi-functional species. The ability to conjugate the thio-albumin to multiple copies of a conjugation partner allows the concentration of molecule to be increased and therefore increase the amount, or volume, of thio-albumin conjugate required for a given purpose relative to a conjugate having only a single copy of the conjugation partner. Advantages of delivering drugs via an albumin fusion protein are discussed in Osborn, et al. (2002). J Pharmacol Exp Ther 303(2): 540-8. It is expected that delivery of drugs via a conjugation of the invention would have similar advantages.

Further details which may or may not be used in accordance with the invention are described below:

Three Dimensional (3D) Models

The above disclosure has been made in relation to the albumin model known as 1A06 (Protein Data Bank) which relates to SEQ ID NO: 1. FIG. 1 gives the amino acid residues for 1AO6.

However, the invention relates to all albumins and their structures. Structures of albumin are available to the skilled person, for example the atomic coordinates for the tertiary structure of human albumin are available at the GenBank DNA database. Structures may be viewed using suitable software such as RasM.1 Chime (Sayle, TIBS 20, 374, 1995). Available albumin coordinates include:

1AO6, 1BM0 (Sugio et al. (1999). *Protein Enq* 12(6): 439-46), which was among the top 17 requested proteins.

1UOR, He & Carter (1992). *Nature* 358(6383): 209-15.

1bj5 and 1bke, Curry et al. (1998). *Nat Struct Biol* 5(9): 827-35.

1e7a, 1e7b, 1e7c, Bhattacharya et al. (2000). *J Biol Chem* 275(49): 38731-8.

1e7e, 1e7f, 1e7g, 1e7h and 1e7i, Bhattacharya et al. (2000). *J Mol Biol* 303(5): 721-32.

1GNJ, Petitpas et al. (2001). *J Mol Biol* 314(5): 955-60.

1HA2 and 1H9Z Petitpas et al. (2001). *J Biol Chem* 276(25): 22804-9.

Albumin

The albumin used in the invention may be a naturally occurring albumin, an albumin-related protein or a variant thereof such as a natural or engineered variant. Variants include polymorphisms, fragments such as domains and sub-domains, fragments and/or fusion proteins. An albumin, of this invention, may comprise the sequence of an albumin protein obtained from any source. Typically the source is mammalian such as human or bovine. In one preferred embodiment the serum albumin is human serum albumin ("HSA"). The term "human serum albumin" includes a serum albumin having an amino acid sequence naturally occurring in humans, and variants thereof. Preferably the albumin has the amino acid sequence of SEQ ID NO: 1 or a variant or fragment thereof, preferably a functional variant or fragment thereof. The HSA coding sequence is obtainable by known methods for isolating cDNA corresponding to human genes, and is also disclosed in, for example, EP 0 073 646 and EP 0 286 424. A fragment or variant may or may not be functional. For example, a fragment or variant may retain the ability to bind to an albumin receptor such as FcRn to at least 10, 20, 30, 40, 50, 60, 70, 80, 90 or 100% of the ability of the parent albumin (from which the fragment or variant derives) to bind to the receptor. Relative binding ability may be determined by methods known in the art such as surface plasmon resonance studies.

The albumin may be a naturally-occurring polymorphic variant of human albumin or of a human albumin analogue. Generally, variants or fragments of human albumin will have at least 5%, 10%, 15%, 20%, 30%, 40%, 50%, 60%, 70%, (preferably at least 80%, 90%, 95%, 100%, 105% or more) of human albumin's ligand binding activity (for example FcRN-binding), mole for mole.

The "albumin" may comprise the sequence of bovine serum albumin. The term "bovine serum albumin" includes a serum albumin having an amino acid sequence naturally occurring in cows, for example as taken from Swissprot accession number P02769, and variants thereof as defined herein. The term "bovine serum albumin" also includes fragments of full-length bovine serum albumin or variants thereof, as defined herein.

A number of proteins are known to exist within the albumin family; a non-exclusive list is shown in Table 1, below. The list indicates full-length of sequences including the mature protein and leader sequence (unless indicated otherwise).

The albumin may comprise the sequence of an albumin derived from one of serum albumin from dog (e.g. see Swissprot accession number P49822-1), pig (e.g. see Swissprot accession number P08835-1), goat (e.g. as available from Sigma as product no. A2514 or A4164), cat (e.g. see Swissprot accession number P49064-1), chicken (e.g. see Swissprot accession number P19121-1), ovalbumin (e.g. chicken ovalbumin) (e.g. see Swissprot accession number P01012-1), turkey ovalbumin (e.g. see Swissprot accession number O73860-1), donkey (e.g. see Swissprot accession number Q5XLE4-1), guinea pig (e.g. see Swissprot accession number Q6WDN9-1), hamster (see DeMarco et al. (2007). International Journal for Parasitology 37(11): 1201-1208), horse (e.g. see Swissprot accession number P35747-1), rhesus monkey (e.g. see Swissprot accession number Q28522-1), mouse (e.g. see Swissprot accession number P07724-1), pigeon (e.g. as defined by Khan et al, 2002, *Int. J. Biol. Macromol.*, 30(3-4), 171-8), rabbit (e.g. see Swissprot accession number P49065-1), rat (e.g. see Swissprot accession number P02770-1) and sheep (e.g. see Swissprot accession number P14639-1) and includes variants and fragments thereof as defined herein.

The albumin may comprise the sequence of an albumin such as a serum albumin or an ovalbumin, for example those shown in Table 1, below, and includes variants and fragments thereof as defined herein.

TABLE 1

Albumins from various species

| Protein | Common Name | Species | SwissProt Accession No | Identity to SEQ ID NO: 1 (Clustal V) | Length (aa) |
|---|---|---|---|---|---|
| SA | African clawed frog | *Xenopus laevis* | P08759-1 | 37.3 | 608 |
| SA | Bovine | *Bos taurus* (SEQ ID NO: 94) | P02769-1 | 76.1 | 607 |
| SA | Cat | *Felis catus* (SEQ ID NO: 95) | P49064-1 | 82.2 | 608 |
| SA | Chicken | *Gallus gallus* | P19121-1 (Version 2 text) | 46.5 | 615 |
| SA | Cobra ALB | *Naja kaouthia* | Q91134-1 | 30.9 | 614 |
| SA | Dog | *Canis lupus familiaris* (SEQ ID NO: 96) | P49822-1 | 80.3 | 608 |
| SA | Donkey | *Equus asinus* (SEQ ID NO: 97) | Q5XLE4-1 | 76.6 | 607 |
| SA | European water frog | *Rana shqiperica* | Q9YGH6-1 | 31.5 | 603 |
| SA | Blood fluke | *Schistosoma mansoni* | AAL08579 Q95VB7-1 | 76.0 | 608 |
| SA | Mongolian Gerbil | *Meriones unguiculatus* (SEQ ID NO: 98) | O35090-1/ JC5838 | 73.2 | 609 |
| SA | Goat | *Capra hircus* (SEQ ID NO: 99) | B3VHM9-1 | 74.3 | 607 |
| SA | Guinea Pig | *Cavia porcellus* (SEQ ID NO: 100) | Q6WDN9-1 | 73.0 | 608 |
| SA | Horse | *Equus caballus* (SEQ ID NO: 101) | P35747-1 | 76.4 | 607 |
| SA | Human | *Homo sapiens* (SEQ ID NO: 102) | P02768-1 | 100.0 | 609 |
| SA | Australian Lungfish | *Neoceratodus forsteri* | P83517-1 | 22.8 | 101 (NL) |
| SA | Macaque (Rhesus Monkey) | *Macaca mulatta* (SEQ ID NO: 103) | Q28522-1 | 93.5 | 608 |
| SA | Mouse | *Mus musculus* (SEQ ID NO: 104) | P07724-1 Version 3. | 72.4 | 608 |

TABLE 1-continued

Albumins from various species

| Protein | Common Name | Species | SwissProt Accession No | Identity to SEQ ID NO: 1 (Clustal V) | Length (aa) |
|---|---|---|---|---|---|
| SA | North American bullfrogs | *Rana catesbeiana* | P21847-1 | 36.1 | 382 (NL) |
| SA | Pig | *Sus scrofa* (SEQ ID NO: 105) | P08835-1 Version 2 | 75.6 | 607 |
| SA | Rabbit | *Oryctolagus cuniculus* (SEQ ID NO: 106) | P49065-1 Version 2 | 75.3 | 608 |
| SA | Rat | *Rattus norvegicus* (SEQ ID NO: 107) | P02770-1 Version 2. | 73.4 | 608 |
| SA | Salamander | *Ambystoma maculatum* | Q8UW05-1 | 38.8 | 626 |
| SA | Salmon ALB1 | *Salmo salar* | P21848-1 | 25.0 | 608 |
| SA-2 | Salmon ALB2 | *Salmo salar* | Q03156-1 | 24.8 | 608 |
| SA | Sea lamprey | *Petromyzon marinus* | Q91274-1 | 16.9 | 1423 |
| SA | Sea lamprey | *Petromyzon marinus*-AS | O42279-1 | 17.4 | 551 |
| SA | Sheep | *Ovis aries* (SEQ ID NO: 108) | P14639-1 | 75.3 | 607 |
| SA | Sumatran Orangutan | *Pongo abelii* | Q5NVH5-1 | 100.0 | 609 |
| SA | Tuatara | *Sphenodon punctatus* | Q8JIA9-1 | 43.8 | 527 (NL) |
| SA | Western clawed frog | *Xenopus* (Silurana) *tropicalis* | Q6DJ95-1 | 10.5 | 572 (NL) |
| OA | Chicken | *Gallus gallus* | P01012-1 Version 2 | 10.9 | 383 (NL) |
| OA | Turkey | *Meleagris gallopavo* | O73860-1 Version 3. | 11.4 | 386 (NL) |

SA: Serum albumin, SA-2: Serum albumin-2, OA: Ovalbumin, NL No Leader sequence

Many naturally occurring mutant forms of albumin are known. Many are described in Peters, (1996, *All About Albumin: Biochemistry, Genetics and Medical Applications*, Academic Press, Inc., San Diego, Calif., p. 170-181). A variant as defined herein may be one of these naturally occurring mutants such as those described in Minchiotti et al. (2008). Hum Mutat 29(8): 1007-16.

A "variant albumin" refers to an albumin protein wherein at one or more positions there have been amino acid insertions, deletions, or substitutions, either conservative or non-conservative, provided that such changes result in an albumin protein for which at least one basic property, for example binding activity (type of and specific activity e.g. binding to bilirubin or a fatty acid such as a long-chain fatty acids, for example oleic (C18:1), palmitic (C16:0), linoleic (C18:2), stearic (C18:0), arachidonic (C20:4) and/or palmitoleic (C16:1)), osmolarity (oncotic pressure, colloid osmotic pressure), behavior in a certain pH-range (pH-stability) has not significantly been changed. "Significantly" in this context means that one skilled in the art would say that the properties of the variant may still be different but would not be unobvious over the ones of the original protein, e.g. the protein from which the variant is derived. Such characteristics may be used as additional selection criteria in the invention.

Typically an albumin variant will have more than 40%, usually at least 50%, more typically at least 60%, preferably at least 70%, more preferably at least 80%, yet more preferably at least 90%, even more preferably at least 95%, most preferably at least 98% or more sequence identity with a naturally occurring albumin such as SEQ ID NO: 1. The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally. The alignment may alternatively be carried out using the Clustal W program or the Clustal V program and therefore allow calculation of % homology between sequences of a multiple alignment and/or calculation of % identity between sequences of a pairwise alignment. The parameters used may be as follows:

Fast pairwise alignment parameters: K-tuple(word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM Custal W: Pairwise alignment parameters: 'Slow-Accurate', Gap Penalty: 10, Gap Length: 0.1, Protein Weight Matrix: Gonnet 250, DNA Weight Matrix: IUB. Multiple Alignment Parameters: Gap penalty 10.00, gap length penalty 0.20, Delay Divergent Seqs (%) 30, DNA transition weight 0.50, Protein weight matrix=Gonnet series, DNA weight matrix=IUB.

Clustal V: Pairwise alignment parameters: Ktuple: 1, Gap Penalty: 3, Window: 5, Diagonals: 5; Multiple alignment parameters: Gap penalty 10, gap length penalty 10.

Conservative Substitution

As used herein, the term "conservative" amino acid substitutions refers to substitutions made within the same group, and which typically do not substantially affect protein function. By "conservative substitutions" is intended combinations such as Gly, Ala; Val, Ile, Leu; Asp, Glu; Asn, Gln; Ser, Thr; Lys, Arg; and Phe, Tyr. Such variants may be made by techniques well known in the art, such as by site-directed mutagenesis as disclosed in U.S. Pat. No. 4,302,386 issued 24 Nov. 1981 to Stevens, incorporated herein by reference.

In one embodiment, the Venn diagram of FIG. 4 may be used to determine conservative amino acid substitutions: Using FIG. 4, a conservation mutation score (ranging from 0 to 5) may be calculated. A score of 0 is the highest conservation, which, for cysteine, is only assigned for substitution of a cysteine residue with another cysteine residue. For changes from any other amino acid to a cysteine, the score may be 1, 2, 3, 4, 5. A score of 1 is a more conservative substitution that a score of 2, 3, 4 or 5. A score of 5 is assigned to the lowest conservation between a substituted amino acid and the cysteine. The score of 0 to 5 is calculated from FIG. 4 as the number of boundaries (i.e. lines) crossed to go from cysteine to the appropriate amino acid. Thus the score for cysteine is 0 as no boundaries are crossed. Likewise, the score of aspartic acid (D) is 3, since 3 boundaries are crossed.

The conservation mutation score (with respect to FIG. 4) for the 20 different amino acids are defined as (using one-letter codes for the amino acids): A=1, C=0, D=3, E=4, F=4, G=2, H=5, I=4, K=4, L=4, M=3, N=2, P=3, Q=3, R=5, S=1, T=1, V=3, W=3, Y=3. With reference to FIGS. 1, 5A, 5B, 5C, and 5D, these scores are provided for each of the amino acid residues in the column labelled 'Conserved Mutation to Cysteine'. Using the conservation mutation score residues with a score of 3 or less, i.e. aspartic acid methionine, proline, glutamine, valine, tryptophan, tyrosine, glycine, asparagine, alanine, serine and threonine are preferred since they are relatively conserved with cysteine. More preferred are those amino acids with a score of 2 or less i.e. glycine, asparagine, alanine, serine, threonine. Most preferred are those with a score of 1, i.e. alanine, serine, threonine. Similarly using the conservation mutation score system of FIG. 4, residues with a score of 4 or more, i.e. glutamic acid, phenylalanine, isoleucine, lysine, leucine, histidine and arginine are less preferred and may not be preferred at all.

Alternatively, or in addition, "conservative" amino acid substitutions refers to substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

For example, a conservative substitution of alanine-2 in SEQ ID NO: 1 can include glycine or serine. Non-conservative substitutions encompass substitutions of amino acids in one group by amino acids in another group. For example, a non-conservative substitution could include the substitution of a polar amino acid for a hydrophobic amino acid.

Fragment

The term "fragment" as used herein includes any fragment of full-length albumin or a variant thereof, so long as at least one basic property, for example binding activity (type of and specific activity e.g. binding to bilirubin), osmolarity (oncotic pressure, colloid osmotic pressure), behavior in a certain pH-range (pH-stability) has not significantly been changed. "Significantly" in this context means that one skilled in the art would say that the properties of the variant may still be different but would not be unobvious over the ones of the original protein. A fragment will typically be at least 50 amino acids long. A fragment may comprise at least one whole sub-domain of albumin. Domains of HSA have been expressed as recombinant proteins (Dockal et al., 1999, J. Biol. Chem., 274, 29303-29310), where domain I was defined as consisting of amino acids 1-197, domain II was defined as consisting of amino acids 189-385 and domain III was defined as consisting of amino acids 381-585. Partial overlap of the domains occurs because of the extended α-helix structure (h10-h1) which exists between domains I and II, and between domains II and III (Peters, 1996, op. cit., Table 2-4). HSA also comprises six sub-domains (sub-domains IA, IB, IIA, IIB, IIIA and IIIB). Sub-domain IA comprises amino acids 6-105, sub-domain IB comprises amino acids 120-177, sub-domain IIA comprises amino acids 200-291, sub-domain IIB comprises amino acids 316-369, sub-domain IIIA comprises amino acids 392-491 and sub-domain IIIB comprises amino acids 512-583. A fragment may comprise a whole or part of one or more domains or sub-domains as defined above, or any combination of those domains and/or sub-domains. A fragment may comprise or consist of at least 50, 60, 70, 75, 80, 85, 90, 95, 96, 97, 98, or 99% of an albumin or of a domain of an albumin.

Additionally, single or multiple heterologous fusions comprising any of the above; or single or multiple heterologous fusions to albumin, or a variant or fragment of any of these may be used. Such fusions include albumin N-terminal fusions, albumin C-terminal fusions and co-N-terminal and C-terminal albumin fusions as exemplified by WO 01/79271.

Homology

FIGS. 2 and 3 show alignments of various albumin family proteins with HSA (SEQ ID NO: 1), identified as 'P02768'. The protein sequences include the albumin leader sequence. These alignments can be used to identify conserved regions and amino acid residues corresponding to those in HSA selected as described above. One or both alignments can also be used to assign a homology score to an amino acid residue in an albumin sequence.

An example of such a procedure is the MegAlign program (version 8.0.2) developed by DNASTAR Inc., part of the Lasergene suite, based on Hein, J. J. (1990) "Unified approach to alignment and phylogenies." In Methods in Enzymology, Vol. 183: pp. 626-645. Using the Jotun Hein Method and the settings GAP PENALTY=11, GAP LENGTH PENALTY=3 for multiple alignments and KTUPLE=2 for pairwise alignments a series of percentage identity values can be calculated. Alternatively the Clustal V Method and the settings GAP PENALTY=10, GAP LENGTH 10 for multiple alignments and KTUPLE=1. GAP PENALTY=3, WINDOW=5 and DIAGONAL=5 for pairwise alignments a series of percentage identity values can be calculated. Alternatively the Clustal W Method and the settings GAP PENALTY=10, GAP LENGTH PENALTY=0.2, DELAY DIVERGENCE=30 DNA transition=0.5 and using GONNET SERIES for Protein Weight matrix and IUB for DNA Weight matrix for multiple alignments, and Slow accurate, GAP PENALTY=10, GAP LENGTH PENALTY=0.1, and using GONNET SERIES for Protein Weight matrix and IUB for DNA Weight matrix for pairwise alignments a series of percentage identity values can be calculated. Alternatively the Clustal V method may be used (above). The alignment of two amino acid sequences may also be determined by using the Needle program from the EMBOSS package version 2.8.0. The Needle program implements the global alignment algorithm described in Needleman and Wunsch (1970) "A general method applicable to the search for similarities in the amino acid sequence of two proteins." J. Mol. Biol. 48, 443-453. The substitution matrix used is BLOSUM62, gap opening penalty is 10, and gap extension penalty is 0.5.

FIG. 2 shows an alignment of sixteen mammalian albumin family proteins including HSA (SEQ ID NO: 1, identified in the alignment as P02768) compiled using MegAlign program (version 8.0.2) based on Clustal W. The protein sequences include the albumin leader sequence. Each sequence is labelled with the animal from which it derives and its database accession number.

FIG. 3 shows alignments of thirty three albumin family (both mammalian and non-mammalian) proteins including HSA (SEQ ID NO: 1, identified in the alignment as P02768) compiled using MegAlign program (version 8.0.2) based on Clustal V. The protein sequences include the albumin leader sequence.

Homology may be determined with reference to FIG. 2 and/or FIG. 3. The degree of identity between a given amino acid sequence and SEQ ID NO: 1 may be calculated as the number of exact matches in an alignment of the two sequences, divided by the length of the shorter of the two sequences. The result may be expressed in percent identity. An exact match occurs when the two sequences have identical amino acid residues in the same positions of the overlap. The length of a sequence is the number of amino acid residues in the sequence.

Conservation of Adjacent Residues

In addition, individual amino acid residues of HSA can be ranked according to their conservation to the amino acids of other albumin family proteins at the same position. FIG. 1, column labelled 'Align 1 (Mamm. W ('mammalian, Clustal W)) provides the homology level for each position of SEQ ID NO: 1 as calculated by the alignment of mammalian albumins given in FIG. 2. The homology level score may be calculated. One method to score the homology level, which is used herein, is calculated by using the strength of the histogram provided by MegAlign program (version 8.0.2) (ranging 0 to 100%); six levels of homology are determined with the highest=100%, decreasing in 20% increments to the lowest (0%) and shown by bar height in FIG. 2. A score of 100 is the highest conservation and indicates there are no changes at that residue when the sequence from human serum albumin is compared with other mammalian albumin sequence, whereas a score of 0 indicates the lowest level of conservation between the aligned sequences.

Similarly, the homology level score for each amino acid residue in HSA (FIG. 1, column labelled 'Align 2 (Var. Sps. V ('various species (i.e. mammalian and non-mammalian), Clustal V')) calculated using the strength of the histogram provided by Megalign when various albumins (including non-mammalian albumins) are aligned using Clustal V. A person skilled in the art will appreciate that a range of different albumin sequences and alignment algorithms may be used to calculate the homology level score.

When using homology scores, such as those described in reference to the alignments of FIGS. 2 and 3, to identify candidate residues for the present invention, preferred residues include those which are not highly conserved (for example those with a score of less than 40, more preferably less than 20 and most preferably 0) are preferred and those with a higher level of homology (for example those with a score of more than 40, more than 60, more than 80 and most preferably 100) are less preferred.

Each of the amino acid residue in HSA (SEQ ID NO: 1) were scored according to whether the adjacent residue was highly (100%) conserved when HSA is aligned with mammalian albumins (FIG. 1, column labelled 'Adj. 100%'s (Align 1). This is because if an amino acid is within a highly conserved domain, it may be important to the structure of function of the protein and thus disruption may be undesirable. In FIG. 1, a score of 0 indicates the residue is not adjacent to any residue with 100% homology (with reference to the alignment of FIG. 2) when HSA is aligned with mammalian albumins; a score of 1 indicates that the residue is adjacent to one residue with 100% homology when HSA is aligned with mammalian albumins; a score of 2 indicates that the residue is adjacent to two residues with 100% homology when HSA is aligned with mammalian albumins. Residues with a score of 0 or 1 are preferred. Residues with a score of 0 are most preferred.

For example, amino acid residues with a score of 2 (such as valine-7 (V7)) are preferably deselected using the method of the invention since these amino acid residues were assumed to occur in a region of high homology which would be unlikely to accept a mutation to an alternative amino acid. Similarly, phenylalanine-11 (F11) is adjacent to one 100% conserved residue, in a region of conserved residues, and is less preferred to a residue, such as alanine-2 (A2), which has no adjacent 100% conserved residues.

In accordance with the invention, additional information such as preferred sites for insertion, deletions or substitutions may also be obtained by alignment analysis. For example, mouse albumin contains 36 cysteine residues, all the cysteines involved in disulphide bonding (by homology to HSA) are present, as is cysteine-34, however a cysteine residue is present at 579 on mature mouse protein but not other mammalian albumin sequences therefore thio-albumin mutein S579C may be preferred as its lack of homology with other mammalian albumins suggests that it may not be particularly important to the structure and/or function of this albumin.

In addition, using the alignments of various mammalian albumin family and Clustal W (FIG. 2) shows that compared to other mammalian albumins, gerbil albumin has an additional alanine residue between alanine-2 (A2) and histidine-3 (H3), indicating that insertion of a cysteine residues after residue 2 (e.g. A2 of SEQ ID NO: 1) and before residue 3 (e.g. H3 of SEQ ID NO: 1) is preferred.

Compared to other mammalian albumins, guinea pig albumin has a serine residue at cysteine-34 (C34). In examples where deletion of the free thiol group at cysteine-34 is required, a mutation such as C34S may be preferred.

Most mammalian albumin sequences (with the exception of human serum albumin) have a sequence which is less than or equal to 584 amino acids in length (less than or equal to 608 amino acids including leader sequence). Using the alignment in FIG. 2 the additional amino acid residue present on human serum albumin appears to be at the C-terminus without any cognate alignment amino acid residues in the other mammalian serum albumin sequences. Thus a thio-albumin variant containing G584C and a deletion of L585 may be preferred.

A number of albumin sequences (Bovine, Donkey, Goat, Horse, Sheep, Pig) are 583 amino acids in length (607 amino acids including leader sequence). Using the alignment in FIG. 2, it can be seen that these species albumin sequences do not have a residue corresponding R117 (R141 including leader sequence) therefore a thio-albumin containing V116C and a deletion of R117 or a thio-albumin containing a deletion of R117 and P118C may be preferred. In such a thio-albumin the length of the amino acid sequence would be reduced relative to SEQ ID NO: 1.

The alignment used in FIG. 2 and the conclusions drawn are in particular with reference to mammalian albumins and Clustal W, the skilled person will appreciate that the teaching applies likewise to other members of the albumin family and to alternative alignment algorithms.

Alignment and Identity

The albumin variant may have at least 40% identity with SEQ ID NO: 1, particularly at least 45%, 50%, 55%, 60%, 65%, 70%, 75%, at least 80%, at least 85%, at least 90%, at least 95%, at least 97%, at least 98% or at least 99% identity.

Identity may be calculated using any method, for example those described herein.

Conjugation

The thio-albumin may optionally be fused to one or more conjugation partners for example through a genetic or chemical fusion. For a thio-albumin which comprises a genetic fusion, the fusion may be at the N- or C-terminus or comprise an insertion.

With respect to genetic fusions of albumin, the skilled person will also appreciate that the open reading frame of any other gene or variant, or part or either, can be utilised as an open reading frame for use with the present invention. For example, the open reading frame may encode a protein comprising any sequence, be it a natural protein (including a zymogen), or a variant, or a fragment (which may, for example, be a domain) of a natural protein; or a totally synthetic protein; or a single or multiple fusion of different proteins (natural or synthetic). Such proteins can be taken, but not exclusively, from the lists provided in WO 01/79258, WO 01/79271, WO 01/79442, WO 01/79443, WO 01/79444 and WO 01/79480, or a variant or fragment thereof; the disclosures of which are incorporated herein by reference. Although these patent applications present the list of proteins in the context of fusion partners for albumin, the present invention is not so limited and, for the purposes of the present invention, any of the proteins listed therein may be presented alone or as fusion partners for albumin or any other protein or fragment or variant of any of the above, as a desired polypeptide. Examples of chemical fusions (also known as conjugations) of albumin are given in Leger et al. (2004) Bioorg Med Chem Lett 14(17): 4395-8; and Thibaudeau et al. (2005). Bioconjug Chem 16(4): 1000-8.

An advantage of using a genetically or chemically fused albumin is that either or all of the molecules which contribute to the fusion may have improved properties relative to the unfused molecule(s) (Balan et al. (2006) Antivir Ther 11(1): 35-45). Albumins and albumin particles are also important for carrying and delivering drugs and prodrugs to their sites of action (Kratz, F. (2008) Journal of Controlled Release, 132 (3), p. 171-183). Fusion and particle technologies offer improved dosing regimes due to improved pharmacokinetic properties, such as half-life extension, and may improve bioavailability and protect the fused conjugation partner, for example bioactive molecule, from inactivation.

The polypeptide may display modified (e.g. reduced) glycosylation, such as, but not limited to reduced N-linked glycosylation or reduced O-linked glycosylation. The N-linked glycosylation pattern of an albumin molecule can be modified by adding/removing amino acid glycosylation consensus sequences such as N-X-S/T, at any or all of the N, X, or S/T position. Albumin polymorphisms exist with N-linked glycosylation. Albumin mutants may have recycling time such that the efficacy of a mutant as a bioactive carrier is improved. Recombinantly expressed proteins can be subject to undesirable post-translational modifications by the producing host cell. For example, the albumin protein sequence of SEQ ID NO: 1 does not contain any sites for N-linked glycosylation and has not been reported to be modified, in nature, by O-linked glycosylation. However, it has been found that recombinant human albumin ("rHA") produced in a number of yeast species can be modified by O-linked glycosylation, generally involving mannose. The mannosylated albumin is able to bind to the lectin Concanavalin A. The amount of mannosylated albumin produced by the yeast can be reduced by using a yeast strain deficient in one or more of the PMT genes (WO 94/04687). The most convenient way of achieving this is to create a yeast which has a defect in its genome such that a reduced level of one of the Pmt proteins is produced. For example, there may be a deletion, insertion or transposition in the coding sequence or the regulatory regions (or in another gene regulating the expression of one of the PMT genes) such that little or no Pmt protein is produced. Alternatively, the yeast could be transformed to produce an anti-Pmt agent, such as an anti-Pmt antibody.

If a yeast other than *S. cerevisiae* is used, disruption of one or more of the genes equivalent to the PMT genes of *S. cerevisiae* is also beneficial, e.g. in *Pichia pastoris* or *Kluyveromyces lactis*. The sequence of PMT1 (or any other PMT gene) isolated from *S. cerevisiae* may be used for the identification or disruption of genes encoding similar enzymatic activities in other fungal species. The cloning of the PMT1 homologue of *Kluyveromyces lactis* is described in WO 94/04687.

The step of "purifying the thus expressed heterologous protein from the cultured host cell or the culture medium" optionally comprises cell immobilization, cell separation and/or cell breakage, but always comprises at least one other purification step different from the step or steps of cell immobilization, separation and/or breakage.

Cell immobilization techniques, such as encasing the cells using calcium alginate beads, are well known in the art. Similarly, cell separation techniques, such as centrifugation, filtration (e.g. cross-flow filtration, expanded bed chromatography and the like are well known in the art. Likewise, methods of cell breakage, including beadmilling, sonication, enzymatic exposure and the like are well known in the art.

The at least one other purification step may be any other step suitable for protein purification known in the art. For example purification techniques for the recovery of recombinantly expressed albumin have been disclosed in: WO 92/04367, removal of matrix-derived dye; EP 464 590, removal of yeast-derived colorants; EP 319 067, alkaline precipitation and subsequent application of the albumin to a lipophilic phase; and WO 96/37515, U.S. Pat. No. 5,728,553 and WO 00/44772, which describe complete purification processes; all of which are incorporated herein by reference. Production of Conjugation Competent Albumin ("Thio-Albumin")

The thio-albumin or fusions of thio-albumin and another protein or proteins can be prepared by methods know to the art (Sanker, (2004), Genetic Eng. News, 24, 22-28, Schmidt, (2004), Appl. Microbiol. Biotechnol., 65, 363-372) including but not limited to expression in mammalian cell culture (Mason et al., (2004), Protein Expr. Purif., 36, 318-326; Mason et al., (2002), Biochemistry, 41, 9448-9454) from cells lines such as CHO (and its variants), NSO, BHK, HEK293, Vero or PERC6 cells by transformation or transient expression; insect cell culture (Lim et al., (2004) Biotechnol. Prog., 20, 1192-1197); plant cell culture from such plants as *Lemna* or *Oryza sativa*; transgenic animals (Dyck et al., (2003) Trends in Biotechnology, 21, 394-399); transgenic plants (Ma et al., (2003) Nature Reviews Genetics, 4, 794-805); Gram positive and Gram negative bacteria such as *Bacillus* and *Escherichia coli* (Steinlein, and Ikeda, (1993), Enzyme Microb. Technol., 15, 193-199); filamentous fungi including but not restricted to *Aspergillus* spp (EP 238023, U.S. Pat. Nos. 5,364,770, 5,578,463, EP184438, EP284603, WO 2000/056900, WO9614413), *Trichoderma* spp and *Fusarium* spp (Navalainen et al., (2005), Trends in Biotechnology, 23, 468-473).

The host cell may be any type of cell. The host cell may or may not be an animal (such as mammalian, avian, insect, etc.), plant (such as *Oryza sativa*), fungal or bacterial cell. Bacterial and fungal, such as yeast, host cells may or may not be preferred.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumor virus long terminal repeat to drive expression of the cloned gene.

Methods well known to those skilled in the art can be used to construct expression vectors containing the coding sequence and, for example appropriate transcriptional or translational controls. One such method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic double stranded oligonucleotide linkers and adaptors. DNA fragments with blunt ends are generated by bacteriophage T4 DNA polymerase or *E. coli* DNA polymerase I which remove protruding 3' termini and fill in recessed 3' ends. Synthetic linkers and pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end. Alternatively a DNA fragment or DNA fragments can be ligated together by the action of DNA ligase in the presence or absence of one or more synthetic double stranded oligonucleotides optionally containing cohesive ends.

Synthetic linkers containing a variety of restriction endonuclease sites are commercially available from a number of sources including Sigma-Genosys Ltd, London Road, Pampisford, Cambridge, United Kingdom.

The thio-albumin or fusions of thio-albumin and another protein or proteins may be expressed from a nucleotide sequence, which may or may not contain one or more introns. Additionally the nucleotide sequence may or may not be codon optimised for the host by methods known to the art.

The thio-albumin or fusions of thio-albumin and another protein or proteins can be expressed as variants with reduced N-linked glycosylation. Accordingly, in case of human serum albumin (HSA), it may be particularly advantageous to use a yeast deficient in one or more protein mannosyl transferases involved in O-glycosylation of proteins, for instance by disruption of the gene coding sequence. Recombinantly expressed proteins can be subject to undesirable post-translational modifications by the producing host cell. The mannosylated albumin would be able to bind to the lectin Concanavalin A. The amount of mannosylated albumin produced by the yeast can be reduced by using a yeast strain deficient in one or more of the PMT genes (WO 94/04687). The most convenient way of achieving this is to create a yeast which has a defect in its genome such that a reduced level of one of the Pmt proteins is produced. For example, there may or may not be a deletion, insertion or transposition in the coding sequence or the regulatory regions (or in another gene regulating the expression of one of the PMT genes) such that little or no Pmt protein is produced. Alternatively, the yeast could be transformed to produce an anti-Pmt agent, such as an anti-Pmt antibody. Alternatively, the yeast could be cultured in the presence of a compound that inhibits the activity of one of the PMT genes (Duffy et al, "Inhibition of protein mannosyltransferase 1 (PMT1) activity in the pathogenic yeast *Candida albicans*", International Conference on Molecular Mechanisms of Fungal Cell Wall Biogenesis, 26-31 Aug. 2001, Monte Verita, Switzerland, Poster Abstract P38). If a yeast other than *S. cerevisiae* is used, disruption of one or more of the genes equivalent to the PMT genes of *S. cerevisiae* is also beneficial, e.g. in *Pichia pastoris* or *Kluyveromyces lactis*. The sequence of PMT1 (or any other PMT gene) isolated from *S. cerevisiae* may be used for the identification or disruption of genes encoding similar enzymatic activities in other fungal species. The cloning of the PMT1 homologue of *Kluyveromyces lactis* is described in WO 94/04687.

The yeast may or may not also have a deletion of the HSP150 and/or YAP3 genes as taught respectively in WO 95/33833 and WO 95/23857.

The HSA variant may be produced by recombinant expression and secretion. Where the expression system (i.e. the host cell) is yeast, such as *Saccharomyces cerevisiae*, suitable promoters for *S. cerevisiae* include those associated with the PGK1 gene, GAL1 or GAL10 genes, TEF1, TEF2, PYK1, PMA1, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, a-mating factor pheromone, the PRB1 promoter, the PRA1 promoter, the GPD1 promoter, and hybrid promoters involving hybrids of parts of 5' regulatory regions with parts of 5' regulatory regions of other promoters or with upstream activation sites (e.g. the promoter of EP-A-258 067).

Suitable transcription termination signals are well known in the art. Where the host cell is eukaryotic, the transcription termination signal is preferably derived from the 3' flanking sequence of a eukaryotic gene, which contains proper signals for transcription termination and polyadenylation. Suitable 3' flanking sequences may, for example, be those of the gene naturally linked to the expression control sequence used, i.e. may correspond to the promoter. Alternatively, they may be different. In that case, and where the host is a yeast, preferably *S. cerevisiae*, then the termination signal of the *S. cerevisiae* ADH1, ADH2, CYC1, or PGK1 genes are preferred.

It may be beneficial for the promoter and open reading frame of the gene encoding the recombinant protein comprising the sequence of an albumin mutant to be flanked by transcription termination sequences so that the transcription termination sequences are located both upstream and downstream of the promoter and open reading frame, in order to prevent transcriptional read-through into any neighboring genes, such as 2 μm genes, and vice versa.

In one embodiment, the favored regulatory sequences in yeast, such as *Saccharomyces cerevisiae*, include: a yeast promoter (e.g. the *Saccharomyces cerevisiae* PRB1 promoter), as taught in EP 431 880; and a transcription terminator, preferably the terminator from *Saccharomyces* ADH1, as taught in EP 60 057.

It may be beneficial for the non-coding region to incorporate more than one DNA sequence encoding a translational stop codon, such as UAA, UAG or UGA, in order to minimise translational read-through and thus avoid the production of elongated, non-natural fusion proteins. The translation stop codon UAA is preferred.

In one preferred embodiment, the recombinant protein comprising the sequence of an albumin mutant is secreted. In that case, a sequence encoding a secretion leader sequence may be included in the open reading frame. Thus, a polynucleotide according to the present invention may comprise a sequence that encodes a recombinant protein comprising the sequence of an albumin mutant operably linked to a polynucleotide sequence that encodes a secretion leader sequence. Leader sequences are usually, although not necessarily, located at the N-terminus of the primary translation product of an ORF and are generally, although not necessarily, cleaved off the protein during the secretion process, to yield the "mature" protein. Thus, in one embodiment, the term "operably linked" in the context of leader sequences includes the meaning that the sequence that encodes a recombinant protein comprising the sequence of an albumin mutant is linked, at its 5' end, and in-frame, to the 3' end of a polynucleotide sequence that encodes a secretion leader sequence. Alternatively, the polynucleotide sequence that encodes a secretion leader sequence may be located, in-frame, within the coding sequence of the recombinant protein comprising the sequence of an albumin mutant, or at the 3' end of the coding sequence of the recombinant protein comprising the sequence of an albumin mutant.

Numerous natural or artificial polypeptide leader sequences (also called secretion pre regions and pre/pro regions) have been used or developed for secreting proteins from host cells. Leader sequences direct a nascent protein towards the machinery of the cell that exports proteins from the cell into the surrounding medium or, in some cases, into the periplasmic space.

For production of proteins in eukaryotic species such as the yeasts *Saccharomyces cerevisiae, Zygosaccharomyces species, Kluyveromyces lactis* and *Pichia pastoris*, a secretion leader sequence may be used. This may comprise a signal (pre) sequence or a prepro leader sequence. Signal sequences are known to be heterogeneous in their amino acid sequence (Nothwehr and Gordon 1990, Bioessays 12, 479-484, or Gierasch 1989, Biochemistry 28, p 923-930). In essence, signal sequences are generally N-terminally located, have a basic n-region, a hydrophobic h-region and a polar c-region. As long as this structure is retained the signal sequence will work, irrespective of the amino acid composition. How well they work, i.e. how much mature protein is secreted, depends upon the amino acid sequence. Accordingly, the term "signal peptide" is understood to mean a presequence which is predominantly hydrophobic in nature and present as an N-terminal sequence of the precursor form of an extracellular protein expressed in yeast. The function of the signal peptide is to allow the expressed protein to be secreted to enter the endoplasmic reticulum. The signal peptide is normally cleaved off in the course of this process. The signal peptide may be heterologous or homologous to the yeast organism producing the protein. Known leader sequences include those from the *S. cerevisiae* acid phosphatase protein (Pho5p) (see EP 366 400), the invertase protein (Suc2p) (see Smith et al. (1985) *Science*, 229, 1219-1224) and heat-shock protein-150 (Hsp150p) (see WO 95/33833). Additionally, leader sequences from the *S. cerevisiae* mating factor alpha-1 protein (MFα-1) and from the human lysozyme and human serum albumin (HSA) protein have been used, the latter having been used especially, although not exclusively, for secreting human albumin. WO 90/01063 discloses a fusion of the MFα-1 and HSA leader sequences (also known as the fusion leader sequence (FL)). In addition, the natural albumin leader sequence may or may not be used to direct secretion of the recombinant protein comprising the sequence of an albumin mutant.

The skilled person will appreciate that any suitable plasmid may be used, such as a centromeric plasmid. The examples provide suitable plasmids (centromeric YCplac33-based vectors) for use to transform yeast host cells of the present invention. Alternatively, any other suitable plasmid may be used, such as a yeast-compatible 2 μm-based plasmid.

Plasmids obtained from one yeast type can be maintained in other yeast types (Irie et al, 1991, *Gene*, 108(1), 139-144; Irie et al, 1991, *Mol. Gen. Genet.*, 225(2), 257-265). For example, pSR1 from *Zygosaccharomyces rouxii* can be maintained in *Saccharomyces cerevisiae*. In one embodiment the plasmid may or may not be a 2 μm-family plasmid and the host cell will be compatible with the 2 μm-family plasmid used (see below for a full description of the following plasmids). For example, where the plasmid is based on pSR1, pSB3 or pSB4 then a suitable yeast cell is *Zygosaccharomyces rouxii*; where the plasmid is based on pSB1 or pSB2 then a suitable yeast cell is *Zygosaccharomyces bailii*; where the plasmid is based on pSM1 then a suitable yeast cell is *Zygosaccharomyces fermentati*; where the plasmid is based on pKD1 then a suitable yeast cell is *Kluyveromyces drosophilarum*; where the plasmid is based on pPM1 then a suitable yeast cell is *Pichia membranaefaciens*; where the plasmid is based on the 2 μm plasmid then a suitable yeast cell is *Saccharomyces cerevisiae* or *Saccharomyces* carlsbergensis. Thus, the plasmid may be based on the 2 μm plasmid and the yeast cell may be *Saccharomyces cerevisiae*. A 2 μm-family plasmid can be said to be "based on" a naturally occurring plasmid if it comprises one, two or preferably three of the genes FLP, REP1 and REP2 having sequences derived from that naturally occurring plasmid.

Useful yeast episomal plasmid vectors are pRS403-406 and pRS413-416 and are generally available from Stratagene Cloning Systems (La Jolla, Calif. 92037, USA), YEp24 (Botstein, D., et al. (1979) Gene 8, 17-24), and YEplac122, YEplac195 and YEplac181 (Gietz, R. D. and Sugino. A. (1988) Gene 74, 527-534). Other yeast plasmids are described in WO 90/01063 and EP 424 117, as well as the "disintegration vectors" of EP-A-286 424 and WO2005061719. Plasmids pRS403, pRS404, pRS405 and pRS406 are Yeast Integrating plasmids (YIps) and incorporate the yeast selectable markers HIS3, TRP1, LEU2 and URA3, as are YIplac204, YIplac211 and YIplac128 (Gietz, R. D. and Sugino. A. (1988) Gene 74, 527-534). Plasmids pRS413-416 are Yeast Centromere plasmids (YCps) as are YCplac22, YCplac33 and YCplac111 (Gietz, R. D. and Sugino. A. (1988) Gene 74, 527-534).

Where one or more of the helper (also known as 'chaperone') protein(s) and/or protein product of choice are encoded by a plasmid-borne polynucleotide sequence, the host cell type may be selected for compatibility with the plasmid type being used. Such plasmids are disclosed in WO2005061719. Preferred helper proteins include PDI1, AHA1, ATP11, CCT2, CCT3, CCT4, CCT5, CCT6, CCT7, CCT8, CNS1, CPR3, CPRE, DER1, DER3, DOA4, ERO1, EUG1, ERV2, EPS1, FKB2, FMO1, HCH1, HRD3, HSP10, HSP12, HSP104, HSP26, HSP30, HSP42, HSP60, HSP78, HSP82, KAR2, JEM1, MDJ1, MDJ2, MPD1, MPD2, PDI1, PFD1, ABC1, APJ1, ATP11, ATP12, BTT1, CDCl$_3$7, CPR7, HSC82, KAR2, LHS1, MGE1, MRS11, NOB1, ECM10, SCJ1, SSA1, SSA2, SSA3, SSA4, SSB1, SSB2, SSC1, SSE2, SIL1, SLS1, ORM1, ORM2, PER1, PTC2, PSE1, UBC7, UB/4 and HAC1 or a truncated intronless HAC1 (Valkonen et al. 2003, *Applied Environ. Micro.*, 69, 2065). Such helper proteins are disclosed in WO 2005/061718, WO 2006/067511 and WO 2006/136831.

Plasmids as defined herein may be introduced into a host through standard techniques. With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual*, 3$^{rd}$ Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. Methods for the transformation of *S. cerevisiae* are taught generally in EP 251 744, EP 258 067 and WO 90/01063, all of which are incorporated herein by reference. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming fungal (including yeast) cell, plant cells, bacterial cells and animal (including vertebrate) cells. Methods for transformation of yeast by electroporation are disclosed in Becker & Guarente (1990) *Methods Enzymol.* 194, 182.

Generally, the plasmid will transform not all of the hosts and it will therefore be necessary to select for transformed host cells. Thus, a plasmid may comprise a selectable marker, including but not limited to bacterial selectable marker and/or a yeast selectable marker. A typical bacterial selectable marker is the β-lactamase gene although many others are known in the art. Typical yeast selectable marker include LEU2, TRP1, HIS3, HIS4, URA3, URA5, SFA1, ADE2, MET15, LYS5, LYS2, ILV2, FBA1, PSE1, PDI1 and PGK1. Those skilled in the art will appreciate that any gene whose chromosomal deletion or inactivation results in an unviable host, so called essential genes, can be used as a selective marker if a functional gene is provided on the plasmid, as demonstrated for PGK1 in a pgk1 yeast strain (Piper and Curran, 1990, *Curr. Genet.* 17, 119). Suitable essential genes can be found within the Stanford Genome Database (SGD). Any essential gene product (e.g. PDI1, PSE1, PGK1 or FBA1) which, when deleted or inactivated, does not result in an auxotrophic (biosynthetic) requirement, can be used as a selectable marker on a plasmid in a host cell that, in the absence of the plasmid, is unable to produce that gene product, to achieve increased plasmid stability without the disadvantage of requiring the cell to be cultured under specific selective conditions. By "auxotrophic (biosynthetic) requirement" we include a deficiency which can be complemented by additions or modifications to the growth medium. Therefore, preferred "essential marker genes" in the context of the present application are those that, when deleted or inactivated in a host cell, result in a deficiency which cannot be complemented by additions or modifications to the growth medium. Additionally, a plasmid may comprise more than one selectable marker.

Transformed host cells may be cultured for a sufficient time and under appropriate conditions known to those skilled in the art, and in view of the teachings disclosed herein, to permit the expression of the helper protein(s) and the protein product of choice.

The culture medium may be non-selective or place a selective pressure on the maintenance of a plasmid.

Methods for culturing prokaryotic host cells, such as *E. coli*, and eukaryotic host cells, such as mammalian cells are well known in the art. Methods for culturing yeast are generally taught in EP 330 451 and EP 361 991.

The thus produced protein product of choice may be present intracellularly or, if secreted, in the culture medium and/or periplasmic space of the host cell.

Preparation of a Polypeptide

The step of "purifying the thus expressed protein product of choice from the cultured host cell, recombinant organism or culture medium" optionally comprises cell immobilisation, cell separation and/or cell breakage, but always comprises at least one other purification step different from the step or steps of cell immobilisation, separation and/or breakage.

Thio-albumin of the invention may be purified from the culture medium by any technique that has been found to be useful for purifying such proteins. Similarly, cell separation techniques, such as centrifugation, filtration (e.g. cross-flow filtration, expanded bed chromatography and the like) are well known in the art. Likewise, methods of cell breakage, including beadmilling, sonication, enzymatic exposure and the like are well known in the art.

The "at least one other purification step" may be any other step suitable for protein purification known in the art. For example purification techniques for the recovery of recombinantly expressed albumin have been disclosed in: WO 92/04367, removal of matrix-derived dye; EP 464 590, removal of yeast-derived colorants; EP 319 067, alkaline precipitation and subsequent application of the albumin to a lipophilic phase; and WO 96/37515, U.S. Pat. No. 5,728,553 and WO 00/44772, which describe complete purification processes; all of which are incorporated herein by reference. Suitable methods include ammonium sulphate or ethanol precipitation, acid or solvent extraction, anion or cation exchange chromatography, phosphocellulose chromatography, hydrophobic interaction chromatography, affinity chromatography, hydroxyapatite chromatography, lectin chromatography, concentration, dilution, pH adjustment, diafiltration, ultrafiltration, high performance liquid chromatography ("HPLC"), reverse phase HPLC, conductivity adjustment and the like.

The polypeptide may be purified to a commercially or industrially acceptable level of purity. By commercially or industrially acceptable level of purity, we include the provision of the thio-albumin and/or thio-albumin-conjugate in which other material (for example, one or more contaminants) are present at a level of less than 50%, 40%, 30%, 20%, 10%, 5%, 4%, 3%, 2%, 1%, 0.5%, 0.1%, 0.01%, 0.001%, 0.0001%, 0.00001%, or 0.000001% and, most preferably at a level of 0%.

A commercially or industrially acceptable level of purity may be obtained by a relatively crude purification method by which the protein product of choice is put into a form suitable for its intended purpose. A protein preparation that has been purified to a commercially or industrially acceptable level of purity may, in addition to the protein product of choice, also comprise, for example, cell culture components such as host cells or debris derived therefrom. Alternatively, high molecular weight components (such as host cells or debris derived therefrom) may or may not be removed (such as by filtration or centrifugation) to obtain a composition comprising the protein product of choice and, optionally, a functionally acceptable level of low molecular weight contaminants derived from the cell culture process.

The protein may or may not be purified to achieve a pharmaceutically acceptable level of purity. A protein has a pharmaceutically acceptable level of purity if it is essentially pyrogen free and can be used for its intended purpose and hence be administered in a pharmaceutically efficacious amount without causing medical effects not associated with the activity of the protein.

The thio-albumin and/or thio-albumin-conjugate may be provided at a concentration of at least $10^{-4}$ g·L$^{-1}$, $10^{-3}$ g·L$^{-1}$, 0.01 g·L$^{-1}$, 0.02 g·L$^{-1}$, 0.03 g·L$^{-1}$, 0.04 g·L$^{-1}$, 0.05 g·L$^{-1}$, 0.06 g·L$^{-1}$, 0.07 g·L$^{-1}$, 0.08 g·L$^{-1}$, 0.09 g·L$^{-1}$, 0.1 g·L$^{-1}$, 0.2 g·L$^{-1}$, 0.3 g·L$^{-1}$, 0.4 g·L$^{-1}$, 0.5 g·L$^{-1}$, 0.6 g·L$^{-1}$, 0.7 g·L$^{-1}$, 0.8 g·L$^{-1}$, 0.9 g·L$^{-1}$, 1 g·L$^{-1}$, 2 g·L$^{-1}$, 3 g·L$^{-1}$, 4 g·L$^{-1}$, 5 g·L$^{-1}$, 6 g·L$^{-1}$, 7 g·L$^{-1}$, 8 g·L$^{-1}$, 9 g·L$^{-1}$, 10 g·L$^{-1}$, 15 g·L$^{-1}$, 20 g·L$^{-1}$, 25 g·L$^{-1}$, 30 g·L$^{-1}$, 40 g·L$^{-1}$, 50 g·L$^{-1}$, 60 g·L$^{-1}$, 70 g·L$^{-1}$, 80 g·L$^{-1}$, 90 g·L$^{-1}$, 100 g·L$^{-1}$, 150 g·L$^{-1}$, 200 g·L$^{-1}$, 250 g·L$^{-1}$, 300 g·L$^{-1}$, 350 g·L$^{-1}$, 400 g·L$^{-1}$, 500 g·L$^{-1}$, 600 g·L$^{-1}$, 700 g·L$^{-1}$, 800 g·L$^{-1}$, 900 g·L$^{-1}$, 1000 g·L$^{-1}$.

A method of the present invention may or may not further comprise the step of formulating the purified protein product of choice with a carrier or diluent and optionally presenting the thus formulated protein in a unit dosage form.

Although it is possible for a therapeutically useful protein obtained by a process of the invention to be administered alone, it is preferable to present it as a pharmaceutical formulation, together with one or more acceptable carriers or diluents. The carrier(s) or diluent(s) must be "acceptable" in the sense of being compatible with the desired protein. Typically, the carriers or diluents will be water or saline which will be sterile and pyrogen free.

Alternatively, a method of the present invention may or may not further comprise the step of lyophilising the thus purified protein product of choice.

Formulation of Thio-Albumin or Conjugate

The thio-albumin may be formulated by strategies given in "Protein Formulation and Delivery", E. J. McNally (Ed.), published by Marcel Dekker Inc. New York 2000 and "Rational Design of Stable Protein Formulations—Theory and Practice"; J. F. Carpenter and M. C. Manning (Ed.) Pharmaceutical Biotechnology Vol 13. Kluwer Academic/Plenum Publishers, New York 2002, Yazdi and Murphy, (1994) Cancer Research 54, 6387-6394, Wdera et al., (2003) Pharmaceutical Research 20, 1231-1238; Lee et al., (2005) Arch. Pharm. Res. 28, 722-729. Examples of formulation methods are as follows:

Method #1: Following purification the free thiol containing albumin mutein of the invention or the conjugate can be stored at 4° C., −20° C. or −80° C. in 0.01 M-0.1 M phosphate buffered saline (pH 7.0-8.0) containing 0.01 M-0.2 M NaCl.

Method #2: Following purification the free thiol containing albumin mutein of the invention or the conjugate can be stored at 4° C., −20° C. or −80° C. in 0.01 M-0.1 M phosphate buffered saline (pH 7.0-8.0) containing 0.01 M-0.2 M NaCl and containing 10-20 mg/L Polysorbate 80.

Method #3: Following purification the free thiol containing albumin mutein of the invention or the conjugate can be stored at 4° C., −20° C. or −80° C. in 0.01 M-0.2 M NaCl (pH 7.0-8.0).

Method #4: Following purification the free thiol containing albumin mutein of the invention or the conjugate can be stored at 4° C., −20° C. or −80° C. in 0.01 M-0.2 M NaCl (pH 7.0-8.0) containing 10-20 mg/L Polysorbate 80.

Freeze-Dried Formulations

Method #5: Following purification the free thiol containing albumin mutein of the invention or the conjugate can be dialysed against water, freeze dried and stored at 4° C., −20° C. or −80° C.

Method #6: Following purification the free thiol containing albumin mutein of the invention or the conjugate can be dialysed against 0.01 M-0.2 M NaCl (pH 7.0-8.0), freeze dried and stored at 4° C., −20° C. or −80° C.

Nanoparticle Formulation

The thio-albumin of the invention (and/or its conjugated form) may be used to produce nanoparticles and/or be entrapped within a nanoparticle or liposome.

The thio-albumin of the invention may be used with and/or in and/or as a nanoparticle and/or liposome. A problem of current conjugation strategies is maintaining both the pharmacological and immunological activity of the conjugation partner, such as a bioactive-targeting ligand conjugate. There is likely to be a maximum number of protein targeting ligand/bioactive moieties (conjugation partners) possible for conjugation to a protein and if this number is exceeded the targeting ligand does not retain its biological activity. Preferably the biological activity of the conjugation partner is not reduced by conjugation to an albumin of the invention.

Liposomes and nanoparticles may be used to entrap bioactive compounds. They provide a mechanism for enhanced delivery of drugs such as bioactive compounds, or uptake by target cells and/or a reduction in the toxicity of the free bioactive to non-target organs which may result in an increased therapeutic index and/or reduced side effects. In addition, many solvent-based formulations required for the delivery of some bioactive compounds (e.g. taxanes) are associated with toxicity which limits the maximum dose which can be given to a patient. Liposome and nanoparticle delivery may also be advantageous for such bioactive compounds, since they would allow larger amounts of the bioactive compound to be delivered whilst avoiding some of the toxicities of solvent-based formulations (Hawkins et al (2008) Advanced Drug Delivery Reviews, 60, 8, p 876-885).

Methods for attaching targeting ligands to liposomes and nanoparticles are known in the art (reviewed in Nobs et al (2004) Journal of Pharmaceutical Sciences Vol 93 p 1980-1992) and may be used in accordance with the invention. Attachment methods may be non-covalent or covalent. Covalent reactions appear to be favorable, because covalent linkage is more stable than noncovalent methods. Lipids for the covalent or non-covalent attachment of proteins, peptides, or drugs to the liposome surface are available commercially (for example Avanti Polar Lipids Inc Alabaster, Ala., USA). There are 3 major classes of functionality: conjugation through disulphide or thioether formation, amide bond formation, or biotin/streptavidin binding, any of these may be used in the invention.

A number of methods relying on covalent coupling ligands to the surface of liposomes via thioether bonds have been described, most commonly utilizing the highly efficient reaction of maleimide with thiol groups. Functionalized lipid anchors commonly added to liposomes, and which may be used in or with the invention, include, but are not limited those containing maleimide such as N-[4-(p-maleimidophenyl) butyramide]-PE (N-MPB]-PE) or N-[4-(p-maleimidomethyl) cyclohexane-carboxamide) (MCC-PE) which allow convenient covalent coupling of the targeting moiety via a stable thioether bond (Martin & Papahadjopoulos (1982) J. Biol. Chem. 257, 286-288).

Method #7: Following purification the free thiol containing albumin mutein of the invention or the conjugate can be formulated into nanoparticles prepared according to known procedures for preparing nanoparticles, such as procedures disclosed in WO 2004/071536 A1 and WO 2008/007146 A1, both incorporated herein by reference.

Similarly materials for the formation of nanoparticles, including but are limited to Poly(lactic acid) (PLA), poly (lactic-co-glycolic acid) (PLGA), and COOH-PLA are commercially available and may be functionalized with maleimide or other known chemistries according to known literature for nanoparticle formation. Any of these may be used in or with the invention.

Another convenient way for covalent coupling of ligands to liposomes involves conjugation of two thiols to form a disulphide; however under the reductive conditions in serum more stable conjugation chemistries involving one free thiol group may be preferred. Chemistries such as (PDP-PE) allow covalent coupling via a disulphide bond. Modification of the ligand to introduce a free thiol group or a functionalized linker may be used. An advantage of the thio-albumin of the invention is that no ligand modification is required. However, ligand modification may optionally be used in addition to the invention.

Frequently thiol groups are not present in proteins, or are not present in sufficient amounts or at the desired location. Thus, most cases of covalent coupling of one of more ligands to a liposome via thioether or disulphide bonds requires the use of heterobifunctional cross linking agents (described herein with reference to conjugation). Some heterobifunctional cross linking agents (such as SPDP and SATA) require a de-protection step. The thio-albumin of the invention overcomes the requirement for this additional processing.

Alternatively thio-albumin could be conjugated to liposomes or nanoparticles by other chemistries, known to the art. For example, thio-albumin could be attached by an amide bond using a functionalised lipid anchor with either amine or carboxyl functional groups (examples include DSPE-PEG-COOH) which reacts with the primary amine of the ligand. Direct cross linking between primary amines and the surface of liposomes may also be used. The one or more free thiol groups of thio-albumin would then be available for conjugation to another conjugation partner.

Following conjugation, a conjugation partner (e.g. bioactive molecule) may show a reduction in its activity (e.g. bioactivity). Thio-albumin described in this invention may overcome this problem by providing a conjugate, nanoparticle and/or liposome in which the conjugation partner is located and/or orientated with respect to a thio-albumin such that the conjugation partner retains at least 10, 20, 30, 40, 50, 60, 70, 80, 90 or 100% of its unconjugated activity.

Conjugation Partner

The term 'conjugation partner' includes bioactive agents, imaging agents, diagnostic agents, contrast agents and therapeutic compounds such as chemotherapeutic drugs and radiopharmaceuticals. A thio-albumin of the invention may be conjugated to one or more conjugation partners.

Imaging Agents, Diagnostic Compounds, Contrast Agents and Therapeutic Compounds

The use of diagnostic agents, imaging agents and biological "contrast" agents are well known to the art. A diagnostic agent is any pharmaceutical product used as part of a diagnostic test (i.e. together with the equipment and procedures that are needed to assess the test result). The diagnostic agent may be used in vivo, ex vivo or in vitro.

The ability of albumin to accumulate in damaged muscle fibres of dystrophic muscle has been well described. For example, a Gadolinium-DTPA-albumin conjugate may be used as a combined diagnostic and therapeutic tool to visualize and monitor, for example, dystrophic muscle by magnetic resonance imaging (MRI) and for the delivery of putative therapeutics bound to albumin for effective targeting to dystrophic muscle (Amthor et al. (2004) Neuromuscular Disorders 14912: 791-796). Malignant tumors often show an increased uptake and metabolism of albumin. The use of gadolinium-albumin conjugate has also been described for improved imaging of malignant tumors and to determine by MRI tumors sensitive to a therapy with drug-conjugated albumin (Kiessling et al. (2002) Investigative Radiology 37(4): 93-198).

Current imaging agents often degrade quickly whilst longer-lasting agents are often toxic. The use of albumin conjugates may be especially useful to increase the half life of imaging agents and would therefore permit imaging over an extended period of time. WO2005/082423 describes the use of serum albumin conjugated to fluorescent substances for imaging.

A thio-albumin of this invention may be conjugated to two or more molecules selected from imaging agents, diagnostic agents, therapeutic compounds and contrast agents.

Tumors (and muscle degeneration) show enhanced uptake of albumin (EPR: Enhanced Permeation and Retention). Albumin conjugates may be used for enhanced imaging, and also to assess whether tumors (or other tissues and organs) would be suitable for albumin conjugated drugs.

Bioactive Compound

The bioactive compound may be a therapeutic or diagnostic compound. The therapeutic compound may be a chemotherapy drug for use in cancer chemotherapy. It may be cytostatic or cytotoxic; it may be a tumor-inhibiting agent.

The bioactive compound may already contain a free thiol group, e.g. a polypeptide containing a Cysteine residue with a free thiol group. Alternatively, the bioactive compound may be modified so as to contain a free thiol group. Thus, the amino acid sequence of a polypeptide may be altered so as to include a Cysteine residue with a free thiol group, or the bioactive compound may be chemically derivatized to include a free thiol group.

The bioactive compound may be a polypeptide (protein), particularly a recombinant protein pharmaceutical. It may be a chemotherapy or radiotherapy drug used to treat cancers and other related diseases.

The free thiol containing albumin mutein of the invention (thio-albumin) can be conjugated via the free thiol group, or groups if the albumin mutein of the invention contains more than one free thiol, to at least one bioactive compound by methods know to the art. The bioactive compound includes but is not limited to, peptides, polypeptides or proteins (either natural, recombinant, or synthetic) (Debinski, (2002) Cancer Investigation 20, 801-809, O'Keefe and Draper et al., (1985) JBC 260, 932-937, Xia et al., (2000) J. Pharmacology Experimental Therapeutics 295, 594-600, Kavimandan et al., (2006) Bioconjugate Chem. 17, 1376-1384, Humphries, et al., (1994) J. Tissue Culture Methods 16, 239-242, Wenning et al., (1998) Biotech. Bioeng. 57, 484-496, Yazdi and Murphy, (1994) Cancer Research 54, 6387-6394, Weaver and Laske (2003) J. Neuro-Oncology 65, 3-13, Wdera et al., (2003) Pharmaceutical Research 20, 1231-1238, Daniels, T. R. et al. (2006) Clinical Immunology 121, 159-176 and the references included therein); therapeutic and diagnostic drugs or compounds (Mishra et al., (2006) J. Drug Targeting 14, 45-53, Lim and Shen, (2004) Pharmaceutical Research 21, 1985-1992, Fritzer et al., (1996) Biochemical Pharmacology 51, 489-493, Lubgan and Jozwiak (2002) Cell. Mol. Biol. Lett. 7, 98, Daniels, T. R. et al. (2006) Clinical Immunology 121, 159-176 and the references included therein); high molecular weight complexes including but not limited to liposomes, viruses and nanoparticles (Mishra et al., (2006) J. Drug Targeting 14, 45-53, Daniels, T. R. et al. (2006) Clinical Immunology 121, 159-176 and the references included therein); nucleic acids and radionuclides, including DNA, RNA (including siRNA) and their analogs (Lee et al., (2005) Arch. Pharm. Res. 28, 722-729, Huang et al., (2007) FASEB J. 21, 1117-1125, Daniels, T. R. et al. (2006) Clinical Immunology 121, 159-176 and the references included therein) and devices (Humphries, et al., (1994) J. Tissue Culture Methods 16, 239-242 and the references included therein). Additionally the entity can itself be modified by methods known to the art.

Therapeutic Compounds 4-1BB ligand, 5-helix, A human C-C chemokine, A human L105 chemokine, A human L105 chemokine designated huL105_3, A monokine induced by gamma-interferon (MIG), A partial CXCR4B protein, A platelet basic protein (PBP), α1-antitrypsin, □□ACRP-30 Homologue; Complement Component Clq C, Adenoid-expressed chemokine (ADEC), aFGF; FGF-1, AGF, AGF Protein, albumin, an etoposide, angiostatin, Anthrax vaccine, Antibodies specific for collapsin, antistasin, Anti-TGF beta family antibodies, antithrombin III, APM-1; ACRP-30; Famoxin, apo-lipoprotein species, Arylsulfatase B, b57 Protein, BCMA, Beta-thromboglobulin protein (beta-TG), bFGF; FGF2, Blood coagulation factors, BMP Processing Enzyme Furin, BMP-10, BMP-12, BMP-15, BMP-17, BMP-18, BMP-2B, BMP-4, BMP-5, BMP-6, BMP-9, Bone Morphogenic Protein-2, calcitonin, Calpain-10a, Calpain-10b, Calpain-10c, Cancer Vaccine, Carboxypeptidase, C-C chemokine, MCP2, CCR5 variant, CCR7, CCR7, CD11a Mab, CD137; 4-1BB Receptor Protein, CD20 Mab, CD27, CD27L, CD30, CD30 ligand, CD33 immunotoxin, CD40, CD40L, CD52 Mab, Cerebus Protein, Chemokine Eotaxin, Chemokine hIL-8, Chemokine hMCP1, Chemokine hMCP1a, Chemokine hMCP1b, Chemokine hMCP2, Chemokine hMCP3, Chemokine hSDF1b, Chemokine MCP-4, chemokine TECK and TECK variant, Chemokine-like protein IL-8M1 Full-Length and Mature, Chemokine-like protein IL-8M10 Full-Length and Mature, Chemokine-like protein IL-8M3, Chemokine-like protein IL-8M8 Full-Length and Mature, Chemokine-like protein IL-8M9 Full-Length and Mature, Chemokine-like protein PF4-414 Full-Length and Mature, Chemokine-like protein PF4-426 Full-Length and Mature, Chemokine-like protein PF4-M2 Full-Length and Mature, Cholera vaccine, Chondromodulin-like protein, c-kit ligand; SCF; Mast cell growth factor; MGF; Fibrosarcoma-derived stem cell factor, CNTF and fragment thereof (such as CNTFAx15' (Axokine™)), coagulation factors in both pre and active forms, collagens, Complement C5 Mab, Connective tissue activating protein-III, CTAA16.88 Mab, CTAP-III, CTLA4-Ig, CTLA-8, CXC3, CXCR3; CXC chemokine receptor 3, cyanovirin-N, Darbepoetin, designated exodus, designated huL105_7, DIL-40, Dnase, EDAR, EGF Receptor Mab, ENA-78, Endostatin, Eotaxin, Epithelial neutrophil activating protein-78, EPO receptor; EPOR, erythropoietin (EPO) and EPO mimics, Eutropin, Exodus protein, Factor IX, Factor VII, Factor VIII, Factor X and Factor XIII, FAS Ligand Inhibitory Protein (DcR3), FasL, FasL, FasL, FGF, FGF-12; Fibroblast growth factor homologous factor-1, FGF-15, FGF-16, FGF-18, FGF-3; INT-2, FGF-4; gelonin, HST-1; HBGF-4, FGF-5, FGF-6; Heparin binding secreted transforming factor-2, FGF-8, FGF-9; Glia activating factor, fibrinogen, flt-1, flt-3 ligand, Follicle stimulating hormone Alpha subunit, Follicle stimulating hormone Beta subunit, Follitropin, Fractalkine, fragment. myofibrillar protein Troponin I, FSH, Galactosidase, Galectin-4, G-CSF, GDF-1, Gene therapy, Glioma-derived growth factor, glucagon, glucagon-like peptides, Glucocerebrosidase, glucose oxidase, Glucosidase, Glycodelin-A; Progesterone-associated endometrial protein, GM-CSF, gonadotropin, Granulocyte chemotactic protein-2 (GCP-2), Granulocyte-macrophage colony stimulating factor, growth hormone, Growth related oncogene-alpha (GRO-alpha), Growth related oncogene-beta (GRO-beta), Growth related oncogene-gamma (GRO-gamma), hAPO-4; TROY, hCG, Hepatitus B surface Antigen, Hepatitus B Vaccine, HER2 Receptor Mab, hirudin, HIV gp120, HIV gp41, HIV Inhibitor Peptide, HIV Inhibitor Peptide, HIV Inhibitor Peptide, HIV protease inhibiting peptides, HIV-1 protease inhibitors, HPV vaccine, Human 6CKine protein, Human Act-2 protein, Human adipogenesis inhibitory factor, human B cell stimulating factor-2 receptor, Human beta-chemokine H1305 (MCP-2), Human C-C chemokine DGWCC, Human CC chemokine ELC protein, Human CC type chemokine interleukin C, Human CCC3 protein, Human CCF18 chemokine, Human CC-type chemokine protein designated SLC (secondary lymphoid chemokine), Human chemokine beta-8 short forms, Human chemokine C10, Human chemokine CC-2, Human chemokine CC-3, Human chemokine CCR-2, Human chemokine Ckbeta-7, Human chemokine ENA-78, Human chemokine eotaxin, Human chemokine GRO alpha, Human chemokine GROalpha, Human chemokine GRObeta, Human chemokine HCC-1, Human chemokine HCC-1, Human chemokine 1-309, Human chemokine IP-10, Human chemokine L105_3, Human chemokine L105_7, Human chemokine MIG, Human chemokine MIG-beta protein, Human chemokine MIP-1alpha, Human chemokine MIP1beta, Human chemokine MIP-3alpha, Human chemokine MIP-3beta, Human chemokine PF4, Human chemokine protein 331D5, Human chemokine protein 61164, Human chemokine receptor CXCR3, Human chemokine SDF1alpha, Human chemokine SDF1beta, Human chemokine ZSIG-35, Human Chr19Kine protein, Human CKbeta-9, Human CKbeta-9, Human CX3C 111 amino acid chemokine, Human DNAX interleukin-40, Human DVic-1 C-C chemokine, Human EDIRF I protein sequence, Human EDIRF II protein sequence, Human eosinocyte CC type chemokine eotaxin, Human eosinophil-expressed chemokine (EEC), Human fast twitch skeletal muscle troponin C, Human fast twitch skeletal muscle troponin I, Human fast twitch skeletal muscle Troponin subunit C, Human fast twitch skeletal muscle Troponin subunit I Protein, Human fast twitch skeletal muscle Troponin subunit T, Human fast twitch skeletal muscle troponin T, Human foetal spleen expressed chemokine, FSEC, Human GM-CSF receptor, Human gro-alpha chemokine, Human gro-beta chemokine, Human gro-gamma chemokine, Human IL-16 protein, Human IL-1RD10 protein sequence, Human IL-1RD9, Human IL-5 receptor alpha chain, Human IL-6 receptor, Human IL-8 receptor protein hIL8RA, Human IL-8 receptor protein hIL8RB, Human IL-9 receptor protein, Human IL-9 receptor protein variant #3, Human IL-9 receptor protein variant fragment, Human IL-9 receptor protein variant fragment #3, Human interleukin 1 delta, Human Interleukin 10, Human Interleukin 10, Human interleukin 18, Human interleukin 18 derivatives, Human interleukin-1 beta precursor, Human interleukin-1 beta precursor, Human interleukin-1 receptor accessory protein, Human interleukin-1 receptor antagonist beta, Human interleukin-1 type-3 receptor, Human Interleukin-10 (precursor), Human Interleukin-10 (precursor), Human interleukin-11 receptor, Human interleukin-12 40 kD subunit, Human interleukin-12 beta-1 receptor, Human interleukin-12 beta-2 receptor, Human Interleukin-12 p35 protein, Human Interleukin-12 p40 protein, Human interleukin-12 receptor, Human interleukin-13 alpha receptor, Human interleukin-13 beta receptor, Human interleukin-15, Human interleukin-15 receptor from clone P1, Human interleukin-17 receptor, Human interleukin-18 protein (IL-18), Human interleukin-3, human interleukin-3 receptor, Human interleukin-3 variant, Human interleukin-4 receptor, Human interleukin-5, Human interleukin-6, Human interleukin-7, Human interleukin-7, Human interleukin-8 (IL-8), Human intracellular IL-1 receptor antagonist, Human IP-10 and HIV-1 gp120 hypervariable region fusion protein, Human IP-10 and human Muc-1 core epitope (VNT) fusion protein, human liver and activation regulated chemokine (LARC), Human Lkn-1 Full-Length and Mature protein, Human mammary associated chemokine (MACK) protein Full-Length and Mature, Human mature chemokine Ckbeta-7, Human mature gro-alpha, Human mature gro-gamma polypeptide used to treat sepsis, Human MCP-3 and human Muc-1 core epitope (VNT) fusion protein, Human MI10 protein, Human MI1A protein, Human monocyte chemoattractant factor hMCP-1, Human monocyte chemoattractant factor hMCP-3, Human monocyte chemotactic proprotein (MCPP) sequence, Human neurotactin chemokine like domain, Human non-ELR CXC chemokine H174, Human non-ELR CXC chemokine IP10, Human non-ELR CXC chemokine Mig, Human PAI-1 mutants, Human protein with IL-16 activity, Human protein with IL-16 activity, Human secondary lymphoid chemokine (SLC), Human SISD protein, Human STOP-1, Human stromal cell-derived chemokine, SDF-1, Human T cell mixed lymphocyte reaction expressed chemokine (TMEC), Human thymus and activation regulated cytokine (TARC), Human thymus expressed, Human TNF-alpha, Human TNF-alpha, Human TNF-beta (LT-alpha), Human type CC chemokine eotaxin 3 protein sequence, Human type II interleukin-1 receptor, Human wild-type interleukin-4 (hIL-4) protein, Human ZCHEMO-8 protein, Humanized Anti-VEGF Antibodies, and fragments thereof, Humanized Anti-VEGF Antibodies, and fragments thereof, Hyaluronidase, ICE 10 kD subunit, ICE 20 kD subunit, ICE 22 kD subunit, Iduronate-2-sulfatase, Iduronidase, IL-1 alpha, IL-1 beta, IL-1 inhibitor (IL-1i), IL-1 mature, IL-10 receptor, IL-11, IL-11, IL-12 p40 subunit, IL-13, IL-14, IL-15, IL-15 receptor, IL-17, IL-17 receptor, Il-17 receptor, Il-17 receptor, IL-19, IL-1i fragments, IL1-receptor antagonist, IL-21 (TIF), IL-3 containing fusion protein, IL-3 mutant proteins, IL-3 variants, IL-3 variants, IL-4, IL-4 mutein, IL-4 mutein Y124G, IL-4 mutein Y124X, IL-4 muteins, Il-5 receptor, IL-6, Il-6 receptor, IL-7 receptor clone, IL-8 receptor, IL-9 mature protein variant (Met117 version), immunoglobulins or immunoglobulin-based molecules or fragment of either (e.g. a Small Modular ImmunoPharmaceutical™ ("SMIP") or dAb, Fab' fragments, F(ab')$_2$, scAb, scFv or scFv fragment), including but not limited to plasminogen, Influenza Vaccine, Inhibin alpha, Inhibin beta, insulin, insulin-like growth factor, Integrin Mab, inter-alpha trypsin inhibitor, inter-alpha trypsin inhibitor, Interferon gamma-inducible protein (IP-10), interferons (such as interferon alpha species and sub-species, interferon beta species and sub-species, interferon gamma species and sub-species), interferons (such as interferon alpha species and sub-species, interferon beta species and sub-species, interferon gamma species and sub-species), Interleukin 6, Interleukin 8 (IL-8) receptor, Interleukin 8 receptor B, Interleukin-1alpha, Interleukin-2 receptor associated protein p43, interleukin-3, interleukin-4 muteins, Interleukin-8 (IL-8) protein, interleukin-9, Interleukin-9 (IL-9) mature protein (Thr117 version), interleukins (such as IL10, IL11 and 1L2), interleukins (such as IL10, IL11 and 1L2), Japanese encephalitis vaccine, Kalikrein Inhibitor, Keratinocyte growth factor, Kunitz domain protein (such as aprotinin, amyloid precursor protein and those described in WO 03/066824, with or without albumin fusions), Kunitz domain protein (such as aprotinin, amyloid precursor protein and those described in WO 03/066824, with or without albumin fusions), LACI, lactoferrin, Latent TGF-beta binding protein II, leptin, Liver expressed chemokine-1 (LVEC-1), Liver expressed chemokine-2 (LVEC-2), LT-alpha, LT-beta, Luteinization Hormone, Lyme Vaccine, Lymphotactin, Macrophage derived chemokine analogue MDC (n+1), Macrophage derived chemokine analogue MDC-eyfy, Macrophage derived chemokine analogue MDC-yl, Macrophage derived chemokine, MDC, Macrophage-derived chemokine (MDC), Maspin; Protease Inhibitor 5, MCP-1 receptor, MCP-1a, MCP-1b, MCP-3, MCP-4 receptor, M-CSF, Melanoma inhibiting protein, Membrane-bound proteins, Met117 human interleukin 9, MIP-3 alpha, MIP-3 beta, MIP-Gamma, MIRAP, Modified Rantes, monoclonal antibody, MP52, Mutant Interleukin 6 S176R, myofibrillar contractile protein Troponin I, Natriuretic Peptide, Nerve Growth Factor-beta, Nerve Growth Factor-beta2, Neuropilin-1, Neuropilin-2, Neurotactin, Neurotrophin-3, Neurotrophin-4, Neurotrophin-4a, Neurotrophin-4b, Neurotrophin-4c, Neurotrophin-4d, Neutrophil activating peptide-2 (NAP-2), NOGO-66 Receptor, NOGO-A, NOGO-B, NOGO-C, Novel beta-chemokine designated PTEC, N-terminal modified chemokine GroHEK/hSDF-1alpha, N-terminal modified chemokine GroHEK/hSDF-1beta., N-terminal modified chemokine met-hSDF-1 alpha, N-terminal modified chemokine met-hSDF-1 beta, OPGL, Osteogenic Protein-1; OP-1; BMP-7, Osteogenic Protein-2, OX40; ACT-4, OX40L, Oxytocin (Neurophysin I), parathyroid hormone, Patched, Patched-2, PDGF-D, Pertussis toxoid, Pituitary expressed chemokine (PGEC), Placental Growth Factor, Placental Growth Factor-2, Plasminogen Activator Inhibitor-1; PAI-1, Plasminogen Activator Inhibitor-2; PAI-2, Plasminogen Activator Inhibitor-2; PAI-2, Platelet derived growth factor, Platelet derived growth factor Bv-sis, Platelet derived growth factor precursor A, Platelet derived growth factor precursor B, Platelet Mab, platelet-derived endothelial cell growth factor (PD-ECGF), Platelet-Derived Growth Factor A chain, Platelet-Derived Growth Factor B chain, polypeptide used to treat sepsis, Preproapolipoprotein "milano" variant, Preproapolipoprotein "paris" variant, pre-thrombin, Primate CC chemokine "ILINCK", Primate CXC chemokine "IBICK", proinsulin, Prolactin, Prolactin2, prosaptide, Protease inhibitor peptides, Protein C, Protein S, pro-thrombin, prourokinase, RANTES, RANTES 8-68, RANTES 9-68, RANTES peptide, RANTES receptor, Recombinant interleukin-16, Resistin, restrictocin, Retroviral protease inhibitors, ricin, Rotavirus Vaccine, RSV Mab, saporin, sarcin, Secreted and Transmembrane polypeptides, Secreted and Transmembrane polypeptides, serum cholinesterase, serum protein (such as a blood clotting factor), Soluble BMP Receptor Kinase Protein-3, Soluble VEGF Receptor, Stem Cell Inhibitory Factor, Straphylococcus Vaccine, Stromal Derived Factor-1 alpha, Stromal Derived Factor-1 beta, Substance P (tachykinin), T1249 peptide, T20 peptide, T4 Endonuclease, TACI, Tarc, TGF-beta 1, TGF-beta 2, Thr117 human interleukin 9, thrombin, thrombopoietin, Thrombopoietin derivative1, Thrombopoietin derivative2, Thrombopoietin derivative3, Thrombopoietin derivative4, Thrombopoietin derivative5, Thrombopoietin derivative6, Thrombopoietin derivative7, Thymus expressed chemokine (TECK), Thyroid stimulating Hormone, tick anticoagulant peptide, Tim-1 protein, TNF-alpha precursor, TNF-R, TNF-RII; TNF p75 Receptor; Death Receptor, tPA, transferrin, transforming growth factor beta, Troponin peptides, Truncated monocyte chemotactic protein 2 (6-76), Truncated monocyte chemotactic protein 2 (6-76), Truncated RANTES protein (3-68), tumor necrosis factor, Urate Oxidase, urokinase, Vasopressin (Neurophysin II), VEGF R-3; flt-4, VEGF Receptor; KDR; flk-1, VEGF-110, VEGF-121, VEGF-138, VEGF-145, VEGF-162, VEGF-165, VEGF-182, VEGF-189, VEGF-206, VEGF-D, VEGF-E; VEGF-X, von Willebrand's factor, Wild type monocyte chemotactic protein 2, Wild type monocyte chemotactic protein 2, ZTGF-beta 9.

Chemotherapy Drugs 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, A, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin diftitox, DepoCyt™, Dexamethasone, Dexamethasone acetate, Dexamethasone Sodium Phosphate, Dexasone, Dexrazoxane, DHAD, DIC, Diodex, Docetaxel, Doxorubicin, Doxorubicin liposomal, Droxia™, DTIC, DTIC-Dome®, Duralone®, Efudex®, Eligard™, Ellence™, Eloxatin™, Elspar®, Emcyt®, Epirubicin, Epoetin alfa, Erbitux™, Erlotinib, Erwinia L-asparaginase, Estramustine, Ethyol, Etopophos®, Etoposide, Etoposide Phosphate, Eulexin®, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar®, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™ STI-571, Streptozocin, SU11248, Sunitinib, Sutent®, Tamoxifen, Tarceva®, Targretin®, Taxol®, Taxotere®, Temodar®, Temozolomide, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Tositumomab, Trastuzumab, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Radiopharmaceuticals

Carbon-11, Carbon-14, Chromium-51, Cobalt-57, Cobalt-58, Erbium-169, Fluorine-18, Gallium-67, Gold-198, Indium-111, Indium-113m, Iodine-123, Iodine-125, Iodine-131, Iron-59, Krypton-81m, Nitrogen-13, Oxygen-15, Phosphorous-32, Rhenium-186, Rubidium-82, Samarium-153, Selenium-75, Strontium-89, Technetium-99m, Thallium-201, Tritium, Xenon-127, Xenon-133, Yttrium-90.

Imaging Agents

Gadolinium, magnetite, manganese, technetium, I125, I131, P32, TI201, Iopamidol, PET-FDG.

Purification Tags

The albumin may also be fused to one or more purification tags such as (Ala-Trp-Trp-Pro)$_n$, avidin/streptavidin/Strep-tag, BCCP, B-tag (VP7 protein region of bluetongue virus), calmodulin binding protein (CBP), cellulose binding domains (CBD's), chitin binding domain, chloramphenicol acetyltransferase, c-myc, dihydrofolate reductase (DHFR), FLAG™ peptide (DYKDDDDK), galactose-binding protein, glutathione-S-transferase (GST), green fluorescent protein (GFP), Growth hormone, N-terminus, hemagglutinin influenza virus (HAI), His-patch thioredoxin, His-tag, HSB-tag, KSI, lacZ (β-Galactosidase), maltose binding protein (MBP), NusA, ompT/ompA/pelB/DsbA/DsbC, polyarginine, polyaspartic acid, polycysteine, polyphenyalanine, S-tag, staphylococcal protein A, streptococcal protein G, T4 gp55, T7gene10, T7-tag, thioredoxin, trpE, ubiquitin.

Ligand Binding

HSA has ligand binding and esterase activities, as described in "All about Albumin", T. Peters Jr., Academic Press N. Y. The ligand binding properties include binding to anionic and neutral ligands such as long-chain fatty acids, bilirubin and other miscellaneous ligands. The long-chain fatty acids, oleic (C18:1), palmitic (C16:0), linoleic (C18:2), stearic (C18:0), arachidonic (C20:4) and palmitoleic (C16:1) are known to bind HSA.

The polypeptide may include insertions, deletions and substitutions, either conservative or non-conservative, where such changes do not substantially reduce the useful ligand-binding, immunological or receptor binding properties of albumin, for example to FcRN, bilirubin and/or a fatty acid. The polypeptide may have at least 5%, 10%, 15%, 20%, 30%, 40% or 50%, 60%, 70%, at least 80%, 90%, 95%, 100%, 105% or more of human serum albumin's receptor binding activity, mole for mole. The polypeptide may have increased affinity for an albumin receptor.

Ligand binding studies can be performed on HSA and thio-albumins using an isothermal titration calorimetry method that had been suitably qualified for this purpose. Samples can be pre-treated by defatting (Sogami, M. and J. F. Foster (1968). *Biochemistry* 7(6): 2172-82, incorporated herein by reference) followed by thiol blocking (Sogami, M., H. A. Petersen, et al. (1969). *Biochemistry* 8(1): 49-58, incorporated herein by reference) and subsequent gel permeation chromatography. The binding curves generated for thio-albumins and HSA with octanoate, for example, may subsequently be compared, and functional similarity established.

Conjugation Methods

The albumin mutein (thio-albumin) of the invention can be covalently linked to one or more conjugation partners such as bioactive compounds by methods known in the art (for example those provided by Pierce, Thermo Fisher Scientific, Rockford, Ill., USA). These include, but are not limited to incorporating or engineering a thiol reactive group into or onto the conjugation partner, for example by incorporating or engineering another free thiol present on the conjugation partner; or by incorporating or engineering a pyridyl disulphide group on the conjugation partner; or by incorporating or engineering an iodoacetyl group on the bioactive compound or by incorporating or engineering a maleimide group on the conjugation partner. For example, N-ethylmaleimide (NEM, Pierce), 2-amino-2'-aminoethanethiolsulfonate (Pierce), N-beta-maleimidoprpionic acid (BMPA Pierce), methyl methane thiosulfonate (MMTS, Pierce), fluorescein-5-maleimide (Pierce), 5-iodoacetamido-fluorescein (5-IAF, Pierce) or N-[6-7-amino-4-methylcoumarin-3-acetamido) hexyl]-3'-[2'-pyridyldithio] propionamide (AMCA-HPDP, Pierce).

If the conjugation partner contains at least one thiol group, then the conjugation partner may be cross-linked to the albumin mutein of the invention by methods known to the art such as, but not limited to, oxidation or by the use of cross-linking reagents such as, but not limited to, 1,4-Bis-maleimidibutane (BMB, Pierce); 1,4-Bis-maleimidyl-2,3-dihydroxybutane (BMDB, Pierce); Bis-maleimidohexane (BMH, Pierce), Bis-maleimidoethane (BMOE, Pierce); 1,8-Bis-Maleimidotriethyleneglycol (BM[PEO]3 Pierce); 1,11-Bis-Maleimidotetraethyleneglycol (BM[PEO]4 Pierce); 1,4-Di-[3'-(2'-pyridyldithio)-propionamido]butane (DPDPB, Pierce); dithuio-bis-maleimidoethane (DTME Pierce); 1,6-Hexane-bis-vinylsulfone (HBVS, Pierce) and Tris-[2-maleimimidoethyl]amine (TMEA, Pierce).

If the conjugation partner does not contain a thiol reactive group then it may be modified to incorporate one or more such groups by either chemical modification or genetic engineering by methods know to the art (Chapman, A. P. (2002) Adv. Drug Deliv. Rev., 54 531-545: Humphreys, D. P. et al. Protein Engineering, Design & Selection vol. 20 no. 5 pp. 227-234, 2007). While these two references describe methodologies to cross-link PEG to an engineered free thiol within an antibody or antibody fragment, the techniques may be used to cross-link a conjugation partner to an engineered free thiol within the albumin mutein of the invention. Alternatively the Drug Affinity Complex (DAC™) technology developed by ConjuChem Inc. (Montreal, Quebec, Canada, H2X 3Y8) may be used, e.g. as described in WO200069902. There are three parts of each DAC™ construct: 1) the drug component (the portion responsible for biologic activity); 2) a linker attached to the drug component, and 3) a reactive chemistry group at the opposite end of the linker, usually a soft electrophile selective for thiols; a maleimide is the most useful embodiment. Other applicable conjugation methods are described in WO2007/071068 incorporated herein by reference.

If the conjugation partner does not contain a thiol reactive group but does contain one or more amino groups then it may be modified to incorporate one or more thiol reactive groups by chemical modification by methods known to the art such as the use of cross-linking reagents such as, but not limited to, N-5-azido-2-nitrobenzoyloxysuccinimide (AMAS, Pierce), N-[beta-maleimidopropyloxy] succinimide ester (BM PS, Pierce), N-eta-maleimidocaproic acid (EMCA, Pierce), N-[eta-maleimidocaproyloxy]succinimide ester (EMCS, Pierce), N-[eta-maleimidocaproyloxy]sulfosuccinimide ester (sulfo-EMCS, Pierce), N-[gamma-maleimidobutyryloxy]succinimide ester (GMBS, Pierce), N-[gamma-maleimidobutyryloxy]sulfosuccinimide ester (sulfo-GM BS, Pierce), N-kappa-maleimidoundecanoic acid (KMUA, Pierce), N-[kappa-maleimidoundecanoic acid]hydrazide (KMUH, Pierce), N-[kappa-maleimidoundecanoyloxy]sulfosuccinimide ester (sulfo-KMUS, Pierce), m-maleimidobenzoyl-N-hydroxysuccinimide (MBS, Pierce), m-maleimidobenzoyl-N-hydroxysulfosuccinimide ester (sulfo-MBS, Pierce), N-succinimidyl S-acetylthio-acetate (SATA, Pierce), N-succinimidyl S-acetylthiopropionate (SATP, Pierce), succinimidyl 3-[bromoacetamido]propionate (SBAP, Pierce), N-succinimidyl iodoacetate (SIA, Pierce), N-succinimidyl[4-iodoacetyl]aminobenzoate (STAB, Pierce), sulfosuccinimidyl[4-iodoacetyl]aminobenzoate (sulfo-SIAB, Pierce), succinimidyl [4-[N-maleimidomethyl]cyclohexane-1-carboxylate (SMCC, Pierce), sulfosuccinimidyl [4-[N-maleimidomethyl]cyclohexane-1-carboxylate (sulfo-SMCC, Pierce), succinimidyl-[4-[N-maleimidomethyl]cyclohexane-1-carboxy46-amidocaproate (LC-SMCC, Pierce), 4-succinimidyloxycarbonyl-methyl-alpha[2-pyridyldithio]toluene (SM PT, Pierce), sulfosuccinimidyl-6-[alpha-methyl-alpha☐2-pyridyldithio)toluamido] hexanoate (sulfo-LC-SMPT, Pierce), succinimidyl 4-[p-maleimidophenyl]-butyrate (SM PB, Pierce), sulfosuccinimidyl 4-[p-maleimidophenyl]-butyrate (sulfo-SMPB, Pierce), succinimidyl-6-[(beta-maleimidopropionamido)hexanoate] (SMPH, Pierce), N-succinimidyl 3-[2-pyridyldithio]propionate (SPDP, Pierce), succinimidyl [3-(2-pyridyldithio)propionamido]hexanoate (LC-SPDP, Pierce), sulfosuccinimidyl [3'-(2-pyridyldithio)propionamido]hexanoate (sulfo-LC-SPDP, Pierce) and N-succinimidyl[4-vinylsulfonyl]benzoate (SVSB Pierce). It may be advantageous to block certain amine residue as described by Kavimandan et al., (2006) Bioconjugate Chem. 17, 1376-1384.

If the conjugation partner does not contain a thiol reactive group but does contain one or more carbonyl (oxidised carbohydrate) groups then it can be modified to incorporate one or more thiol reactive groups by chemical modification by methods known to the art such as the use of cross-linking reagents such as, but not limited to, N-[eta-maleimidocaproic acid]hydrazide (EMCH, Pierce), 4-[N-maleimidomethyl]cyclohexane-lcarboxylhydrazide.HCl.½ dioxane (M2C2H, Pierce), 3-maleimidophenyl boronic acid (MPBH, Pierce) and 3-[2-pyridyldithio]propionyl hydrazide (PDPH, Pierce).

If the conjugation partner does not contain a thiol reactive group but does contain one or more hydroxyl groups then it may be modified to incorporate one or more thiol reactive groups by chemical modification by methods known to the art such as the use of cross-linking reagents such as, but not limited to, N-[p-maleimidophenyl]isocyanate (PMPI, Pierce).

Conjugation Competence of Albumin Variant

The conjugation competence of polypeptides of the invention may be tested by fluorescent labelling and cellular uptake, as described by McGraw et al., (1987), *The Journal of Cell Biology*, 105, 207-214 and Presley et al., (1993), *The Journal of Cell Biology*, 122, 1231-1241. Other methods of testing conjugation competence include conjugating the albumin to another molecule such as HRP. Subsequently, the mass of the resultant conjugate and/or the activity of the conjugated compound may be assayed, for example by mass spectrometry or by enzyme assay.

Microorganism.

A host strain suitable for use in the present invention includes an hsp150-deficient version of DXY1, disclosed in S. M. Kerry-Williams et al. (1998) Yeast 14:161-169. WO 95/33833 teaches the skilled person how to prepare hsp150-deficient yeast. This host strain may be referred to as 'Strain 1'.

All documents cited are incorporated by reference in their entirety.

The invention is described by way of example only with reference to the following examples:

EXAMPLES

Example 1: Construction of Albumin Mutein Expression Plasmids

The HSA coding sequence is obtainable by known methods for isolating cDNA corresponding to human genes, and is also disclosed in, for example, EP 0 073 646 and EP 0 286 424. Expression plasmids for albumin variants of this invention can be constructed in a similar way to pDB2244 described in WO 00/44772 or pDB2305 described in WO/2006/013859 for expression of human serum albumin from *S. cerevisiae*. Plasmid pDB2305 contains the HSA sequence codon-optimised for expression in *S. cerevisiae*. Alternative codon optimisation methods may be used for the particular host organism selected for thio-albumin production. Expression plasmids for albumin variants of this invention can also be constructed in a similar way to those described in WO 2005/061719 A1 for improved expression of human serum albumin from *S. cerevisiae*.

Thio-albumin muteins can be made following modification of plasmid pDB2244 (FIG. 7) or pDB2305 by site directed mutagenesis. Overlapping mutagenic oligonucleotide sequences can be used to modify the codon of the selected residue(s) to any DNA sequence which encodes a cysteine residue (TGT or TGC) using the procedures indicated by a commercially available kit (such as Stratagene's Quikchange™ Kit). Alternatively, synthetic DNA fragments can be manufactured containing the desired modifications to the polynucleotide sequence.

Construction of a thio-albumin mutant expression plasmids

Subcloning plasmids which may be used to create plasmid pDB2244 (FIG. 7) are plasmid pDB2243 (FIG. 8) (described in WO 00/44772) and pSAC35 (described in EP 286424). Plasmids pDB2243 and pDB2244 contain the native HSA gene. A skilled person will appreciate that the expression cassette may or may not be codon optimised; methods for constructing expression plasmids containing HSA codon optimised for expression in *S. cerevisiae* are described in WO/2006/013859. The native nucleotide sequence encoding HSA is provided in SEQ ID NO: 2. A HSA nucleotide sequence codon-optimised for expression in *S. cerevisiae* is provided as SEQ ID NO: 3.

Plasmid pDB2243 (6.203 kb) was digested to completion using restriction endonucleases NotI to release the 2.992 kb human serum albumin expression cassette.

Figure 7:
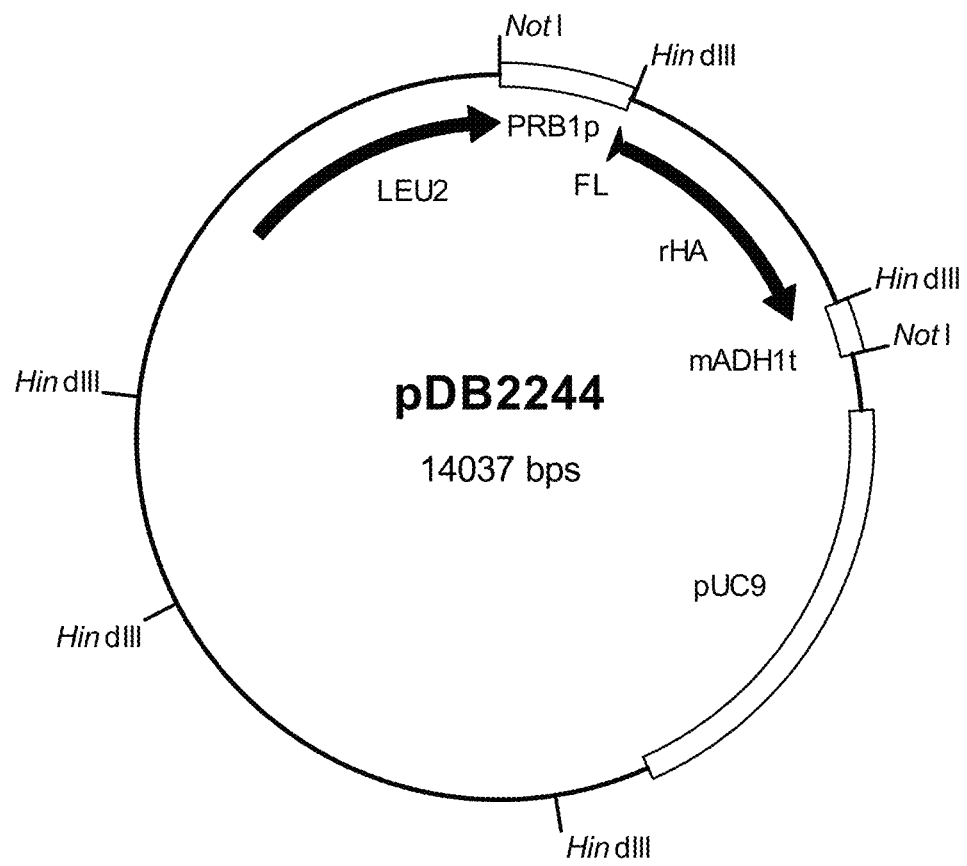
FIG. 7. is a map of plasmid pDB2244.
Figure 8:
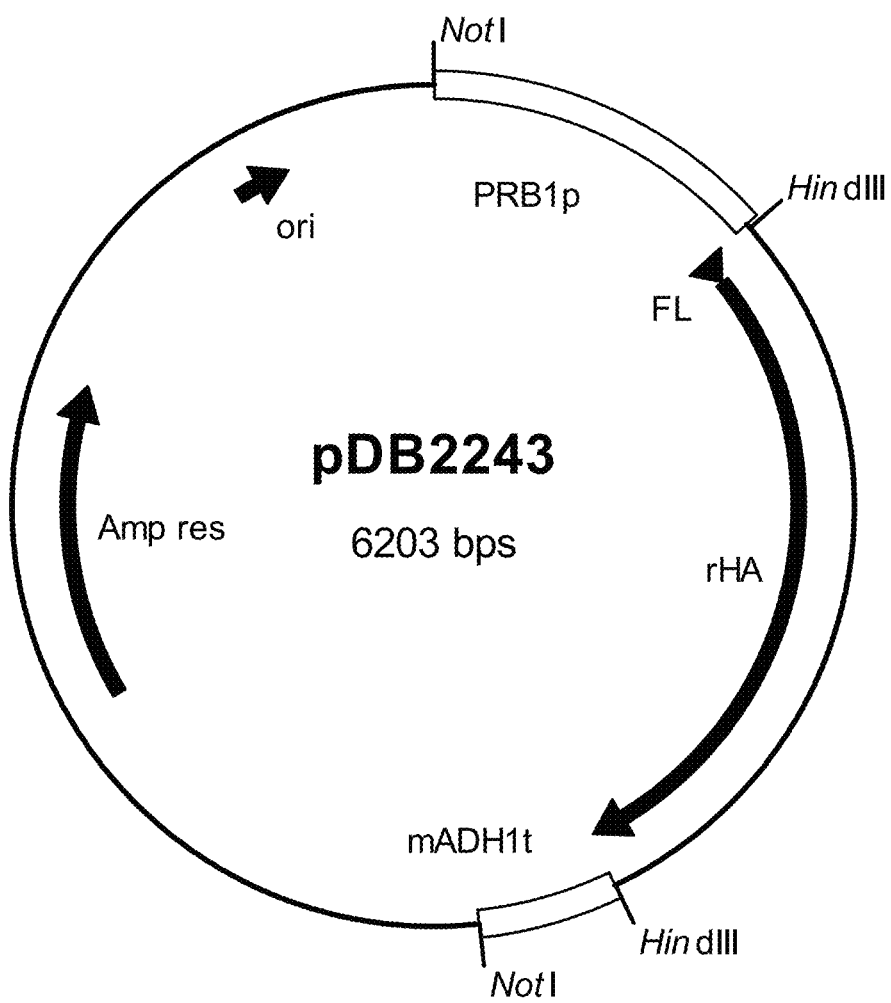
FIG. 8 is a map of plasmid pDB2243.

Plasmid pSAC35 is derivative of pSAC3 by Chinery and Hinchliffe (1989) *Curr. Genet.* 16, 21-25, and in EP 286424. Plasmid pSAC35 (11.037 kb) was digested to completion with restriction endonuclease NotI and dephosphorylated using calf alkaline intestinal phosphatase and ligated with the 2.992 kb NotI human serum albumin expression cassette to produce 14.037 kb pDB2244 which has the human serum albumin expression cassette orientated in the same direction as the LEU2 gene (FIG. 7). A person skilled in the art will appreciate that the expression cassette may or may not be codon optimised and that the expression cassette may or may not be cloned in either orientation in the expression vector as part of this invention.

Figure 9:
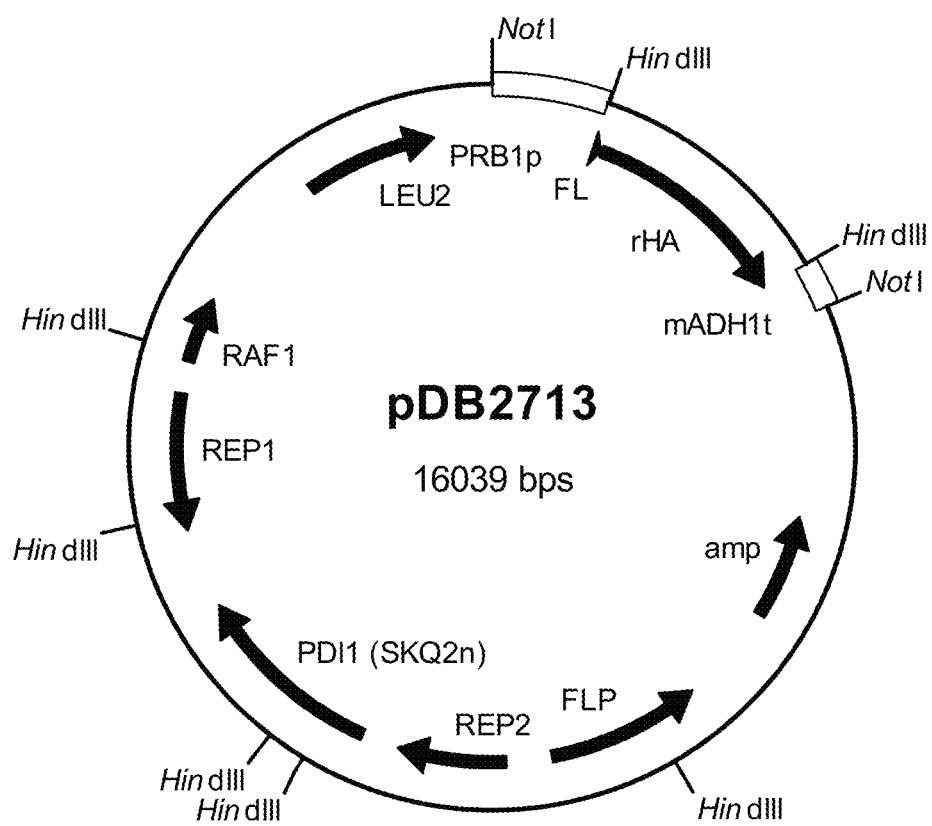
FIG. 9. is a map of plasmid pDB2713.

Alternatively plasmid pDB2690 may be used. The construction of plasmid pDB2690 is described in WO/2005061719 A1. Plasmid pDB2690 (13.018 kb) was digested to completion with restriction endonuclease NotI and dephosphorylated using calf alkaline intestinal phosphatase and ligated with the 2.992 kb NotI human serum albumin expression cassette to produce a 16.039 kb plasmid pDB2713 which has the human serum albumin expression cassette orientated in the same direction as the LEU2 gene (FIG. 9). A person skilled in the art will appreciate that the expression cassette may or may not be codon optimised and that the expression cassette may or may not be cloned in either orientation in the expression vector as part of this invention.

As an alternative to site-directed mutagenesis expression plasmids for thio-albumin (i.e. conjugation competent albumin) variants of this invention could be made by subcloning synthesized DNA fragments into plasmid pDB2243 (FIG. 8) prior to cloning into pSAC35 or pDB2690. A method for the construction of a thio-albumin subcloning plasmid containing one extra conjugation competent cysteine (relative to SEQ ID NO: 1) is described, by way of example only, below.

The albumin DNA sequence of pDB2243 includes two HindIII restriction endonuclease sites.

The synthetic DNA may be modified such that the human serum albumin protein encoding sequence is modified at a selected codon to a cysteine codon, or an existing cysteine codon is deleted or modified to a codon for another amino acid. Alternatively, the coding sequence for the mature thio-albumin may be extended at the 5' or 3' end(s) or insertions made within the polypeptide to add novel sequence(s) coding for cysteine or polypeptides containing one or more cysteine.

Alternatively synthetic DNA may be modified such that the human serum albumin protein encoding sequence is modified at a selected cysteine codon to an alternative codon to create an unpaired cysteine. Alternatively synthetic DNA may be modified such that the human serum albumin protein encoding sequence is modified by substitution of two codons at a specified site to a cysteine codon (the amino acid chain length is reduced). Alternatively synthetic DNA may be modified such that the human serum albumin protein encoding sequence (e.g. SEQ ID NO: 2 or SEQ ID NO: 3 in relation to HSA) is modified by insertion of a cysteine codon at a specified site (the amino acid chain length is increased). Plasmid pDB2243 may be digested to completion with HindIII restriction endonuclease and the fragment (approximately 4.383 kb) is recovered and dephosphorylated, the synthetic DNA containing the appropriate modification to the human serum albumin encoding sequence may then be cloned to produce the required thio-albumin subcloning plasmid. The thio-albumin subcloning plasmid may then be digested to produce an expression cassette, which may be cloned into a suitable expression plasmid in a similar manner to the construction of pDB2244, pDB2305 or pDB2713.

Those skilled in the art will appreciate that expression cassette for thio-albumin variants with additional modifications to the albumin protein sequence could be produced using a similar method to that described for the construction of a thio-albumin subcloning plasmid containing one extra conjugation competent cysteine (relative to SEQ ID NO: 1).

A *S. cerevisiae* strain, e.g. Strain 1, may be transformed to leucine prototrophy with pDB2244 (WO 00/44772), or pDB2305 (WO/2006/013859) for expression of human serum albumin or the appropriate thio-albumin expression plasmids. Yeast may be transformed using a modified lithium acetate method (Sigma yeast transformation kit, YEAST-1, protocol 2; Ito et al, 1983, J. Bacteriol., 153, 16; Elble, 1992, Biotechniques, 13, 18). Transformants may be selected on BMMD-agar plates, and subsequently patched out on BMMD-agar plates. The composition of BMMD is described by Sleep et al., 2002, Yeast, 18, 403. Cryopreserved stocks may be prepared in 20% (w/v) trehalose from 10 mL BMMD shake flask cultures (24 hours, 30° C., 200 rpm).

Example 2: Expression of Albumin Muteins with Single Amino Acid Changes Compared to HSA Thio-albumin variants with single amino acid changes were selected from Tables 5A, 5B and 6A. These variants were identified as the preferred mutations according to the methods described above. Details of each variant are given in FIG. 11, which provides a Construct Reference (e.g. TA1 for rHA A2C), the name of the plasmid encoding each thio-albumin variant expression construct and flanking sequences required for in vivo recombination by gap-repair, and the number given to a cryopreserved yeast stock (the yeast stock number) producing each thio-albumin variant. Details of the mutant codons compared to SEQ ID NO: 2 are also provided, as are the SEQ ID numbers for each thio-albumin variant (DNA and protein).

Figure 12:
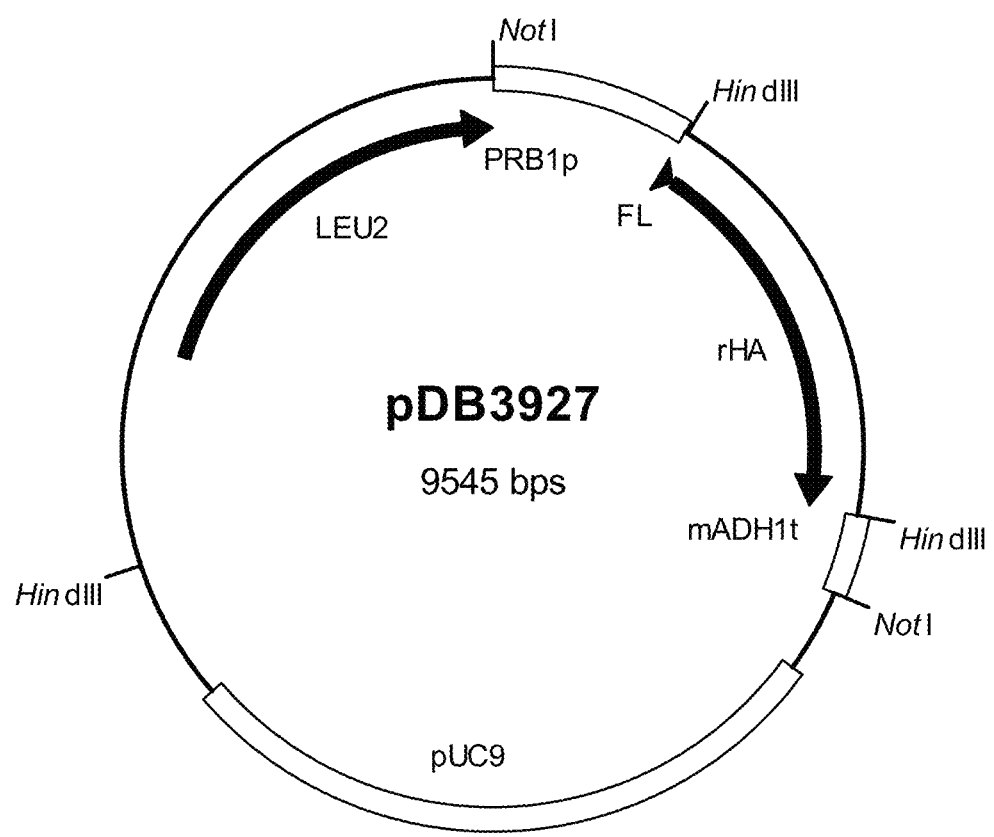
FIG. 12 is a map of plasmid pDB3927.
Figure 13:
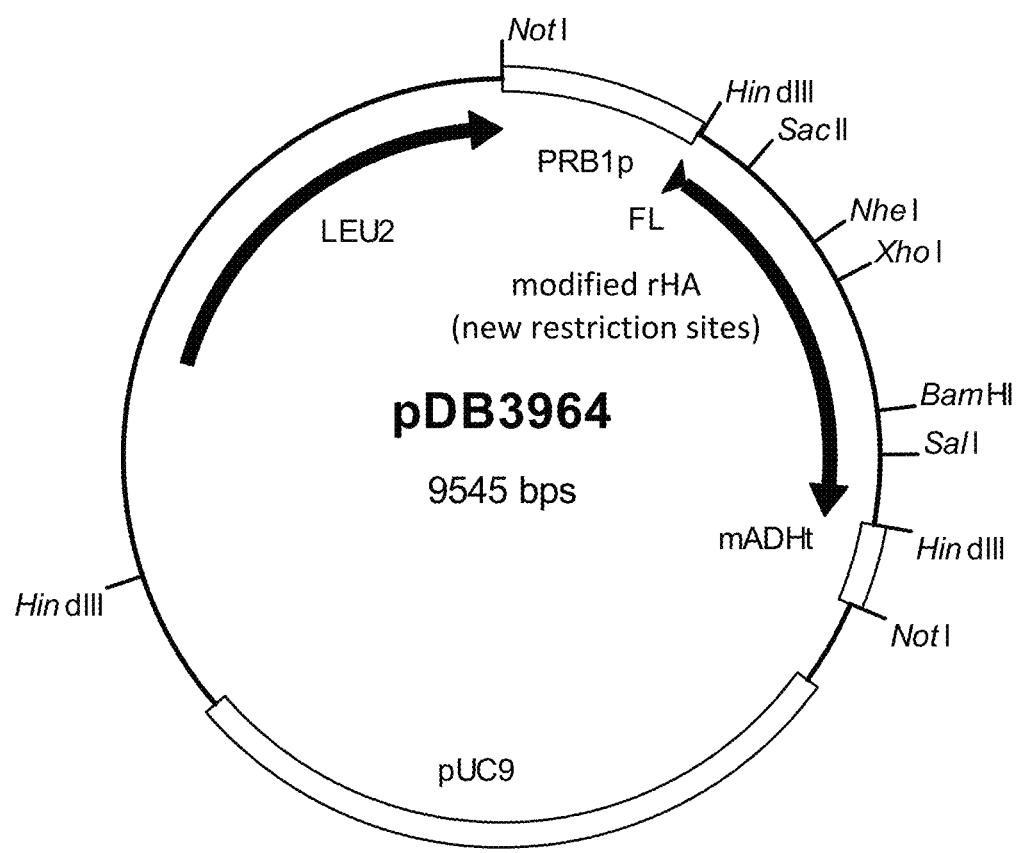
FIG. 13 is a map of plasmid pDB3964.

To modify the amino acids in non-human serum albumins, the equivalent positions to a particular position in HSA may be determined from an alignment including human serum albumin (SEQ ID NO: 1) such as FIGS. 2 and 3. The skilled person is familiar with alignments and can readily determine whether or not an amino acid in a sequence is equivalent to an amino acid in another sequence. For example, the position of the amino acid in the nonhuman albumin is not necessarily the same relative to the N-terminal end of HSA. For example, from FIG. 2 position 239 of HSA is an alanine residue, whereas the corresponding residue of the bovine sequence is serine-238. Similarly, valine-479 of HSA corresponds to leucine-478 of sheep albumin. The plasmid pDB3927 (FIG. 12) was constructed from plasmid pDB2244 (FIG. 7, WO 0044772A, 'FL': fusion leader sequence). pDB2244 was digested with restriction enzymes SwaI and HpaI (both produce blunt ends) and self-ligated to form pDB3927. To create plasmid pDB3964 (FIG. 13) restriction enzyme sites were modified in the albumin DNA sequence (SEQ ID NO: 2) of pDB3927 without modifying the protein sequence, as outlined below. The resultant DNA sequence is sequence ID No. 4.

1) Introduced enzyme sites: (basepair positions in brackets refer to positions in SEQ ID NO: 4)

| Restriction site | SEQ ID NO: | | SEQ ID NO: 4 | Position |
|---|---|---|---|---|
| a SacII: | GAGTCAGCTGAA AA SEQ ID NO: 126) | →(to) | GAGTCCGCGGAA AA (SEQ ID NO: 127) | (bp 173-178) |
| b NheI/BmtI: | AAGGCTTCGTCT GC (SEQ ID NO: 128) | →(to) | AAGGCTAGCTCT GC (SEQ ID NO: 129) | (bp 571-576) |
| c XhoI: | TCTGCTTGAATG TGC (SEQ ID NO: 130) | →(to) | TCTGCTCGAGTG TGC (SEQ ID NO: 131) | (bp 751-756) |
| d BamHI: | GTGGGCAGCAAA T (SEQ ID NO: 132) | →(to) | GTGGGATCCAAA T (SEQ ID NO: 133) | (bp 751-756) |

-continued

| Restriction site | SEQ ID NO: | | SEQ ID NO: 4 | Position |
|---|---|---|---|---|
| e SalI: | GGAAGTCGATGAA7 (SEQ ID NO: 134) | →(to) | GGAAGTCGACGAAA (SEQ ID NO: 135) | (bp 1477-1482) |

The coding sequence of HSA in pDB3964 is provided as SEQ ID NO: 4. DNA synthesis and cloning was used to generate pDB3964 from pDB3927 (DNA2.0 Inc, USA). Synthetic DNA fragments were designed to alter specific amino acid codons within the albumin gene of pDB3964, or with combinations of modifications (see Example 3 below). DNA fragments containing these modifications were synthesised (DNA 2.0 Inc, USA) and cloned into pDB3964 to produce plasmids containing the thio-albumin sequences (FIG. 11). These synthetic genes and flanking regions were excised with restriction enzymes BstEII and BsrBI from the plasmids named in FIG. 11 for each of the thio-albumin variants and the controls pDB3927, pDB3964 and pDB2244, before purification of the resulting DNA fragments (PCR purification kit, Qiagen). The DNA fragments were used in the yeast transformation procedure described below to allow gap-repair in vivo with linearised pDB3936.

The plasmid pDB3853 (not shown) was constructed from base vector pDB2690 (Ref DB88/WO2005/061719A1) and the synthetic linker described below. The synthetic linker was constructed from two oligonucleotides (Sigma-Genosys) annealed in distilled water using a temperature gradient from 96° C. to room temperature (1 min per 1° C.). pDB2690 was digested using KpnI and NotI, and purified by gel extraction (Qiagen), before ligation of the annealed linker:

```
'KpnI (linker) BamHI NotI'
                                      (SEQ ID NO: 136)
5'-CGCTAGCCTCGAGGTTTAAACGCTAGCGAGCTCGGATCC-3'

(SEQ ID NO: 137)
3'-CATGGCGATCGGAGCTCCAAATTTGCGATCGCTCGAGCCTAG

GCCGG-5'
```

Figure 14:
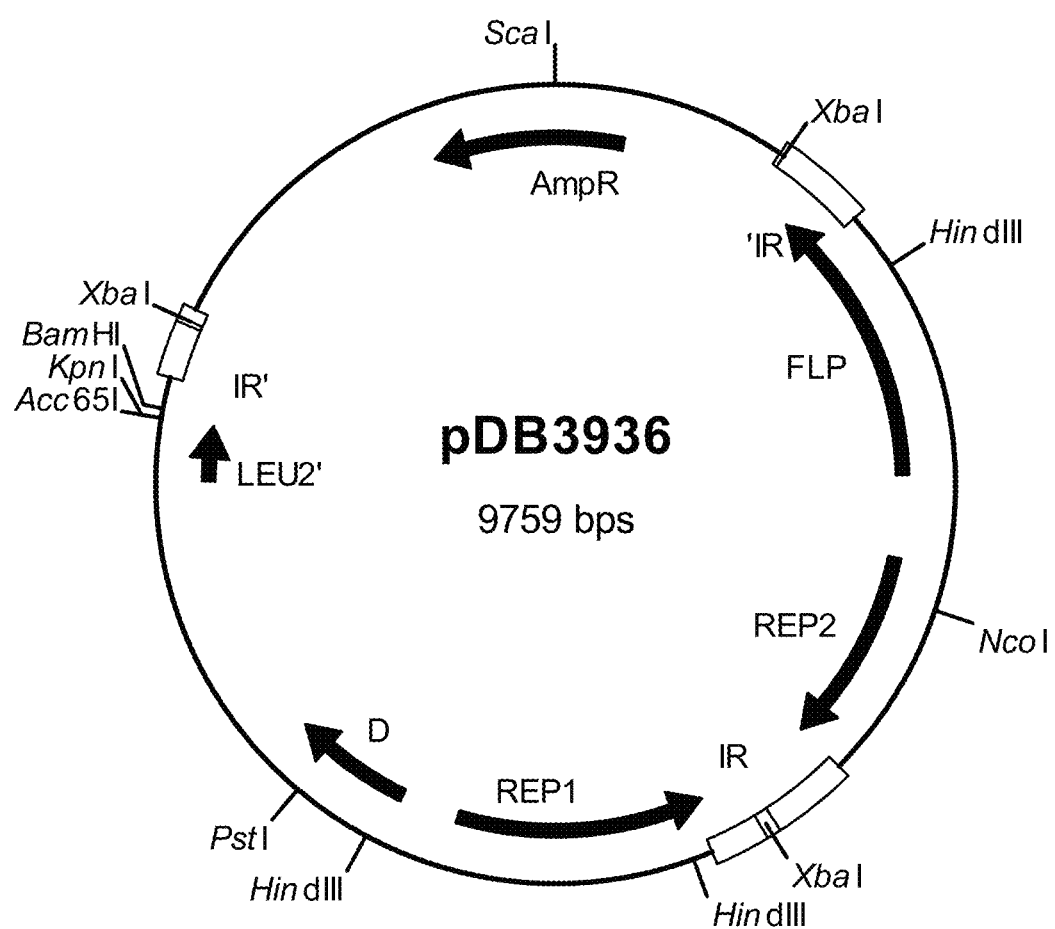
FIG. 14 is a map of plasmid pBD3936.

Following the construction of pDB3853, the linker was excised using PstI and ScaI (3787 bp fragment) before ligation into the gel extracted PstI/ScaI cut pSAC35 plasmid (WO 0044772A and WO2005/061719A1)), to form pDB3936 (FIG. 14).

pDB3936 was linearised with restriction enzymes Acc65I and BamHI before purification of the 9721 bp fragment following separation by agarose gel electrophoresis. For the yeast transformation procedure to allow gap-repair in vivo (described below) the concentrations of the linearised pDB3936 and each of the BsrBI-BstEII fragments encoding the thio-albumin coding sequences was calculated and 100 ng of each use for each yeast transformation reaction.

Saccharomyces cerevisiae strain BXP10 was used as the expression host throughout (So-low, S. P., J. Sengbusch, et al. (2005). "Heterologous protein production from the inducible MET25 promoter in Saccharomyces cerevisiae." Biotechnol Prog 21(2): 617-20.), although alternative expression hosts are also be suitable.

Cryopreserved stocks of S. cerevisiae BXP10 were prepared from 10 mL YEPPD (1% w/v yeast extract, 2% w/v plant peptone, 2% w/v dextrose)) shake flask cultures (grown for 24 hours, 30° C., 200 rpm) mixed with an equal volume of 40% w/v sterile trehalose solution and dispensed in 1 mL aliquots for storage at −80° C. 10 mL BMMD, YEPPD and LB (1% w/v bacteriological tryptone, 0.5% w/v yeast extract, 0.5% w/v NaCl) shake flasks were inoculated with 100 µL cryopreserved yeast stock and incubated for four days at 30° C., 200 rpm as above before being observed microscopically to confirm they were axenic.

Frozen competent S. cerevisiae BXP10 cells were prepared by inoculating 100 µL cryopreserved yeast stock into 10 mL YEPPD which were incubated for two days at 30° C., 200 rpm, before being used to inoculate 300 mL YEPPD to an OD600=0.3. The cells were incubated as above for approximately 4 hours or until a doubling of $OD_{600}$ had been achieved. The cells were harvested by centrifugation (3000× g, 5 min, room temperature) before resuspension in 120 mL distilled water followed by a further centrifugation step. The pellet was resuspended in 3 mL TE/LiAc (10 mM Tris, 1 mM EDTA, pH7; 500 mM lithium acetate) and glycerol added to a final concentration of 15% (v/v), before storage in aliquots at −80° C.

S. cerevisiae BXP10 cells were transformed to leucine prototrophy using a modified lithium acetate method (Elble, R. "A simple and efficient procedure for transformation of yeasts." Biotechniques 13.1 (1992): 18-20. Ito, H., et al. "Transformation of intact yeast cells treated with alkali cations." J. Bacteriol. 153.1 (1983): 163-68.). 50p1 of thawed competent cells were aliquoted into a 48-well microtitre plate (Nunc) before the addition of DNA fragments for gap-repair, as described above. The plate was mixed by swirling of the plate while flat on a benchtop. 300 µl of PEG/LiAc (40% w/v PEG 3350, 100 mM lithium acetate) was added to each well and was mixed again. The plate was incubated at 30° C. with shaking at 200 rpm for 1 hour before transfer to static incubation at 42° C. for 30 min. After 1 min incubation on ice, the plate was centrifuged (2000×g, 5 min, room temperature) followed by removal of the supernatant and resuspension of the pellet in 200 µl 1M sorbitol. The full volume was inoculated onto BMMD agar plates with CSM-Leu nutritional supplement (MP Biomedicals, Bio 101) and incubated for 4 days at 30° C.

Single colony transformants were picked and patched onto fresh BMMD agar plates for short term storage. These patches were grown at 30° C. and cells then inoculated into 10 mL BMMD shake flask cultures and cryopreserved as described earlier. 10p1 of yeast stock was inoculated into a 48-well plate containing 0.5 mL BMMD per well. Growth of cultures in microtitre plates was achieved in a humidity chamber which was a sealed Perspex box containing wet paper towels to provide ~100% humidity and evaporative loss below 0.25% over 5 days under growth conditions. The plates were incubated in the shaking humidity chamber (30° C., 200 rpm,) for 5 days at 30° C. The 48-well plate was centrifuged to pellet cells (2000×g, 10 min, room temperature) and the supernatant was harvested.

The concentration of the thio-albumin variants in the culture supernatants was determined by Gel Permeation High Pressure Liquid Chromatography (GP-HPLC). Protein concentrations were determined using a LC2010 HPLC system (Shimadzu) equipped with UV detection under Shimadzu VP7.3 client server software control. Injections of 25 µL were made onto a 7.8 mm internal diameter×300 mm length TSK G3000SWXL column (Tosoh Bioscience), with a 6.0 mm internal diameter×40 mm length TSK SW guard column (Tosoh Bioscience). Samples were chromatographed in 25 mM sodium phosphate, 100 mM sodium sulphate, 0.05% (w/v) sodium azide, pH 7.0 at 1 mL·min$^{-1}$, with a run time of 15 minutes. Samples were quantified by UV detection at 280 nm, by peak height, relative to a recombinant human albumin standard of known concentration (10 mg/mL).

Figure 15:
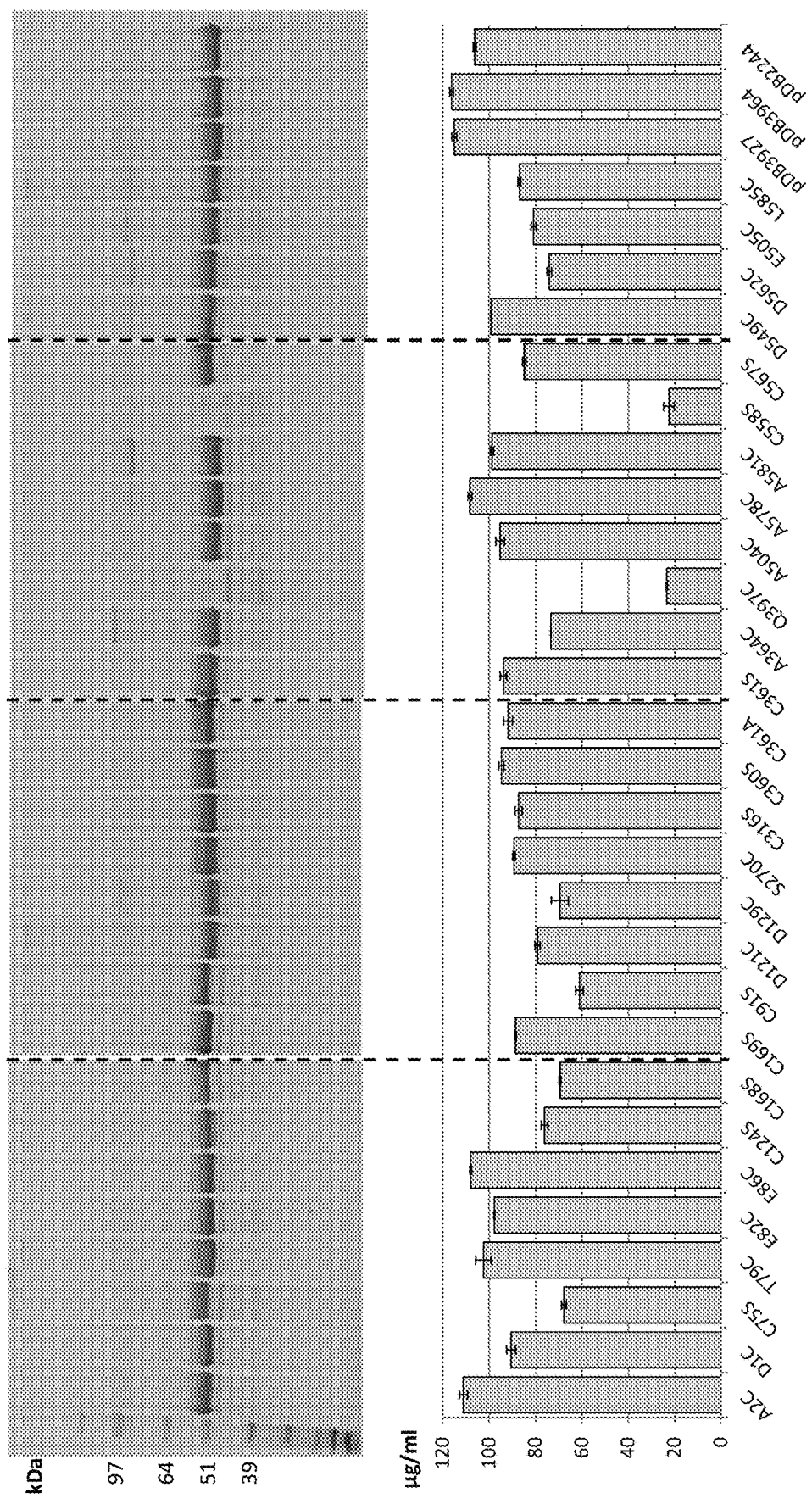
FIG. 15 shows SDS-PAGE analysis, and HPLC data (bar chart), showing the expression (µg/ml with standard deviation) of albumin molecules having a free thiol group at Cys-34 of SEQ ID NO: 1 and an additional free-thiol at the position indicated below the bar chart.

A non-reducing SDS-PAGE analysis and the expression titres (by GP-HPLC) for each of the thio-albumin variants with single mutations are compared against controls in FIG. 15. It is evident that all of the thio-albumin variants have been successfully secreted from S. cerevisiae BXP10. Preferred mutations have high expression titres and show a sharp Coomassie stained band equivalent to rHA controls by non-reducing SDS-PAGE analysis.

Example 3: Expression of Additional Thio-Albumin Variants

FIG. 16 describes an additional selection of thio-albumin variants with two or more free-thiol groups. Mutations shown to be expressed in Example 2 above were combined to generate sequences designed to have multiple free-thiol groups available for conjugation. This selection includes thio-albumin variants designed to have up to five free-thiol groups, thio-albumin variants designed to have free-thiol groups from within one Selection Group or from more than one Selection Group, thio-albumin variants designed to have free-thiol groups with and without the naturally occurring free-thiol at C34 of HSA, thio-albumin variants designed to have free-thiol groups from a range of Proximity Groups, and thio-albumin variants designed to have free-thiol groups derived from insertions, extensions, additions and/or deletions. It represents a sub-set of thio-albumins with multiple conjugation competent cysteine residues. The details of these thio-albumin variants, the plasmids encoding them and the SEQ ID NO for their DNA and protein sequences are described in FIG. 16, in a similar manner to those of FIG. 11 for the thio-albumin variants with single modifications. Methods for plasmid construction and expression from S. cerevisiae BXP10 are similar to those described above.

Figure 17:
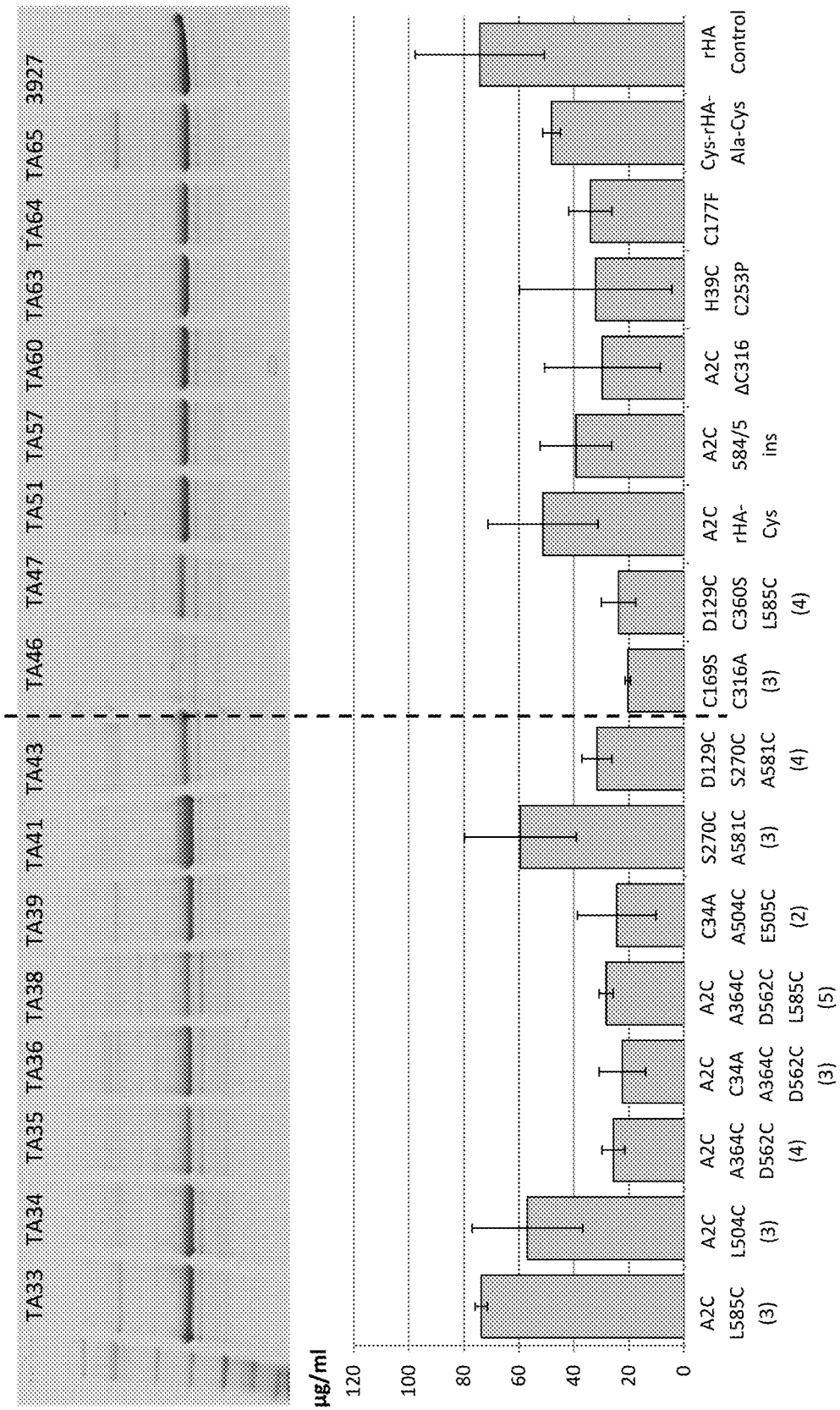
FIG. 17 shows SDS-PAGE analysis, and HPLC data (bar chart), showing the expression (µg/ml with standard deviation of albumin molecules having one or more free thiol groups in addition to Cys-34 of native human serum albumin and/or having Cys-34 removed.

FIG. 17 shows a non-reducing SDS-PAGE analysis and the expression titres (by GP-HPLC) for each of these additional thio-albumin variants compared against an rHA control (pDB3927 coding sequence). Again, it is evident that all of the thio-albumin variants have been successfully secreted from S. cerevisiae BXP10. It therefore confirms that the selection criteria allow suitable thio-albumin variants to be generated and therefore indicates that there is no problem with undersirable mis-folding or aggregation. Again, preferred combinations of mutations have high expression titres and show a sharp Coomassie stained band equivalent to rHA controls by non-reducing SDS-PAGE analysis.

Example 4: Production, Purification and Conjugation of Thio-Albumin Variants

Five cryopreserved yeast stocks (9116, 9118, 9124, 9125 and 9130; FIG. 11) each in 1 mL aliquots were inoculated into shake flasks containing 100 mL BMMS growth medium (yeast nitrogen base without amino acids and $(NH_4)_2SO_4$, Difco 1.7 g/L; citric acid monohydrate 6.09 g/L; anhydrous $Na_2HPO_4$ 20.16 g/L; $(NH_4)_2SO_4$ 5.0 g/L; pH6.5±0.2; sucrose added to 20 g/L). Cells were transferred from the shake flask to the fermenter (10 L working volume, Sartorius Biostat C 10-3 fermenter) when the concentration of cells in the shake flask has reached 0.8-1.2 g/L achieving a cell inocula concentration of ≥10 mg/L (greater than or equal to 10 mg/L) in the fermenter.

The thio-albumin variants proteins were produced by axenic culture of each of the five yeast strains in high cell density (HCD) fed-batch fermentation. The aim of the fermentation was to achieve maximum biomass and productivity by controlling feed rate addition so that formation of byproducts such as ethanol and acetate were avoided. Further details of the fermentation process are described in WO96/37515. The temperature and pH were controlled at 30° C. and pH5.5 respectively. Culture supernatant was harvested by centrifugation using a Sorvall RC 3C centrifuge (DuPont) and frozen for storage, before being thawed for subsequent purification. Final product concentrations were determined by GP HPLC using a LC2010 HPLC system (Shimadzu) equipped with UV detection under Shimadzu VP7.3 client server software control as described above. FIG. 18 provides the yields of each thio-albumin variant (in g/L culture supernatant) and shows that high product titres of greater that 1 g/L culture supernatant were obtained in all cases.

A single step chromatography procedure was used to prepare material suitable for mass spectrometry. This purification step used a column (bed volume approximately 200 µL) packed with AlbuPure™ matrix (ProMetic BioSciences Ltd, Cambridge UK or Novozymes Biophama UK Ltd.). This was equilibrated with 50 mM sodium phosphate, pH5.3, and loaded with neat culture supernatants, at approximately pH5.5-6.5, to approximately 40 mg protein/mL matrix. The column was washed with approximately 3 column volumes each of 50 mM sodium phosphate, pH5.3, and 50 mM ammonium acetate, pH8.0, respectively. Bound protein was eluted using approximately 5 column volumes of 50 mM ammonium acetate, 10 mM octanoate, pH7.0. The flow rate for the load step was 137 µL/min, while the wash and elution steps were performed by means of centrifugal force, using a Heraeus Multifuge 3 centrifuge at 300 rpm. Final concentrations were in the range 1.8-4.0 mg/mL and samples were approximately 2 mL volume. Free thiol determination was performed immediately after sample elution by following the procedure described below.

The number of free thiols on a protein can be determined spectrophotometrically using Ellman's reagent. Ellman's reagent (5'5'-dithio-bis(2-nitronenzoic acid) (DTNB)) is an aromatic disulphide which reacts with thiol groups to form a mixed disulphide of the protein and one mole of 5-thio-2-nitrobenzoic acid (TNB) (per mole of protein sulfhydryl group). This reaction also results in a yellow color from free TNB being released in solution. Alternatively the number of free thiols on a protein can be determined using mass spectrometric analysis of protein sample treated with DTNB reagent. 5-thio-2-nitrobenzoic acid (TNB) has a molecular weight of 199 Da, thus an increase in mass of 197 Da (TNB minus H2 lost during disulphide bond formation with the free thiol group on the test protein) indicates the presence of one free thiol group on the protein sample.

700 µL of the test protein sample was added to 100 µl Buffer 2 (4 mg/mL DTNB and 500 mM Sodium Phosphate, pH 7.0) and 900 µL Buffer 1 (0.1M Tris-HCl, 100 mM EDTA, pH8.0). The preparation was allowed to mix for 25 minutes at ambient temperature (21-25° C.) followed by filtration through a low molecular mass cut-off filter (Vivaspin 2-10000 MWCO Sartorius Stedim Germany). The filter was washed with two volumes of 0.1% Triflu-oroacetic acid (TFA) and the sample was resuspended in 1 ml of 0.1% TFA. TNB labelled and unlabelled samples were prepared for mass spectrometric analysis by desalt-ing/concentrating using Solid Phase Extaction (SPE). SPE columns were prepared by first wetting with 1 mL of 70% Acetonitrile (ACN Fisher)/0.1% TFA and then equilibrating ready for loading with 0.1% TFA. 1 mL of sample was loaded on the equilibrated SPE columns al-lowing time for the protein to bind. The bound protein and SPE columns were then washed three times in 1 mL of 0.1% Formic acid (Merck). Finally the bound protein was eluted into pre-washed 1 mL microfuge tube with 0.5 mL 70% ACN/0.1% FA.

For Time-of-Flight mass spectrometry 30 μL of sample was introduced into a hybrid quadru-pole time-of flight mass spectrometer (QqOaTOF, Applied Biosystems, QSTAR-XL®), equipped with an IonSpray™ source in positive ion mode, using flow injection analysis (FIA). The only instrument parameter that is actively tuned is the Decoupling Potential (DP), typically set to 250 V. Typically 2 minutes of sample scans are averaged. For protein analysis the TOF analyser is calibrated against protonated molecular ions of equine myoglobin (Sigma) and resolution is typically >14,000. Instrument control and data acquisition and processing were performed using Analyst™ QS v1.1 software (Applied Biosystems).

The results of the above analysis of the purified thio-albumin samples are described below. On addition of DTNB all samples quickly turned yellow as expected due to the presence of numerous free thiols. When the samples were visually compared to an equivalent sample of rHA, containing a single free thiol, the color change observed for the thio-albumin samples was significantly more intense, strongly indicating the presence of multiple free thiols on each thio-albumin molecule. Results are summarised in FIG. 18, with increasing color intensity increasing denoted by increased number of "+".

The thio-albumin variants produced at higher fermentation yields were preferred for analysis by the mass spectroscopy method described above. Therefore, the recombinant proteins rHA (A2C, L585C) (total of 3 free thiols), rHA (D129C, C360S, L585C) (total of 4 free thiols), and A2C rHA-Cys (total of 3 free thiols) were analysed by ESI TOF (electrospray ionsation time of flight) mass spectrometry pre- and post-DTNB treatment to determine the numbers of free thiols present on each molecule.

Figure 19:
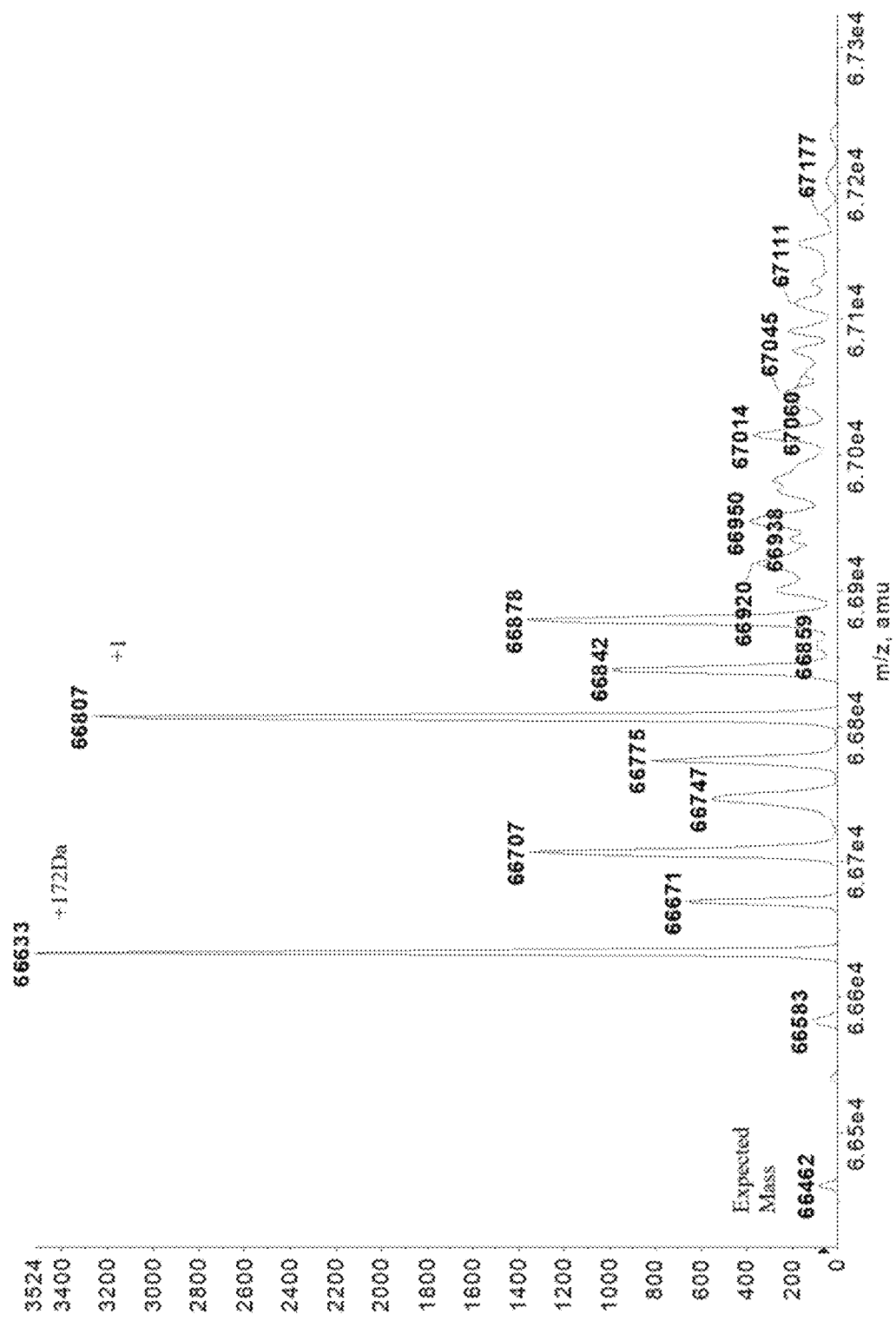
FIG. 19 is a mass spectrogram of a rHA molecule designed to have three free-thiols (Cys-34, A2C and L585C) before treatment with DTNB.
Figure 20:
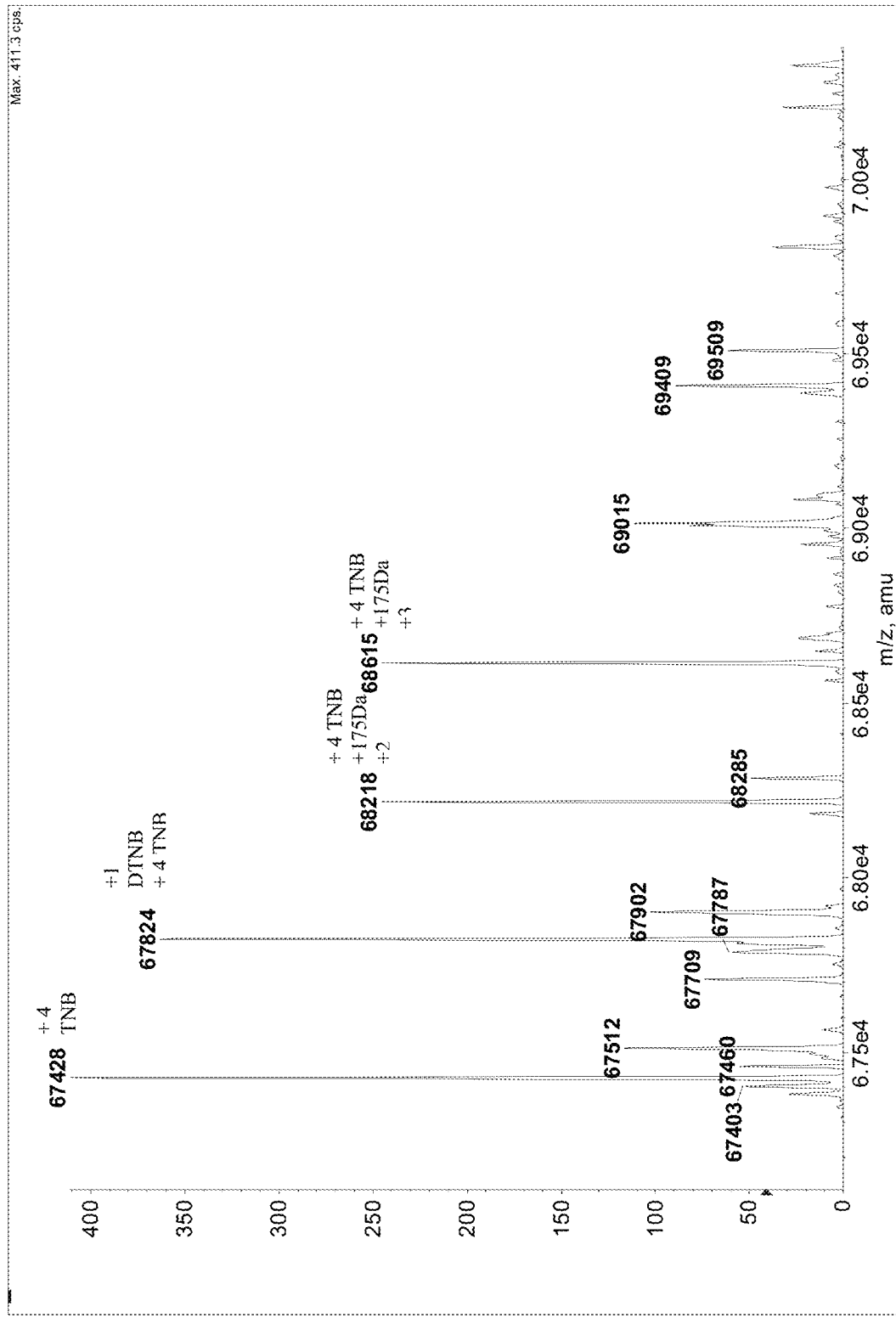
FIG. 20 is a mass spectrogram of a rHA molecule designed to have three free-thiols (Cys-34, A2C and L585C) after treatment with DTNB.

When rHA (A2C, L585C) was analysed pre-DTNB treatment (FIG. 19) the major deconvoluted peaks observed were at 66633 Da and 66807 Da which corresponds to 172 Da and 346 Da above the expected mass of 66461 Da. These modifications were likely to be due to species, of ~172 Da present in the growth media cross linking to the free thiols in rHA (A2C, L585C). Post DTNB treatment mass spectrometric analysis (FIG. 20) resulted in a major a deconvoluted peak at 67428 Da which was 376 Da above the expected mass for the protein with 3 free thiols. This extra mass is most likely to be due to an extra TNB linked to a free thiol and a further 179 Da, this strongly suggests the presence of a 4 free thiols and a possible a further thiol blocked with a species of ~179 Da. Hence, the rHA (A2C, L558C) thio-albumin variant is particularly surprising in that it provides more than the expected number of reactive groups available for conjugation. Also present is a series of peaks ~396 Da apart which are due to excess DTNB still present at the time of ionisation causing DTNB adduct formation with the labelled rHA (A2C, L558C) molecule. This adduct formation is known to occur in the presence of excess DTNB.

Figure 21:
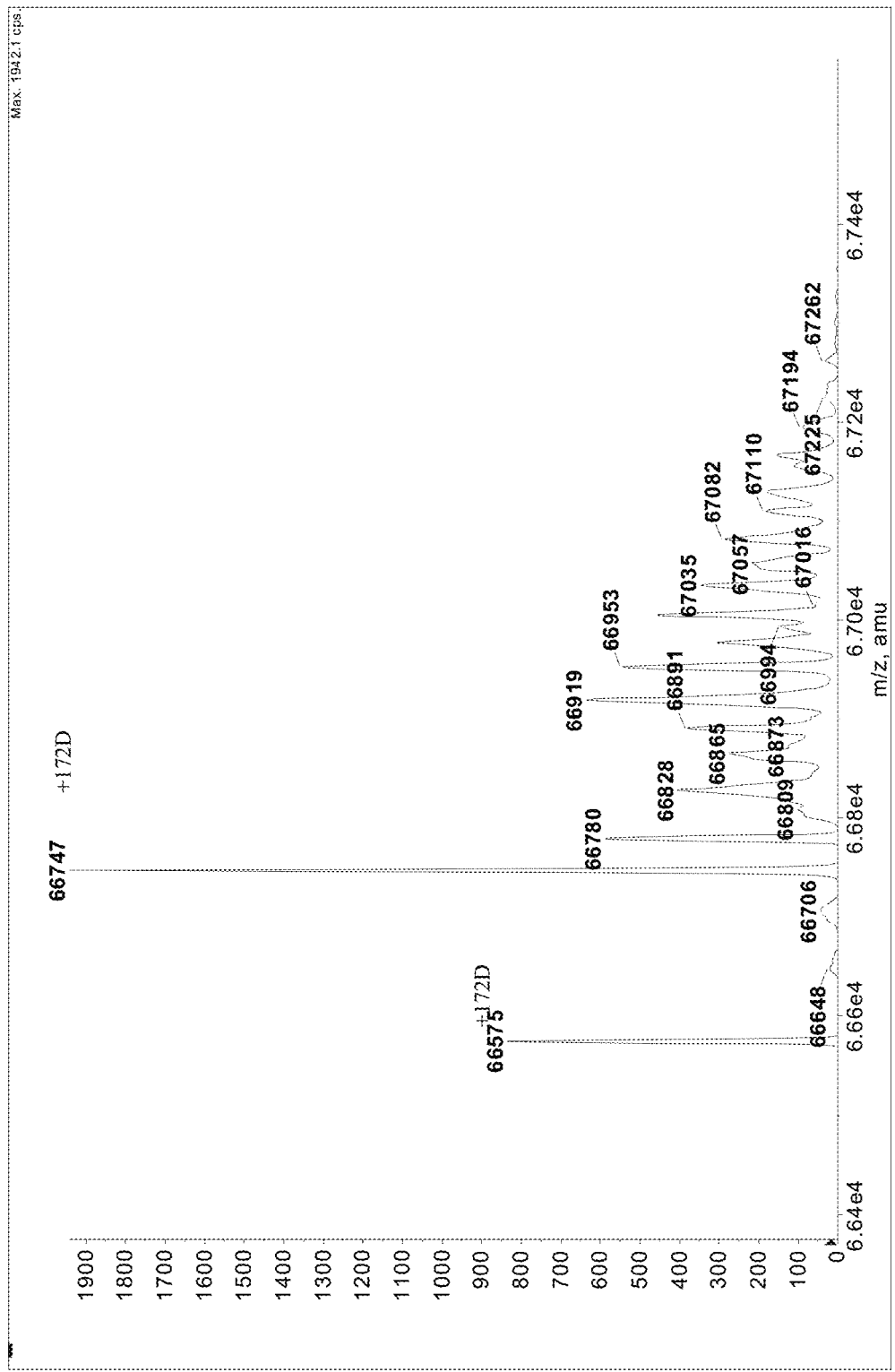
FIG. 21 is a mass spectrogram of a rHA molecule designed to have four free-thiols (Cys-34, D129C, C360S and L585C) before treatment with DTNB.
Figure 22:
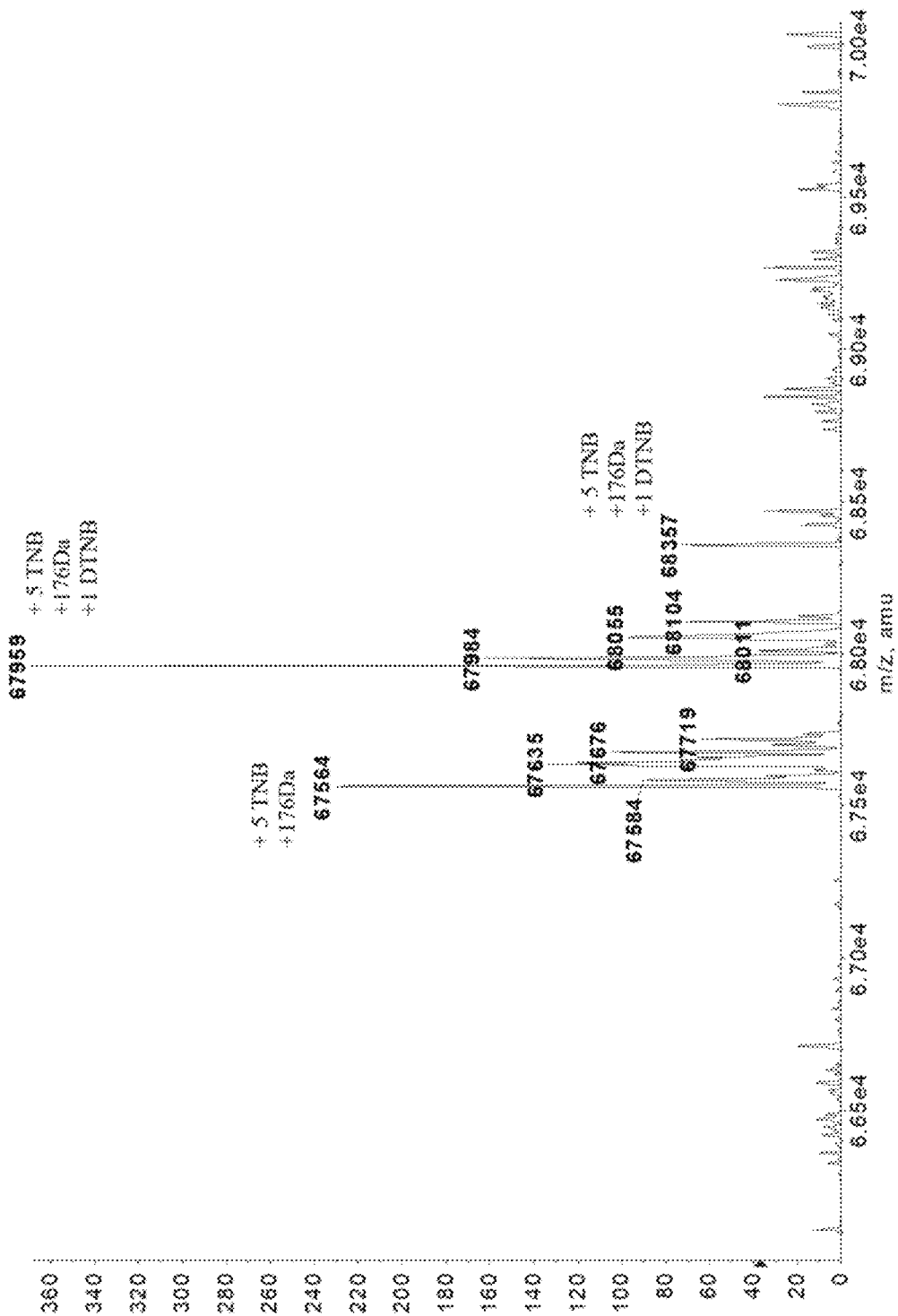
FIG. 22 is a mass spectrogram of a rHA molecule designed to have four free-thiols (Cys-34, D129C, C360S and L585C) after treatment with DTNB.

When rHA (D129C, C360S, L585C) (total of 4 free thiols) was analysed pre-DTNB treatment (FIG. 21) the major deconvoluted peaks observed were at 66575 Da and 66747 Da which corresponds to 172 Da and 344 Da above the expected mass of 66403 Da. These modifications were likely to be due to molecules of ~172 Da present in the growth media cross linking to the free thiols in rHA (D129C, C360S, L585C). Post DTNB treatment mass spectrometric analysis (FIG. 22) resulted in a major a deconvoluted peak at 67564 Da which was 373 Da above the expected mass for the protein with 4 free thiols. This extra mass is most likely to be due to an extra TNB linked to a free thiol and a further 176 Da, this strongly suggests the presence of a 5 free thiols and a possible a further thiol blocked with a species of ~176 Da. Hence, the rHA (D129C, C360S, L585C) thio-albumin variant is particularly surprising in that it has provided more than the expected number of groups available for conjugation. Also present are a series of peaks ~396 Da apart these are due to excess DTNB still present at the time of ionisation causing DTNB adduct formation with the labelled rHA D129C, C360S, L585C. This adduct formation is known to occur in the presence of excess DTNB.

Figure 23:
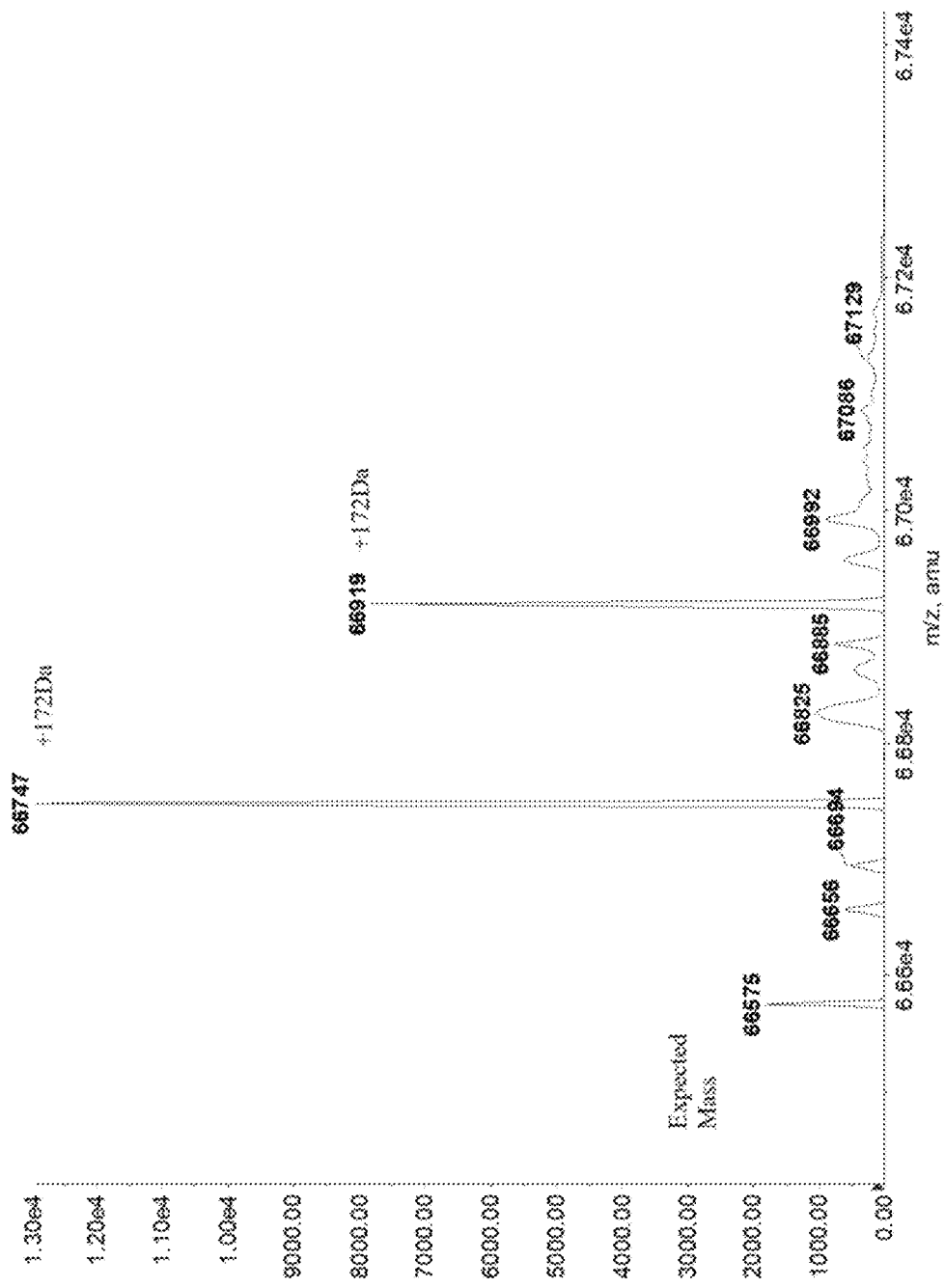
FIG. 23 is a mass spectrogram of a rHA molecule designed to have three free-thiols (Cys-34, A2C and a C-terminal free-thiol) before treatment with DTNB.
Figure 24:
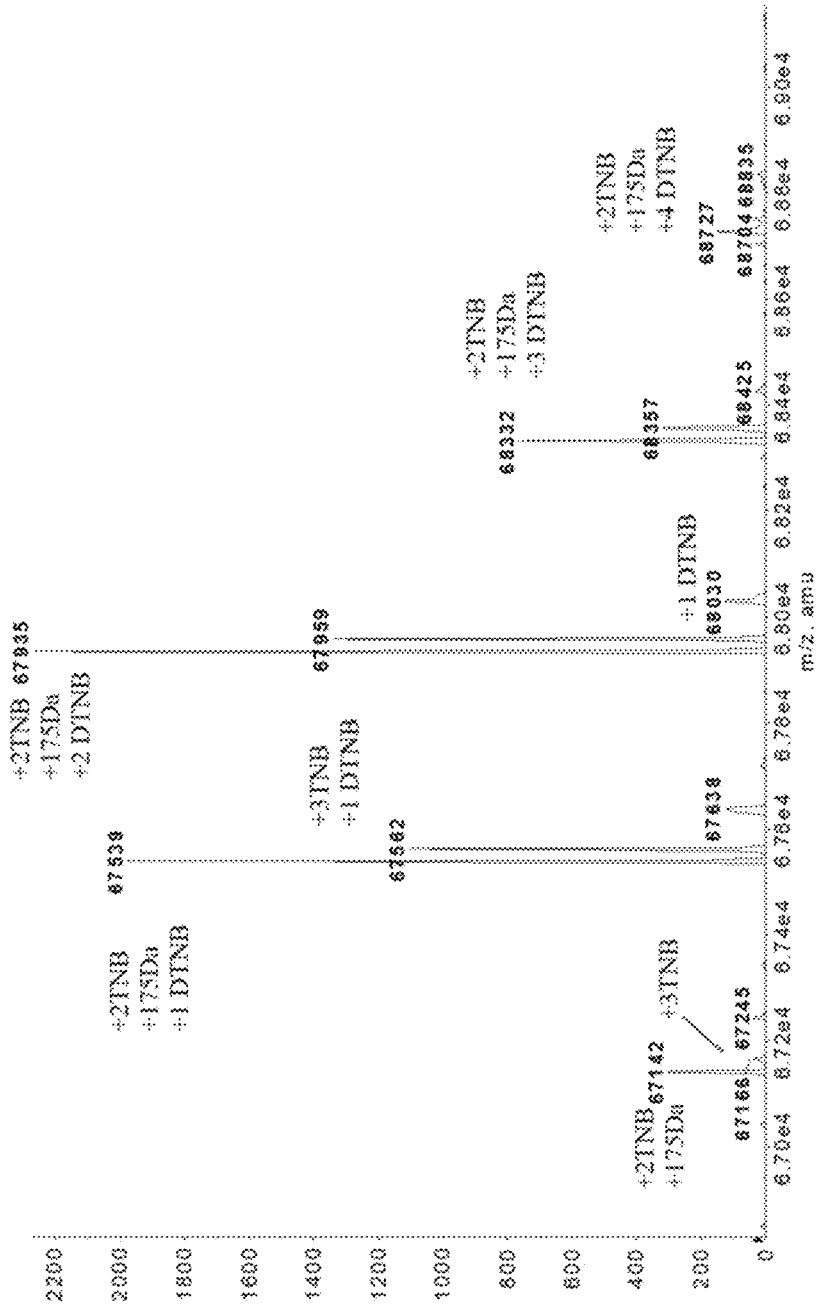
FIG. 24 is a mass spectrogram of a rHA molecule designed to have three free-thiols (Cys-34, A2C and a C-terminal free-thiol).

Finally when A2C rHA-Cys (total of 3 free thiols) was analysed pre-DTNB treatment (FIG. 23) the major deconvoluted peaks observed were at 66747 Da and 66919 Da which corresponds to 172 Da and 344 Da above the expected mass of 66574 Da. However also present was a smaller peak corresponding to the expected unmodified mass at 66575 Da. This mass spectra indicates the blocking of some free thiols while a proportion of the molecule is present containing the expected 3 free thiols. Post DTNB treatment mass spectrometric analysis (FIG. 24) resulted in a major a deconvoluted peak at 67142 Da which was 23 Da below the expected mass of 67165 Da of the protein labelled with 3 TNB molecules, this was likely due to the presence of two TNB molecules and a 175 Da modification, suggesting the presence of 3 thiols, one of which was blocked by the unknown ~175 Da species. However on closer inspection of FIG. 24 the presence of secondary peaks 23 Da above each species can be seen. These secondary peaks correspond to small shoulders in the raw data (data not shown) which are likely to indicate the presence of the molecule modified with 3 TNB molecules, indicating 3 free thiols. The other major species present are due to excess DTNB still present at the time of ionisation causing DTNB adduct formation with the labelled rHA D129C, C360S, L585C. This adduct formation is known to occur in the presence of excess DTNB.

In conclusion, a range of thio-albumin variants have been produced with three or more conjugation competent cysteine residues. The conjugation competent cysteines can be in regions of that may or may not have secondary structure, and/or may or may not be generated from natural disulphide bonds, and/or may or may not be additional cysteines residues (such as cysteine residues extending from the natural C-terminus of HSA).

Example 5: Formation of Gels from Thio-Albumin Variants

Samples of TA35 (i.e. A2C, A364, D562 in addition to naturally occurring C34) and TA33 (i.e. A2C, L585C in addition to naturally occurring C34) were incubated at room-temperature for 24 hours and both formed gels.

The invention claimed is:

1. A conjugation competent polypeptide comprising an amino acid sequence which is at least 90% identical to a human albumin having the sequence set forth in SEQ ID NO: 1, in which a position corresponding to position E294 of SEQ ID NO: 1 there is:
   (a) a substitution to cysteine,
   (b) an insertion of a cysteine at the N' side of the residue located at the position, or
   (c) an insertion of a cysteine at the C' side of the residue located at the position.

2. The polypeptide according to claim 1, wherein the polypeptide comprises 2, 3, 4, or 5 conjugation competent cysteine residues.

3. The polypeptide according to claim 2, in which the distance between two or more conjugation competent cysteine residues is at least 10 Angstroms.

4. The polypeptide according to claim 1, in which at a position corresponding to position 34 of SEQ ID NO: 1 there is a cysteine residue.

5. The polypeptide according to claim 1, in which at a position corresponding to position 34 of SEQ ID NO: 1 there is a residue other than cysteine.

6. The polypeptide according to claim 1, in which the polypeptide further comprises a linker to which a bioactive compound may be linked.

7. A polynucleotide which encodes the polypeptide to claim 1.

8. A plasmid comprising the polynucleotide of claim 7.

9. A host cell comprising a polynucleotide of claim 8.

10. The host cell of claim 9, which is a yeast cell.

11. A conjugate which comprises a bioactive compound and a polypeptide according to claim 2, wherein the bioactive compound is linked to the polypeptide through a conjugation competent cysteine residue of the polypeptide.

12. The conjugate according to claim 11, further comprising one or more further bioactive compounds, each of the one or more further bioactive compounds being linked to the polypeptide through a conjugation competent cysteine residue of the polypeptide.

13. A method of producing a polypeptide of claim 1, comprising:
   culturing the host cell of claim 10 under conditions that allow expression of the polypeptide; and
   recovering the polypeptide from the host cell and/or from host cell growth medium.

14. A method of preparing a conjugation-competent polypeptide, comprising:
   providing a three-dimensional model comprising at least one instance of an albumin sequence and, optionally, providing an amino acid sequence of that albumin sequence,
   selecting an amino acid residue in the albumin sequence which corresponds to residue E294 of SEQ ID NO: 1,
   substituting the selected residue with cysteine or inserting Cysteine at the N-side or C-side of the selected residue,
   optionally, making additional alterations to the albumin sequence where each alteration is an amino acid deletion, substitution, or insertion, and
   preparing a polypeptide having the resulting amino acid sequence.

15. A method of producing the conjugate of claim 11, comprising linking a bioactive compound to the polypeptide of claim 1 through a conjugation competent cysteine residue of the polypeptide.

16. A composition comprising a conjugate of claim 11 and at least one pharmaceutically acceptable carrier or diluent.

17. A method of therapy comprising providing the conjugate of claim 11 to a subject.

* * * * *

UNITED STATES PATENT AND TRADEMARK OFFICE
CERTIFICATE OF CORRECTION

PATENT NO. : 11,555,061 B2  
APPLICATION NO. : 16/827356  
DATED : January 17, 2023  
INVENTOR(S) : Christopher John Arthur Finnis Page 1 of 5

It is certified that error appears in the above-identified patent and that said Letters Patent is hereby corrected as shown below:

On the Title Page

Page 3, Column 2 (Item (56) Other Publications), Line 2, Delete "genertion" and insert -- generation --.

Page 3, Column 2 (Item (56) Other Publications), Line 16, Delete "MCH" and insert -- MHC --.

Page 3, Column 2 (Item (56) Other Publications), Line 71, Delete "Rc" and insert -- Fc --.

Page 4, Column 1 (Item (56) Other Publications), Line 5, Delete "TCR-lg" and insert -- TCR-Ig --.

Page 4, Column 1 (Item (56) Other Publications), Line 25, Delete "Common.," and insert -- Commun., --.

Page 4, Column 2 (Item (56) Other Publications), Line 11, Delete "A" and insert -- Å --.

Page 5, Column 1 (Item (56) Other Publications), Line 56, Delete "maleeimide" and insert -- maleimide --.

Page 6, Column 1 (Item (56) Other Publications), Line 28, Delete "1581 -1591." and insert -- 1581-1591. --.

Page 6, Column 2 (Item (56) Other Publications), Line 61, Delete "low-loaded,covalently" and insert -- low-loaded, covalently --.

Page 7, Column 1 (Item (56) Other Publications), Line 54, Delete "Lttrs," and insert -- Letters, --.

Page 7, Column 1 (Item (56) Other Publications), Line 56, Delete "Chern" and insert -- Chem --.

Page 7, Column 1 (Item (56) Other Publications), Line 56, Delete "Lttrs," and insert -- Letters, --.

Signed and Sealed this  
Twentieth Day of June, 2023

Katherine Kelly Vidal  
*Director of the United States Patent and Trademark Office*

CERTIFICATE OF CORRECTION (continued)  Page 2 of 5
U.S. Pat. No. 11,555,061 B2

Page 7, Column 1 (Item (56) Other Publications), Line 60, Delete "Inti" and insert -- Intl --.

Page 7, Column 2 (Item (56) Other Publications), Line 5, Delete "Enediyene" and insert
-- Enediyne --.

Page 7, Column 2 (Item (56) Other Publications), Line 6, Delete "theta11" and insert -- theta1 --.

Page 7, Column 2 (Item (56) Other Publications), Line 52, Delete "Gllu," and insert -- Glu, --.

Page 7, Column 2 (Item (56) Other Publications), Line 52, Delete "Bioph" and insert -- Biophys --.

Page 8, Column 1 (Item (56) Other Publications), Line 58, Delete "Postransitional" and insert
-- Post-transitional --.

Page 8, Column 2 (Item (56) Other Publications), Line 39, Delete "byt" and insert -- but --.

Page 9, Column 1 (Item (56) Other Publications), Line 36, Delete "Vsc" and insert -- Vasc --.

Page 9, Column 1 (Item (56) Other Publications), Line 48, Delete "µ m" and insert -- µm --.

Page 9, Column 1 (Item (56) Other Publications), Line 48, After "plasmid" insert -- copy --.

Page 9, Column 1 (Item (56) Other Publications), Line 54, Delete "Biochimca" and insert
-- Biochimica --.

Page 9, Column 2 (Item (56) Other Publications), Line 26, Delete "Fc- Fusion" and insert
-- Fc-Fusion --.

Page 9, Column 2 (Item (56) Other Publications), Line 53, Delete "antihaemophilic" and insert
-- antihemophilic --.

Page 9, Column 2 (Item (56) Other Publications), Line 68, Delete "3T3-L 1" and insert -- 3T3-L1 --.

Page 10, Column 1 (Item (56) Other Publications), Line 18, Delete "3T3-L 1" and insert -- 3T3-L1 --.

Page 10, Column 1 (Item (56) Other Publications), Line 27, Delete "he" and insert -- the --.

Page 10, Column 1 (Item (56) Other Publications), Line 43, Delete "HeLac" and insert -- HeLa --.

Page 10, Column 1 (Item (56) Other Publications), Line 44, Delete "Biotechol" and insert
-- Biotechnol --.

Page 10, Column 1 (Item (56) Other Publications), Line 50, Delete "GCSF-transferring" and insert
-- G-CSF-transferrin --.

Page 10, Column 2 (Item (56) Other Publications), Line 16, Delete "agricultre" and insert -- agriculture --.

In the Specification

Column 2, Line 53, Delete "1." and insert -- 1 --.

Column 2, Line 57, Delete "2." and insert -- 2 --.

Column 3, Line 6, Delete "3. Is" and insert -- 3 is --.

Column 3, Line 42, Delete "4." and insert -- 4 --.

Column 3, Line 52, Delete "7." and insert -- 7 --.

Column 3, Line 54, Delete "9." and insert -- 9 --.

Column 4, Line 44, Delete "varant'" and insert -- variant' --.

Column 7, Line 53, Delete "1." and insert -- 1 --.

Column 7, Line 66, Delete "HSA HSA" and insert -- HSA (i.e. HSA --.

Column 8, Line 1, Delete "1." and insert -- 1 --.

Column 12, Line 64, Delete "Macacque" and insert -- Macaque --.

Column 14, Line 6, Delete "C567." and insert -- C567; --.

Column 14, Line 10-19, Delete "such that the net result of the substitution, deletion, addition or insertion events of (a), (b), (c) and (d) is that the number of conjugation competent cysteine residues of the polypeptide sequence is increased relative to the polypeptide prior to the substitution, insertion, deletion and addition events. Within (a) to (d), above, the residues all of the residues are preferred. However, within each of (a), (b), (c) and (d), the residues are listed in order of decreasing preference." and insert the same on Column 14, Line 9, as a continuation of the same paragraph.

Column 16, Line 66, Delete "descrive" and insert -- describe --.

Column 23-24, Line 39 (TABLE 1), Delete "Fells" and insert -- Felis --.

Column 33, Line 10, Delete "Biorad" and insert -- Bio-Rad --.

Column 36, Line 61, Delete "(Ylps)" and insert -- (YIps) --.

Column 37, Line 8, Delete "CPRE," and insert -- CPR6, --.

Column 37, Line 12, Delete "CDCl$_3$7," and insert -- CDC37, --.

CERTIFICATE OF CORRECTION (continued)
U.S. Pat. No. 11,555,061 B2

Column 37, Line 16, Delete "UB/4" and insert -- UBI4 --.

Column 41, Line 5, Delete "(N-MPB]-PE)" and insert -- (N-MPB-PE) --.

Column 44, Line 23, Delete "Hepatitus" and insert -- Hepatitis --.

Column 44, Line 24, Delete "Hepatitus" and insert -- Hepatitis --.

Column 45, Line 43, Delete "STOP-1," and insert -- STCP-1, --.

Column 45, Line 67, Delete "F(ab′)$_2$," and insert -- F(ab′)2, --.

Column 46, Line 15, Delete "1L2)," and insert -- IL2), --.

Column 46, Line 16, Delete "1L2)," and insert -- IL2), --.

Column 47, Line 5, Delete "Straphylococcus" and insert -- Staphylococcus --.

Column 49, Line 9, Delete "polyphenyalanine," and insert -- polyphenylalanine, --.

Column 49, Line 58, Delete "maleimidoprpionic" and insert -- maleimidopropionic --.

Column 50, Line 8, Delete "dithuio" and insert -- dithio --.

Column 50, Line 9-10, Delete "maleimimidoethyl]amine" and insert -- maleimidoethyl]amine --.

Column 50, Line 46, Delete "GM BS," and insert -- GMBS, --.

Column 50, Line 64, Delete "(SM PT," and insert -- (SMPT, --.

Column 50, Line 67, Delete "(SM PB," and insert -- (SMPB, --.

Column 51, Line 2, Delete "SM PB," and insert -- SMPB, --.

Column 56, Line 56, Delete "10p1" and insert -- 10 μl --.

Column 57, Line 57, Delete "undersirable" and insert -- undesirable --.

Column 58, Line 33, Delete "Biophama" and insert -- Biopharma --.

Column 58, Line 51, Delete "nitronenzoic" and insert -- nitrobenzoic --.

Column 59, Line 4, Delete "Triflu-oroacetic" and insert -- Trifluoroacetic --.

Column 59, Line 7, Delete "desalt-ing/" and insert -- desalting/ --.

Column 59, Line 8, Delete "Extaction" and insert -- Extraction --.

Column 59, Line 47, Delete "ionsation" and insert -- ionisation --.

In the Claims

Column 389, Line 61, In Claim 7, delete "to" and insert -- according to --.

Column 389, Line 67, In Claim 11, delete "claim 2" and insert -- claim 1 --.

Column 390, Line 57, In Claim 14, delete "Cysteine" and insert -- cysteine --.